United States Patent
Lu et al.

(10) Patent No.: US 6,984,648 B2
(45) Date of Patent: Jan. 10, 2006

(54) CYCLIC β-AMINO ACID DERIVATIVES AS INHIBITORS OF MATRIX METALLOPROTEASES AND TNF-α

(75) Inventors: Zhonghui Lu, Wilmington, DE (US); Thomas P. Maduskuie, Jr., Wilmington, DE (US); Matthew E. Voss, Lincoln Univ., PA (US); Chu-Biao Xue, Hockessin, DE (US); Jingwu Duan, Newark, DE (US); Gregory Ott, Philadelphia, PA (US); Lihua Chen, Wilmington, DE (US); Carl Decicco, Kennett Square, PA (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 0 days.

(21) Appl. No.: 10/779,539

(22) Filed: Feb. 13, 2004

(65) Prior Publication Data
US 2004/0162426 A1 Aug. 19, 2004

Related U.S. Application Data

(62) Division of application No. 09/811,233, filed on Mar. 16, 2001, now Pat. No. 6,743,807.
(60) Provisional application No. 60/190,182, filed on Mar. 17, 2000, provisional application No. 60/233,373, filed on Sep. 18, 2000, and provisional application No. 60/255,539, filed on Dec. 14, 2000.

(51) Int. Cl.
| | |
|---|---|
| A61K 31/47 | (2006.01) |
| A61K 31/445 | (2006.01) |
| C07D 215/02 | (2006.01) |
| C07D 413/00 | (2006.01) |
| C07D 211/68 | (2006.01) |

(52) U.S. Cl. .................. 514/314; 544/127; 546/166; 546/135; 546/194; 514/318
(58) Field of Classification Search .............. 544/127; 514/314, 318; 546/166, 194, 139, 141, 152, 546/158, 164, 165, 171, 181, 268.1
See application file for complete search history.

(56) References Cited

U.S. PATENT DOCUMENTS
5,212,182 A    5/1993   Musser et al.

FOREIGN PATENT DOCUMENTS
| | | |
|---|---|---|
| EP | 780386 A | 6/1997 |
| EP | 818442 A | 1/1998 |
| WO | WO 9720824 A | 6/1997 |
| WO | WO 9808815 A | 3/1998 |
| WO | WO 9919296 A | 4/1999 |
| WO | WO 0059865 A | 10/2000 |
| WO | WO 0063165 A | 10/2000 |
| WO | WO 0063197 A | 10/2000 |

OTHER PUBLICATIONS

Mohamed, M. M. et al. "Studies on the cyclization of the products of Stobbe condensation with 2,4-dimethylacetophenone", *Rev. Roum. Chim.* (1981), 26(3), 441-8.

*Primary Examiner*—Cecilia J. Tsang
*Assistant Examiner*—Binta Robinson
(74) *Attorney, Agent, or Firm*—Jing G. Sun; David H. Vance

(57) ABSTRACT

The present application describes novel cyclic β-amino acid derivatives of formula I:

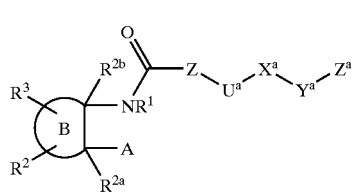

or pharmaceutically acceptable salt forms thereof, wherein ring B is a 5–7 membered cyclic system containing from 0–2 heteroatoms selected from O, N, $NR^a$, and $S(O)_p$, and 0–1 carbonyl groups and the other variables are defined in the present specification, which are useful as metalloprotease and/or as TNF-α inhibitors.

21 Claims, No Drawings

CYCLIC β-AMINO ACID DERIVATIVES AS INHIBITORS OF MATRIX METALLOPROTEASES AND TNF-α

The present application is a divisional application of U.S. application Ser. No. 09/811,233, filed Mar. 16, 2001 now U.S. Pat. No. 6,743,807, which claims the benefit of U.S. Provisional Application Ser. No. 60/190,182, filed Mar. 17, 2000, U.S. Provisional Application 60/233,373 filed, Sep. 18, 2000, and U.S. Provisional Application 60/255,539, filed Dec. 14, 2000. The contents of each application are incorporated herein by reference.

FIELD OF THE INVENTION

This invention relates generally to novel cyclic β-amino acid derivatives as matrix metalloproteases and TNF-α inhibitors, pharmaceutical compositions containing the same, and methods of using the same.

BACKGROUND OF THE INVENTION

There is now a body of evidence that metalloproteases (MP) are important in the uncontrolled breakdown of connective tissue, including proteoglycan and collagen, leading to resorption of the extracellular matrix. This is a feature of many pathological conditions, such as rheumatoid and osteoarthritis, corneal, epidermal or gastric ulceration; tumor metastasis or invasion; periodontal disease and bone disease. Normally these catabolic enzymes are tightly regulated at the level of their synthesis as well as at their level of extracellular activity through the action of specific inhibitors, such as alpha-2-macroglobulins and TIMPs (tissue inhibitors of metalloprotease), which form inactive complexes with the MP's.

Osteo- and Rheumatoid Arthritis (OA and RA respectively) are destructive diseases of articular cartilage characterized by localized erosion of the cartilage surface. Findings have shown that articular cartilage from the femoral heads of patients with OA, for example, had a reduced incorporation of radiolabeled sulfate over controls, suggesting that there must be an enhanced rate of cartilage degradation in OA (Mankin et al. J. Bone Joint Surg. 52A, 1970, 424–434). There are four classes of protein degradative enzymes in mammalian cells: serine, cysteine, aspartic and metalloproteases. The available evidence supports that it is the metalloproteases which are responsible for the degradation of the extracellular matrix of articular cartilage in OA and RA. Increased activities of collagenases and stromelysin have been found in OA cartilage and the activity correlates with severity of the lesion (Mankin et al. Arthritis Rheum. 21, 1978, 761–766, Woessner et al. Arthritis Rheum. 26, 1983, 63–68 and Ibid. 27, 1984, 305–312). In addition, aggrecanase has been identified as providing the specific cleavage product of proteoglycan found in RA and OA patients (Lohmander L. S. et al. Arthritis Rheum. 36, 1993, 1214–22).

Therefore, metalloproteases (MP) have been implicated as the key enzymes in the destruction of mammalian cartilage and bone. It can be expected that the pathogenesis of such diseases can be modified in a beneficial manner by the administration of MP inhibitors, and many compounds have been suggested for this purpose (see Wahl et al. Ann. Rep. Med. Chem. 25, 175–184, AP, San Diego, 1990).

Tumor necrosis factor (TNF) is a cell-associated cytokine that is processed from a 26 kd precursor form to a 17 kd active form. TNF has been shown to be a primary mediator in humans and in animals, of inflammation, fever, and acute phase responses, similar to those observed during acute infection and shock. Excess TNF has been shown to be lethal. There is now considerable evidence that blocking the effects of TNF with specific antibodies can be beneficial in a variety of circumstances including autoimmune diseases such as rheumatoid arthritis (Feldman et al, Lancet, 1994, 344, 1105) and non-insulin dependent diabetes melitus. (Lohmander L. S. et al. Arthritis Rheum. 36, 1993, 1214–22) and Crohn's disease (MacDonald T. et al. Clin. Exp. Immunol. 81, 1990, 301).

Compounds which inhibit the production of TNF are therefore of therapeutic importance for the treatment of inflammatory disorders. Recently, TNF-α converting enzyme (TACE), the enzyme responsible for TNF-α release from cells, were purified and sequenced (Black et al Nature 1997, 385, 729; Moss et al Nature 1997, 385, 733). This invention describes molecules that inhibit this enzyme and hence the secretion of active TNF-α from cells. These novel molecules provide a means of mechanism based therapeutic intervention for diseases including but not restricted to septic shock, haemodynamic shock, sepsis syndrome, post ischemic reperfusion injury, malaria, Crohn's disease, inflammatory bowel diseases, mycobacterial infection, meningitis, psoriasis, congestive heart failure, fibrotic diseases, cachexia, graft rejection, cancer, diseases involving angiogenesis, autoimmune diseases, skin inflammatory diseases, OA, RA, multiple sclerosis, radiation damage, hyperoxic alveolar injury, periodontal disease, HIV and non-insulin dependent diabetes melitus.

Since excessive TNF production has been noted in several disease conditions also characterized by MMP-mediated tissue degradation, compounds which inhibit both MMPs and TNF production may also have a particular advantage in diseases where both mechanisms are involved.

EP 0,780,286 describes MMP inhibitors of formula A:

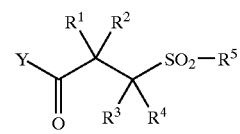

wherein Y can be NHOH, $R^1$ and $R^2$ can combine to form a cycloalkyl or heterocyclo alkyl group, $R^3$ and $R^4$ can be a variety of groups including H, and $R^5$ can be substituted aryl.

WO 97/20824 depicts MMP inhibitors of formula B:

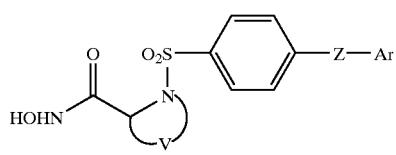

wherein ring V contains six atoms, Z is O or S, and Ar is an aryl or heteroaryl group. Ar is preferably a monocyclic aryl group with an optional para substituent or an unsubstituted monocyclic heteroaryl group.

EP 0,818,442 illustrates MMP inhibitors of formula C:

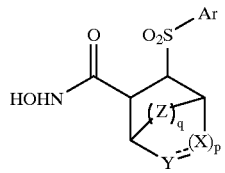

wherein Ar is optionally substituted phenyl or naphthyl, Z can be absent and X and Y can be a variety of substituents. Compounds of this sort are not considered to be part of the present invention.

The compounds of the present invention act as inhibitors of MPs, in particular TNF-α, MMPs, and/or aggrecanase. These novel molecules are provided as anti-inflammatory compounds and cartilage protecting therapeutics. The inhibition of aggrecanase, TNF-C, and other metalloproteases by molecules of the present invention indicates they are anti-inflammatory and should prevent the degradation of cartilage by these enzymes, thereby alleviating the pathological conditions of OA and RA.

SUMMARY OF THE INVENTION

Accordingly, one object of the present invention is to provide novel cyclic hydroxamic acids useful as metalloprotease inhibitors or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating inflammatory disorders, comprising: administering to a host, in need of such treatment, a therapeutically effective amount of at least one of the compounds of the present invention or a pharmaceutically acceptable salt or prodrug form thereof.

It is another object of the present invention to provide novel compounds of the present invention for use in therapy.

It is another object of the present invention to provide the use of novel compounds of the present invention for the manufacture of a medicament for the treatment of a condition or disease mediated by MMPs, TNF, aggrecanase, or a combination thereof.

These and other objects, which will become apparent during the following detailed description, have been achieved by the inventors' discovery that compounds of formula (I):

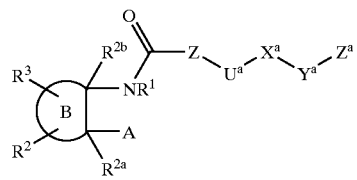

or pharmaceutically acceptable salt or prodrug forms thereof, wherein A, B, $R^1$, $R^2$, $R^{2a}$, $R^{2b}$, and $R^3$ are defined below, are effective metalloprotease inhibitors.

DETAILED DESCRIPTION OF PREFERRED EMBODIMENTS

[1] Thus, in an embodiment, the present invention provides a novel compound of formula I:

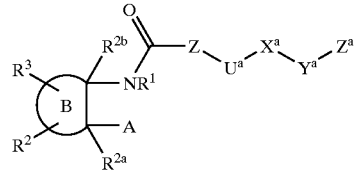

or a stereoisomer or pharmaceutically acceptable salt form thereof, wherein;

A is selected from —$COR^5$, —$CO_2H$, $CH_2CO_2H$, —$CO_2R^6$, —CONHOH, —$CONHOR^5$, —$CONHOR^6$, —$N(OH)COR^5$, —N(OH)CHO, —SH, —$CH_2SH$, —S(O)(=NH)$R^a$, —$SN_2H_2R^a$, —$PO(OH)_2$, and —PO(OH)$NHR^a$;

ring B is a 3–13 membered non-aromatic carbocyclic or heterocyclic ring comprising: carbon atoms, 0–3 carbonyl groups, 0–4 double bonds, and from 0–2 ring heteroatoms selected from O, N, $NR^2$, and S(O)$_p$, provided that ring B contains other than a S—S, O—O, or S—O bond;

Z is absent or selected from a $C_{3-13}$ carbocycle substituted with 0–5 $R^b$ and a 5–14 membered heterocycle comprising: carbon atoms and 1–4 heteroatoms selected from the group consisting of N, O, and S(O)$_p$ and substituted with 0–5 $R^b$;

$U^a$ is absent or is selected from: O, $NR^{a^1}$, C(O), C(O)O, OC(O), C(O)$NR^{a^1}$, $NR^{a^1}$C(O), OC(O)O, OC(O)$NR^{a^1}$, $NR^{a^1}$C(O)O, $NR^{a^1}$C(O)$NR^{a^1}$, S(O)$_p$, S(O)$_p$$NR^{a^1}$, $NR^{a^1}$S(O)$_p$, and $NR^{a^1}SO_2NR^{a^1}$;

$X^a$ is absent or selected from $C_{1-10}$ alkylene, $C_{2-10}$ alkenylene, and $C_{2-10}$ alkynylene;

$Y^a$ is absent or selected from O, $NR^{a^1}$, S(O)$_p$, and C(O);

$Z^a$ is selected from H, a $C_{3-13}$ carbocycle substituted with 0–5 $R^c$ and a 5–14 membered heterocycle comprising: carbon atoms and 1–4 heteroatoms selected from the group consisting of N, O, and S(O)$_p$ and substituted with 0–5 $R^c$;

provided that Z, $U^a$, $Y^a$, and $Z^a$ do not combine to form a N—N, N—O, O—N, O—O, S(O)$_p$—O, O—S(O)$_p$ or S(O)$_p$—S(O)$_p$ group;

$R^1$ is selected from H, $C_{1-4}$ alkyl, phenyl, and benzyl;

$R^2$ is selected from Q, Cl, F, $C_{1-10}$ alkylene-Q substituted with 0–3 $R^{b1}$, $C_{2-10}$ alkenylene-Q substituted with 0–3 $R^{b1}$, $C_{2-10}$ alkynylene-Q substituted with 0–3 $R^{b1}$, $(CR^aR^{a^1})_{r^1}O(CR^aR^{a^1})_r$-Q, $(CR^aR^{a^1})_{r^1}NR^a(CR^aR^{a^1}))_r$-Q, $(CR^aR^{a^1})_{r^1}C(O)(CR^aR^{a^1})_r$-Q, $(CR^aR^{a^1})_{r^1}C(O)O(CR^aR^{a^1})_r$-Q, $(CR^aR^{a^1})_r$C(O)O—$C_{2-5}$ alkenylene, $(CR^aR^{a^1})_r$C(O)O—$C_{2-5}$ alkynylene, $(CR^aR^{a^1})_{r^1}OC(O)(CR^aR^{a^1})_r$-Q, $(CR^aR^{a^1})_{r^1}C(O)NR^aR^{a^1}$, $(CR^aR^{a^1})_{r^1}C(O)NR^a(CR^aR^{a^1})_r$-Q, $(CR^aR^{a^1})_{r^1}NR^aC(O)(CR^aR^{a^1})_r$-Q, $(CR^aR^{a^1})_{r^1}OC(O)O(CR^aR^{a^1})_r$-Q, $(CR^aR^{a^1})_{r^1}OC(O)NR^a(CR^aR^{a^1})_r$-Q, $(CR^aR^{a^1})_{r^1}NR^aC(O)O(CR^aR^{a^1})_r$-Q, $(CR^aR^{a^1})_{r^1}NR^aC(O)NR^a(CR^aR^{a^1})_r$-Q, $(CR^aR^{a^1})_{r^1}S(O)_p(CR^aR^{a^1})_r$-Q, $(CR^aR^{a^1})_{r^1}SO_2NR^a(CR^aR^{a^1})_r$-Q, $(CR^aR^{a^1})_{r^1}NR^aSO_2(CR^aR^{a^1})_r$-Q, and $(CR^aR^{a^1})_{r^1}NR^aSO_2NR^a(CR^aR^{a^1})_r$-Q;

$R^{2a}$ is selected from H, $C_{1-6}$ alkyl, $OR^a$, $NR^aR^{a^1}$, and S(O)$_p$$R^a$;

$R^{2b}$ is H or $C_{1-6}$ alkyl;

Q is selected from H, a $C_{3-13}$ carbocycle substituted with 0–5 $R^d$ and a 5–14 membered heterocycle comprising: carbon atoms and 1–4 heteroatoms selected from the group consisting of N, O, and $S(O)_p$ and substituted with 0–5 $R^d$;

$R^3$ is selected from $Q^1$, Cl, F, $C_{1-6}$ alkylene-$Q^1$, $C_{2-6}$ alkenylene-$Q^1$, $C_{2-6}$ alkynylene-$Q^1$, $(CR^aR^{a^1})_rO(CR^aR^{a^1})_r$-$Q^1$, $(CR^aR^{a^1})_{r^1}NR^a(CR^aR^{a^1})_r$-$Q^1$, $(CR^aR^{a^1})_{r^1}NR^aC(O)(CR^aR^{a^1})_r$-$Q^1$, $(CR^aR^{a^1})_{r^1}C(O)NR^a(CR^aR^{a^1})_r$-$Q^1$, $(CR^aR^{a^1})_{r^1}C(O)(CR^aR^{a^1})_r$-$Q^1$, $(CR^aR^{a^1})_{r^1}C(O)O(CR^aR^{a^1})_r$-$Q^1$, $(CR^aR^{a^1}{}_2)_{r^1}S(O)_p(CR^aR^{a^1})_r$-$Q^1$, and $(CR^aR^{a^1})_{r^1}SO_2NR^a(CR^aR^{a^1})_r$-$Q^1$;

$Q^1$ is selected from H, phenyl substituted with 0–3 $R^d$, naphthyl substituted with 0–3 $R^d$ and a 5–10 membered heteroaryl comprising: carbon atoms and 1–4 heteroatoms selected from the group consisting of N, O, and $S(O)_p$ and substituted with 0–3 $R^d$;

$R^a$, at each occurrence, is independently selected from H, $C_{1-4}$ alkyl, phenyl and benzyl;

$R^{a^1}$, at each occurrence, is independently selected from H and $C_{1-4}$ alkyl;

alternatively, $R^a$ and $R^{a^1}$ when attached to a nitrogen are taken together with the nitrogen to which they are attached to form a 5 or 6 membered ring comprising carbon atoms and from 0–1 additional heteroatoms selected from the group consisting of N, O, and $S(O)_p$;

$R^{a^2}$, at each occurrence, is independently selected from $C_{1-4}$ alkyl, phenyl and benzyl;

$R^b$, at each occurrence, is independently selected from $C_{1-6}$ alkyl, $OR^a$, Cl, F, Br, I, =O, —CN, $NO_2$, $NR^aR^{a^1}$, $C(O)R^a$, $C(O)OR^a$, $C(O)NR^aR^{a^1}$, $R^aNC(O)NR^aR^{a^1}$, $OC(O)NR^aR^{a^1}$, $R^aNC(O)O$, $S(O)_2NR^aR^{a^1}$, $NR^aS(O)_2R^{a^2}$, $NR^aS(O)_2NR^aR^{a^1}$, $OS(O)_2NR^aR^{a^1}$, $NR^aS(O)_2R^{a^2}$, $S(O)_pR^{a^2}$, $CF_3$, and $CF_2CF_3$;

$R^{b^1}$, at each occurrence, is independently selected from $OR^a$, Cl, F, Br, I, =O, —CN, $NLO_2$, and $NR^aR^{a^1}$;

$R^c$, at each occurrence, is independently selected from $C_{1-6}$ alkyl, $OR^a$, Cl, F, Br, I, =O, —CN, $NO_2$, $NR^{a^1}a^1$, $C(O)R^a$, $C(O)OR^a$, $C(O)NR^aR^{a^1}$, $R^aNC(O)NR^aR^{a^1}$, $OC(O)NR^aR^{a^1}$, $R^aNC(O)O$, $S(O)_2NR^aR^{a^1}$, $NR^aS(O)_2R^{a^2}$, $NR^aS(O)_2NR^aR^{a^1}$, $OS(O)_2NR^aR^{a^1}$, $NR^aS(O)_2R^{a^2}$, $S(O)_pR^{a^2}$, $CF_3$, $CF_2CF_3$, $C_{3-10}$ carbocycle substituted with 0–3 $R^{c^1}$ and a 5–14 membered heterocycle comprising: carbon atoms and 1–4 heteroatoms selected from the group consisting of N, O, and $S(O)_p$ and substituted with 0–3 $R^{c^1}$;

$R^{c^1}$, at each occurrence, is independently selected from $C_{1-6}$ alkyl, $OR^a$, Cl, F, Br, I, =O, —CN, $NO_2$, $NR^aR^{a^1}a^1$, $C(O)R^a$, $C(O)OR^a$, $C(O)NR^aR^{a^1}$, $R^aNC(O)NR^aR^{a^1}$, $OC(O)NR^aR^{a^1}$, $R^aNC(O)O$, $S(O)_2NR^aR^{a^1}$, $NR^aS(O)_2R^{a^2}$, $NR^aS(O)_2NR^aR^{a^1}$, $OS(O)_2NR^aR^{a^1}$, $NR^aS(O)_2R^{a^2}$, $S(O)_pR^{a^2}$, $CF_3$, and $CF_2CF_3$;

$R^d$, at each occurrence, is independently selected from $C_{1-6}$ alkyl, $OR^a$, Cl, F, Br, I, =O, —CN, $NO_2$, $NR^aR^1a^1$, $C(O)R^a$, $C(O)OR^a$, $C(O)NR^aR^{a^1}$, $R^aNC(O)NR^aR^{a^1}$, $OC(O)NR^aR^{a^1}$, $R^aNC(O)O$, $S(O)_2NR^aR^{a^1}$, $NR^aS(O)_2R^{a^2}$, $NR^aS(O)_2NR^aR^{a^1}$, $OS(O)_2NR^aR^{a^1}$, $NR^aS(O)_2R^{a^2}$, $S(O)_pR^{a^2}$, $CF_3$, $CF_2CF_3$, $C_{3-10}$ carbocycle and a 5–14 membered heterocycle comprising: carbon atoms and 1–4 heteroatoms selected from the group consisting of N, O, and $S(O)_p$;

$R^5$, at each occurrence, is selected from $C_{1-10}$ alkyl substituted with 0–2 $R^b$, and $C_{1-8}$ alkyl substituted with 0–2 $R^e$;

$R^e$, at each occurrence, is selected from phenyl substituted with 0–2 $R^b$ and biphenyl substituted with 0–2 $R^b$;

$R^6$, at each occurrence, is selected from phenyl, naphthyl, $C_{1-10}$ alkyl-phenyl-$C_{1-6}$ alkyl-, $C_{3-11}$ cycloalkyl, $C_{1-6}$ alkylcarbonyloxy-$C_{1-3}$ alkyl-, $C_{1-6}$ alkoxycarbonyloxy-$C_{1-3}$ alkyl-, $C_{2-10}$ alkoxycarbonyl, $C_{3-6}$ cycloalkylcarbonyloxy-$C_{1-3}$ alkyl-, $C_{3-6}$ cycloalkoxycarbonyloxy-$C_{1-3}$ alkyl-, $C_{3-6}$ cycloalkoxycarbonyl, phenoxycarbonyl, phenyloxycarbonyloxy-$C_{1-3}$ alkyl-, phenylcarbonyloxy-$C_{1-3}$ alkyl-, $C_{1-6}$ alkoxy-$C_{1-6}$ alkylcarbonyloxy-$C_{1-3}$ alkyl-, [5-($C_1$–$C_5$ alkyl)-1,3-dioxa-cyclopenten-2-one-yl]methyl, [5-($R^a$)-1,3-dioxa-cyclopenten-2-one-yl]methyl, (5-aryl-1,3-dioxa-cyclopenten-2-one-yl)methyl, —$C_{1-10}$ alkyl-$NR^7R^{7a}$, —$CH(R^8)OC(=O)R^9$, and —$CH(R^8)OC(=O)OR^9$;

$R^7$ is selected from H and $C_{1-10}$ alkyl, $C_{2-6}$ alkenyl, $C_{3-6}$ cycloalkyl-$C_{1-3}$ alkyl-, and phenyl-$C_{1-6}$ alkyl-;

$R^{7a}$ is selected from H and $C_{1-10}$ alkyl, $C_{2-6}$ alkenyl, $C_{3-6}$ cycloalkyl-$C_{1-3}$ alkyl-, and phenyl-$C_{1-6}$ alkyl-;

$R^8$ is selected from H and $C_{1-4}$ linear alkyl;

$R^9$ is selected from H, $C_{1-8}$ alkyl substituted with 1–2 $R^f$, $C_{3-8}$ cycloalkyl substituted with 1–2 $R^f$, and phenyl substituted with 0–2 $R^b$;

$R^f$, at each occurrence, is selected from $C_{1-4}$ alkyl, $C_{3-8}$ cycloalkyl, $C_{1-5}$ alkoxy, and phenyl substituted with 0–2 $R^b$;

p, at each occurrence, is selected from 0, 1, and 2;

r, at each occurrence, is selected from 0, 1, 2, 3, and 4; and, $r^1$, at each occurrence, is selected from 0, 1, 2, 3, and 4.

[2] In a preferred embodiment, the present invention provides a novel compound of formula II:

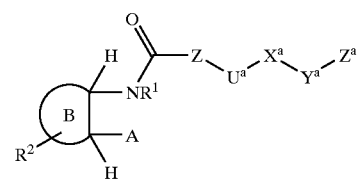

or a stereoisomer or pharmaceutically acceptable salt form thereof, wherein;

A is selected from —$CO_2H$, $CH_2CO_2H$, —CONHOH, —$CONHOR^5$, —$CONHOR^6$, —$N(OH)COR^5$, —N(OH)CHO, —SH, and —$CH_2SH$;

ring B is a 4–7 membered non-aromatic carbocyclic or heterocyclic ring comprising: carbon atoms, 0–1 carbonyl groups, 0–1 double bonds, and from 0–2 ring heteroatoms selected from O, N, and $NR^2$, provided that ring B contains other than a O—O bond;

Z is absent or selected from a $C_{3-11}$ carbocycle substituted with 0–4 $R^b$ and a 5–11 membered heterocycle comprising: carbon atoms and 1–4 heteroatoms selected from the group consisting of N, O, and $S(O)_p$ and substituted with 0–3 $R^b$;

$U^a$ is absent or is selected from: O, $NR^{a^1}$, C(O), C(O)O, C(O)$NR^{a^1}$, $NR^{a^1}$C(O), $S(O)_p$, and $S(O)_pNR^{a^1}$;

$X^a$ is absent or selected from $C_{1-4}$ alkylene, $C_{2-4}$ alkenylene, and $C_{2-4}$ alkynylene;

$Y^a$ is absent or selected from O and $NR^{a^1}$;

$Z^a$ is selected from H, a $C_{3-10}$ carbocycle substituted with 0–5 $R^c$ and a 5–10 membered heterocycle comprising:

carbon atoms and 1–4 heteroatoms selected from the group consisting of N, O, and S(O)$_p$ and substituted with 0–5 R$^c$;

provided that Z, U$^a$, Y$^a$, and Z$^a$ do not combine to form a N—N, N—O, O—N, O—O, S(O)$_p$—O, O—S(O)$_p$ or S(O)$_p$—S(O)$_p$ group;

R$^1$ is selected from H, C$_{1-4}$ alkyl, phenyl, and benzyl;

R$^2$ is selected from Q, C$_{1-6}$ alkylene-Q, C$_{2-6}$ alkenylene-Q, C$_{2-6}$ alkynylene-Q, (CR$^a$R$^{a^1}$)$_{r^1}$O(CR$^a$R$^{a^1}$)$_r$-Q, (CR$^a$R$^{a^1}$)$_{r^1}$NR$^a$(CR$^a$R$^{a^1}$)$_r$-Q, (CR$^a$R$^{a^1}$)$_{r^1}$C(O)(CR$^a$R$^{a^1}$)$_r$-Q, (CR$^a$R$^{a^1}$)$_{r^1}$C(O)O(CR$^a$R$^{a^1}$)$_r$-Q, (CR$^a$R$^{a^1}$)$_{r^1}$C(O)NR$^a$R$^{a^1}$, (CR$^a$R$^{a^1}$)$_{r^1}$C(O)NR$^a$(CR$^a$R$^{a^1}$)$_r$-Q, (CR$^a$R$^{a^1}$)$_{r^1}$S(O)$_p$(CR$^a$R$^{a^1}$)$_r$-Q, and (CR$^a$R$^{a^1}$)$_{r^1}$SO$_2$NR$^a$(CR$^a$R$^{a^1}$)$_r$-Q;

Q is selected from H, a C$_{3-6}$ carbocycle substituted with 0–5 R$^d$, and a 5–10 membered heterocycle comprising: carbon atoms and 1–4 heteroatoms selected from the group consisting of N, O, and S(O)$_p$ and substituted with 0–5 R$^d$;

R$^a$, at each occurrence, is independently selected from H, C$_{1-4}$ alkyl, phenyl and benzyl;

R$^{a^1}$, at each occurrence, is independently selected from H and C$_{1-4}$ alkyl;

alternatively, R$^a$ and R$^{a^1}$ when attached to a nitrogen are taken together with the nitrogen to which they are attached to form a 5 or 6 membered ring comprising carbon atoms and from 0–1 additional heteroatoms selected from the group consisting of N, O, and S(O)$_p$;

R$^{a^2}$, at each occurrence, is independently selected from C$_{1-4}$ alkyl, phenyl and benzyl;

R$^b$, at each occurrence, is independently selected from C$_{1-6}$ alkyl, OR$^a$, Cl, F, Br, =O, —CN, NR$^a$R$^{a^1}$, C(O)R$^a$, C(O)OR$^a$, C(O)NR$^a$R$^{a^1}$, S(O)$_2$NR$^a$R$^{a^1}$, S(O)$_p$R$^{a^2}$, and CF$_3$;

R$^c$, at each occurrence, is independently selected from C$_{1-6}$ alkyl, OR$^a$, Cl, F, Br, =O, —CN, NR$^a$R$^{a^1}$, C(O)R$^a$, C(O)OR$^a$, C(O)NR$^a$R$^{a^1}$, S(O)$_2$NR$^a$R$^{a^1}$, S(O)$_p$R$^{a^2}$, CF$_3$, C$_{3-6}$ carbocycle and a 5–6 membered heterocycle comprising: carbon atoms and 1–4 heteroatoms selected from the group consisting of N, O, and S(O)$_p$;

R$_d$, at each occurrence, is independently selected from C$_{1-6}$ alkyl, OR$^a$, Cl, F, Br, =O, —CN, NR$^a$R$^{a^1}$, C(O)R$^a$, C(O)OR$^a$, C(O)NR$^a$R$^{a^1}$, S(O)$_2$NR$^a$R$^{a^1}$, S(O)$_p$R$^{a^2}$, CF$_3$, C$_{3-6}$ carbocycle and a 5–6 membered heterocycle comprising: carbon atoms and 1–4 heteroatoms selected from the group consisting of N, O, and S(O)$_p$;

R$^5$, at each occurrence, is selected from C$_{1-6}$ alkyl substituted with 0–2 R$^b$, and C$_{1-4}$ alkyl substituted with 0–2 R$^e$;

R$^e$, at each occurrence, is selected from phenyl substituted with 0–2 R$^b$ and biphenyl substituted with 0–2 R$^b$;

R$^6$, at each occurrence, is selected from phenyl, naphthyl, C$_{1-10}$ alkyl-phenyl-C$_{1-6}$ alkyl-, C$_{3-11}$ cycloalkyl, C$_{1-6}$ alkylcarbonyloxy-C$_{1-3}$ alkyl-, C$_{1-6}$ alkoxycarbonyloxy-C$_{1-3}$ alkyl-, C$_{2-10}$ alkoxycarbonyl, C$_{3-6}$ cycloalkylcarbonyloxy-C$_{1-3}$ alkyl-, C$_{3-6}$ cycloalkoxycarbonyloxy-C$_{1-3}$ alkyl-, C$_{3-6}$ cycloalkoxycarbonyl, phenoxycarbonyl, phenyloxycarbonyloxy-C$_{1-3}$ alkyl-, phenylcarbonyloxy-C$_{1-3}$ alkyl-, C$_{1-6}$ alkoxy-C$_{1-6}$ alkylcarbonyloxy-C$_{1-3}$ alkyl-, [5-(C$_1$-C$_5$ alkyl)-1,3-dioxa-cyclopenten-2-one-yl]methyl, [5-(R$^a$)-1,3-dioxa-cyclopenten-2-one-yl]methyl, (5-aryl-1,3-dioxa-cyclopenten-2-one-yl)methyl, —C$_{1-10}$ alkyl-NR$^7$R$^{7a}$, —CH(R$^8$)OC(=O)R$^9$, and —CH(R$^8$)OC(=O)OR$^9$;

R$^7$ is selected from H and C$_{1-6}$ alkyl, C$_{2-6}$ alkenyl, C$_{3-6}$ cycloalkyl-C$_{1-3}$ alkyl-, and phenyl-C$_{1-6}$ alkyl-;

R$^{7a}$ is selected from H and C$_{1-6}$ alkyl, C$_{2-6}$ alkenyl, C$_{3-6}$ cycloalkyl-C$_{1-3}$ alkyl-, and phenyl-C$_{1-6}$ alkyl-;

R$^8$ is selected from H and C$_{1-4}$ linear alkyl;

R$^9$ is selected from H, C$_{1-6}$ alkyl substituted with 1–2 R$^f$, C$_{3-6}$ cycloalkyl substituted with 1–2 R$^f$, and phenyl substituted with 0–2 R$^b$;

R$^f$, at each occurrence, is selected from C$_{1-4}$ alkyl, C$_{3-6}$ cycloalkyl, C$_{1-5}$ alkoxy, and phenyl substituted with 0–2 R$^b$;

p, at each occurrence, is selected from 0, 1, and 2;

r, at each occurrence, is selected from 0, 1, 2, 3, and 4; and, r$^1$, at each occurrence, is selected from 0, 1, 2, 3, and 4.

[3] In a more preferred embodiment, the present invention provides a novel compound of formula IIIa or IIIb:

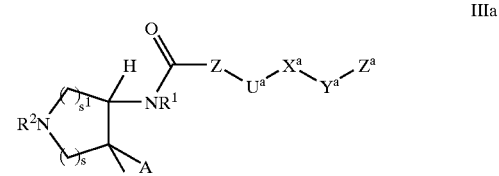

IIIa

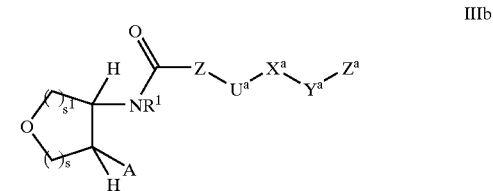

IIIb or a stereoisomer or pharmaceutically acceptable salt form thereof, wherein;

A is selected from —CO$_2$H, CH$_2$CO$_2$H, —CONHOH, —CONHOR$^5$, —N(OH)CHO, and —N(OH)COR$^5$;

Z is absent or selected from a C$_{5-6}$ carbocycle substituted with 0–3 R$^b$ and a 5–6 membered heteroaryl comprising carbon atoms and from 1–4 heteroatoms selected from the group consisting of N, O, and S(O)$_p$ and substituted with 0–3 R$^b$;

U$^a$ is absent or is selected from: O, NR$^{a^1}$, C(O), C(O)NR$^{a^1}$, S(O)$_p$, and S(O)$_p$NR$^{a^1}$;

X$^a$ is absent or selected from C$_{1-4}$ alkylene, C$_{2-4}$ alkenylene, and C$_{2-4}$ alkynylene Y$^a$ is absent or selected from O and NR$^{a^1}$;

Z$^a$ is selected from H, a C$_{5-6}$ carbocycle substituted with 0–3 R$^c$ and a 5–10 membered heteroaryl comprising carbon atoms and from 1–4 heteroatoms selected from the group consisting of N, O, and S(O)$_p$ and substituted with 0–3 R$^c$;

provided that Z, U$^a$, Y$^a$, and Z$^a$ do not combine to form a N—N, N—O, O—N, O—O, S(O)$_p$—O, O—S(O)$_p$ or S(O)$_p$—S(O)$_p$ group;

R$^1$ is selected from H C$_{1-4}$ alkyl, phenyl, and benzyl;

R$^2$ is selected from Q, C$_{1-6}$ alkylene-Q, C$_{2-6}$ alkenylene-Q, C$_{2-6}$ alkynylene-Q, (CR$^a$R$^{a^1}$)$_{r^1}$C(O)(CR$^a$R$^{a^1}$)$_r$-Q, (CR$^a$R$^{a^1}$)$_{r^1}$C(O)O(CR$^a$R$^{a^1}$)$_r$-Q, (CR$^a$R$^{a^1}$)$_{r^1}$C(O)NR$^a$R$^{a^1}$, (CR$^a$R$^{a^1}$)$_{r^1}$C(O)NR$^a$(CR$^a$R$^{a^1}$)$_r$-Q, and (CR$^a$R$^{a^1}$)$_{r^1}$S(O)$_p$(CR$^a$R$^{a^1}$)$_r$-Q;

Q is selected from H, a C$_{3-6}$ carbocycle substituted with 0–3 R$^d$ and a 5–10 membered heterocycle comprising: carbon atoms and 1–4 heteroatoms selected from the group consisting of N, O, and S(O)$_p$ and substituted with 0–3 R$^d$;

$R^a$, at each occurrence, is independently selected from H, $C_{1-4}$ alkyl, phenyl and benzyl;

$R^{a1}$, at each occurrence, is independently selected from H and $C_{1-4}$ alkyl;

$R^{a2}$, at each occurrence, is independently selected from $C_{1-4}$ alkyl, phenyl, and benzyl;

$R_b$, at each occurrence, is independently selected from $C_{1-4}$ alkyl, $OR^a$, Cl, F, =O, $NR^aR^{a1}$, $C(O)R^a$, $C(O)OR^a$, $C(O)NR^aR^{a1}$, $S(O)_2NR^aR^{a1}$, $S(O)_pR^{a^2}$, and $CF_3$;

$R^c$, at each occurrence, is independently selected from $C_{1-6}$ alkyl, $OR^a$, Cl, F, Br, =O, $NR^aR^{a1}$, $C(O)R^a$, $C(O)NR^aR^{a1}$, $S(O)_2NR^aR^{a1}$, $S(O)_pR^{a^2}$, and $CF_3$;

$R^d$, at each occurrence, is independently selected from $C_{1-6}$ alkyl, $OR^a$, Cl, F, Br, =O, $NR^aR^{a1}$, $C(O)R^a$, $C(O)NR^aR^{a1}$, $S(O)_2NR^aR^{a1}$, $S(O)_pR^{a^2}$, $CF_3$, and phenyl;

$R^5$, at each occurrence, is selected from $C_{1-4}$ alkyl substituted with 0–2 $R^b$, and $C_{1-4}$ alkyl substituted with 0–2 $R^e$;

$R^e$, at each occurrence, is selected from phenyl substituted with 0–2 $R^b$ and biphenyl substituted with 0–2 $R^b$;

p, at each occurrence, is selected from 0, 1, and 2;

r, at each occurrence, is selected from 0, 1, 2, 3, and 4;

$r^1$, at each occurrence, is selected from 0, 1, 2, 3, and 4; and, s and $s^1$ combine to total 2, 3, or 4.

[4] In a further preferred embodiment, the present invention provides a novel compound of formula IVa or IVb:

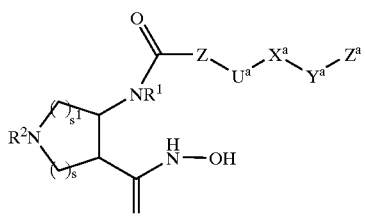

IVa

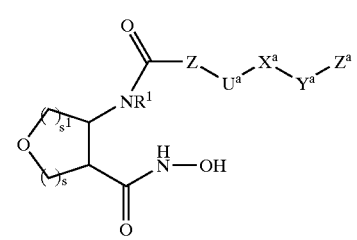

IVb or a stereoisomer or pharmaceutically acceptable salt form thereof, wherein;

Z is absent or selected from phenyl substituted with 0–3 $R^b$ and pyridyl substituted with 0–3 $R^b$;

$U^a$ is absent or is O;

$X^a$ is absent or is $CH_2$ or $CH_2CH_2$;

$Y^a$ is absent or is O;

$Z^a$ is selected from H, phenyl substituted with 0–3 $R^c$, pyridyl substituted with 0–3 $R^c$, and quinolinyl substituted with 0–3 $R^c$;

provided that Z, $U^a$, $Y^a$, and $Z^a$ do not combine to form a N—N, N—O, O—N, or O—O group;

$R^1$ is selected from H, $CH_3$, and $CH_2CH_3$;

$R^2$ is selected from Q, $C_{1-6}$ alkylene-Q, $C_{2-6}$ alkynylene-Q, $C(O)(CR^aR^{a1})_r$-Q, $C(O)O(CR^aR^{a1})_r$-Q, $C(O)NR^a(CR^aR^{a1})_r$-Q, and $S(O)_p(CR^aR^{a1})_r$-Q;

Q is selected from H, cyclopropyl substituted with 0–1 $R^d$, cyclobutyl substituted with 0–1 $R^d$, cyclopentyl substituted with 0–1 $R^d$, cyclohexyl substituted with 0–1 $R^d$, phenyl substituted with 0–2 $R^d$ and a heteroaryl substituted with 0–3 $R^d$, wherein the heteroaryl is selected from pyridyl, quinolinyl, thiazolyl, furanyl, imidazolyl, and isoxazolyl;

$R^a$, at each occurrence, is independently selected from H, $CH_3$, and $CH_2CH_3$;

$R^{a1}$, at each occurrence, is independently selected from H, $CH_3$, and $CH_2CH_3$;

$R^{a2}$, at each occurrence, is independently selected from H, $CH_3$, and $CH_2CH_3$;

$R^b$, at each occurrence, is independently selected from $C_{1-4}$ alkyl, $OR^a$, Cl, F, =O, $NR^aR^{a1}$, $C(O)R^a$, $C(O)OR^a$, $C(O)NR^aR^{a1}$, $S(O)_2NR^aR^{a1}$, $S(O)_pR^{a^2}$, and $CF_3$;

$R^c$, at each occurrence, is independently selected from $C_{1-6}$ alkyl, $OR^a$, Cl, F, Br, =O, $NR^aR^{a1}$, $C(O)R^a$, $C(O)NR^aR^{a1}$, $S(O)_2NR^aR^{a1}$, $S(O)_pR^{a^2}$, and $CF_3$;

$R^d$, at each occurrence, is independently selected from $C_{1-6}$ alkyl, $OR^a$, Cl, F, Br, =O, $NR^aR^{a1}$, $C(O)R^a$, $C(O)NR^aR^{a1}$, $S(O)_2NR^aR^{a1}$, $S(O)_pR^{a^2}$, $CF_3$ and phenyl;

p, at each occurrence, is selected from 0, 1, and 2;

r, at each occurrence, is selected from 0, 1, 2, and 3;

$r^1$, at each occurrence, is selected from 0, 1, 2, and 3; and, s and $s^1$ combine to total 2, 3, or 4.

[5] In another more preferred embodiment, the present invention provides a novel compound of formula II, wherein;

A is selected from —$CO_2H$, $CH_2CO_2H$, —CONHOH, —$CONHOR^5$, —N(OH)CHO, and —$N(OH)COR^5$;

ring B is a 4–7 membered non-aromatic carbocyclic or heterocyclic ring comprising: carbon atoms, 0–1 carbonyl groups, 0–1 double bonds, and from 0–2 ring heteroatoms selected from O, N, and $NR^2$, provided that ring B contains other than a O—O bond;

Z is absent or selected from a $C_{5-6}$ carbocycle substituted with 0–3 $R^b$ and a 5–6 membered heteroaryl comprising carbon atoms and from 1–4 heteroatoms selected from the group consisting of N, O, and $S(O)_p$ and substituted with 0–3 $R^b$;

$U^a$ is absent or is selected from: O, $NR^{a1}$, C(O), C(O)$NR^{a1}$, $S(O)_p$, and $S(O)_pNR^{a1}$;

$X^a$ is absent or selected from $C_{1-2}$ alkylene, $C_{2-4}$ alkenylene, and $C_{2-4}$ alkynylene $Y^a$ is absent or selected from O and $NR^{a1}$;

$Z^a$ is selected from H, a $C_{5-6}$ carbocycle substituted with 0–3 $R^c$ and a 5–10 membered heteroaryl comprising carbon atoms and from 1–4 heteroatoms selected from the group consisting of N, O, and $S(O)_p$ and substituted with 0–3 $R^c$;

provided that Z, $U^a$, $Y^a$, and $Z^a$ do not combine to form a N—N, N—O, O—N, O—O, $S(O)_p$—O, O—$S(O)_p$ or $S(O)_p$—$S(O)_p$ group;

$R^1$ is selected from H, $C_{1-4}$ alkyl, phenyl, and benzyl;

$R^2$ is $(CR^aR^{a1})_{r1}O(CR^aR^{a1})_r$-Q or $(CR^aR^{a1})_{r1}NR^a(CR^aR^{a1})_r$-Q;

Q is selected from H, a $C_{3-6}$ carbocycle substituted with 0–3 $R^d$ and a 5–10 membered heterocycle comprising: carbon atoms and 1–4 heteroatoms selected from the group consisting of N, O, and $S(O)_p$ and substituted with 0–3 $R^d$;

$R^a$, at each occurrence, is independently selected from H, $C_{1-4}$ alkyl, phenyl and benzyl;

$R^{a^1}$, at each occurrence, is independently selected from H and $C_{1-4}$ alkyl;

$R^{a^2}$, at each occurrence, is independently selected from $C_{1-4}$ alkyl, phenyl and benzyl;

$R^b$, at each occurrence, is independently selected from $C_{1-4}$ alkyl, $OR^a$, Cl, F, =O, $NR^aR^{a^1}$, $C(O)R^a$, $C(O)OR^a$, $C(O)NR^aR^{a^1}$, $S(O)_2NR^aR^{a^1}$, $S(O)_pR^{a^2}$, and $CF_3$;

$R^c$, at each occurrence, is independently selected from $C_{1-6}$ alkyl, $OR^a$, Cl, F, Br, =O, $NR^aR^{a^1}$, $C(O)R^a$, $C(O)NR^aR^{a^1}$, $S(O)_2NR^aR^{a^1}$, $S(O)_pR^{a^2}$, and $CF_3$;

$R^d$, at each occurrence, is independently selected from $C_{1-6}$ alkyl, $OR^a$, Cl, F, Br, =O, $NR^aR^{a^1}$, $C(O)R^a$, $C(O)NR^aR^{a^1}$, $S(O)_2NR^aR^{a^1}$, $S(O)_pR^{a^2}$, $CF_3$ and phenyl;

$R^5$, at each occurrence, is selected from $C_{1-4}$ alkyl substituted with 0–2 $R^b$, and $C_{1-4}$ alkyl substituted with 0–2 $R^e$;

$R^e$, at each occurrence, is selected from phenyl substituted with 0–2 $R^b$ and biphenyl substituted with 0–2 $R^b$;

p, at each occurrence, is selected from 0, 1, and 2;

r, at each occurrence, is selected from 0, 1, 2, 3, and 4; and, $r^1$, at each occurrence, is selected from 0, 1, 2, 3, and 4.

[6] In another further preferred embodiment, the present invention provides a novel compound of formula II, wherein;

A is —CONHOH;

ring B is a 5–6 membered non-aromatic carbocyclic or heterocyclic ring comprising: carbon atoms, 0–1 carbonyl groups, 0–1 double bonds, and from 0–2 ring heteroatoms selected from O, N, and $NR^2$, provided that ring B contains other than a O—O bond;

Z is absent or selected from phenyl substituted with 0–3 $R^b$ and pyridyl substituted with 0–3 $R^b$;

$U^a$ is absent or is O;

$X^a$ is absent or is $CH_2$ or $CH_2CH_2$;

$Y^a$ is absent or is O;

$Z^a$ is selected from H, phenyl substituted with 0–3 $R^c$, pyridyl substituted with 0–3 $R^c$, and quinolinyl substituted with 0–3 $R^c$;

provided that Z, $U^a$, $Y^a$, and $Z^a$ do not combine to form a N—N, N—O, O—N, or O—O group;

$R^1$ is selected from H, $CH_3$, and $CH_2CH_3$;

$R^2$ is $(CR^aR^{a^1})_{r^1}O(CR^aR^{a^1})_r$-Q or $(CR^aR^{a^1})_{r^1}NR^a(CR^aR^{a^1})_r$-Q;

Q is selected from H, cyclopropyl substituted with 0–1 $R^d$, cyclobutyl substituted with 0–1 $R^d$, cyclopentyl substituted with 0–1 $R^d$, cyclohexyl substituted with 0–1 $R^d$, phenyl substituted with 0–2 $R^d$, and a heteroaryl substituted with 0–3 $R^d$, wherein the heteroaryl is selected from pyridyl, quinolinyl, thiazolyl, furanyl, imidazolyl, and isoxazolyl;

$R^a$, at each occurrence, is independently selected from H, $CH_3$, and $CH_2CH_3$;

$R^{a^1}$, at each occurrence, is independently selected from H, $CH_3$, and $CH_2CH_3$;

$R^{a^2}$, at each occurrence, is independently selected from H, $CH_3$, and $CH_2CH_3$;

$R^b$, at each occurrence, is independently selected from $C_{1-4}$ alkyl, $OR^a$, Cl, F, =O, $NR^aR^{a^1}$, $C(O)R^a$, $C(O)OR^a$, $C(O)NR^aR^{a^1}$, $S(O)_2NR^aR^{a^1}$, $S(O)_pR^{a^2}$, and $CF_3$;

$R^c$, at each occurrence, is independently selected from $C_{1-6}$ alkyl, $OR^a$, Cl, F, Br, =O, $NR^aR^{a^1}$, $C(O)R^a$, $C(O)NR^aR^{a^1}$, $S(O)_2NR^aR^{a^1}$, $S(O)_pR^{a^2}$, and $CF_3$;

$R^d$, at each occurrence, is independently selected from $C_{1-6}$ alkyl, $OR^a$, Cl, F, Br, =O, $NR^aR^{a^1}$, $C(O)R^a$, $C(O)NR^aR^{a^1}$, $S(O)_2NR^aR^{a^1}$, $S(O)_pR^{a^2}$, $CF_3$ and phenyl;

p, at each occurrence, is selected from 0, 1, and 2;

r, at each occurrence, is selected from 0, 1, 2, and 3; and, $r^1$, at each occurrence, is selected from 0, 1, 2, and 3.

[7] In another preferred embodiment, the present invention provides a compound selected from the group:

N-{(1R,2S)-2-[(hydroxyamino)carbonyl]cyclopentyl}-2'-(trifluoromethyl)[1,1'-biphenyl]-4-carboxamide N-{(1R,2S)-2-[(hydroxyamino)carbonyl]cyclopentyl}-4-[2-(trifluoromethyl)phenoxy]benzamide N-{(1R,2S)-2-[(hydroxyamino)carbonyl]cyclopentyl}-4-(3-methyl-2-pyridinyl)benzamide N-{(1R,2S)-2-[(hydroxyamino)carbonyl]cyclopentyl}[1,1'-biphenyl]-4-carboxamide N-{(1R,2S)-2-[(hydroxyamino)carbonyl]cyclopentyl}-4-phenoxybenzamide 4-(benzyloxy)-N-{(1R,2S)-2-[(hydroxyamino)carbonyl]cyclopentyl}benzamide N-{(1R,2S)-2-[(hydroxyamino)carbonyl]cyclopentyl}-2'-methoxy[1,1'-biphenyl]-4-carboxamide N-{(1R,2S)-2-[(hydroxyamino)carbonyl]cyclopentyl}-2'-methyl[1,1'-biphenyl]-4-carboxamide N-{(1R,2S)-2-[(hydroxyamino)carbonyl]cyclopentyl}-4-(2-methoxyphenoxy)benzamide N-{(1R,2S)-2-[(hydroxyamino)carbonyl]cyclopentyl}-4-(2-methylphenoxy)benzamide N-{(1R,2S)-2-[(hydroxyamino)carbonyl]cyclopentyl}-4-(3-methylphenoxy)benzamide 4-(5,8-dihydro-4-quinolinyl)-N-{(1R,2S)-2-[(hydroxyamino)carbonyl]cyclopentyl}benzamide N-{(1R,2S)-2-[(hydroxyamino)carbonyl]cyclopentyl}-3',5'-dimethyl[1,1'-biphenyl]-4-carboxamide N-{(1R,2S)-2-[(hydroxyamino)carbonyl]cyclopentyl}-6-(2-methylphenyl)nicotinamide N-{(1R,2S)-2-[(hydroxyamino)carbonyl]cyclopentyl}-6-(2-methoxyphenyl)nicotinamide (3S,4S)-N-hydroxy-1-isopropyl-4-({4-[(2-methyl-4-quinolinyl)methoxy]benzoyl}amino)-3-pyrrolidinecarboxamide (3S,4S)-1-(2,2-dimethylpropanoyl)-N-hydroxy-4-({4-[(2-methyl-4-quinolinyl)methoxy]benzoyl}amino)-3-pyrrolidinecarboxamide (3S,4S)-N-hydroxy-4-({4-[(2-methyl-4-quinolinyl)methoxy]benzoyl}amino)-1-(methylsulfonyl)-3-pyrrolidinecarboxamide (3S,4S)-N-hydroxy-1-methyl-4-({4-[(2-methyl-4-quinolinyl)methoxy]benzoyl}amino)-3-pyrrolidinecarboxamide tert-butyl (3S,4S)-3-[(hydroxyamino)carbonyl]-4-({4-[(2-methyl-4-quinolinyl)methoxy]benzoyl}amino)-1-pyrrolidinecarboxylate (3S,4S)-N-hydroxy-4-({4-[(2-methyl-4-quinolinyl)methoxy]benzoyl}amino)-3-pyrrolidinecarboxamide tert-butyl 4-[cis-3-[(hydroxyamino)carbonyl]-4-({4-[(2-methyl-4-quinolinyl)methoxy]benzoyl}amino)pyrrolidinyl]-1-piperidinecarboxylate cis-N-hydroxy-4-({4-[(2-methyl-4-quinolinyl)methoxy]benzoyl}amino)-1-(4-piperidinyl)-3-pyrrolidinecarboxamide cis-1-[3-[(1,1-dimethylethoxy)carbonyl]pyrollidinyl]-N-hydroxy-3-[[[4-[(2-methyl-4-quinolinyl)methoxy]phenyl]carbonyl]amino]-4-pyrollidinecarboxamide cis-N-hydroxy-1-[3-pyrollidinyl]-3-[[[4-[(2-methyl-4-quinolinyl)methoxy]phenyl]carbonyl]amino]-4-pyrollidinecarboxamide tert-butyl (3R,4R)-3-[(hydroxyamino)carbonyl]-4-({4-[(2-methyl-4-quinolinyl)methoxy]benzoyl}amino)-1-pyrrolidinecarboxylate tert-butyl (3S,4R)-3-[(hydroxyamino)carbonyl]-4-({4-[(2-methyl-4-quinolinyl)methoxy]benzoyl}amino)-1-pyrrolidinecarboxylate (3S,4R)-N-hydroxy-4-({4-[(2-methyl-4-quinolinyl)methoxy]benzoyl}amino)-3-pyrrolidinecarboxamide tert-butyl (3R,4S)-3-[(hydroxyamino)carbonyl]-4-({4-[(2-methyl-4-quinolinyl)methoxy]benzoyl}amino)-1-pyrrolidinecarboxylate (3R,4S)-N-hydroxy-4-({4-[(2-methyl-4-quinolinyl)methoxy]benzoyl}amino)-3-pyrrolidinecarboxamide N-{(1R,2S)-2-[(hydroxyamino)carbonyl]cyclopentyl}-4-(4-pyridinyl)benzamide (3S,4S)-1-(1,1-dimethyl-2-propynyl)-N-hydroxy-4-({4-[(2-methyl-4-quinolinyl)methoxy]benzoyl}amino)-3-pyrrolidinecarboxamide (3S,4S)-N-hydroxy-4-({4-[(2-methyl-4-quinolinyl)methoxy]benzoyl}amino)-1-(2-propynyl)-3-pyrrolidinecarboxamide (3S,4S)-1-allyl-N-hydroxy-4-({4-[(2-methyl-4-quinolinyl)methoxy]benzoyl}amino)-3-pyrrolidinecarboxamide (3S,4S)-N-hydroxy-4-({4-[(2-methyl-4-quinolinyl)methoxy]benzoyl}amino)-1-propyl-3-pyrrolidinecarboxamide (3S,4S)-N-hydroxy-1-(2-methyl-2-propenyl)-4-({4-[(2-methyl-4-quinolinyl)methoxy]benzoyl}amino)-3-pyrrolidinecarboxamide (3S,4S)-1-(1,1-dimethyl-2-propenyl)-N-hydroxy-4-({4-[(2-methyl-4-quinolinyl)methoxy]benzoyl}amino)-3-pyrrolidinecarboxamide (3S,4S)-N-hydroxy-4-({4-[(2-methyl-4-quinolinyl)methoxy]benzoyl}amino)-1-tert-pentyl-3-pyrrolidinecarboxamide (3S,4S)-N-hydroxy-1-isopentyl-4-({4-[(2-methyl-4-quinolinyl)methoxy]benzoyl}amino)-3-pyrrolidinecarboxamide (3S,4S)-N-hydroxy-4-({4-[(2-methyl-4-quinolinyl)methoxy]benzoyl}amino)-1-neopentyl-3-pyrrolidinecarboxamide (3S,4S)-1-butyl-N-hydroxy-4-({4-[(2-methyl-4-quinolinyl)methoxy]benzoyl}amino)-3-pyrrolidinecarboxamide (3S,4S)-1-(3-butenyl)-N-hydroxy-4-({4-[(2-methyl-4-quinolinyl)methoxy]benzoyl}amino)-3-pyrrolidinecarboxamide (3S,4S)-1-(2-butynyl)-N-hydroxy-4-({4-[(2-methyl-4-quinolinyl)methoxy]benzoyl}amino)-3-pyrrolidinecarboxamide (3S,4S)-1-(2-furylmethyl)-N-hydroxy-4-({4-[(2-methyl-4-quinolinyl)methoxy]benzoyl}amino)-3-pyrrolidinecarboxamide (3S,4S)-N-hydroxy-1-[(5-methyl-2-furyl)methyl]-4-({4-[(2-methyl-4-quinolinyl)methoxy]benzoyl}amino)-3-pyrrolidinecarboxamide (3R,4S)-N-hydroxy-4-({4-[(2-methyl-4-quinolinyl)methoxy]benzoyl}amino)tetrahydro-3-furancarboxamide (3S,4R)-N-hydroxy-4-({4-[(2-methyl-4-quinolinyl)methoxy]benzoyl}amino)tetrahydro-3-furancarboxamide (3S,4S)-N-hydroxy-4-({4-[(2-methyl-4-quinolinyl)methoxy]benzoyl}amino)-1-(1,3-thiazol-2-ylmethyl)-3-pyrrolidinecarboxamide (3S,4S)-1-acetyl-N-hydroxy-4-({4-[(2-methyl-4-quinolinyl)methoxy]benzoyl}amino)-3-pyrrolidinecarboxamide (3S,4S)-N-hydroxy-1-isobutyryl-4-({4-[(2-methyl-4-quinolinyl)methoxy]benzoyl}amino)-3-pyrrolidinecarboxamide (3S,4S)-N-hydroxy-1-(3-methylbutanoyl)-4-({4-[(2-methyl-4-quinolinyl)methoxy]benzoyl}amino)-3-pyrrolidinecarboxamide (3S,4S)-1-(cyclopropylcarbonyl)-N-hydroxy-4-({4-[(2-methyl-4-quinolinyl)methoxy]benzoyl}amino)-3-pyrrolidinecarboxamide (3S,4S)-1-(cyclobutylcarbonyl)-N-hydroxy-4-({4-[(2-methyl-4-quinolinyl)methoxy]benzoyl}amino)-3-pyrrolidinecarboxamide (3S,4S)-N-hydroxy-1-(methoxyacetyl)-4-({4-[(2-methyl-4-quinolinyl)methoxy]benzoyl}amino)-3-pyrrolidinecarboxamide (3S,4S)-1-(2-furoyl)-N-hydroxy-4-({4-[(2-methyl-4-quinolinyl)methoxy]benzoyl}amino)-3-pyrrolidinecarboxamide (3S,4S)-N-hydroxy-4-({4-[(2-methyl-4-quinolinyl)methoxy]benzoyl}amino)-1(2-thienylcarbonyl)-3-pyrrolidinecarboxamide (3S,4S)-N-hydroxy-4-({4-[(2-methyl-4-quinolinyl)methoxy]benzoyl}amino)-1-propionyl-3-pyrrolidinecarboxamide (3R,4S)-4-{[4-(2-butynyloxy)benzoyl]amino}-N-hydroxy-tetrahydro-3-furancarboxamide N-{(1R,2S)-2-[(hydroxyamino)carbonyl]-4-oxocyclopentyl}-4-[(2-methyl-4-quinolinyl)methoxy]benzamide N-{(1R,2S,4R)-4-hydroxy-2-[(hydroxyamino)carbonyl]cyclopentyl}-4-[(2-methyl-4-quinolinyl)methoxy]benzamide N-{(1R,2S,4S)-4-hydroxy-2-[(hydroxyamino)carbonyl]cyclopentyl}-4-[(2-methyl-4-quinolinyl)methoxy]benzamide (3S,4S)-N-hydroxy-4-({4-[(2-methyl-4-quinolinyl)methoxy]benzoyl}amino)-1-tetrahydro-2H-pyran-4-yl-3-pyrrolidinecarboxamide methyl (3S,4S)-3-[(hydroxyamino)carbonyl]-4-({4-[(2-methyl-4-quinolinyl)methoxy]benzoyl}amino)-1-pyrrolidinecarboxylate ethyl (3S,4S)-3-[(hydroxyamino)carbonyl]-4-({4-[(2-methyl-4-quinolinyl)methoxy]benzoyl}amino)-1-pyrrolidinecarboxylate propyl (3S,4S)-3-[(hydroxyamino)carbonyl]-4-({4-[(2-methyl-4-quinolinyl)methoxy]benzoyl}amino)-1-pyrrolidinecarboxylate allyl (3S,4S)-3-[(hydroxyamino)carbonyl]-4-({4-[(2-itethyl-4-quinolinyl)methoxy]benzoyl}amino)-1-pyrrolidinecarboxylate isopropyl (3S,4S)-3-[(hydroxyamino)carbonyl]-4-({4-[(2-methyl-4-quinolinyl)methoxy]benzoyl}amino)-1-pyrrolidinecarboxylate 2-propynyl (3S,4S)-3-[(hydroxyamino)carbonyl]-4-({4-[(2-methyl-4-quinolinyl)methoxy]benzoyl}amino)-1-pyrrolidinecarboxylate 2-butynyl (3S,4S)-3-[(hydroxyamino)carbonyl]-4-({4-[(2-methyl-4-quinolinyl)methoxy]benzoyl}amino)-1-pyrrolidinecarboxylate 3-butenyl (3S,4S)-3-[(hydroxyamino)carbonyl]-4-({4-[(2-methyl-4-quinolinyl)methoxy]benzoyl}amino)-1-pyrrolidinecarboxylate benzyl (3S,4S)-3-[(hydroxyamino)carbonyl]-4-({4-[(2-methyl-4-quinolinyl)methoxy]benzoyl}amino)-1-pyrrolidinecarboxylate N-{(1R,2S)-4-(dimethylamino)-2-[(hydroxyamino)carbonyl]cyclopentyl}-4-[(2-methyl-4-quinolinyl)methoxy]benzamide (3S,4S)-4-{[4-(2-butynyloxy)benzoyl]amino}-N-hydroxy-1-isopropyl-3-pyrrolidinecarboxamide N-{(1R,2S)-4,4-difluoro-2-[(hydroxyamino)carbonyl]cyclopentyl}-4-[(2-methyl-4-quinolinyl)methoxy]benzamide (3S,4S)-N-hydroxy-1-isopropyl-4-{[4-(2-methylphenoxy)benzoyl]amino}-3-pyrrolidinecarboxamide cis-N-hydroxy-2-[[[4-[(2-methyl-4-quinolinyl)methoxy]phenyl]carbonyl]amino]-1-cyclopentanecarboxamide trans-N-hydroxy-2-[[[4-[(2-methyl-4-quinolinyl)methoxy]phenyl]carbonyl]amino]-1-cyclopentanecarboxamide (1S,2R)-N-hydroxy-2-[[[4-[(2-methyl-4-quinolinyl)methoxy]phenyl]carbonyl]amino]-1-cyclopentanecarboxamide (1R,2S)-N-hydroxy-2-[[[4-[(2-methyl-4-quinolinyl)methoxy]phenyl]carbonyl]amino]-1-cyclopentanecarboxamide cis-N-hydroxy-2-[[[4-[(2-methyl-4-quinolinyl)methoxy]phenyl]carbonyl]amino]-1-cyclohexanecarboxamide trans-N-hydroxy-2-[[[4-[(2-methyl-4-quinolinyl)methoxy]phenyl]carbonyl]amino]-1-cyclohexanecarboxamide trans-1-[[(1,1-dimethylethyl)oxy]carbonyl]-N-hydroxy-3-[[[4-[(2-methyl-4-quinolinyl)methoxy]phenyl]carbonyl]amino]-4-pyrrolidinecarboxamide trans-N-hydroxy-3-[[[4-[(2-methyl-4-quinolinyl)methoxy]phenyl]carbonyl]amino]-4-pyrrolidinecarboxamide cis-1-[[(1,1-dimethylethyl)oxy]carbonyl]-N-hydroxy-3-[[[4-[(2-methyl-4-quinolinyl)methoxy]phenyl]carbonyl]amino]-4-pyrrolidinecarboxamide cis-N-hydroxy-3-[[[4-[(2-methyl-4-quinolinyl)methoxy]phenyl]carbonyl]amino]-4-pyrrolidinecarboxamide (3S,4R)-1-[[(1,1-dimethylethyl)oxy]carbonyl]-N-hydroxy-4-[[[4-[(2-methyl-4-quinolinyl)methoxy]phenyl]carbonyl]amino]-3-piperidinecarboxamide (3S,4S)-1-[[(1,1-dimethylethyl)oxy]carbonyl]-N-hydroxy-4-[[[4-[(2-methyl-4-quinolinyl)methoxy]phenyl]carbonyl]amino]-3-piperidinecarboxamide (3S,4S)-N-hydroxy-4-[[[4-[(2-methyl-4-quinolinyl)methoxy]phenyl]carbonyl]amino]-3-piperidinecarboxamide (3S,4R)-N-hydroxy-4-[[[4-[(2-methyl-4-quinolinyl)methoxy]phenyl]carbonyl]amino]-3-piperidinecarboxamide (3S,4R)-1-[(butoxy)carbonyl]-N-hydroxy-4-[[[4-[(2-methyl-4-quinolinyl)methoxy]phenyl]carbonyl]amino]-3-piperidinecarboxamide (3S,4R)-N-hydroxy-1-[[(1-methylethyl)oxy]carbonyl]-4-[[[4-[(2-methyl-4-quinolinyl)methoxy]phenyl]carbonyl]amino]-3-piperidinecarboxamide (3S,4R)-N-hydroxy-1-(methylsulfonyl)-4-[[[4-[(2-methyl-4-quinolinyl)methoxy]phenyl]carbonyl]amino]-3-piperidinecarboxamide (3S,4R)-N-hydroxy-4-[[[4-[(2-methyl-4-quinolinyl)methoxy]phenyl]carbonyl]amino]-1-(phenylsulfonyl)-3-piperidinecarboxamide (3S,4R)-1-acetyl-N-hydroxy-4-[[[4-[(2-methyl-4-quinolinyl)methoxy]phenyl]carbonyl]amino]-3-piperidinecarboxamide (3S,4R)-1-benzoyl-N-hydroxy-4-[[[4-[(2-methyl-4-quinolinyl)methoxy]phenyl]carbonyl]amino]-3-piperidinecarboxamide (3S,4R)-1-(2,2-dimethylpripionyl)-N-hydroxy-4-[[[4-[(2-methyl-4-quinolinyl)methoxy]phenyl]carbonyl]amino]-3-piperidinecarboxamide (3S,4R)-1-(3,3-dimethylbutanoyl)-N-hydroxy-4-[[[4-[(2-methyl-4-quinolinyl)methoxy]phenyl]carbonyl]amino]-3-piperidinecarboxamide (3S,4R)-N-hydroxy-4-[[[4-[(2-methyl-4-quinolinyl)methoxy]phenyl]carbonyl]amino]-1-(4-morpholinecarbonyl)-3-piperidinecarboxamide (3S,4R)-1-(dimethylcarbamyl)-N-hydroxy-4-[[[4-[(2-methyl-4-quinolinyl)methoxy]phenyl]carbonyl]amino]-3-piperidinecarboxamide (3S,4R)-N-hydroxy-1-methyl-4-[[[4-[(2-methyl-4-quinolinyl)methoxy]phenyl]carbonyl]amino]-3-piperidinecarboxamide (3S,4R)-1-ethyl-N-hydroxy-4-[[[4-[(2-methyl-4-quinolinyl)methoxy]phenyl]carbonyl]amino]-3-piperidinecarboxamide (3S,4R)-N-hydroxy-4-[[[4-[(2-methyl-4-quinolinyl)methoxy]phenyl]carbonyl]amino]-1-propyl-3-piperidinecarboxamide (3S,4R)-N-hydroxy-1-(1-methylethyl)-4-[[[4-[(2-methyl-4-quinolinyl)methoxy]phenyl]carbonyl]amino]-3-piperidinecarboxamide (3S,4R)-1-(cyclopropylmethyl)-N-hydroxy-4-[[[4-[(2-methyl-4-quinolinyl)methoxy]phenyl]carbonyl]amino]-3-piperidinecarboxamide (3S,4R)-1-(2,2-dimethylpropyl)-N-hydroxy-4-[[[4-[(2-methyl-4-quinolinyl)methoxy]phenyl]carbonyl]amino]-3-piperidinecarboxamide (3S,4R)-1-benzyl-N-hydroxy-4-[[[4-[(2-methyl-4-quinolinyl)methoxy]phenyl]carbonyl]amino]-3-piperidinecarboxamide (3S,4R)-1-(2-thiazolylmethyl)-N-hydroxy-4-[[[4-[(2-methyl-4-quinolinyl)methoxy]phenyl]carbonyl]amino]-3-piperidinecarboxamide (3S,4S)-1-[[(1,1-dimethylethyl)oxy]carbonyl]-N-hydroxy-3-[[[4-[(2-methyl-4-quinolinyl)methoxy]phenyl]carbonyl]amino]-4-piperidinecarboxamide (3R,4S)-1-[[(1,1-dimethylethyl)oxy]carbonyl]-N-hydroxy-3-[[[4-[(2-methyl-4-quinolinyl)methoxy]phenyl]carbonyl]amino]-4-piperidinecarboxamide (3R,4S)-N-hydroxy-3-[[[4-[(2-methyl-4-quinolinyl)methoxy]phenyl]carbonyl]amino]-4-piperidinecarboxamide (3S,4S)-N-hydroxy-3-[[[4-[(2-methyl-4-quinolinyl)methoxy]phenyl]carbonyl]amino]-4-piperidinecarboxamide (3S,4S)-N-hydroxy-1-[[(2-methylpropyl)oxy]carbonyl]-3-[[[4-[(2-methyl-4-quinolinyl)methoxy]phenyl]carbonyl]amino]-4-piperidinecarboxamide (3S,4S)-N-hydroxy-1-(methoxycarbohyl)-3-[[[4-[(2-methyl-4-quinolinyl)methoxy]phenyl]carbonyl]amino]-4-piperidinecarboxamide (3S,4S)-N-hydroxy-1-[(1-methylethoxy)carbonyl]-3-[[[4-[(2-methyl-4-quinolinyl)methoxy]phenyl]carbonyl]amino]-4-piperidinecarboxamide (3S,4S)-N-hydroxy-1-(methylsulfonyl)-3-[[[4-[(2-methyl-4-quinolinyl)methoxy]phenyl]carbonyl]amino]-4-piperidinecarboxamide (3S,4S)-N-hydroxy-3-[[[4-[(2-methyl-4-quinolinyl)methoxy]phenyl]carbonyl]amino]-1-(phenylsulfonyl)-4-piperidinecarboxamide (3S,4S)-1-(3,3-dimethylbutanoyl)-N-hydroxy-3-[[[4-[(2-methyl-4-quinolinyl)methoxy]phenyl]carbonyl]amino]-4-piperidinecarboxamide (3S,4S)-1-(2,2-dimethylpropionyl)-N-hydroxy-3-[[[4-[(2-methyl-4-quinolinyl)methoxy]phenyl]carbonyl]amino]-4-piperidinecarboxamide (3S,4S)-1-benzoyl-N-hydroxy-3-[[[4-[(2-methyl-4-quinolinyl)methoxy]phenyl]carbonyl]amino]-4-piperidinecarboxamide (3S,4S)-1-[(pyridin-3-yl)carbonyl]-N-hydroxy-3-[[[4-[(2-methyl-4-quinolinyl)methoxy]phenyl]carbonyl]amino]-4-piperidinecarboxamide (3S,4S)-N-hydroxy-3-[[[4-[(2-methyl-4-quinolinyl)methoxy]phenyl]carbonyl]amino]-1-(2-thiophenecarbonyl)-4-piperidinecarboxamide (3S,4S)-1-(dimethylcarbamyl)-N-hydroxy-3-[[[4-[(2-methyl-4-quinolinyl)methoxy]phenyl]carbonyl]amino]-4-piperidinecarboxamide (3S,4S)-N-hydroxy-3-[[[4-[(2-methyl-4-quinolinyl)methoxy]phenyl]carbonyl]amino]-1-(4-morpholinecarbonyl)-4-piperidinecarboxamide (3S,4S)-N-hydroxy-3-[[[4-[(2-methyl-4-quinolinyl)methoxy]phenyl]carbonyl]amino]-1-[[2-(2-thienyl)ethyl]carbamyl]-4-piperidinecarboxamide (3S,4S)-1-[(1,1-dimethylethyl)carbamyl]-N-hydroxy-3-[[[4-[(2-methyl-4-quinolinyl)methoxy]phenyl]carbonyl]amino]-4-piperidinecarboxamide (3S,4S)-N-hydroxy-1-methyl-3-[[[4-[(2-methyl-4-quinolinyl)methoxy]phenyl]carbonyl]amino]-4-piperidinecarboxamide (3S,4S)-1-ethyl-N-hydroxy-3-[[[4-[(2-methyl-4-quinolinyl)methoxy]phenyl]carbonyl]amino]-4-piperidinecarboxamide (3S,4S)-N-hydroxy-3-[[[4-[(2-methyl-4-quinolinyl)methoxy]phenyl]carbonyl]amino]-1-propyl-4-piperidinecarboxamide (3S,4S)-N-hydroxy-1-(1-methylethyl)-3-[[[4-[(2-methyl-4-quinolinyl)methoxy]phenyl]carbonyl]amino]-4-piperidinecarboxamide (3S,4S)-1-cyclobutyl-N-hydroxy-3-[[[4-[(2-methyl-4-quinolinyl)methoxy]phenyl]carbonyl]amino]-4-piperidinecarboxamide (3S,4S)-1-butyl-N-hydroxy-3-[[[4-[(2-methyl-4-quinolinyl)methoxy]phenyl]carbonyl]amino]-4-piperidinecarboxamide (3S,4S)-N-hydroxy-3-[[[4-[(2-methyl-4-quinolinyl)methoxy]phenyl]carbonyl]amino]-1-(2-methylpropyl)-4-piperidinecarboxamide (3S,4S)-1-(cyclopropylmethyl)-N-hydroxy-3-[[[4-[(2-methyl-4-quinolinyl)methoxy]phenyl]carbonyl]amino]-4-piperidinecarboxamide (3S,4S)-1-(2,2-dimethylpropyl)-N-hydroxy-3-[[[4-[(2-methyl-4-quinolinyl)methoxy]phenyl]carbonyl]amino]-4-piperidinecarboxamide (3S,4S)-1-cyclopentyl-N-hydroxy-3-[[[4-[(2-methyl-4-quinolinyl)methoxy]phenyl]carbonyl]amino]-4-piperidinecarboxamide (3S,4S)-N-hydroxy-3-[[[4-[(2-methyl-4-quinolinyl)methoxy]phenyl]carbonyl]amino]-1-(4-tetrahydropyranyl)-4-piperidinecarboxamide (3S,4S)-1-benzyl-N-hydroxy-3-[[[4-[(2-methyl-4-quinolinyl)methoxy]phenyl]carbonyl]amino]-4-piperidinecarboxamide (3S,4S)-N-hydroxy-3-[[[4-[(2-methyl-4-quinolinyl)methoxy]phenyl]carbonyl]amino]-1-(2-thiazolylmethyl)-4-piperidinecarboxamide (3S,4S)-N-hydroxy-3-[[[4-[(2-methyl-4-quinolinyl)methoxy]phenyl]carbonyl]amino]-1-(4-pyridinylmethyl)-4-piperidinecarboxamide (3S,4S)-N-hydroxy-3-[[[4-[(2-methyl-4-quinolinyl)methoxy]phenyl]carbonyl]amino]-1-(2-pyridinylmethyl)-4-piperidinecarboxamide (3S,4S)-N-hydroxy-3-[[[4-[(2-methyl-4-quinolinyl)methoxy]phenyl]carbonyl]amino]-1-(3-pyridinylmethyl)-4-piperidinecarboxamide (3S,4S)-N-hydroxy-3-[[[4-[(2-methyl-4-quinolinyl)methoxy]phenyl]carbonyl]amino]-1-(trans-3-phenyl-2-propenyl)-4-piperidinecarboxamide (3S,4S)-N-hydroxy-3-[[[4-[(2-methyl-4-quinolinyl)methoxy]phenyl]carbonyl]amino]-1-phenyl-4-piperidinecarboxamide (3R,4S)-1-(2,2-dimethylpropionyl)-N-hydroxy-3-[[[4-[(2-methyl-4-quinolinyl)methoxy]phenyl]carbonyl]amino]-4-piperidinecarboxamide (3R,4S)-N-hydroxy-3-[[[4-[(2-methyl-4-quinolinyl)methoxy]phenyl]carbonyl]amino]-1-methyl-4-piperidinecarboxamide (3R,4S)-1-(dimethylcarbamyl)-N-hydroxy-3-[[[4-[(2-methyl-4-quinolinyl)methoxy]phenyl]carbonyl]amino]-4-piperidinecarboxamide (3S,4S)-1-hexyl-N-hydroxy-3-[[[4-[(2-methyl-4-quinolinyl)methoxy]phenyl]carbonyl]amino]-4-piperidinecarboxamide (3S,4S)-1-(2-fluoroethyl)-N-hydroxy-3-[[[4-[(2-methyl-4-quinolinyl)methoxy]phenyl]carbonyl]amino]-4-piperidinecarboxamide (3S,4S)-1-(2,2-difluoroethyl)-N-hydroxy-3-[[[4-[(2-methyl-4-quinolinyl)methoxy]phenyl]carbonyl]amino]-4-piperidinecarboxamide (3S,4S)-N-hydroxy-1-(1-methylpropyl)-3-[[[4-[(2-methyl-4-quinolinyl)methoxy]phenyl]carbonyl]amino]-4-piperidinecarboxamide (3S,4S)-1-(1-ethylpropyl)-N-hydroxy-3-[[[4-[(2-methyl-4-quinolinyl)methoxy]phenyl]carbonyl]amino]-4-piperidinecarboxamide (3S,4S)-1-[1-[[(1,1-dimethylethyl)oxy]carbonyl]-4-tetrahydropiperidinyl]-N-hydroxy-3-[[[4-[(2-methyl-4-quinolinyl)methoxy]phenyl]carbonyl]amino]-4-piperidinecarboxamide (3S,4S)-N-hydroxy-3-[[[4-[(2-methyl-4-quinolinyl)methoxy]phenyl]carbonyl]amino]-1-(4-tetrahydropiperidinyl)-4-piperidinecarboxamide (3S,4S)-1-[1-[[(1,1-dimethylethyl)oxy]carbonyl]-3-tetrahydropyrrolidinyl]-N-hydroxy-3-[[[4-[(2-methyl- 4-quinolinyl)methoxy]phenyl]carbonyl]amino]-4-piperidinecarboxamide (3S,4S)-N-hydroxy-3-[[[4-[(2-methyl-4-quinolinyl)methoxy]phenyl]carbonyl]amino]-1-(3-tetrahydropyrrolidinyl)-4-piperidinecarboxamide (3S,4S)-1-(1,1-dimethyl-2-propynyl)-N-hydroxy-3-[[[4-[(2-methyl-4-quinolinyl)methoxy]phenyl]carbonyl]amino]-4-piperidinecarboxamide (3S,4S)-N-hydroxy-3-[[[4-[(2-methyl-4-quinolinyl)methoxy]phenyl]carbonyl]amino]-1-(3-thiophenylmethyl)-4-piperidinecarboxamide (3S,4S)-N-hydroxy-1-(1-methylethyl)-3-[[[4-[(2-methyl-4-quinolinyl)methoxy]phenyl]carbonyl]amino]-1-oxo-4-piperidinecarboxamide (3S,4S)-N-hydroxy-1-(1-methylethyl)-3-[[[4-[(2-methyl-1-oxo-4-quinolinyl)methoxy]phenyl]carbonyl]amino]-4-piperidinecarboxamide (3S,4S)-N-hydroxy-1-(1-methylethyl)-3-[[[4-[(2-methyl-1-oxo-4-quinolinyl)methoxy]phenyl]carbonyl]amino]-1-oxo-4-piperidinecarboxamide (3S,4S)-N-hydroxy-3-[[[4-[(2-methyl-4-quinolinyl)methoxy]phenyl]carbonyl]amino]-1-[2-(4-morpholinyl)-2-oxoethyl]-4-piperidinecarboxamide (3S,4S)-1-[2-(N,N-dimethylamino)-2-oxoethyl]-N-hydroxy-3-[[[4-[(2-methyl-4-quinolinyl)methoxy]phenyl]carbonyl]amino]-4-piperidinecarboxamide (3S,4S)-1-(t-butylsulfonyl)-N-hydroxy-3-[[[4-[(2-methyl-4-quinolinyl)methoxy]phenyl]carbonyl]amino]-4-piperidinecarboxamide (3S,4S)-1-(t-butylsulfonyl)-N-hydroxy-3-[[[4-[(2-methyl-1-oxo-4-quinolinyl)methoxy]phenyl]carbonyl]amino]-4-piperidinecarboxamide (3S,4S)-1-(benzenesulfonyl)-N-hydroxy-3-[[[4-[(2-methyl-4-quinolinyl)methoxy]phenyl]carbonyl]amino]-4-piperidinecarboxamide (3S,4S)-1-(t-butylsulfinyl)-N-hydroxy-3-[[[4-[(2-methyl-4-quinolinyl)methoxy]phenyl]carbonyl]amino]-4-piperidinecarboxamide (3S,4S)-N-hydroxy-1-(2-hydroxyethyl)-3-[[[4-[(2-methyl-4-quinolinyl)methoxy]phenyl]carbonyl]amino]-4-piperidinecarboxamide (3S,4S)-1-[2-[[[(1,1-dimethylethyl)oxy]carbonyl]amino]ethyl]-N-hydroxy-3-[[[4-[(2-methyl-4-quinolinyl)methoxy]phenyl]carbonyl]amino]-4-piperidinecarboxamide (3S,4S)-1-(2-aminoethyl)-N-hydroxy-3-[[[4-[(2-methyl-4-quinolinyl)methoxy]phenyl]carbonyl]amino]-4-piperidinecarboxamide (3S,4S)-1-[2-(N,N-dimethylamino)ethyl]-N-hydroxy-3-[[[4-[(2-methyl-4-quinolinyl)methoxy]phenyl]carbonyl]amino]-4-piperidinecarboxamide (3S,4S)-1-[(2S)-2-aminopropyl]-N-hydroxy-3-[[[4-[(2-methyl-4-quinolinyl)methoxy]phenyl]carbonyl]amino]-4-piperidinecarboxamide (3S,4S)-1-[(2R)-2-amino-3-hydroxypropyl]-N-hydroxy-3-[[[4-[(2-methyl-4-quinolinyl)methoxy]phenyl]carbonyl]amino]-4-piperidinecarboxamide (3S,4S)-N-hydroxy-3-[[[4-[(2-methyl-4-quinolinyl)methoxy]phenyl]carbonyl]amino]-1-[[(2R)-2-pyrrolidinyl]methyl]-4-piperidinecarboxamide (3S,4R)-N-hydroxy-1-(2-hydroxyethyl)-4-[[[4-[(2-methyl-4-quinolinyl)methoxy]phenyl]carbonyl]amino]-3-piperidinecarboxamide (3S,4R)-1-(2-aminoethyl)-N-hydroxy-4-[[[4-[(2-methyl-4-quinolinyl)methoxy]phenyl]carbonyl]amino]-3-piperidinecarboxamide (3S,4R)-1-cyclobutyl-N-hydroxy-4-[[[4-[(2-methyl-4-quinolinyl)methoxy]phenyl]carbonyl]amino]-3-piperidinecarboxamide (3R,4R)-N-hydroxy-4-({4-[(2-methyl-4-quinolinyl)methoxy]benzoyl}amino)tetrahydro-2H-pyran-3-carboxamide (3S,4S)-1-tert-butyl-N-hydroxy-3-({4-[(2-methyl-4-quinolinyl)methoxy]benzoyl}amino)-4-piperidinecarboxamide tert-butyl 2-[(3S,4S)-4-[(hydroxyamino)carbonyl]-3-({4-[(2-methyl-4-quinolinyl)methoxy]benzoyl}amino)piperidinyl]-2-methylpropanoate 2-[(3S,4S)-4-[(hydroxyamino)carbonyl]-3-({4-[(2-methyl-4-quinolinyl)methoxy]benzoyl}amino)piperidinyl]-2-methylpropanoic acid methyl 2-[(3S,4S)-4-[(hydroxyamino)carbonyl]-3-({4-[(2-methyl-4-quinolinyl)methoxy]benzoyl}amino)piperidinyl]-2-methylpropanoate (3S,4S)-N-hydroxy-3-({4-[(2-methyl-4-quinolinyl)methoxy]benzoyl}amino)-1-[2-(4-morpholinyl)-2-oxoethyl]-4-piperidinecarboxamide (3S,4S)-1-[2-(dimethylamino)-2-oxoethyl]-N-hydroxy-3-({4-[(2-methyl-4-quinolinyl)methoxy]benzoyl}amino)-4-piperidinecarboxamide (3S,4S)-1-(1,1-dimethyl-2-propenyl)-N-hydroxy-3-({4-[(2-methyl-4-quinolinyl)methoxy]benzoyl}amino)-4-piperidinecarboxamide (3S,4S)-N-hydroxy-3-({4-[(2-methyl-4-quinolinyl)methoxy]benzoyl}amino)-1-tert-pentyl-4-piperidinecarboxamide (3S,4S)-N-hydroxy-3-({4-[(2-methyl-4-quinolinyl)methoxy]benzoyl}amino)-1-(2-propynyl)-4-piperidinecarboxamide (3S,4S)-1-allyl-N-hydroxy-3-({4-[(2-methyl-4-quinolinyl)methoxy]benzoyl}amino)-4-piperidinecarboxamide (3S,4S)-N-hydroxy-1-(1-methyl-2-propynyl)-3-({4-[(2-methyl-4-quinolinyl)methoxy]benzoyl}amino)-4-piperidinecarboxamide (3S,4S)-N-hydroxy-1-(1-methyl-2-propenyl)-3-({4-[(2-methyl-4-quinolinyl)methoxy]benzoyl}amino)-4-piperidinecarboxamide N-{(1R,2S)-4,5-dihydroxy-2-[(hydroxyamino)carbonyl]cyclohexyl}-4-[(2-methyl-4-quinolinyl)methoxy]benzamide (5S)-N-hydroxy-5-({4-[(2-methyl-4-quinolinyl)methoxy]benzoyl}amino)-2-oxo-4-piperidinecarboxamide (3S,4S)-N-hydroxy-3-({4-[(2-methyl-4-quinolinyl)methoxy]benzoyl}amino)-2-oxo-4-piperidinecarboxamide (3S,4S)-3-{[4-(2-butynyloxy)benzoyl]amino}-N-hydroxy-1-isopropyl-4-piperidinecarboxamide (3S,4S)-3-{[4-(2-butynyloxy)benzoyl]amino}-N-hydroxy-4-piperidinecarboxamide tert-butyl (3S,4S)-4-[(hydroxyamino)carbonyl]-3-({4-[(2-methyl-3-pyridinyl)methoxy]benzoyl}amino)-1-piperidinecarboxylate (3S,4S)-N-hydroxy-3-({4-[(2-methyl-3-pyridinyl)methoxy]benzoyl}amino)-4-piperidinecarboxamide tert-butyl (3S,4S)-3-({4-[(2,5-dimethylbenzyl)oxy]benzoyl}amino)-4-[(hydroxyamino)carbonyl]-1-piperidinecarboxylate (3S,4S)-3-({4-[(2,5-dimethylbenzyl)oxy]
benzoyl}amino)-N-hydroxy-4-piperidinecarboxamide
(cis,cis)-3-Amino-2-[[[4-[(2-methyl-4-quinolinyl)
methoxy]phenyl]carbonyl]amino]-(N-hydroxy)
cyclohexylcarboxamide
(cis,cis)-3-Methylamino-2-[[[4-[(2-methyl-4-quinolinyl)
methoxy]phenyl]carbonyl]amino]-(N-hydroxy)
cyclohexylcarboxamide
(cis,cis)-3-Dimethylmino-2-[[[4-[(2-methyl-4-
quinolinyl)methoxy]phenyl]carbonyl]amino]-1-(N-
hydroxy)cyclohexylcarboxamide
(cis,trans)-3-Amino-2-[[[4-[(2-methyl-4-quinolinyl)
methoxy]phenyl]carbonyl]amino]-1-(N-hydroxy)
cyclohexylcarboxamide
(cis,trans)-3-Dimethylmino-2-[[[4-[(2-methyl-4-
quinolinyl)methoxy]phenyl]carbonyl]amino]-(N-
hydroxy)cyclohexylcarboxamide
(cis,trans)-3-(1-Methyl-1-ethylmino)-2-[[[4-[(2-methyl-
4-quinolinyl)methoxy]phenyl]carbonyl]amino]-(N-
hydroxy)cyclohexylcarboxamide
(cis,trans)-3-Methylamino-2-[[[4-[(2-methyl-4-
quinolinyl)methoxy]phenyl]carbonyl]amino]-(N-
hydrloxy)cyclohexylcarboxamide
(cis,cis)-3-Hydroxy-2-[[[4-[(2-methyl-4-quinolinyl)
methoxy]phenyl]carbonyl]amino]-(N-hydroxy)
cyclohexylcarboxamide
N-{cis-2-[(Hydroxyamino)carbonyl]cyclopentyl}-4-{[(2-
methyl-4-quinolinyl)methyl]amino}benzamide
N-{cis-2-[(Hydroxyamino)carbonyl]cyclopentyl}-4-
{methyl[(2-methyl-4-quinolinyl)methyl]
amino}benzamide
N-{cis-2-[(Hydroxyamino)carbonyl]cyclopentyl}-4-(3-
phenyl-4,5-dihydro-5-isoxazolyl)benzamide
N-{cis-2-[(Hydroxyamino)carbonyl]cyclopentyl}-4-[3-
(4-pyridinyl)-4,5-dihydro-5-isoxazolyl]benzamide
N-{cis-2-[(Hydroxyamino)carbonyl]cyclopentyl}-4-[3-
(3-pyridinyl)-4,5-dihydro-5-isoxazolyl]benzamide
N-{cis-2-[(Hydroxyamino)carbonyl]cyclopentyl}-4-[3-
(2-pyridinyl)-4,5-dihydro-5-isoxazolyl]benzamide
N-{cis-2-[(Hydroxyamino)carbonyl]cyclopentyl}-4-[3-
(4-quinolinyl)-4,5-dihydro-5-isoxazolyl]benzamide
4-[3-(2,6-Dimethyl-4-pyridinyl)-4,5-dihydro-5-
isoxazolyl]-N-{cis-2-[(hydroxyamino)carbonyl]
cyclopentyl}benzamide
N-{cis-2-[(Hydroxyamino)carbonyl]cyclopentyl}-3-
methoxy-4-[3-(4-pyridinyl)-4,5-dihydro-5-isoxazolyl]
benzamide
3-Hydroxy-N-{cis-2-[(hydroxyamino)carbonyl]
cyclopentyl}-4-[3-(4-pyridinyl)-4,5-dihydro-5-
isoxazolyl]benzamide
N-{cis-2-[(Hydroxyamino)carbonyl]cyclopentyl}-4-[5-
(2-pyridinyl)-4,5-dihydro-3-isoxazolyl]benzamide
N-{cis-2-[(Hydroxyamino)carbonyl]cyclopentyl}-4-[5-
(4-pyridinyl)-4,5-dihydro-3-isoxazolyl]benzamide
N-{4-[(hydroxyamino)carbonyl]-3-pyrrolidinyl}-1-[(2-
methyl-4-quinolinyl)methyl]-1H-indole-5-
carboxamide
N-{2-[(hydroxyamino)carbonyl]cyclopentyl}-1-[(2-
methyl-4-quinolinyl)methyl]-1H-indole-5-
carboxamide
N-hydroxy-3-({6-[(2-methyl-4-quinolinyl)methoxy]-1-
naphthoyl}amino)-4-piperidinecarboxamide
N-{2-[(hydroxyamino)carbonyl]cyclopentyl}-6-[(2-
methyl-4-quinolinyl)methoxy]-1-naphthamide
N-{2-[(hydroxyamino)carbonyl]cyclopentyl}-6-[(2-
methyl-4-quinolinyl)methoxy]-2-naphthamide
N-{2-[(hydroxyamino)carbonyl]cyclopentyl}-6-[(2-
methyl-4-quinolinyl)methoxy]-1,2,3,4-tetrahydro-1-
isoquinolinecarboxamide
N-{2-[(hydroxyamino)carbonyl]cyclopentyl}-1-[(2-
methyl-4-quinolinyl)methyl]-1H-benzimidazole-5-
carboxamide
N-{2-[(hydroxyamino)carbonyl]cyclopentyl}-1-[(2-
methyl-4-quinolinyl)methyl]-1H-indole-4-
carboxamide
(±)-cis-N-hydroxy-2-[[4-[(2-methyl-4-quinolinyl)
methoxy]benzoyl]amino]-1-cycloheptanecarboxamide
(±)-trans-N-hydroxy-2-[[4-[(2-methyl-4-quinolinyl)
methoxy]benzoyl]amino]-1-cycloheptanecarboxamide
(4S,5R)-N-hydroxy-5-({4-[(2-methyl-4-quinolinyl)
methoxy]benzoyl}amino)-2-oxohexahydro-1-azepine-
4-carboxamide
(3S,4S)-N-hydroxy-3-({4-[(2-methyl-4-quinolinyl)
methoxy]benzoyl}amino)-7-oxohexahydro-1H-
azepine-4-carboxamide
(3S,4R)-N-hydroxy-4-({4-[(2-methyl-4-quinolinyl)
methoxy]benzoyl}amino)-7-oxohexahydro-1H-
azepine-3-carboxamide
(4S,5R)-N-hydroxy-5-({4-[(2-methyl-4-quinolinyl)
methoxy]benzoyl}amino)-7-oxohexahydro-1H-
azepine-4-carboxamide
(2S,3R)-N-hydroxy-3-({4-[(2-methyl-4-quinolinyl)
methoxy]benzoyl}amino)-2-pyrrolidinecarboxamide
(2R,3R)-N-hydroxy-3-({4-[(2-methyl-4-quinolinyl)
methoxy]benzoyl}amino)-2-pyrrolidinecarboxamide,
and
tert-butyl (2S,3R)-2-[(hydroxyamino)carbonyl]-3-({4-
[(2-methyl-4-quinolinyl)methoxy]benzoyl}amino)-1-
pyrrolidinecarboxylate
or a pharmaceutically acceptable salt form thereof.

In another embodiment, the present invention provides a novel pharmaceutical composition, comprising: a pharmaceutically acceptable carrier and a therapeutically effective amount of a compound of the present invention or a pharmaceutically acceptable salt form thereof.

In another embodiment, the present invention provides a novel method for treating or preventing an inflammatory disorder, comprising: administering to a patient in need thereof a therapeutically effective amount of a compound of the present invention or a pharmaceutically acceptable salt form thereof.

In another embodiment, the present invention provides a novel method of treating a condition or disease mediated by MMPs, TNF, aggrecanase, or a combination thereof in a mammal, comprising: administering to the mammal in need of such treatment a therapeutically effective amount of a compound of the present invention or a pharmaceutically acceptable salt form thereof.

In another embodiment, the present invention provides a novel method of treating, wherein the disease or condition is referred to as acute infection, acute phase response, age related macular degeneration, alcoholism, anorexia, asthma, autoimmune disease, autoimmune hepatitis, Bechet's disease, cachexia, calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthropathy, Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pydoderma gangrenosum, relapsing polychondritis, Reiter's syndrome, rheumatic fever, rheumatoid arthritis, sarcoidosis, scleroderma, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

In another embodiment, the present invention provides novel compounds of the present invention for use in therapy.

In another embodiment, the present invention provides the use of novel compounds of the present invention for the manufacture of a medicament for the treatment of a condition or disease mediated by MMPs, TNF, aggrecanase, or a combination thereof.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Geometric isomers of double bonds such as olefins and C=N double bonds can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R^b$) occurs more than one time in any constituent or formula for a compound, its definition at each occurrence is independent of its definition at every other occurrence. Thus, for example, if a group is shown to be substituted with 0–2 $R^6$, then said group may optionally be substituted with up to two $R^6$ groups and $R^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" or "alkylene" is intended to include both branched and straight-chain saturated aliphatic hydrocarbon groups having the specified number of carbon atoms. $C_{1-10}$ alkyl (or alkylene), is intended to include $C_1$, $C_2$, $C_3$, $C_4$, $C_5$, $C_6$, $C_7$, $C_8$, $C_9$, and $C_{10}$ alkyl groups. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2 v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. $C_{1-10}$ alkoxy, is intended to include $C_1$, $C_2$, $C_3$, $C_4$, $C_5$, $C_6$, $C_7$, $C_8$, $C_9$, and $C_{10}$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. $C_{3-7}$ cycloalkyl, is intended to include $C_3$, $C_4$, $C_5$, $C_6$, and $C_7$ cycloalkyl groups. "Alkenyl" or "alkenylene" is intended to include hydrocarbon chains of either a straight or branched configuration and one or more unsaturated carbon-carbon bonds which may occur in any stable point along the chain, such as ethenyl and propenyl. $C_{2-10}$ alkenyl (or alkenylene), is intended to include $C_2$, $C_3$, $C_4$, $C_5$, $C_6$, $C_7$, $C_8$, $C_9$, and $C_{10}$ alkenyl groups. "Alkynyl" or "alkynylene" is intended to include hydrocarbon chains of either a straight or branched configuration and one or more triple carbon-carbon bonds which may occur in any stable point along the chain, such as ethynyl and propynyl. $C_{2-10}$ alkynyl (or alkynylene), is intended to include $C_2$, $C_3$, $C_4$, $C_5$, $C_6$, $C_7$, $C_8$, $C_9$, and $C_{10}$ alkynyl groups.

"Halo" or "halogen" as used herein refers to fluoro, chloro, bromo, and iodo; and "counterion" is used to represent a small, negatively charged species such as chloride, bromide, hydroxide, acetate, and sulfate.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane, [2.2.2] bicyclooctane, fluorenyl, phenyl, naphthyl, indanyl, adamantyl, and tetrahydronaphthyl.

As used herein, the term "heterocycle" or "heterocyclic group" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic group" or "heteroaryl" is intended to mean a stable 5, 6, or 7-membered monocyclic or bicyclic or 7, 8, 9, or 10-membered bicyclic heterocyclic aromatic ring which consists of carbon atoms and 1, 2, 3, or 4 heterotams independently selected from the group consisting of N, O and S. It is to be noted that total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc . . . ) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers which release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent.

"Therapeutically effective amount" is intended to include an amount of a compound of the present invention or an amount of the combination of compounds claimed effective to inhibit a desired metalloprotease in a host. The combination of compounds is preferably a synergistic combination. Synergy, as described for example by Chou and Talalay, Adv. Enzyme Regul. 22:27–55 (1984), occurs when the effect (in this case, inhibition of the desired target) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased antiviral effect, or some other beneficial effect of the combination compared with the individual components.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

A variety of compounds of formula (I) wherein A is hydroxamic acid group are prepared from the corresponding esters via several routes known in the literature (Scheme 1). The methyl ester of 1 ($R^{11}$=Me) is directly converted to hydroxamic acid 2 by treatment with hydroxylamine under basic conditions such as KOH or NaOMe in solvents such as methanol. The methyl ester of 1 ($R^{11}$=Me) can also be converted to O-benzyl protected hydroxamic acid with O-benzylhydroxylamine under similar conditions or using Weinreb's trimethylalluminum conditions (Levin, J. I.; Turos, E.; Weinreb, S. M. *Syn. Commun.* 1982, 12, 989) or Roskamp's bis[bis(trimethylsilyl)amido]tin reagent (Wang, W.-B.; Roskamp, E. J. *J. Org. Chem.* 1992, 57, 6101). The benzyl ether is removed by methods well known in the literature such as hydrogenation using palladium on barium sulfate in hydrogen, to give compound 2. Alternatively, 2 can be prepared through the carboxylic intermediate 3. Carboxylic acid 3 is converted to 2 via coupling with hydroxylamine, or O-benzylhydroxylamine followed by deprotection.

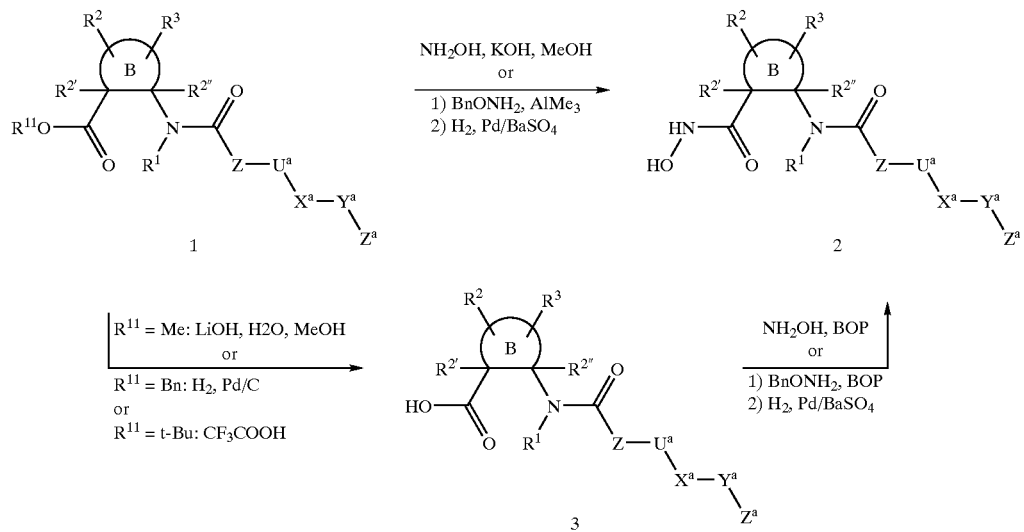

Scheme 1

The β-amino acid moiety in formula (I) can be synthesized following a variety of literature routes as reviewed in "Enantioselective Synthesis of β-Amino Acids" (E. Juaristi, Ed. Wiley-VCH, 1997). One representative approach using Davies protocol is summarized in Scheme 2 (*J. Chem. Soc. Perkin Trans I*, 1994, 1411). Michael addition of lithium amide 5 to 4 gives cis product 6. The stereochemical configuration of 6 is governed by the chirality of 5. De-benzylation of 6 provides cis-β-amino acid 7. The trans-β-amino acid 9 can be prepared by epimerization of 6 followed by de-benzylation. Since both amine enantiomers of 5 are commercially available, this approach provides ready access to both cis and trans isomers (7 and 9), as well as their antipodes.

Scheme 2

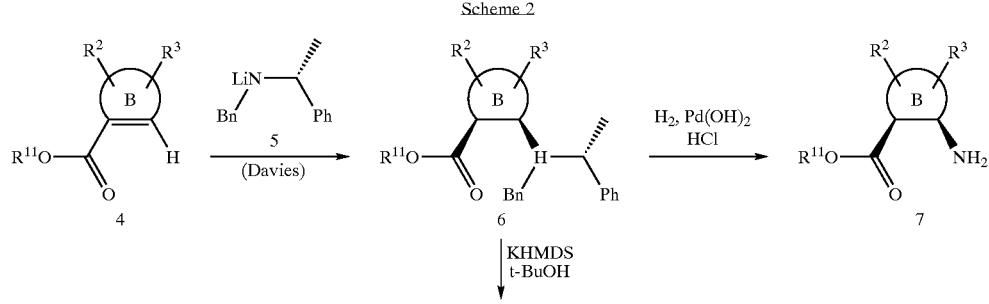

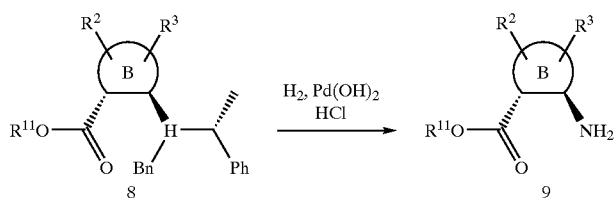

Alternatively, these β-amino acids can be prepared from the corresponding dicarboxylate derivatives (Scheme 3). The dicarboxylate derivatives can be de-symmetrized through enzymatic resolution (for an example with lipase, see Gais, H.-J. et al, *J. Am. Chem. Soc.* 1989, 54, 5115), or through chemical resolution (for an example with TADOLates, see Seebach, D. et al, *Angew Chem Int. Ed. Engl.* 1995, 34, 2395). The optically pure mono-ester 11 is converted to Cbz protected β-amino acid ester 12 through Curtius rearrangement (for a related example, see Kobayashi, S. et al, *Tetrahedron Lett.* 1984, 25, 2557).

Removal of Cbz protecting group provides cis amino acid ester 13. The corresponding trans analogue of 13 can be prepared from the ester of trans di-carboxylic acid of 10 following same sequence.

Scheme 3

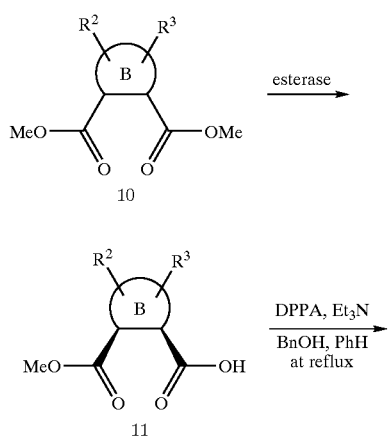

-continued

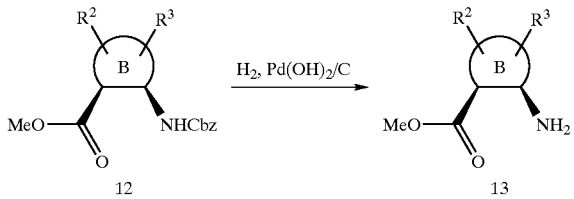

A series of compounds of formula (I) wherein ring B is pyrrolidine are prepared following the sequence outlined in Scheme 4. Pyrrolidine 15 is prepared following a dipolar addition procedure documented in the literature (Joucla, M.; Mortier, J., *J. Chem. Commun.* 1985, 1566). Protecting group manipulations and Curtius rearrangement (for a related example, see Kobayashi, S. et al, *Tetrahedron Lett.* 1984, 25, 2557) give intermediate 17. Hydrogenolysis gives amino acid ester 18. 18 is coupled with acid 20 to provide 21 with $R^1$ as H. To prepare analogues of 21 when $R^1$ is not a hydrogen, 18 is first converted to 19 by alkylation or reductive amination, then coupled with 20. The pyrrolidine nitrogen in 21 is unmasked and functionalized to various tertiary amines, amides, carbamides, ureas, sulfonamides and sulfonyl ureas following procedures well known in the literature. Ester 23 is converted to hydroxamic acid following sequence outlined in Scheme 1. Following the same sequence, the cis isomer of 23 can be prepared using benzyl methyl maleate as the starting material.

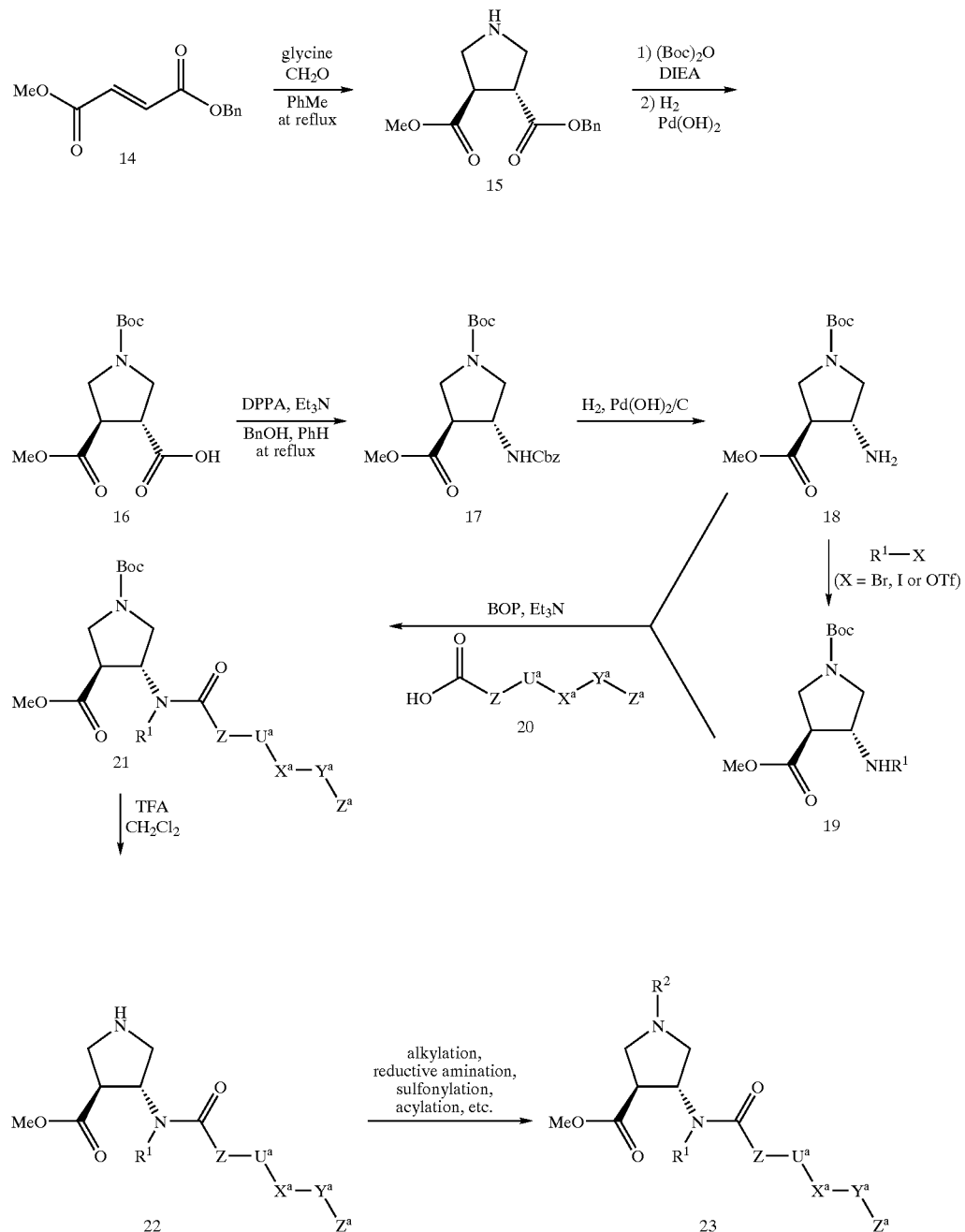

Scheme 4

A series of compounds of formula (I) wherein ring B is piperidine are prepared following the sequence outlined in Scheme 5. The β-amino acid moiety is prepared by reduction of enamine 27. Optically pure α-methylbenzylamine (26) is used to induce diastereoselectivity in the reduction (Cimarelli, C. et. al, *J. Org. Chem.* 1996, 61, 5557). Hydrogenolysis gives amino acid ester 29. 29 is coupled with acid 20 to provide 31 with $R^1$ as H. To prepare analogues of 31 when $R^1$ is not a hydrogen, 29 is first converted to 30 by alkylation or reductive amination, then coupled with 20. The piperidine nitrogen in 31 is unmasked and functionalized to various tertiary amines, amides, carbamides, ureas, sulfonamides and sulfonyl ureas following procedures well known in the literature. Ester 33 is converted to hydroxamic acid following sequence outlined in Scheme 1. Regio-isomers of 33 with piperidine nitrogen transposed to other positions are prepared following a similar sequence. The antipode of 33 can be prepared using the S enantiomer of 26. The trans-isomer of 33 is prepared by epimerization of 31 or 33 under basic conditions (e.g., DBU, PhMe, at reflux).

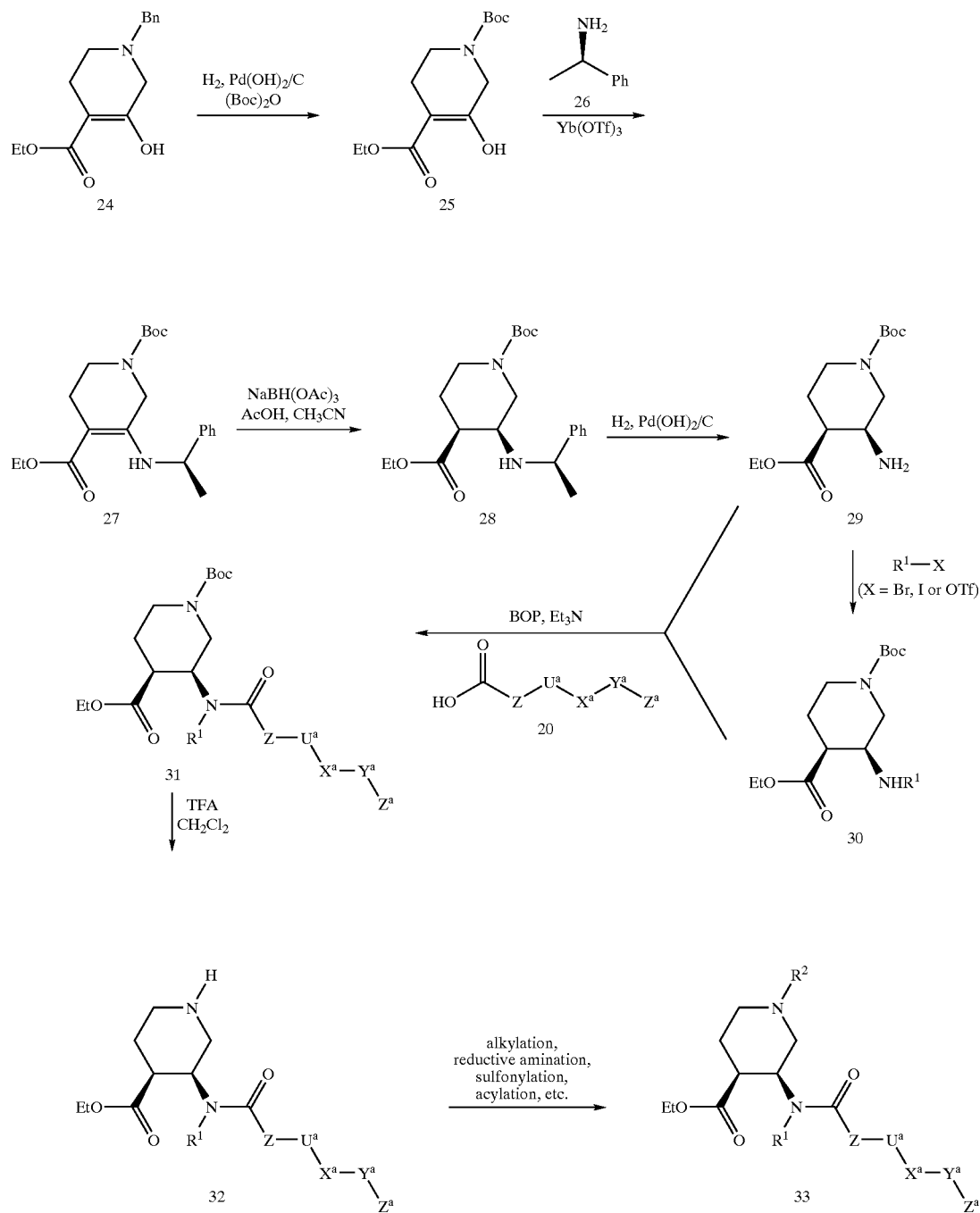

Scheme 5

A series of compounds of formula (I) wherein ring B is piperidine and $R^{2a}$ is hydroxy are prepared following the sequence outlined in Scheme 6. Ketone 34 is converted to enol triflate 35 following McMurry triflimide conditions (McMurry, J. E.; Scott, W. J. *Tetrahedron Lett.* 1983, 24, 979). Palladium-catalyzed carbonylation in methanol provides methyl ester 36. Epoxidation, epoxide opening with NaN3 and hydrogenation give intermediate 39 with amino and ester groups in cis relationship. The isomer with trans stereochemistry (43) is prepared using Sharpless asymmetric aminohydroxylation and subsequent removal of Cbz group (Li, G.; Angert, H. H.; Sharpless, K. B. *Angew. Chem. Int. Ed. Engl.* 1996, 35, 2813). Coupling of 39 and 43 with acid 20 provides 40 and 44, respectively. Esters 40 and 44 are converted to hydroxamic acids following sequence outlined in Scheme 1.

Scheme 6

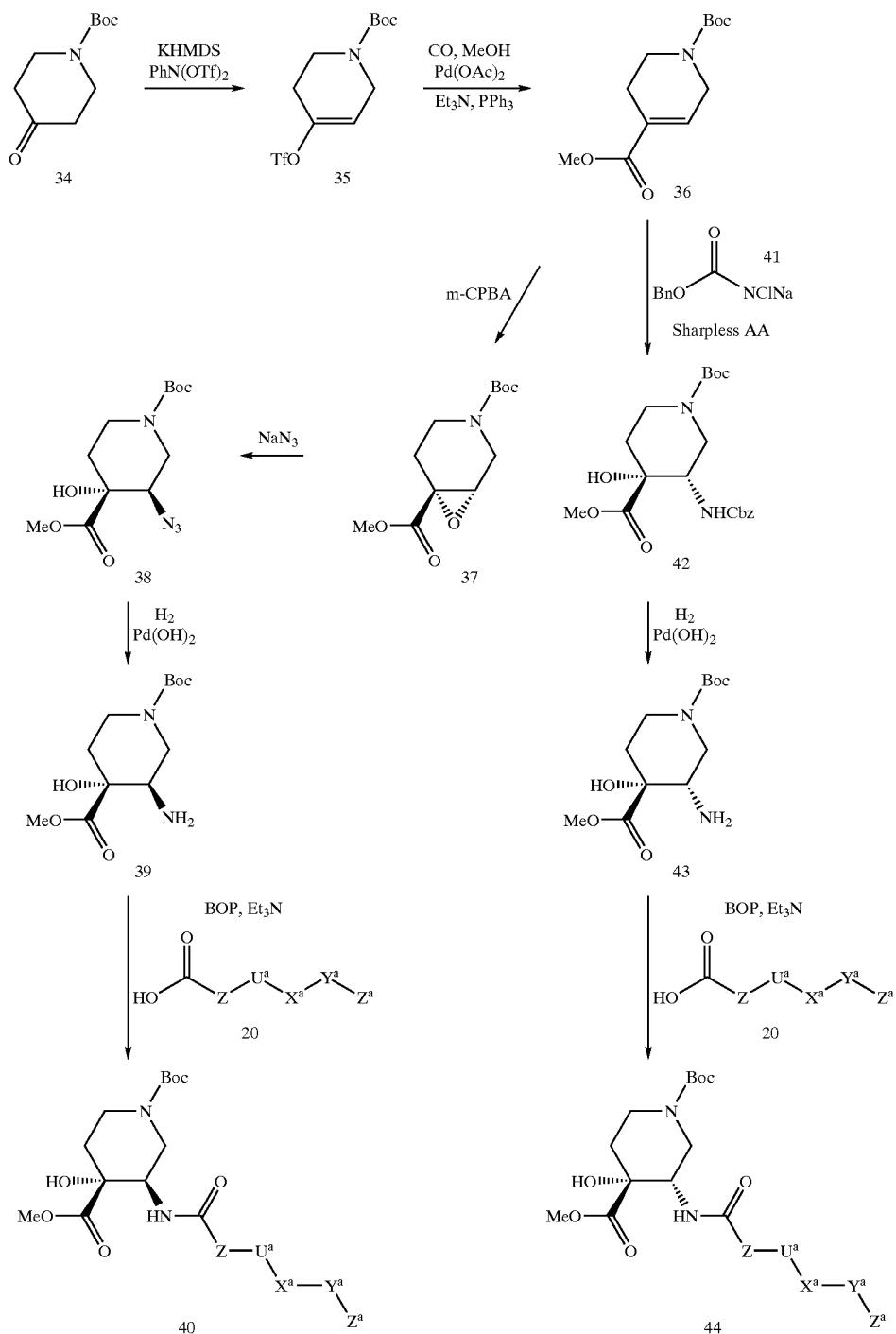

A series of compounds of formula (I) wherein A is N-formylhydroxylamino group are prepared following the sequence outlined in Scheme 7. Starting from trans-hydroxy ester 45, Wenreib or Roskamp amide formation with O-t-butylhydroxylamine gives 46 (Levin, J. I.; Turos, E.; Weinreb, S. M. *Syn. Commun.* 1982, 12, 989 and Wang, W.-B.; Roskamp, E. J. *J. Org. Chem.* 1992, 57, 6101). β-Lactam is formed under Mitsunobu conditions (Mitsunobu, O. *Synthesis*, 1981, 1). Opening of lactam 47 with methylamine followed by N-formylation provide 49. The N-methyl amide moiety of 49 is converted to carboxylic acid by nitrosation with N2O4 or NaNO2, and hydrolysis with LiOOH (Evans, D. A.; Carter, P. H.; Dinsmore, C. J.; Barrow, J. C.; Katz, J. L.; Kung, D. W. *Tetrahedron Lett.* 1997, 38, 4535). Acid 50 is converted to 53 as described previously. Acid hydrolysis of t-Butyl group in 53 completes the synthesis.

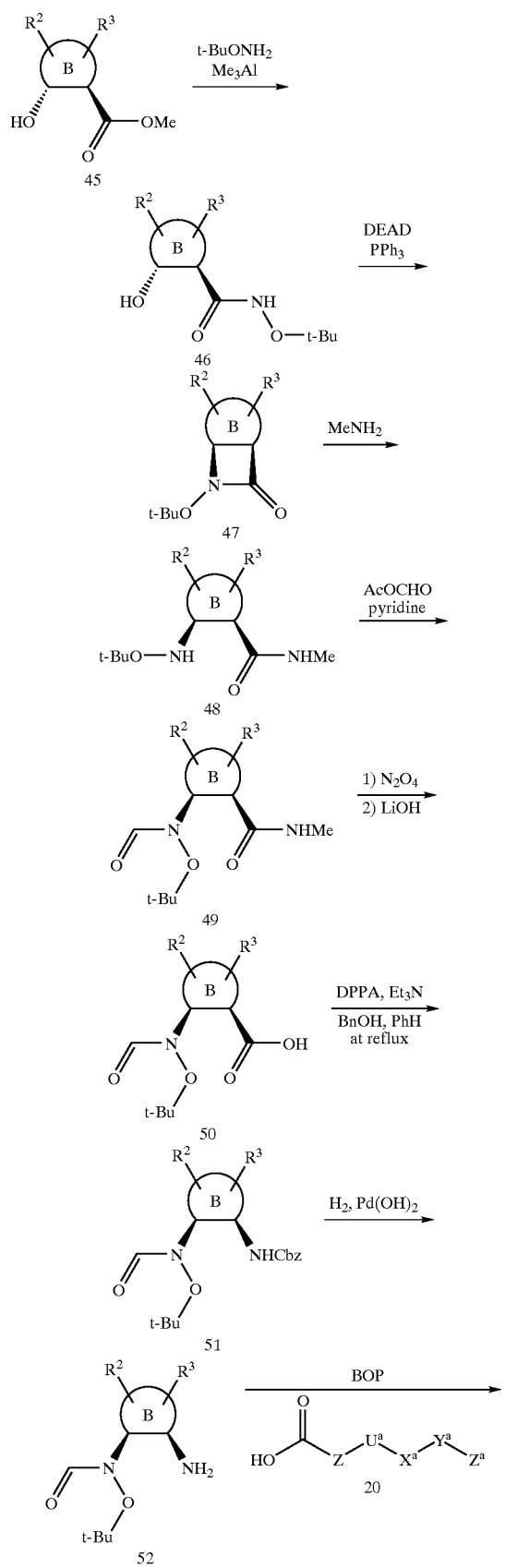
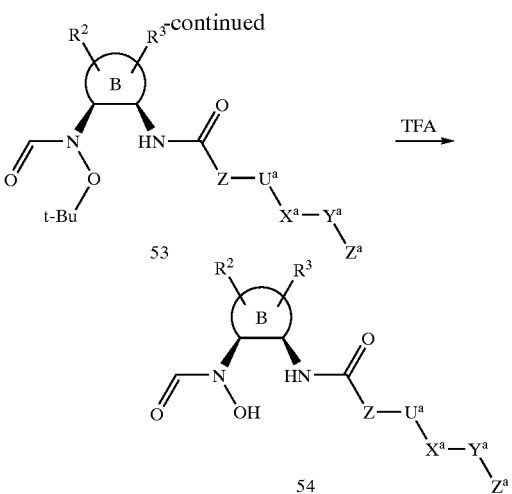
A series of compounds of formula (I) wherein A is mercaptomethyl group are prepared following the sequence outlined in Scheme 8. Saponification and hydroboration of 55 give alcohol 57. Mitsunobu reaction with thioacetic acid followed by lithium hydroxide hydrolysis provides the desired thiol 59.
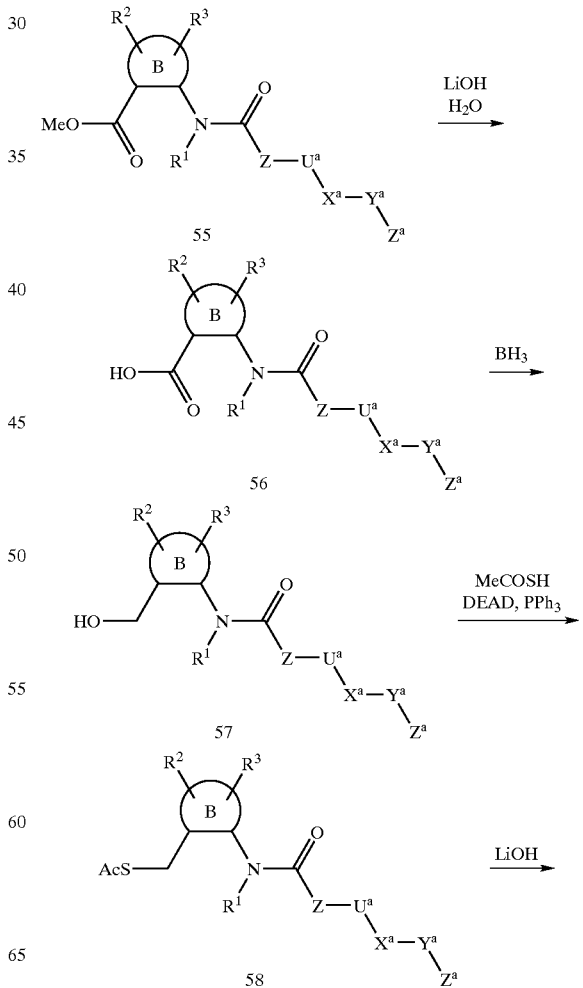

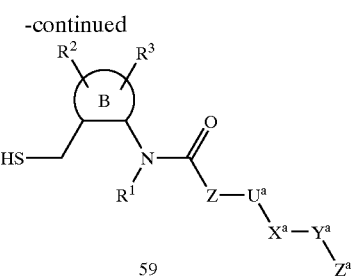

A variety of compounds of formula (I) wherein Z-$U^a$—$X^a$—$Y^a$-$Z^a$ is a functionalized phenyl group can be prepared by methods described in Scheme 9. Intermediate 60, available from schemes described previously, is converted to phenol 61 by hydrogenolysis. Phenol 61 is used as common intermediates for structure diversification. Reaction of 61 with $R^{10}$—X provides 62, an alternative is the reaction of 61 with $R^{10}$—OH under Mitsunobu conditions to produce 62. $R^{10}$ can be appended directly to the aromatic ring by converting 61 to an aryl triflate then reaction with an organometallic in the presence of a palladium (O) catalyst to give 63. 61 can also be reacted with acyl halides or isocyanates to afford 66. Biaryl ethers 65 can be produced by treatment of 61 with aryl boronic acids in the presence of a copper catalyst. Esters 62–63 and 65–66 are converted to the hydroxamic acids following the sequences outlined in Scheme 1.

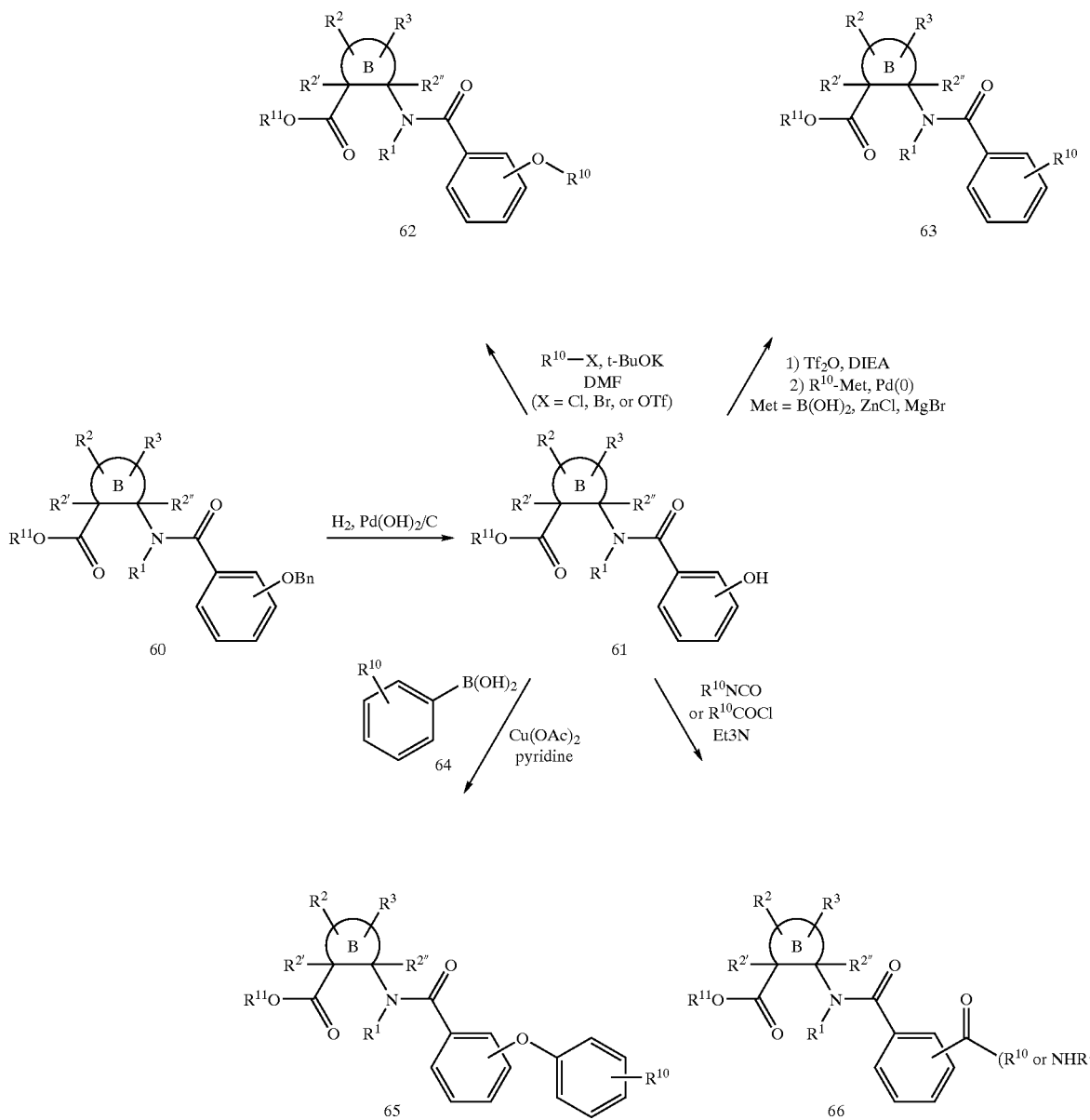

Compounds of formula 76 can be prepared starting from the commercially available 3-hydroxy-2-nitrobenzoic acid 67 (Scheme 10). Conversion of the carboxylic acid to an ester such as an ethyl ester 68 can be accomplished by refluxing in EtOH/benzene in the presence of sulfuric acid. Ester 68 can be reduced to a saturated cyclohexyl ring 69 by hydrogenation in acidic aqueous solution using a catalyst such as $PtO_2$. Coupling of 69 with a benzoic acid derivative 70 using a coupling agent such as BOP produces the amide derivative 71 as the major diastereomer with a cis, cis-stereochemistry. The hydroxyl group of 71 can be oxidized using an oxidizing agent such as the Dess-Martin periodinane to give a ketone derivative 72. Reductive amination of 72 with ammonium acetate or a primary amine using a reducing agent such as $Na(OAc)_3BH$ affords the amino derivative 73. After Boc protection at the amino using di-tert-butyl-dicarbonate, saponification of the ethyl ester 74 at an elevated temperature using a base such as KOH in $MeOH/H_2O$ followed by coupling of the resulting carboxylic acid with hydroxylamine hydrochloride using a coupling agent such as BOP produces the hydroxamic acid 75. Removal of the Boc group using an acid such $TFA/CH_2Cl_2$ or 4 N HCl in dioxane affords the final compounds of formula 76.

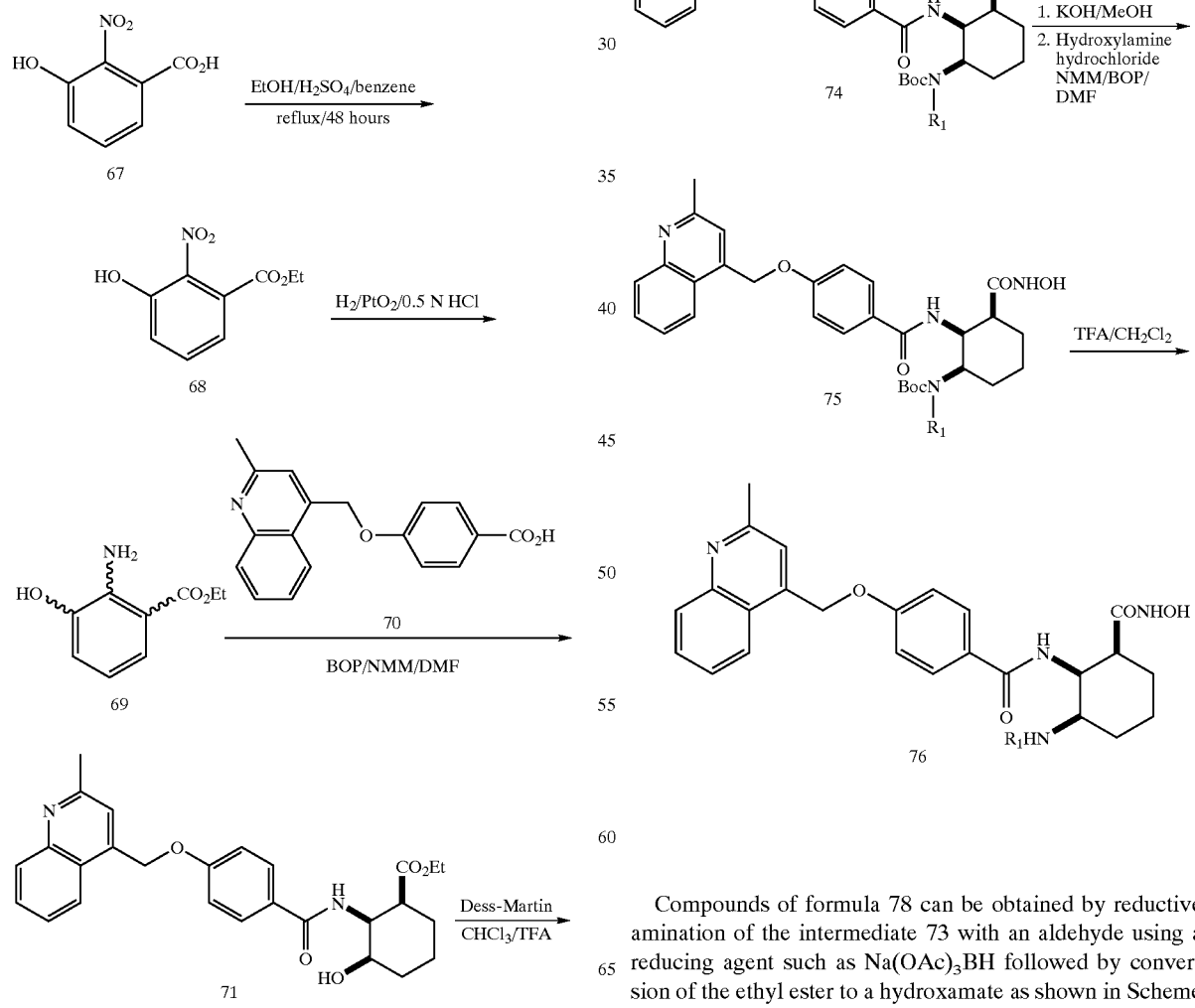

Compounds of formula 78 can be obtained by reductive amination of the intermediate 73 with an aldehyde using a reducing agent such as $Na(OAc)_3BH$ followed by conversion of the ethyl ester to a hydroxamate as shown in Scheme 11.

Scheme 11

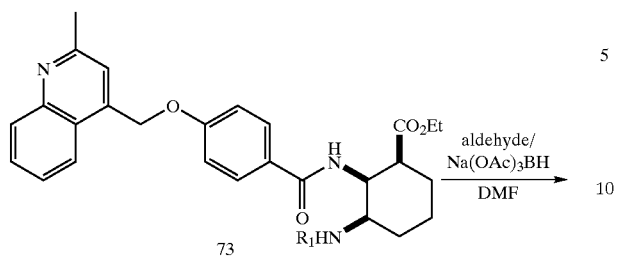

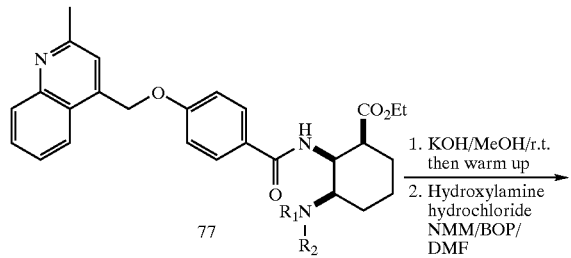

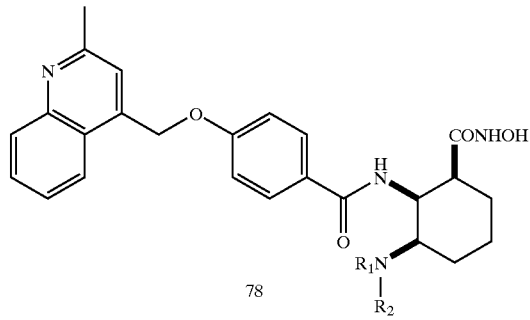

Compounds of formula 80 can be obtained by reductive amination of the intermediate 72 with a cycloamine such as azetidine, pyrrolidine, piperidine or morpholine using a reducing agent such as Na(OAc)$_3$BH followed by conversion of the ethyl ester to a hydroxamate as shown in Scheme 12.

Scheme 12

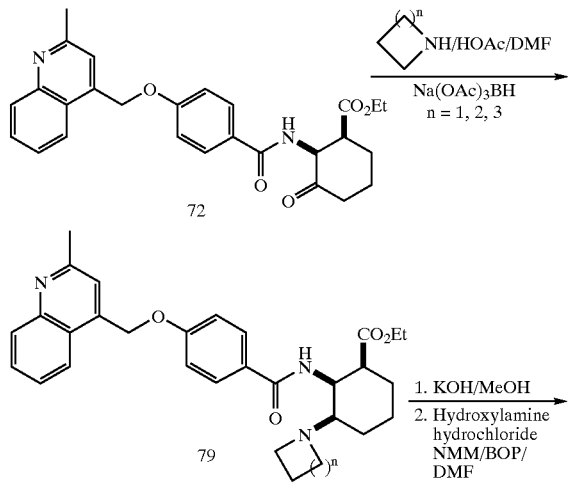

Compound of formula 89 can be synthesized starting from the intermediate 69 which is coupled with 4-benzyloxybenzoic acid 81 using a coupling agent such as BOP, producing 82 as the major diastereomer with a cis, cis-stereochemistry (Scheme 13). The hydroxyl group can be converted to a sulfonate such as a mesylate 83. Displacement of 83 with sodium azide produces the azido derivative 84 which is subjected to a hydrogenolysis using a catalyst such as Pd—C to give the primary amine 85. Mono Boc protection at the amino group is accomplished by reaction of 85 with di-tert-butyl-dicarbonate in THF/H$_2$O using a mixed base such as NaOH/NaHCO$_3$. Alkylation of 86 with 4-chloromethyl-2-methylquinoline using a base such as potassium carbonate in acetone at reflux affords the intermediate 87. Following saponification using a base such as KOH in MeOH/H$_2$O at an elevated temperature, the resulting carboxylic acid 88 is coupled with hydroxylamine hydrochloride using a coupling agent such as BOP. Removal of the Boc group using an acid such as TFA/CH$_2$Cl$_2$ produces the final compound 89.

Scheme 13

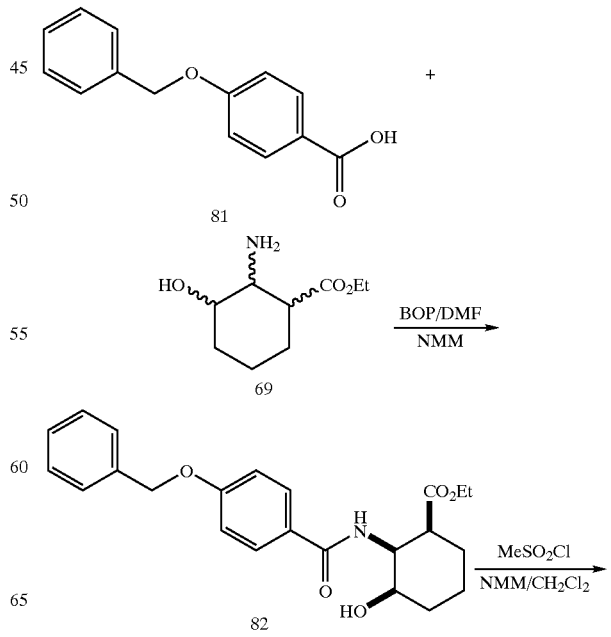

-continued

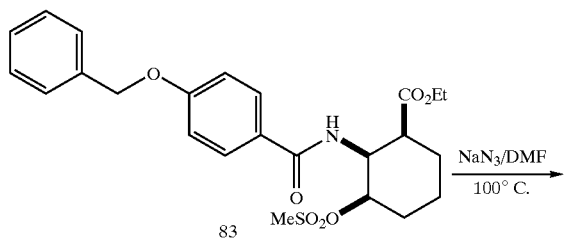

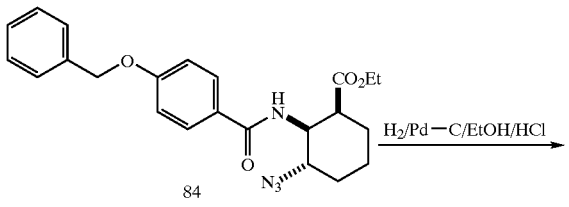

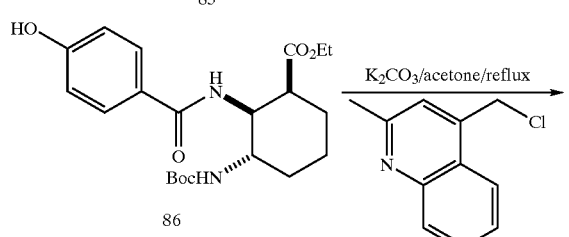

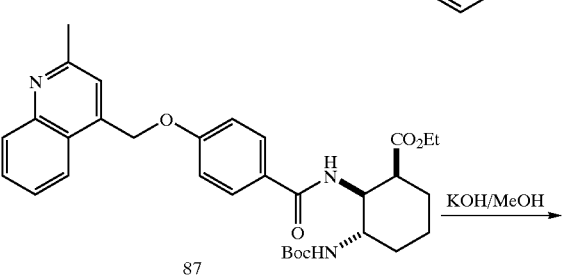

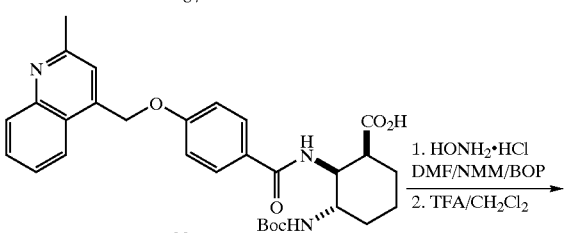

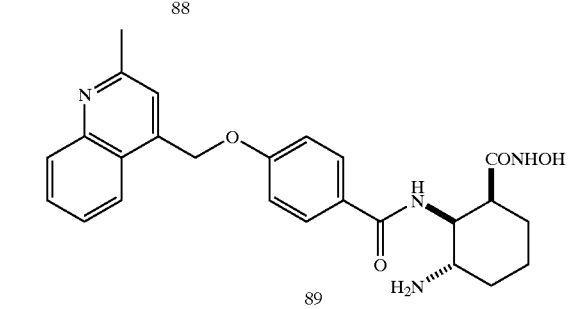

Compounds of formula 92 can be prepared starting from the intermediate 87 (Scheme 14). Saponification using a base such as KOH in MeOH at an elevated temperature followed by deprotection of the Boc group using an acid such as TFA in $CH_2Cl_2$ produces the amino-carboxylic acid intermediate 90. Reductive amination of 90 with a ketone using a reducing agent such as $Na(OAc)_3BH$ produces the secondary amine 91. The hydroxamic acids of formula 92 can be obtained by coupling the carboxylic acid with hydroxylamine hydrochloride using a coupling agent such as BOP.

Scheme 14

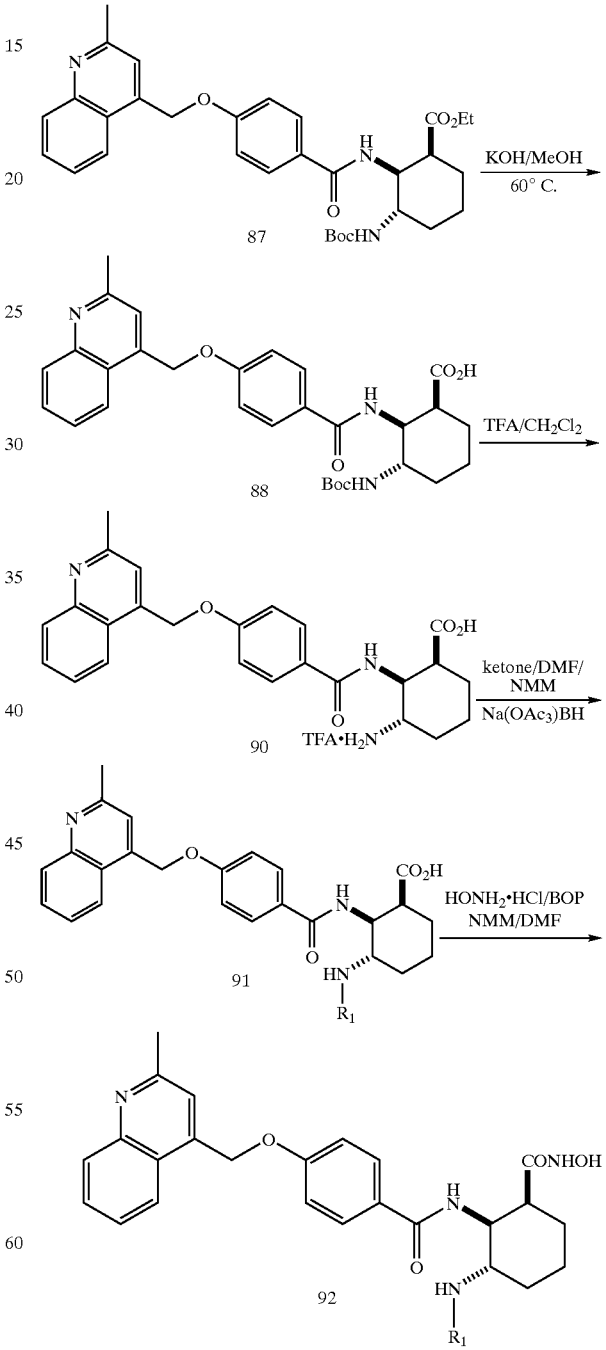

Compounds of formula 95 can be obtained by reductive amination of the intermediate 90 with an aldehyde using a reducing agent such as Na(OAc)₃BH followed by conversion of the carboxylic acid to a hydroxamic acid as shown in Scheme 15.

Compounds of formula 103 can be prepared starting from the intermediate 85 (Scheme 16). The mono-benzylated amino derivative 97 can be obtained by reductive amination of the intermediate 85 with excess benzaldehyde using a reducing agent such as Na(OAc)₃BH followed by hydrogenation under atmospheric pressure using a catalyst such as Pd—C. Further alkylation at the benzylamino group by reductive amination with an aldehyde using a reducing agent such as Na(OAc)₃BH produces the tertiary amino derivative 98. After removal of the benzyl group by hydrogenation, the secondary amine is protected by reaction with di-tert-butyl-dicarbonate. Alkylation of the phenol derivative 100 with 4-chloromethyl-2-methylquinoline is followed by saponification of the ethyl ester using a base such as KOH in MeOH at reflux. Conversion of the carboxylic acid to a hydroxamic acid followed by acid deprotection of the Boc group affords compounds of formula 103.

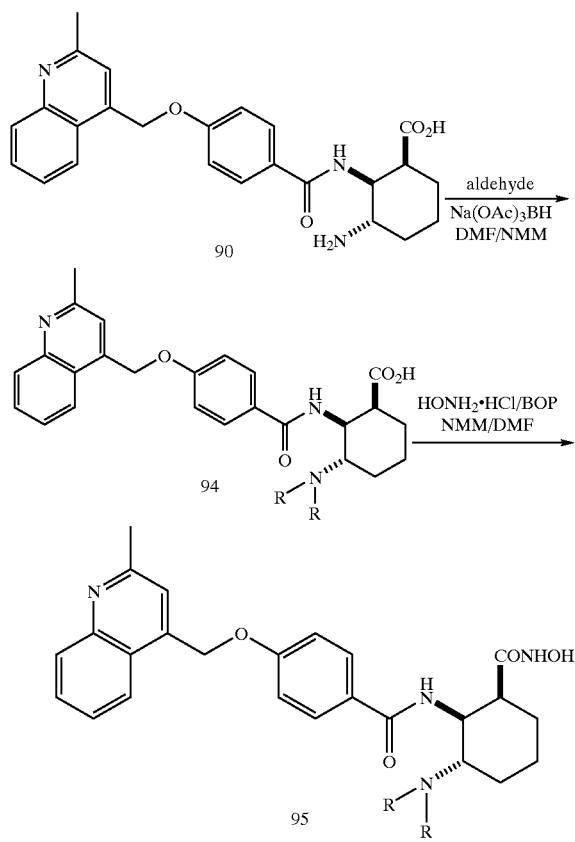

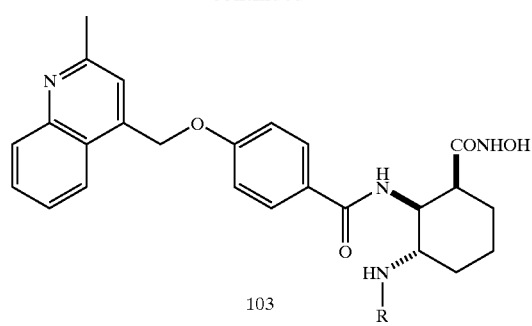

103

Compounds of formula 108 can be prepared starting from the intermediate 83 (Scheme 17). Displacement of 83 with ArOH produces the aryl ether 104. After removal of the benzyl group by hydrogenation using a catalyst such as Pd—C, the phenol moiety is alkylated with 4-chloromethyl-2-methylquinoline. Saponification of the ethyl ester using a base such as KOH in MeOH at reflux followed by coupling of the resulting carboxylic acid with hydroxylamine hydrochloride using a coupling agent such as BOP affords compounds of formula 108.

Scheme 17

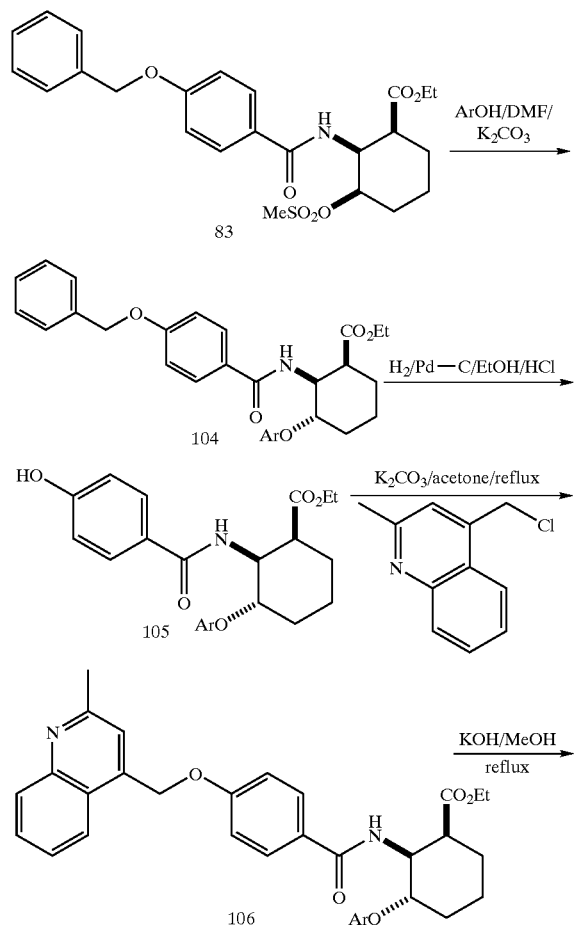

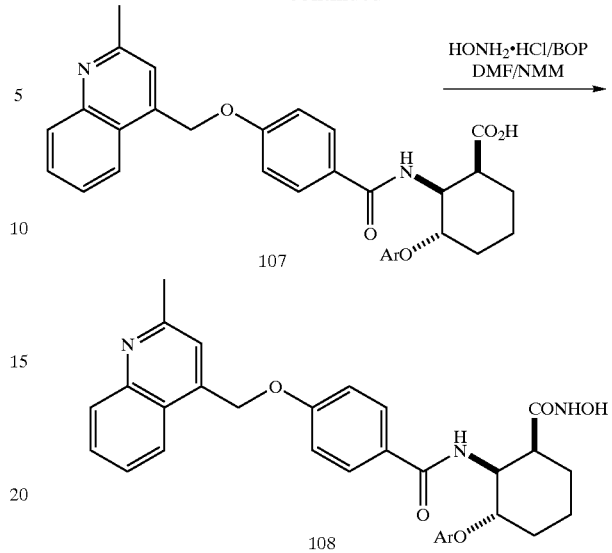

The 3-hydroxyl analog of formula 110 can be prepared starting from the intermediate 71. Saponification using a base such as LiOH followed by coupling the resulting carboxylic acid with hydroxylamine hydrochloride using a coupling agent such as BOP provides the the final product with a cis, cis-stereochemistry.

Scheme 18

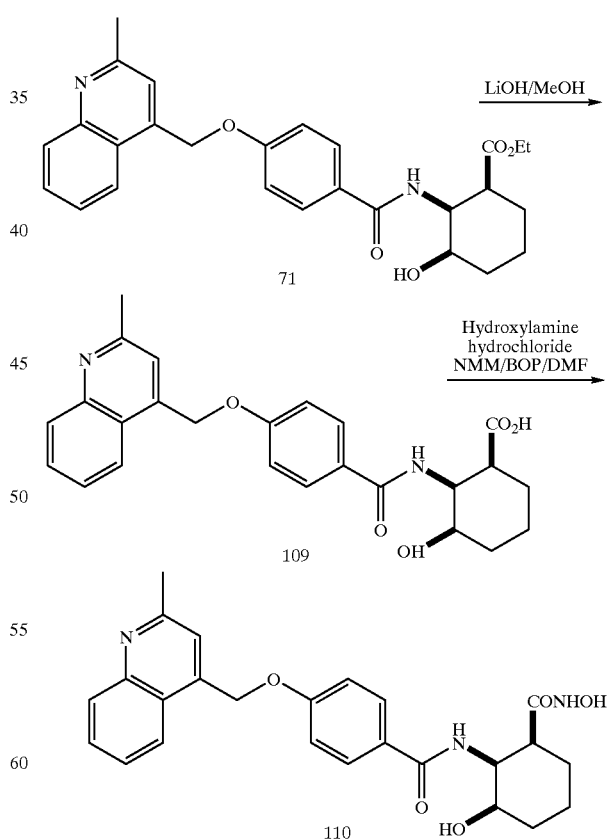

The cis-trans-diastereomeric analog of 110 can be prepared starting from the same intermediate 71. Inversion of the chirality at the 3-hydroxyl position can be accomplished by a Mitsunobu reaction with 4-nitrobenzoic acid. Hydrolysis using a base such as KOH removes the 4-nitrobenzoyl moiety and saponifies the ethyl ester. Coupling of the resulting carboxylic acid with hydroxylamine hydrochloride using a coupling agent such as BOP provides compound of formula 112.

Scheme 19

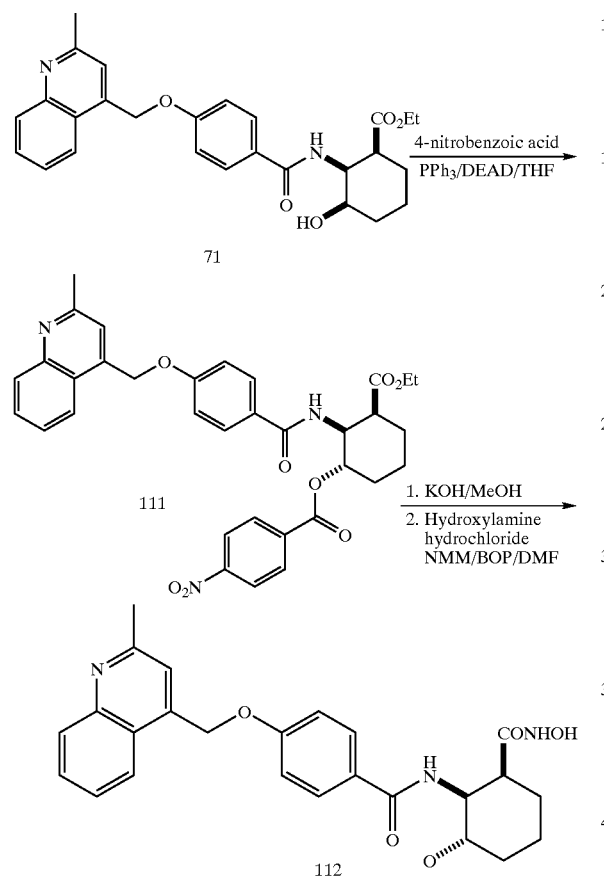

A series of compound of formula (I) where ring B is tetrahydropyran are prepared following the sequence outlined in Scheme 20. Treatment of the enolate of tetrahydropyranone 113 with Mander's reagent provides β-keto ester 114. Condensation of 114 with amine 115 gives enamine 116. Reduction of 116 with sodium (triacetoxy)borohydride proceeds stereoselectively to give desired amine 117. Hydrogenolysis and coupling with acid 20 provides ester 119. Ester 119 is converted to hydroxamic acid following sequence outline in Scheme 1.

Scheme 20

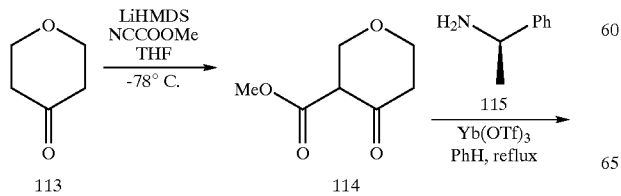

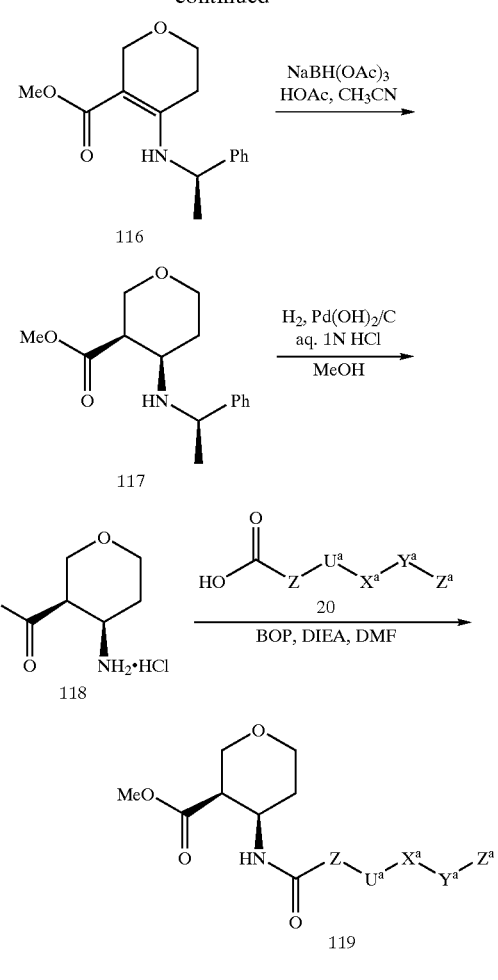

Compounds of formula (I) wherein ring B is a tetrahydrofuran are prepared as outlined in Schemes 21 and 22. Michael addition of the sodium salt of methyl glycolate 120 to methyl acrylate and concomitant Dieckman cyclization provides the keto-ester 121. Enamine formation with (R)-α-methylbenzyl amine 115 and diastereoselective reduction gives 123. Hydrogenolysis gives the amino acid ester 124. 124 is coupled to acid 20 and converted to the hydroxamate 126.

Scheme 21

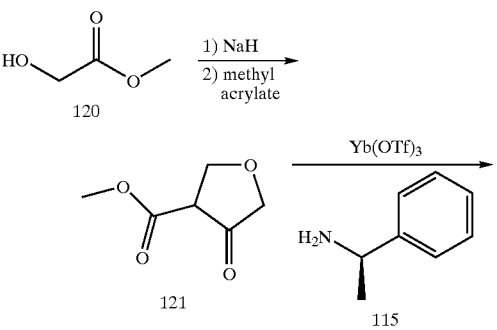

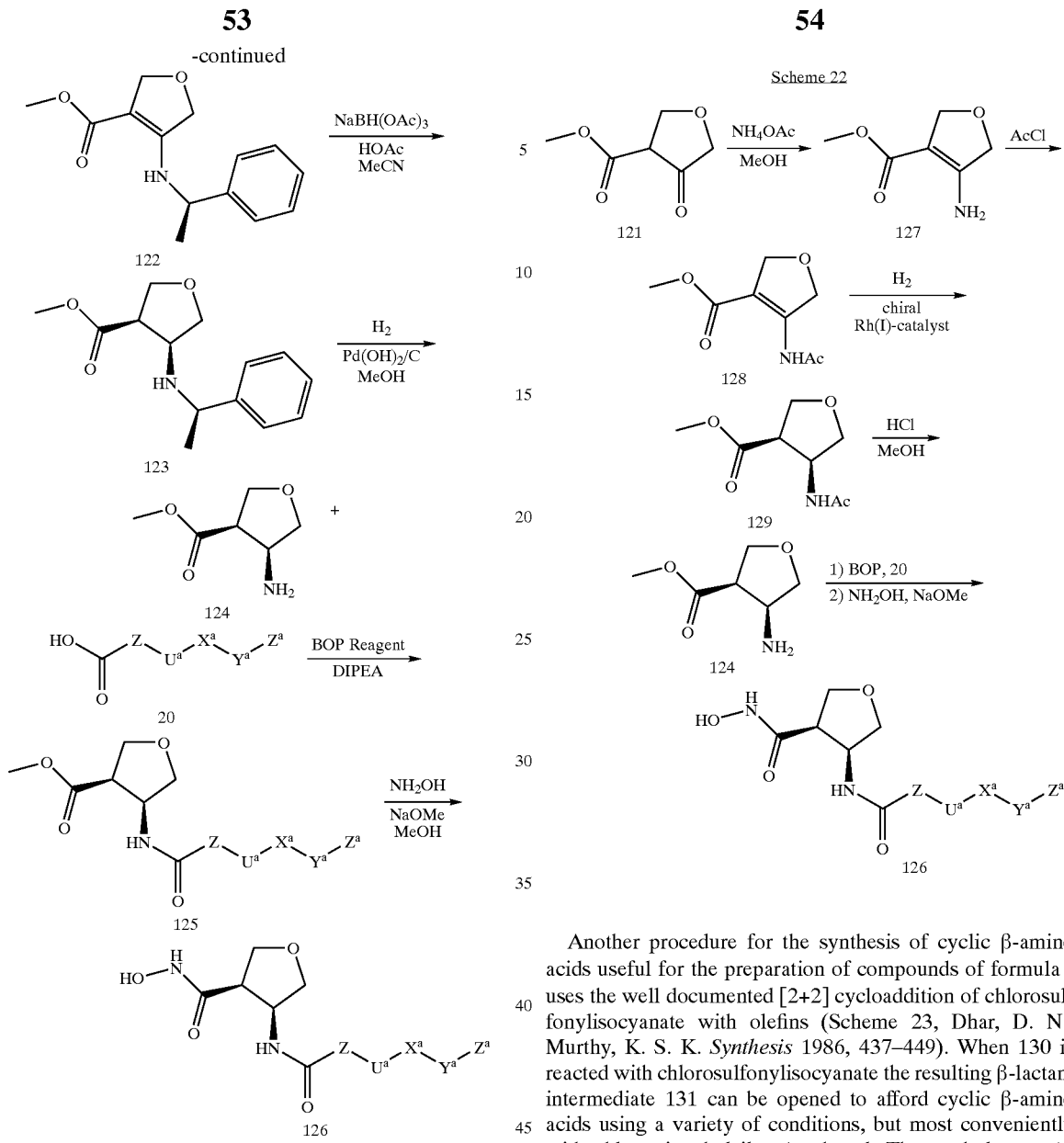

An alternative preparation (Scheme 22) of the amino acid ester 124 begins with the intermediate 121. Enamine formation with $NH_4OAc$ and acetylation gives 128. Asymmetric hydrogenation using a chiral rhodium catalyst (*J. Am. Cem. Soc.* 1995, 117, 9375) and de-acetylation would yield 124 that could be converted similarly to hydroxamate 126.

Another procedure for the synthesis of cyclic β-amino acids useful for the preparation of compounds of formula I uses the well documented [2+2] cycloaddition of chlorosulfonylisocyanate with olefins (Scheme 23, Dhar, D. N.; Murthy, K. S. K. *Synthesis* 1986, 437–449). When 130 is reacted with chlorosulfonylisocyanate the resulting β-lactam intermediate 131 can be opened to afford cyclic β-amino acids using a variety of conditions, but most conveniently with chlorotrimethylsilane/methanol. The methyl ester 13 can then be converted to compounds of formula I followed our usual procedure of attaching carboxcylic acid 20 to provide 132 then hydroxamic acid 133 is formed by our standard conditions. The trans β-amino acids 134 are available by equilibration of cis amide ester 132 under basic conditions.

Scheme 23

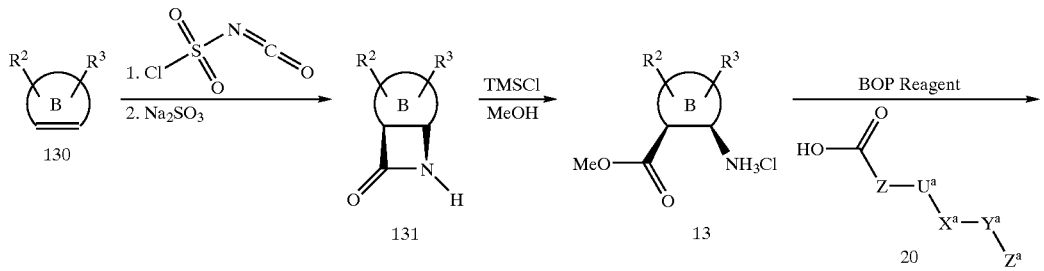

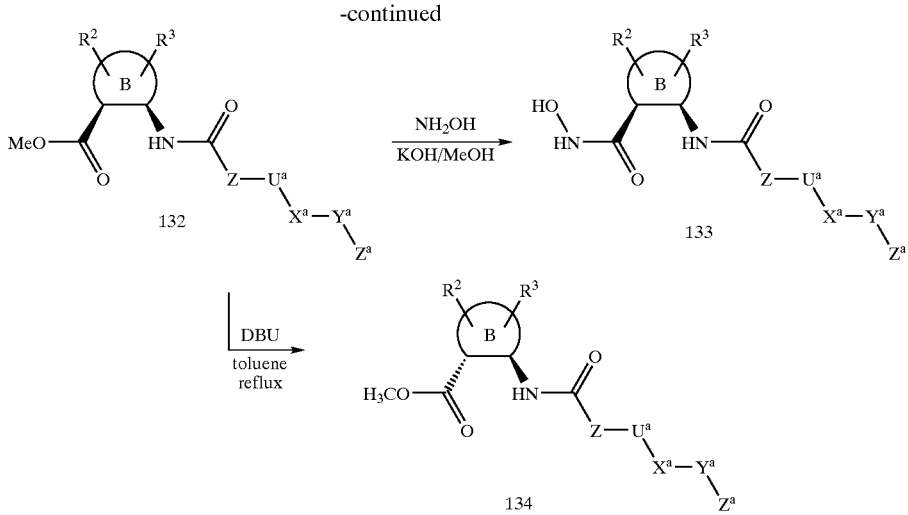

An alternative synthesis of 133 begins with formation of benzyl hydroxamate 136 from trans β-hydroxy carboxylate 135 (Scheme 24). Intramolecular cyclization of 136 under Mitsunobu conditions (Bellettini, J. R.; Miller, M. J. Tetrahedron Letters 1997, 38, 167–168) then affords benzyl protected hydroxy β-lactam 137. Removal of the benzyl group by hydrogenolysis and reduction of the intermediate N-hydroxy β-lactam provides 131, which can be converted to final products as shown in the previous scheme.

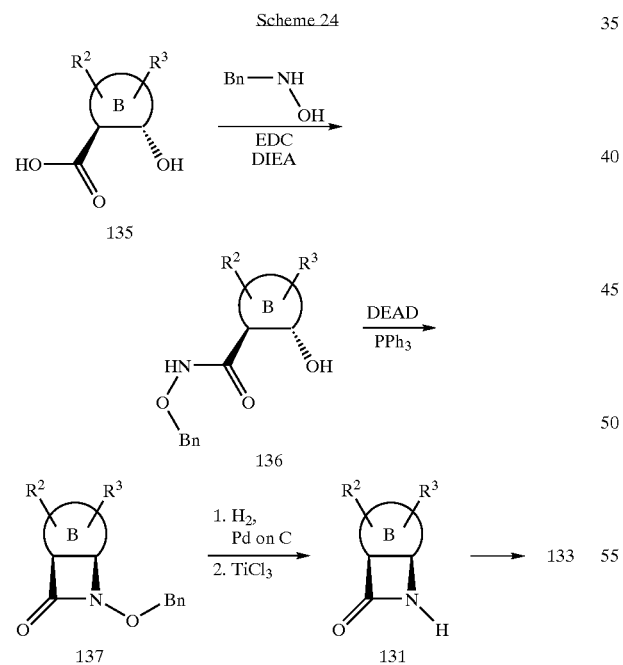

A synthesis of cyclic lactam β-amino acids begins conveniently with ketone 138 (Scheme 25). Oxime 139 is formed with hydroxylamine hydrochloride, sodium bicarbonate in refluxing methanol and is then treated with p-toluenesulfonyl chloride to give Beckmann rearrangement precursor 140. The rearrangement can be driven by a variety of conditions with silica gel/chloroform providing a straightforward mild procedure to form lactam 141. Conversion of 141 to hydroxamate 142 uses conditions outline in previous schemes.

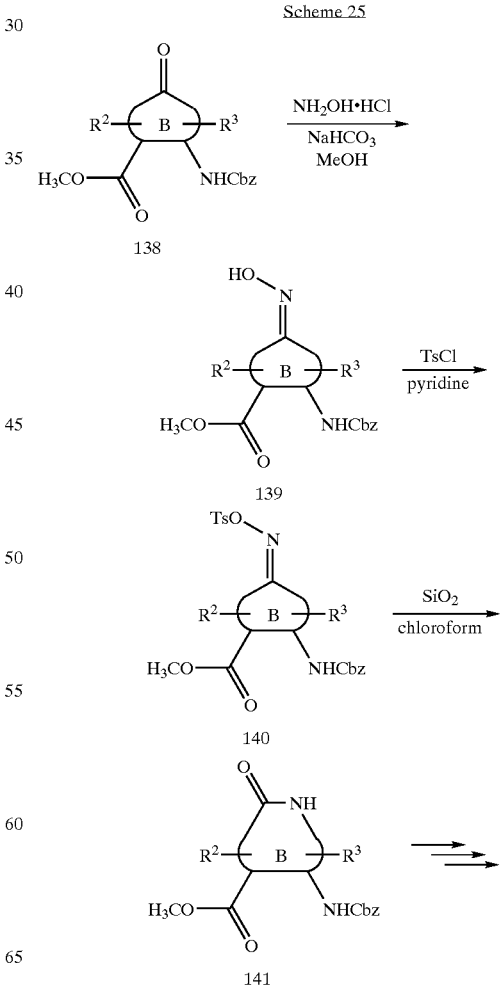

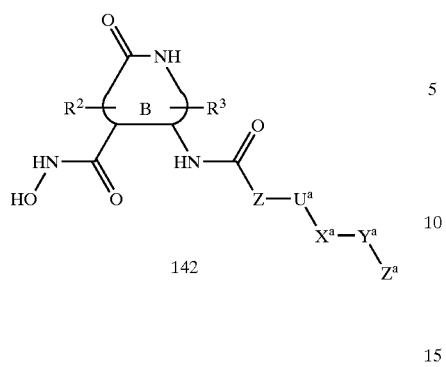

142

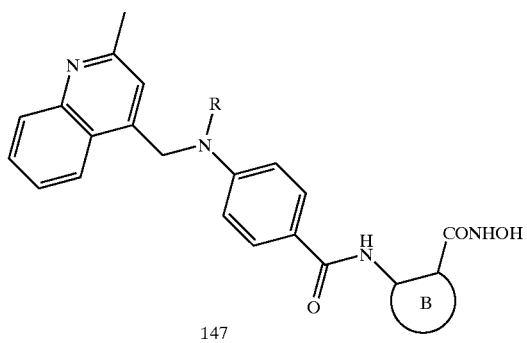

147

R = H, Me

Compounds of formula 147 can be prepared using the protocol described in Scheme 26. Alkylation of methyl 4-aminobenzoate or methyl 4-methylaminobenzoate 143 with 4-chloromethyl-2-methylquinoline using $K_2CO_3$ in DMF at 100 °C produced the secondary or tertiary amine 144. Following saponification, the resulting carboxylic acid 145 was coupled with a cyclic β-aminoacid derivative using a coupling agent such as BOP to give the amide 146. Conversion of the ester in 146 to a hydroxamic acid using hydroxylamine afforded the final product 147.

Compounds of formula 154 can be prepared according to Scheme 27. An aldehyde 148 was treated with hydroxylamine to provide an oxime 149. Cycloaddition of 149 with an olefin 150 using bleach produced the isoxazoline derivative 151. Hydrolysis of the ester followed by coupling with a cyclic β-aminoacid derivative afforded the amide 153. Treatment of 153 with a hydroxylamine solution produced the hydroxamic acid 154.

Scheme 26

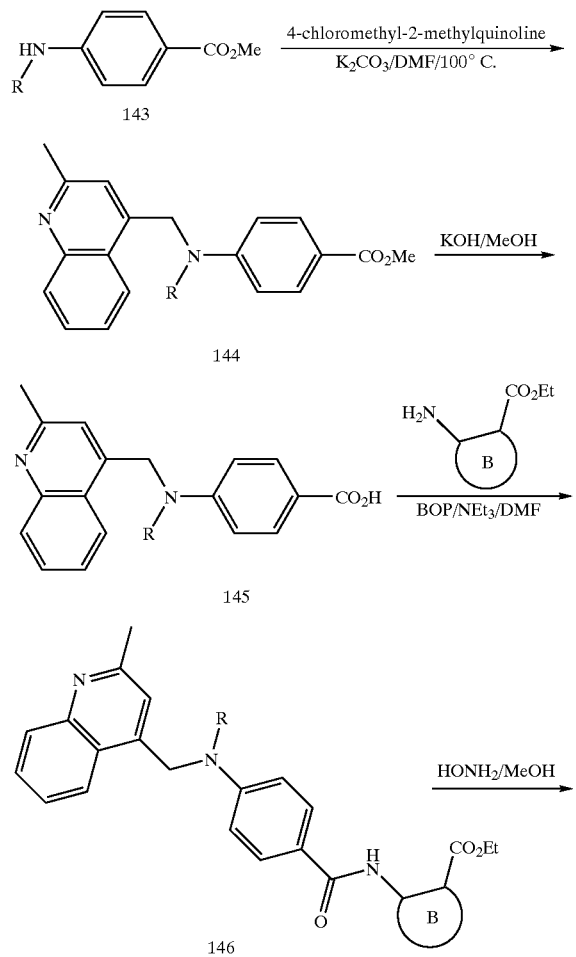

Scheme 27

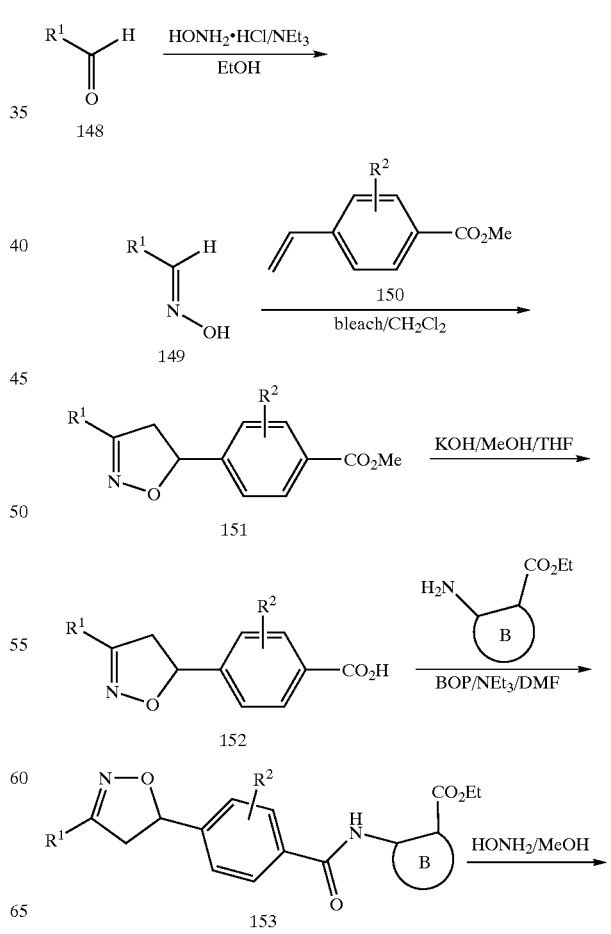

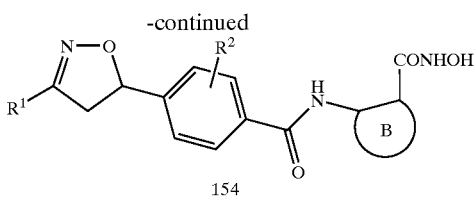

154

R$^1$ = aryl, heteroaryl, alkyl, carbocycle, heterocycle

Compounds of formula 161 can be prepared using the sequence as illustrated in Scheme 28. An aldehyde 155 was treated with hydroxylamine to give an oxime 156. Cycloaddition of 146 with an olefin 157 using bleach produced the isoxazoline derivative 158. Following saponification, the resulting carboxylic acid 159 was condensed with a cyclic β-aminoacid to give the amide 160. Treatment of 160 with a hydroxylamine solution afforded the hydroxamic acid 161.

Scheme 28

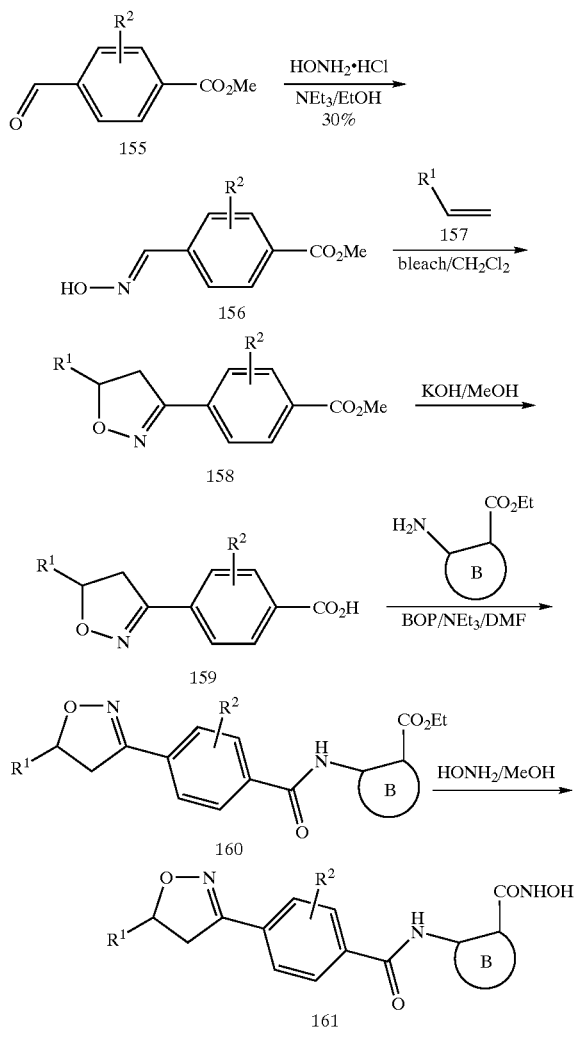

R$^1$ = aryl, heteroaryl, alkyl, carbocycle, heterocycle

One diastereomer of a compound of Formula I may display superior activity compared with the others. Thus, the following stereochemistries are considered to be a part of the present invention.

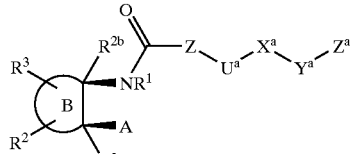

Ia

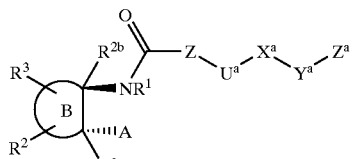

Ib

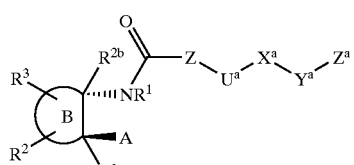

Ic

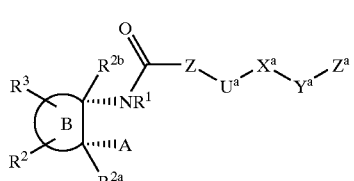

Id

When required, separation of the racemic material can be achieved by HPLC using a chiral column or by a resolution using a resolving agent such as camphonic chloride as in Steven D. Young, et al, *Antimicrobial Agents and Chemotheraphy*, 1995, 2602–2605. A chiral compound of Formula I may also be directly synthesized using a chiral catalyst or a chiral ligand, e.g., Andrew S. Thompson, et al, *Tetr. Lett*. 1995, 36, 8937–8940.

Other features of the invention will become apparent in the course of the following descriptions of exemplary embodiments that are given for illustration of the invention and are not intended to be limiting thereof.

EXAMPLES

Abbreviations used in the Examples are defined as follows: "1×" for once, "2×" for twice, "3×" for thrice, "° C." for degrees Celsius, "eq" for equivalent or equivalents, "g" for gram or grams, "mg" for milligram or milligrams, "mL" for milliliter or milliliters, "$^1$H" for proton, "h" for hour or hours, "M" for molar, "min" for minute or minutes, "MHz" for megahertz, "MS" for mass spectroscopy, "NMR" for nuclear magnetic resonance spectroscopy, "rt" for room temperature, "tlc" for thin layer chromatography, "v/v" for volume to volume ratio. "α", "β", "R" and "S" are stereochemical designations familiar to those skilled in the art.

Example 1

N-{(1R,2S)-2-[(hydroxyamino)carbonyl]cyclopentyl}-2'-(trifluoromethyl)[1,1'-biphenyl]-4-carboxamide (1a) Tetrakis(triphenylphosphine)palladium(0) (168 g, 0.1 eq) was added to a mixture of methyl-4-iodobenzoate (0.384 g, 1.44 mmol), 2-trifluoromethylphenylboronic acid (0.3 g, 1.1 eq), sodium carbonate (2 M, 2 eq), ethanol (1.5 mL) and benzene (1.5 mL) at rt. The mixture was heated to 70° C. for 24 h and cooled to rt. The mixture was diluted with ether (20 mL) and washed with water and brine (10 mL each), dried ($MgSO_4$) and concentrated. Silica gel column chromatography (ethyl acetate-hexane, 5:95) yielded the desired product (364 mg, 90%). MS found: $(M-H)^-=279$.

(1b) The ester (364 mg, 1.3 mmol) from reaction (1a), lithium hydroxide (1 M, 10 eq) and methanol (13 mL) were stirred at 40° C. for 4.5 h. The pH of the mixture was adjusted to pH=3 with 1 N HCl and then extracted with ethyl acetate (2×30 mL), washed with brine (25 mL) dried ($MgSO_4$) and concentrated. Silica gel column chromatography (ethyl acetate-hexane, 1:1) yielded the desired product (247 mg, 71%). MS found: $(M-H)^-=265$.

(1c) BOP reagent (239 mg, 1.2 eq) was added to a mixture of (1S,2R)-2-carbomethoxycyclopentyl amine hydrochloride (81 mg, 0.45 mmol), the carboxylic acid (120 mg, 1 eq) from reaction (1b), N,N-diisopropylethylamine (0.12 mL, 2.5 eq) and N,N-dimethylformamide (2.5 mL) at rt. After 2.5 h at rt saturated aqueous ammonium chloride (25 mL) was added and the mixture extracted with ethyl acetate (2×20 mL). The mixture was washed with water (10 mL), brine (10 mL), dried ($MgSO_4$) and concentrated. Silica gel column chromatography (ethyl acetate-hexane, 1:3) yielded the desired product (147 mg, 83%). MS found: $(M+H)^+=392$.

(1d) Preparation of hydroxylamine/potassium hydroxide solution: A solution of potassium hydroxide (2.81 g, 1.5 eq) in methanol (7 mL) was added to a hot solution of hydroxylamine hydrochloride (2.34 g, 33.7 mmol) in methanol (12 mL). After the mixture was cooled to room temperature, the precipitate was removed by filtration. The filtrate was used fresh and assumed hydroxylamine concentration of 1.76 M.

The above freshly prepared 1.76 M hydroxylamine solution (0.5 mL, 4 eq) was added to the methyl ester (80 mg, 0.20 mmol) from reaction (1c) in methanol (1 mL) and stirred at room temperature for 5 h. The mixture was adjusted to pH 7 with 1 N hydrochloric and diluted with ethyl acetate (10 mL). The organic layer was washed with brine (5 mL), dried ($MgSO_4$) and concentrated. Reverse phase HPLC purification (gradient elution, water/acetonitrile 85-15 to 10-90) provided the hydroxamic acid (50 mg, 63%). MS found: $(M+H)^+=393$.

Example 2

N-{(1R,2S)-2-[(hydroxyamino)carbonyl]cyclopentyl}-4-[2-(trifluoromethyl)phenoxy]benzamide (2a) 4-hydroxybenzoic acid (240 mg, 1.6 mmol), 2-trifluoromethylphenylboronic acid (300 mg, 1 eq), pyridine (0.68 mL, 5 eq), 4A molecular sieves (100 mg), copper (II) acetate (0.32 g, 1 eq) and dichloromethane (15 mL) were stirred under air atmosphere for 4 days. The mixture was filtered through Celite and the bed washed with ethyl acetate-hexane (1:9, 50 mL) and concentrated. Silica gel column chromatography (ethyl acetate-hexane, 1:10) yielded the desired product (49 mg, 10%). MS found: $(M+H)^+=296$.

(2b) Using procedures analogous to those described for reactions (1b)–(1d), the methyl ester (49 mg, 0.162 mmol) from reaction (2a) was converted to the desired hydroxamic acid (2.6 mg, 4% for 3 steps). MS found: $(M+H)^+=409$.

Example 3

N-{(1R,2S)-2-[(hydroxyamino)carbonyl]cyclopentyl}-4-(3-methyl-2-pyridinyl)benzamide (3a) Using procedures analogous to those described for reactions (1a)–(1d), 4-carbomethoxyphenylboronic acid (0.72 g, 2 eq) and 2-bromo-3-methylpyridine (0.34 g, 2.0 mmol) were converted to the desired hydroxamic acid (40 mg, 10% for 4 steps). MS found: $(M+H)^+=340$.

Example 4

N-{(1R,2S)-2-[(hydroxyamino)carbonyl]cyclopentyl}[1,1'-biphenyl]-4-carboxamide (4a) Using procedures analogous to those described for reactions (1c)–(1d), the amine hydrochloride (106 mg, 0.59 mmol) and 4-biphenylcarboxylic acid (117 mg, 1 eq) were converted to the desired hydroxamic acid (46.6 mg, 36% for 2 steps). MS found: $(M+H)^+=325$.

Example 5

N-{(1R,2S)-2-[(hydroxyamino)carbonyl]cyclopentyl}-4-phenoxybenzamide (5a) Using procedures analogous to those described for reactions (1c)–(1d), the amine hydrochloride (111 mg) and 4-phenoxybenzoic acid (132 mg, 1 eq) were converted to the desired hydroxamic acid (24.2 mg, 36% for 2 steps). MS found: $(M+H)^+=341$.

Example 6

4-(benzyloxy)-N-{(1R,2S)-2-[(hydroxyamino)carbonyl]cyclopentyl}benzamide (6a) Using procedures analogous to those described for reactions (1c)–(1d), the amine hydrochloride (101 mg, 0.56 mmol), 4-benzyloxybenzoic acid (129 mg, 1 eq) were converted to the desired hydroxamic acid (19.1 mg, 26% for 2 steps). MS found: $(M+H)^+=355$.

Example 7

N-{(1R,2S)-2-[(hydroxyamino)carbonyl]cyclopentyl}-2'-methoxy[1,1'-biphenyl]-4-carboxamide (7a) Using procedures analogous to those described for reactions (1a)–(1d), 2-methoxyphenylboronic acid (0.163 g, 1.1 eq), methyl 4-iodobenzoate (265 mg, 1.0 mmol) were converted to the desired hydroxamic acid (30 mg, 9% for 4 steps). MS found: $(M+H)^+=355$.

Example 8

N-{(1R,2S)-2-[(hydroxyamino)carbonyl]cyclopentyl}-2'-methyl[1,1'-biphenyl]-4-carboxamide (8a) Using procedures analogous to those described for reactions (1a)–(1d), methyl 4-iodobenzoate (0.100 g, 0.4 mmol) and 2-methylphenylboronic acid (0.066 g, 1.2 eq) were reacted to give the desired hydroxamic acid (9.5 mg, 7% for 4 steps). MS found: $(M+H)^+=339$.

Example 9

N-{(1R,2S)-2-[(hydroxyamino)carbonyl]cyclopentyl}-4-(2-methoxyphenoxy)benzamide (9a) Using procedures analogous to those described for reactions (2a), (1b)–(1d), 4-hydroxybenzoic acid (152 mg, 1.0 mmol) and 2-methoxyphenylboronic acid (304 mg, 2 eq), were reacted to give the desired hydroxamic acid (5.1 mg, 14% for 4 steps). MS found: $(M+H)^+=371$.

Example 10

N-{(1R,2S)-2-[(hydroxyamino)carbonyl] cyclopentyl}-4-(2-methylphenoxy)benzamide (10a) Using procedures analogous to those described for reactions (2a), (1b)–(1d), 4-hydroxybenzoic acid (152 mg, 1.0 mmol) and 2-methylphenylboronic acid (272 mg, 2 eq) were reacted to give the desired hydroxamic acid (23 mg, 7% for 4 steps). MS found: $(M+H)^+=355$.

Example 11

N-{(1R,2S)-2-[(hydroxyamino)carbonyl] cyclopentyl}-4-(3-methylphenoxy)benzamide (11a) Using procedures analogous to those described for reactions (1a)–(1d), methyl 4-iodobenzoate (0.663 g, 0.2.5 mmol) and 3-methylphenylboronic acid (0.408 g, 1.2 eq) were reacted to give the desired hydroxamic acid (91.9 mg, 46% for 4 steps). MS found: $(M+H)^+=339$.

Example 12

4-(5,8-dihydro-4-quinolinyl)-N-{(1R,2S)-2-[(hydroxyamino)carbonyl]cyclopentyl}benzamide (12a) Using procedures analogous to those described for reactions (1a)–(1d), 4-carbomethoxyphenylboronic acid (298 mg, 2 eq) and 4-bromoquinoline were reacted to give the desired hydroxamic acid (25 mg, 9% for 4 steps). MS found: $(M+H)^+=376$.

Example 13

N-{(1R,2S)-2-[(hydroxyamino)carbonyl] cyclopentyl}-3',5'-dimethyl[1,1'-biphenyl]-4-carboxamide (13a) Using procedures analogous to those described for reactions (1a)–(1d), 4-carbomethoxyphenylboronic acid (0.72 g, 2 eq) and 4-bromo-meta-xylene (0.37 g, 2.0 mmol) were reacted to give the desired hydroxamic acid (22 mg, 14% for 4 steps). MS found: $(M+H)^+=353$.

Example 14

N-{(1R,2S)-2-[(hydroxyamino)carbonyl] cyclopentyl}-6-(2-methylphenyl)nicotinamide (14a) Using procedures analogous to those described for reactions (1a)–(1d), methyl 6-(3-methylphenyl)nicotinate (0.3 g, 1.4 mmol) and 2-methylphenylboronic acid (0.21 g, 1.1 eq) were reacted to give the desired product (18 mg, 17% for 4 steps). MS found: $(M+H)^+=340$.

Example 15

N-{(1R,2S)-2-[(hydroxyamino)carbonyl] cyclopentyl}-6-(2-methoxyphenyl)nicotinamide (15a) Using procedures analogous to those described for reactions (1a)–(1d), methyl 6-(3-methylphenyl)nicotinate (378 mg, 1.75 mmol) and 2-methoxyphenylboronic acid (292 mg, 1.1 eq) were reacted to give the desired product (10 mg, 6% for 4 steps). MS found: $(M+H)^+=356$.

Example 16

(3S,4S)-N-hydroxy-1-isopropyl-4-({4-[(2-methyl-4-quinolinyl)methoxy]benzoyl}amino)-3-pyrrolidinecarboxamide (16a) A solution of benzyl methyl maleate (15.0 g, 68.2 mmol) in benzene (1 L) at reflux was treated with a mixture of glycine (8.3 g, 2 eq) and para-formaldehyde (8.3 g, 4 eq) portionwise over 1 h. The mixture was heated at reflux for 2 h further. The mixture was filtered through a plug of silica and concentrated providing the desired amine (19.3 g, 100%). MS found: $(M+H)^+=264$.

(16b) The amine from reaction (16a) (7.3 g, 27.5 mmol) in N,N-dimethylformamide was treated with di-t-butyl dicarbonate (9.0 g, 1.5 eq), triethylamine (5.8 mL, 1.5 eq), and hydroxylamine hydrochloride (0.2 g, 0.1 eq) and stirred for 17 h. The mixture was partitioned between water and ether (100 mL each) and the aqueous layer further extracted with ether (100 mL). The combined ether layers were washed with water and brine (100 mL each) dried ($MgSO_4$) and concentrated. Silica gel column chromatography (ethyl acetate-hexane, 3:2) yielded the desired ester (6.39 g, 64%). MS found: (M–Bu)=308.

(16c) The ester from reaction (16b) (8.3 g, 22.9 mmol) in methanol (100 mL) was treated with 10% palladium hydroxide on carbon (2.28 g, 0.1 eq) and stirred under a balloon of hydrogen for 3.5 h. The mixture was purged with nitrogen, filtered through a plug of Celite®, washed with excess methanol, and the filtrate concentrated providing the desired acid (6.0 g, 96%). MS found: $(M+Na)^+=296$.

(16d) The acid from reaction (16c) (2.73 g, 0.01 mmol) in benzene (100 mL) was treated with triethylamine (2.1 mL, 1.5 eq) and diphenylphosphorylazide (2.58 mL, 1.2 eq) and stirred at room temperature for 1 h. Benzyl alcohol (1.03 mL, 1.0 eq) was added and the mixture heated to reflux for 1.5 h. The mixture was cooled and partitioned between ethyl acetate and saturated aqueous $NaHCO_3$ (100 mL each). The organic layer was washed further with $NaHCO_3$ and brine (100 mL each), dried ($MgSO_4$), and concentrated. Silica gel column chromatography (ethyl acetate-hexane, 3:2) yielded the desired carbamate (2.86 g, 76%). MS found: $(M+H)^+=379$.

(16e) The carbamate from reaction (16d) (2.86 g, 7.6 mmol) in methanol (38 mL) was treated with 10% palladium hydroxide on carbon (0.53 g, 0.1 eq) and stirred under a balloon of hydrogen for 1.5 h. The mixture was purged with nitrogen, filtered through a plug of Celite®, washing with excess methanol, and the filtrate concentrated providing the desired amine (1.85 g, 100%). MS found: (M–Bu)=189.

(16f) The amine from reaction (16e) (11 g, 45 mmol) in DMF (225 mL) was treated with 4-[(2-methyl-4-quinolinyl)methoxy]benzoic acid (19.8 g, 1.5 eq), BOP reagent (32.1 g, 1.6 eq) and N,N-diisopropylethylamine (20 mL, 2.5 eq) and stirred for 5 h. The mixture was partitioned between saturated aqueous $NH_4Cl$ and ethyl acetate (500 mL each). The aqueous layer was further extracted with ethyl acetate (3×500 mL). The combined layers were dried ($MgSO_4$) and concentrated. Silica gel column chromatography (ethyl acetate) yielded the desired racemic amide (13 g). Chiral HPLC separation provided the (3S,4S)-enantiomer (5.5 g, 23%, >98% ee), MS found: $(M+H)^+=520$, and the (3R,4R)-enantiomer (4.5 g, 19%). MS found: $(M+H)^+=520$.

(16g) The (3S,4S)-enantiomer from reaction (16f) (2.11 g, 4.06 mmol) in dichloromethane/trifluoracetic acid (1:1, 16 mL) was stirred for 1 h and concentrated. The residue was dissolved in water and lyophilized to provide the desired amine as the bis(trifluoroacetate) salt (2.6 g, 100%). MS found: (M+H)$^+$=420.

(16h) The amine from reaction (16g) (699 mg, 1.08 mmol) in dichloromethane (10 mL) was treated with N,N-diisopropylethylamine (0.77 mL, 4 eq), acetone (0.16 mL, 2 eq) and stirred at rt for 10 min. Na(OAc)$_3$BH (0.46 g, 2 eq) was then added and the mixture stirred for 1 h. The mixture was partitioned between ethyl acetate and saturated aqueous NaHCO$_3$ and then further extracted with ethyl acetate (4×). The organic layers were dried (MgSO$_4$) and concentrated. Silica gel column chromatography (methanol/dichloromethane, 1:4) yielded the desired amine (0.411 g, 89%). MS Found: (M+H)$^+$=462.

(16i) Preparation of hydroxylamine/potassium hydroxide solution: A solution of potassium hydroxide (2.81 g, 1.5 eq) in methanol (7 mL) was added to a hot solution of hydroxylamine hydrochloride (2.34 g, 33.7 mmol) in methanol (12 mL). After the mixture was cooled to room temperature, the precipitate was removed by filtration. The filtrate was used fresh and assumed hydroxylamine concentration of 1.76 M.

The above freshly prepared 1.76 M hydroxylamine solution (7.6 mL, 15 eq) was added to the methyl ester (400 mg, 0.88 mmol) from reaction (16h) in methanol (9 mL) and stirred at room temperature for 0.5 h. The mixture was adjusted to pH 7 with 1 N hydrochloric acid and diluted with brine (50 mL) and extracted with dichloromethane (5×60 mL). The organic layers were dried (MgSO$_4$) and concentrated. Reverse phase HPLC purification (gradient elution, water/acetonitrile 85-15 to 60-40, 0.1% TFA) provided the hydroxamic acid (207 mg, 34%). MS found: (M+H)$^+$=463.

Example 17

(3S,4S)-1-(2,2-dimethylpropanoyl)-N-hydroxy-4-({4-[(2-methyl-4-quinolinyl)methoxy]benzoyl}amino)-3-pyrrolidinecarboxamide (17a) The amine from reaction (16g) (270 mg, 0.42 mmol) in dichloromethane (4 mL) was treated with triethylamine (0.57 mL, 10 eq), trimethylacetyl chloride (0.1 mL, 2 eq) and stirred at rt for 1 h. The mixture was partitioned between ethyl acetate and saturated aqueous NaHCO$_3$ and then further extracted with ethyl acetate (4×). The organic layers were dried (MgSO$_4$) and concentrated. Silica gel column chromatography (methanol/dichloromethane, 1:4) yielded the desired amide (189 mg, 90%). MS Found: (M+H)$^+$=504.

(17b) Using procedures analogous to reaction (16i) the methyl ester from reaction (17a) (0.3 g, 6.0 mmol) was converted to the desired hydroxamic acid (107 mg, 30%). MS Found: (M+H)$^+$=505.

Example 18

(3S, 4S)-N-hydroxy-4-({4-[(2-methyl-4-quinolinyl)methoxy]benzoyl}amino)-1-(methylsulfonyl)-3-pyrrolidinecarboxamide (18a) The amine from reaction (16g) (206 mg, 0.33 mmol) in dichloromethane (3.3 mL) was treated with triethylamine (0.5 mL, 10 eq), methanesulfonyl chloride (0.05 mL, 2 eq) and stirred at rt for 1 h. The mixture was partitioned between ethyl acetate and saturated aqueous NaHCO$_3$ and then further extracted with ethyl acetate (4×). The organic layers were dried (MgSO$_4$) and concentrated. Silica gel column chromatography (methanol/dichloromethane, 1:4) yielded the desired amide (128 mg, 57%). MS Found: (M)$^+$=498.

(18b) Using procedures analogous to reaction (16i), the methyl ester from reaction (18a) (224 mg, 4.5 mmol) was converted to the desired hydroxamic acid (104 mg, 37%). MS Found: (M+H)$^+$=499

Example 19

(3S,4S)-N-hydroxy-1-methyl-4-({4-[(2-methyl-4-quinolinyl)methoxy]benzoyl}amino)-3-pyrrolidinecarboxamide (19a) Using procedures analogous to those described for example (16h-i), the amine from reaction (16g) (0.324 g, 0.5 mmol) and formaldehyde (37%, 0.06 mL, 1.5 eq) were converted to the desired hydroxamic acid (155 mg, 25% 2 steps). MS Found: (M+H)$^+$=435.

Example 20 tert-butyl (3S,4S)-3-[(hydroxyamino)carbonyl]-4-({4-[(2-methyl-4-quinolinyl)methoxy]benzoyl}amino)-1-pyrrolidinecarboxylate (20a) 1,3-Pyrrolidinedicarboxylic acid, 4-oxo-1-(1,1-dimethylethyl) 3-methyl ester (2.45 g, 10.1 mmol) in benzene (50 mL) was treated with (R)-alpha-methylbenzyl amine (1.7 mL, 1.3 eq) and Yttrbium triflate (0.12 g, 0.02 eq) and heated to reflux for 3 h. Concentration, followed by silica gel column chromatography (ethyl acetate/hexane, 1:4) yielded the desired amine (2.49 g, 67%). MS Found: (M+H)$^+$=347.

(20b) The product from reaction (20a) (1.0 g, 2.9 mmol) in acetonitrile/acetic acid (1:1, 5.8 mL) was treated with NaBH$_3$CN and stirred for 0.5 h. The mixture was quenched with NaHCO$_3$ (aq) until pH 7 and extracted with ethyl acetate (3×100 mL). The combined layers were dried (MgSO$_4$) and concentrated. Silica gel column chromatography (ethyl acetate/hexane, 3:1) yielded the (3S, 4S) amine (59.4 mg, 6%), MS Found: (M)$^+$=349, the (3S,4R) amine (415 mg, 41% mmol) MS Found: (M)$^+$=349 and the (3R,4S) amine (246 mg, 24%) MS Found: (M)$^+$=349.

(20c) The (3S,4S) amine from reaction (20b) (59.4 mg, 0.17 mmol) in methanol/water/acetic acid (10:1:0.25, 1 mL) was treated with 10% palladium hydroxide on carbon (12 mg, 0.1 eq) and stirred under a balloon of hydrogen for 1.5 h. The mixture was purged with nitrogen, filtered through a plug of Celite®, washing with excess methanol and the filtrate concentrated providing the crude amine (37.9 mg) that was used without purification. In an analogous reaction to (1f) the crude amine was converted to the desired amide (64.5 mg, 72% two steps). MS Found: (M+H)$^+$=520.

(20d) Using procedures analogous to reaction (16i), the methyl ester from reaction (20c) (60 mg, 0.12 mmol) was converted to the desired hydroxamic acid (42.4 mg, 58%). MS Found: (M+H)$^+$=521.

Example 21

(3S,4S)-N-hydroxy-4-({4-[(2-methyl-4-quinolinyl)methoxy]benzoyl}amino)-3-pyrrolidinecarboxamide (21a) In an analogous procedure to (16g) the product from reaction (20d) (12 mg, 0.02 mmol) was converted to the desired amine (8.7 mg, 72%). MS Found: (M+H)$^+$=421.

Example 22 tert-butyl 4-[cis-3-[(hydroxyamino)carbonyl]-4-({4-[(2-methyl-4-quinolinyl)methoxy]benzoyl}amino)pyrrolidinyl]-1-piperidinecarboxylate (22a) In an analogous procedure to (16g) the racemic product from reaction (16h–16i) (0.25 g, 0.4 mmol) and Boc-4-piperidone (1.15 mg, 1.5 eq) was converted to the desired hydroxamic acid (49.4 mg, 18% 2 steps). MS Found: (M+H)$^+$=604.

Example 23 cis-N-hydroxy-4-({4-[(2-methyl-4-quinolinyl)methoxy]benzoyl}amino)-1-(4-piperidinyl)-3-pyrrolidinecarboxamide (23a) In an analogous procedure to (16g) the product from reaction (22a) (25.2 mg, 0.03 mmol) was converted to the desired amine (21.4 mg, 82%). MS Found: (M+H)$^+$=504.

Example 24 cis-1-[3-[(1,1-dimethylethoxy)carbonyl]pyrollidinyl]-N-hydroxy-3-[[[4-[(2-methyl-4-quinolinyl)methoxy]phenyl]carbonyl]amino]-4-pyrollidinecarboxamide bis(trifluoroacetate)

(24a) In an analogous procedure to (1g) the racemic product from reaction (16h–16i) (0.25 g, 0.4 mmol) and Boc-3-pyrollidinone (107 mg, 1.5 eq) was converted to the desired hydroxamic acid (73.1 mg, 26% 2 steps). MS Found: (M+H)$^+$=590.

Example 25 cis-N-hydroxy-1-[3-pyrollidinyl]-3-[[[4-[(2-methyl-4-quinolinyl)methoxy]phenyl]carbonyl]amino]-4-pyrollidinecarboxamide tris(trifluoroacetate)

(25a) In an analogous procedure to (16g), the product from reaction (24a) (31 mg, 0.04 mmol) was converted to the title compound (27.0 mg, 86%). MS Found: (M+H)$^+$=490.

Example 26 tert-butyl (3R,4R)-3-[(hydroxyamino)carbonyl]-4-({4-[(2-methyl-4-quinolinyl)methoxy]benzoyl}amino)-1-pyrrolidinecarboxylate (26a) In an analogous procedure to (16h), the (3R,4R)-enantiomer from reaction (16f) (0.2 g, 0.4 mmol) was converted to the desired hydroxamic acid (18.3 mg, 7%). MS Found: (M+H)$^+$=521.

Example 27 tert-butyl (3S,4R)-3-[(hydroxyamino)carbonyl]-4-({4-[(2-methyl-4-quinolinyl)methoxy]benzoyl}amino)-1-pyrrolidinecarboxylate (27a) In an analogous procedure to (20c–d), the (3S,4R)-amine from reaction (20b) (0.4 g, 1.2 mmol) was converted to the hydroxamic acid (53.6 mg, 20%, 2 steps). MS Found: (M+H)$^+$=521.

Example 28

(3S,4R)-N-hydroxy-4-({4-[(2-methyl-4-quinolinyl)methoxy]benzoyl}amino)-3-pyrrolidinecarboxamide (28a) In an analogous procedure to (16g), the product from reaction (27a) (11 mg, 0.02 mmol) was converted to the desired amine (5 mg, 45%). MS Found: (M+H)$^+$=421.

Example 29 tert-butyl (3R,4S)-3-[(hydroxyamino)carbonyl]-4-({4-[(2-methyl-4-quinolinyl)methoxy]benzoyl}amino)-1-pyrrolidinecarboxylate (29a) In an analogous procedure to (20c–d), the (3R,4S)-amine from reaction (20b) (0.2 g, 0.6 mmol) was converted to the hydroxamic acid (132 mg, 59%, 2 steps). MS Found: (M+H)$^+$=521.

Example 30

(3R,4S)-N-hydroxy-4-({4-[(2-methyl-4-quinolinyl)methoxy]benzoyl}amino)-3-pyrrolidinecarboxamide (30a) In an analogous procedure to (16g), the product from reaction (29a) (10 mg, 0.02 mmol) was converted to the desired amine (9.8 mg, 98%). MS Found: (M+H)$^+$=421.

Example 31

N-{(1R,2S)-2-[(hydroxyamino)carbonyl]cyclopentyl}-4-(4-pyridinyl)benzamide trifluoroacetate (31a) Tetrakis(triphenylphosphine)palladium(0) (0.64 g, 0.1 eq) was added to a mixture of 4-methoxycarbonylphenylboronic acid (2.0 g, 11.1 mmol), 4-bromopyridine hydrochloride (1.03 g, 1 eq), sodium carbonate (2 M, 2 eq), methanol (10 mL) and benzene (10 mL) at rt. The mixture was heated to 70° C. for 2 h and cooled to rt. The mixture was diluted with ethyl acetate and saturated aqueous sodium bicarbonate (100 mL ea).

The organic layers were washed with water and brine (100 mL each), dried (MgSO$_4$), and concentrated. Silica gel column chromatography (ethyl acetate-hexane, 1:1) yielded the desired product (1.0 g, 85%). MS found: (M+H)$^+$=214.

(31b) The ester (1.0 mg, 4.7 mmol) from reaction (31a), lithium hydroxide (1 M, 10 eq) and methanol (50 mL) were stirred at 40° C. for 2 h. The pH of the mixture was adjusted to pH=7 with 1 N HCl and then extracted with ethyl acetate (2×100 mL), dried (MgSO$_4$), and concentrated, yielding the desired acid (400 mg, 43%). MS found: (M+H)$^+$=200.

(31c) BOP reagent (266 mg, 1.2 eq) was added to a mixture of (1R,2S)-2-carbomethoxycyclopentyl amine hydrochloride (90 mg, 0.50 mmol), the carboxylic acid (100 mg, 1 eq) from reaction (31b), N,N-diisopropylethylamine (0.22 mL, 2.5 eq) and N,N-dimethylformamide (1 mL) at rt. After 2.5 h at rt, saturated aqueous ammonium chloride (25 mL) was added and the mixture extracted with ethyl acetate (2×20 mL). The mixture was washed with water (10 mL), brine (10 mL), dried (MgSO$_4$), and concentrated. Silica gel column chromatography (ethyl acetate) yielded the desired product (113 mg, 69%). MS found: (M+H)$^+$=325.

(31d) Freshly prepared 1.76 M hydroxylamine solution (8 mL, 20 eq) was added to the methyl ester (233 mg, 0.7 mmol) from reaction (31c) in methanol (1 mL) and stirred at room temperature for 0.5 h. The mixture was adjusted to pH 7 with 1 N hydrochloric acid and diluted with ethyl acetate (10 mL). The organic layer was washed with brine (5 mL), dried (MgSO$_4$), and concentrated. Reverse phase HPLC purification (gradient elution, water/acetonitrile 85-15 to 10-90) provided the desired hydroxamic acid (83 mg, 35%). MS found: (M+H)$^+$=326.

Example 32

(3S,4S)-1-(1,1-dimethyl-2-propynyl)-N-hydroxy-4-({4-[(2-methyl-4-quinolinyl)methoxy]benzoyl}amino)-3-pyrrolidinecarboxamide bis(trifluoroacetate)

(32a) The amine from reaction (16g) (224 mg, 0.34 mmol) in dichloromethane (3 mL) was treated with triethylamine (0.24 mL, 5 eq), 3,3-dimethylpropargyl chloride (0.05 mL, 1.2 eq), water (1.5 mL), catalytic copper(I) chloride and catalytic copper turnings and stirred at rt for 1 h. The mixture was diluted with dichloromethane and washed with water (50 mL each), dried (MgSO$_4$) and concentrated. Silica gel column chromatography (methanol/dichloromethane, 1:4) yielded the desired amine (150 mg, 89%). MS Found: (M+H)$^+$=486.

(32b) In an analogous procedure to (16i) the ester from reaction (32a) (150 mg, 0.3 mmol) was converted to the desired hydroxamic acid (8.4 mg, 6%). MS Found: (M+H)$^+$=487.

Example 33

(3S,4S)-N-hydroxy-4-({4-[(2-methyl-4-quinolinyl)methoxy]benzoyl}amino)-1-(2-propynyl)-3-pyrrolidinecarboxamide bis(trifluoroacetate)

(33a) The amine from reaction (16g) (204 mg, 0.32 mmol) in dichloromethane (3 mL) was treated with triethylamine (0.18 mL, 4 eq), propargyl bromide (80% wt. in toluene, 0.04 mL, 1.1 eq) and stirred for 4 h. The mixture was partitioned between ethyl acetate and water (25 mL, ea) and the organic layer dried (MgSO$_4$), filtered and concentrated. Silica gel column chromatography (methanol/dichloromethane, 1:4) yielded the desired amine (38 mg, 26%). MS Found: (M+H)$^+$=458.

(33b) In an analogous procedure to (16i), the ester from reaction (33a) (38 mg, 0.08 mmol) was converted to the desired hydroxamic acid (5 mg, 13%). MS Found: (M+H)$^+$=459.

Example 34

(3S,4S)-1-allyl-N-hydroxy-4-({4-[(2-methyl-4-quinolinyl)methoxy]benzoyl}amino)-3-pyrrolidinecarboxamide bis(trifluoroacetate)

(34a) Using analogous procedures to (33a–b), the amine from reaction (16g) (250 mg, 0.39 mmol) and allyl bromide (2 eq) was converted to the desired amine and then to the desired hydroxamate (92 mg, 47% 2 steps). MS Found: (M+H)$^+$=461.

Example 35

(3S,4S)-N-hydroxy-4-({4-[(2-methyl-4-quinolinyl)methoxy]benzoyl}amino)-1-propyl-3-pyrrolidinecarboxamide bis(trifluoroacetate)

(35a) Using analogous procedures to (16h–i), the amine from reaction (16g) (250 mg, 0.39 mmol) and propanal (2 eq) was converted to the desired amine and then to the desired hydroxamic acid (38 mg, 22% 2 steps). MS Found: (M+H)$^+$=463.

Example 36

(3S,4S)-N-hydroxy-1-(2-methyl-2-propenyl)-4-({4-[(2-methyl-4-quinolinyl)methoxy]benzoyl}amino)-3-pyrrolidinecarboxamide bis(trifluoroacetate)

(36a) Using analogous procedures to (33a), the amine from reaction (16g) (224 mg, 0.35 mmol) and 1-bromo-2-methyl propene (1.1 eq) was converted to the desired ester (110 mg, 67%). MS Found: (M+H)$^+$=474.

(36b) Preparation of hydroxylamine/sodium methoxide solution: hydroxylamine hydrochloride (2.4 g, 34.5 mmol) and MeOH (9 mL) were heated to 55° C. Sodium methoxide (25% wt in MeOH, 11.85 mL, 1.5 eq) was added, the mixture stirred at 55° C. for 5 minutes and cooled to room temperature then 0° C. Filtration afforded a clear solution assumed to be ca. 1.64 M. The solution is prepared and used fresh.

A solution of 1.64 M hydroxylamine solution (3 mL, 20 eq) was added to the amine from reaction (36a) (110 mg, 0.45 mmol) in MeOH (3 mL) then stirred for 1 h. The mixture was adjusted to pH 7 with 1 N hydrochloric acid (3 mL). Reverse phase HPLC purification (gradient elution, water/acetonitrile 85-15 to 60-40, 0.1% TFA) provided the hydroxamic acid (67 mg, 25%, 2 steps). MS Found: (M+H)$^+$=475.

Example 37

(3S,4S)-1-(1,1-dimethyl-2-propenyl)-N-hydroxy-4-({4-[(2-methyl-4-quinolinyl)methoxy]benzoyl}amino)-3-pyrrolidinecarboxamide bis(trifluoroacetate)

(37a) The amine from reaction (32a) (268 mg, 0.55 mmol) was treated with 5% Pd/BaSO$_4$ (0.1 eq) in methanol (5.5 mL) and stirred under a balloon of hydrogen. The catalyst was removed by filtration and the mixture concentrated. Silica gel column chromatography (methanol/dichloromethane, 1:4) yielded the desired olefin (150 mg, 56%) MS Found: (M+H)$^+$=488.

(37b) In an analogous procedure to (16i) the ester from reaction (37a) (106 mg, 0.2 mmol) was converted to the desired hydroxamic acid (50 mg, 32%). MS Found: (M+H)$^+$=489.

Example 38

(3S,4S)-N-hydroxy-4-({4-[(2-methyl-4-quinolinyl)methoxy]benzoyl}amino)-1-tert-pentyl-3-pyrrolidinecarboxamide bis(trifluoroacetate)

(38a) The amine from reaction (37a) (61 mg, 0.13 mmol) was treated with 5% Rh/C (0.1 eq) in methanol (1.3 mL) and stirred under a balloon of hydrogen. The catalyst was removed by filtration and the mixture concentrated. Silica gel column chromatography (methanol/dichloromethane, 1:4) yielded the desired amine (37 mg, 60%) MS Found: (M+H)$^+$=490.

(38b) In an analogous procedure to (16i), the ester from reaction (38a) (37 mg, 0.08 mmol) was converted to the desired hydroxamic acid (14 mg, 25%). MS Found: (M+H)$^+$=491.

Example 39

(3S,4S)-N-hydroxy-1-isopentyl-4-({4-[(2-methyl-4-quinolinyl)methoxy]benzoyl}amino)-3-pyrrolidinecarboxamide bis(trifluoroacetate)

(39a) Using analogous procedures to (16h and 36b), the amine from reaction (16g) (102 mg, 0.16 mmol) and isovaleraldehyde (3 eq) were converted to the desired amine and then to the desired hydroxamic acid (65 mg, 58% 2 steps). MS Found: (M+H)$^+$=491.

Example 40

(3S,4S)-N-hydroxy-4-({4-[(2-methyl-4-quinolinyl)methoxy]benzoyl}amino)-1-neopentyl-3-pyrrolidinecarboxamide bis(trifluoroacetate)

(40a) Using analogous procedures to (16h and 36b), the amine from reaction (16g) (60 mg, 0.1 mmol) and pival-

Example 41

(3S,4S)-1-butyl-N-hydroxy-4-({4-[(2-methyl-4-quinolinyl)methoxy]benzoyl}amino)-3-pyrrolidinecarboxamide bis(trifluoroacetate)

(41a) Using analogous procedures to (16h and 36b), the amine from reaction (16g) (120 mg, 0.19 mmol) and butyraldehyde (2 eq) were converted to the desired amine and then to the desired hydroxamic acid (20 mg, 15% 2 steps). MS Found: (M+H)$^+$=477.

Example 42

(3S,4S)-1-(3-butenyl)-N-hydroxy-4-({4-[(2-methyl-4-quinolinyl)methoxy]benzoyl}amino)-3-pyrrolidinecarboxamide bis(trifluoroacetate)

(42a) Using analogous procedures to (33a and 36b), the amine from reaction (16g) (216 mg, 0.33 mmol) and 4-bromo-1-butene (2 eq) were converted to the desired amine and then to the desired hydroxamic acid (68 mg, 30% 2 steps). MS Found: (M+H)$^+$=475.

Example 43

(3S,4S)-1-(2-butynyl)-N-hydroxy-4-({4-[(2-methyl-4-quinolinyl)methoxy]benzoyl}amino)-3-pyrrolidinecarboxamide bis(trifluoroacetate)

(43a) Using analogous procedures to (33a and 36b), the amine from reaction (16g) (140 mg, 0.22 mmol) and 1-bromo-2-butyne (1.2 eq) were converted to the desired amine and then to the desired hydroxamic acid (50 mg, 32% 2 steps). MS Found: (M+H)$^+$=473.

Example 44

(3S,4S)-1-(2-furylmethyl)-N-hydroxy-4-({4-[(2-methyl-4-quinolinyl)methoxy]benzoyl}amino)-3-pyrrolidinecarboxamide bis(trifluoroacetate)

(44a) Using analogous procedures to (16h and 36b), the amine from reaction (16g) (202 mg, 0.48 mmol) and furfural (1.5 eq) were converted to the desired amine and then to the desired hydroxamic acid (110 mg, 32% 2 steps). MS Found: (M+H)$^+$=501.

Example 45

(3S,4S)-N-hydroxy-1-[(5-methyl-2-furyl)methyl]-4-({4-[(2-methyl-4-quinolinyl)methoxy]benzoyl}amino)-3-pyrrolidinecarboxamide bis(trifluoroacetate)

(45a) Using analogous procedures to (16h and 36b), the amine from reaction (16g) (223 mg, 0.53 mmol) and 5-methyl-furfural (1.5 eq) were converted to the desired amine and then to the desired hydroxamic acid (131 mg, 34% 2 steps). MS Found: (M+H)$^+$=515.

Example 46

(3R,4S)-N-hydroxy-4-({4-[(2-methyl-4-quinolinyl)methoxy]benzoyl}amino)tetrahydro-3-furancarboxamide trifluoroacetate (46a) Sodium hydride (60% dispersion in mineral oil) (5.28 g, 1.1 eq) in ether (120 mL) was treated with methyl glycolate (10.8 g, 120 mmol) dropwise, slowly. The mixture was stirred for 30 min and cooled to 0° C. Methyl acrylate (12.39 g, 1.2 eq) was added dropwise to the 0° C. solution. The mixture was stirred for 15 min, warmed to room temperature and stirred for 1 h. The reaction was cooled to 0° C. and quenched by addition of 5% aqueous H$_2$SO$_4$ (200 mL). The layers were separated and the aqueous layer extracted with ether (2×250 mL). The combined ether layers were washed with brine (150 mL), dried with MgSO$_4$, filtered and concentrated. Flash chromatography (ethyl acetate/hexanes, 75:25) provided the desired keto-ester (9.9 g, 57%).

(46b) The keto-ester (3.3 g, 23.0 mmol) from reaction (46a) in benzene (100 mL) was treated with (R)-alpha-methylbenzyl amine (3.0 mL, 1.02 eq) and yttrbium(III) triflate (0.29 g, 0.02 eq) and heated to reflux using Dean-Stark conditions for 3 h, then treated with more (R)-alpha-methylbenzyl amine (0.5 mL) and heated 1 h further. The solution was cooled to room temperature and washed with water (50 mL), dried with MgSO$_4$, filtered and concentrated. Flash chromatography (ethyl acetate/hexanes, 40:60) provided the desired enamine (2.7 g, 48%). MS found: (M+H)$^+$=248.

(46c) The enamine (3.43 g, 13.9 mmol) from reaction (46b) in acetic acid/dichloromethane/acetonitrile (1:1:1, 42 mL) was treated with NaBH(OAc)$_3$ and stirred for 5 h. The reaction was cooled to 0° C. and neutralized with saturated aqueous NaHCO$_3$ and extracted with dichloromethane (3×100 mL), dried (MgSO$_4$), filtered and concentrated. Flash chromatography (ethyl acetate/hexanes, 30:70) provided the desired amine (1.01 g, 29%) as a 3:1 mixture of diastereomers. MS found: (M+H)$^+$=250.

(46d) A mixture of the amine (838 mg, 3.38 mmol) from reaction (46c), 20% palladium hydroxide on carbon (240 mg, 0.1 eq) in methanol was shaken on a Parr apparatus under 50 psi of hydrogen for 2 h. The mixture was filtered and concentrated to provide the amine (495 mg, 100%). MS found: (M+H)$^+$=146.

(46e) A mixture of the amine (274 mg, 1.89 mmol) from reaction (46d) in DMF (10 mL) was treated with 4-[(2-methyl-4-quinolinyl)methoxy]benzoic acid (691 mg, 1.25 eq), BOP reagent (1.23 g, 1.5 eq), N,N-diisopropylethylamine (1.0 mL, 3.0 eq) and stirred for 5 h. The mixture was partitioned between saturated aqueous NH4Cl and ethyl acetate (25 mL each). The aqueous layer was further extracted with ethyl acetate (3×50 mL). The combined layers were dried (MgSO$_4$) and concentrated. Silica gel column chromatography (gradient elution: ethyl acetate to methanol/ethyl acetate 1:10) yielded the desired amide (600 mg, 76%). MS found (M+H)$^+$=421. Analytical chiral HPLC (Chiracel OD column, 1:1 hexane/ethanol, 0.75 mL/min, 254 nm) revealed a 77:23 mixture of enantiomers, which were separated on preparative scale (Chiracel OD column, 98:2 methanol/water) providing the faster running isomer (3S,4R)-enantiomer (120 mg, 15%, >98% ee)and the slower running (3R,4S)-enantiomer (440 g, 55%, >98% ee).

(46f) Using conditions similar to those described for reaction (36b), the slower running (3R,4S) isomer (130 mg, 0.3 mmol) was converted to the desired hydroxamic acid (108 mg, 65%). MS Found: (M+H)$^+$=422.

Example 47

(3S,4R)-N-hydroxy-4-({4-[(2-methyl-4-quinolinyl)methoxy]benzoyl}amino)tetrahydro-3-furancarboxamide trifluoroacetate (47a) Using conditions similar to those described for reaction (36b), the faster running (3S,4R) isomer (38 mg, 0.09

Example 48

(3S,4S)-N-hydroxy-4-({4-[(2-methyl-4-quinolinyl)methoxy]benzoyl}amino)-1-(1,3-thiazol-2-ylmethyl)-3-pyrrolidinecarboxamide bis(trifluoroacetate)

(48a) Using analogous procedures to (16h) and (36b), the amine from reaction (16g) (229 mg, 0.55 mmol) and 2-thiazolecarboxaldehyde (1.5 eq) were converted to the desired amine and then to the desired hydroxamic acid (186 mg, 46%, 2 steps). MS Found: $(M+H)^+$=518.

Example 49

(3S,4S)-1-acetyl-N-hydroxy-4-({4-[(2-methyl-4-quinolinyl)methoxy]benzoyl}amino)-3-pyrrolidinecarboxamide trifluoracetate (49a) A BIO-RAD Poly-Prep® chromatography column (0.8×4 cm) vessel was charged with a solution of the free base of the amine from reaction (16g) (0.1 g, 0.24 mmol) in dichloromethane (4 mL). The mixture was then treated with PS-DIEA resin (Argonaut Technologies) (215 mg, 3 eq) followed by acetyl chloride (0.026 mL, 1.5 eq). The vessel was sealed and rotated on a Labquake® rotisserie (Barnstead/Thermolyne) for 2 h. PS-Trisamine resin (Argonaut Technologies) (300 mg, 3 eq) was then added, the vessel sealed and rotated for 1 h. The reaction mixture was then filtered and the resins rinsed with dichloromethane (4 mL). The filtrate was concentrated in a test tube to give the desired amide as a white solid that was taken on without further purification. MS found: $(M+H)^+$=462.

(49b) The crude amide from reaction (49a), in a test tube, was treated with a 1.64M solution of $NH_2OH/NaOMe/MeOH$, as prepared in example (36b) (2.9 mL, 20 eq), at 0° C. and warmed to ambient temperature while agitating on a Vortex (1 h). The mixture was quenched with 1N HCl (2.9 ml) and the ensuing precipitate filtered affording a white solid. The product was converted to its TFA salt by dissolution in 0.2 N TFA (5 mL), filtration through a 0.45μ PTFE membrane, and freeze-drying yielding the desired hydroxamate as a white amorphous solid (90.7 mg, 66% yield, 2 steps). MS Found: $(M+H)^+$=463.

Example 50

(3S,4S)-N-hydroxy-1-isobutyryl-4-({4-[(2-methyl-4-quinolinyl)methoxy]benzoyl}amino)-3-pyrrolidinecarboxamide trifluoracetate (50a) Using procedures analogous to (49a)–(49b), the free base of the amine from reaction (16g) (0.1 g, 0.24 mmol) and isobutyryl chloride (0.038 mL, 1.5 eq) were converted to the desired amide and then to the desired hydroxamic acid (112 mg, 77% yield, 2 steps). MS Found $(M+H)^+$=491.

Example 51

(3S,4S)-N-hydroxy-1-(3-methylbutanoyl)-4-({4-[(2-methyl-4-quinolinyl)methoxy]benzoyl}amino)-3-pyrrolidinecarboxamide trifluoracetate (51a) Using procedures analogous to (49a)–(49b), the free base of the amine from reaction (16g) (0.1 g, 0.24 mmol) and 3-methylbutanoyl chloride (0.044 mL, 1.5 eq) were converted to the desired amide and then to the desired hydroxamic acid (116 mg, 78% yield, 2 steps). MS Found $(M+H)^+$=505.

Example 52

(3S,4S)-1-(cyclopropylcarbonyl)-N-hydroxy-4-({4-[(2-methyl-4-quinolinyl)methoxy]benzoyl}amino)-3-pyrrolidinecarboxamide trifluoracetate (52a) Using procedures analogous to (49a)–(49b), the free base of the amine from reaction (16g) (0.1 g, 0.24 mmol) and cyclopropanecarbonyl chloride (0.033 mL, 1.5 eq) were converted to the desired amide and then to the desired hydroxamic acid (40 mg, 28% yield, 2 steps). MS Found $(M+H)^+$=489

Example 53

(3S,4S)-1-(cyclobutylcarbonyl)-N-hydroxy-4-({4-[(2-methyl-4-quinolinyl)methoxy]benzoyl}amino)-3-pyrrolidinecarboxamide trifluoracetate (53a) Using procedures analogous to (49a)–(49b), the free base of the amine from reaction (16g) (0.1 g, 0.24 mmol) and cyclobutanecarbonyl chloride (0.042 mL, 1.5 eq) were converted to the desired amide and then to the desired hydroxamic acid (83 mg, 56% yield, 2 steps). MS Found $(M+H)^+$=503.

Example 54

(3S,4S)-N-hydroxy-1-(methoxyacetyl)-4-({4-[(2-methyl-4-quinolinyl)methoxy]benzoyl}amino)-3-pyrrolidinecarboxamide trifluoracetate (54a) Using procedures analogous to (49a)–(49b), the free base of the amine from reaction (16g) (0.1 g, 0.24 mmol) and methoxyacetyl chloride (0.033 mL, 1.5 eq) were converted to the desired amide and then to the desired hydroxamic acid (85 mg, 59% yield, 2 steps). MS Found $(M+H)^+$=493.

Example 55

(3S,4S)-1-(2-furoyl)-N-hydroxy-4-({4-[(2-methyl-4-quinolinyl)methoxy]benzoyl}amino)-3-pyrrolidinecarboxamide trifluoracetate (55a) Using procedures analogous to (49a)–(49b), the free base of the amine from reaction (16g) (0.1 g, 0.24 mmol) and 2-furoyl chloride (0.036 mL, 1.5 eq) were converted to the desired amide and then to the desired hydroxamic acid (75 mg, 50% yield, 2 steps). MS Found $(M+H)^+$=515.

Example 56

(3S,4S)-N-hydroxy-4-({4-[(2-methyl-4-quinolinyl)methoxy]benzoyl}amino)-1-(2-thienylcarbonyl)-3-pyrrolidinecarboxamide trifluoracetate (56a) Using procedures analogous to (49a)–(49b), the free base of the amine from reaction (16g) (0.1 g, 0.24 mmol) and 2-thienylcarbonyl chloride (0.039 mL, 1.5 eq) were converted to the desired amide and then to the desired hydroxamic acid (70 mg, 46% yield, 2 steps). MS Found $(M+H)^+$=531.

Example 57

(3S,4S)-N-hydroxy-4-({4-[(2-methyl-4-quinolinyl)methoxy]benzoyl}amino)-1-propionyl-3-pyrrolidinecarboxamide trifluoracetate (57a) Using procedures analogous to (49a)–(49b), the free base of the amine from reaction (16g) (0.1 g, 0.24 mmol) and propionyl chloride (0.031, 1.5 eq) were converted to the desired amide and then to the desired hydroxamic acid (71 mg, 51% yield, 2 steps). MS Found (M+H)$^+$=477.

Example 58

(3R,4S)-4-{[4-(2-butynyloxy)benzoyl]amino}-N-hydroxy-tetrahydro-3-furancarboxamide (58a) Using procedures analogous to (1c) and (16i) the amine from reaction (46d) (31 mg, 0.21 mmol, 52% ee) and (49 mg, 1.2 eq) were converted the amide and then hydroxamic acid (22 mg, 33%). MS Found (M+H)$^+$=319.

Example 59

N-{(1R,2S)-2-[(hydroxyamino)carbonyl]-4-oxocyclopentyl}-4-[(2-methyl-4-quinolinyl)methoxy]benzamide trifluoroacetate (59a) 1-(3-Dimethylaminopropyl)-3-ethylcarbodiimide hydrochloride (73.0 g, 1.5 eq) was added to a mixture of (1S,2R)-1-methyl cis-1,2,3,6-tetrahydrophthalate (46.8 g, 254.2 mmol), benzyl alcohol (30.2 g, 1.1 eq) and 4-dimethylaminopyridine (3.0 g, 0.1 eq) in dichloromethane (470 mL) at 0° C. and let warm to room temperature. After 3 h, the solution was cooled to 0° C. and 1N HCl (300 mL) was added. The mixture was extracted with dichloromethene (2×300 mL). The organic layer was washed successively with brine (200 mL), dried (MgSO$_4$) and concentrated. 70 g of crude product was obtained and purified by silica gel column chromatography (ethyl acetate-hexane (1:10). The desired compound was obtained as colorless oil (68.8 g, 99%). MS found: (M+H)$^+$=275.

(59b) The olefin from reaction (59a) (68.8 g, 251 mmol) was added dropwise to a solution of potassium permanganate (125 g, 3.2 eq) in water (400 mL) at 0° C. After 20 min stirring at 0° C., TLC showed the presence of starting olefin. Another portion of water (400 mL) and potassium permanganate (125 g) were added. After 20 min the reaction was complete (by TLC). Sulfur dioxide was bubbled through the mixture at 0° C. until the color of the solution turned pink from purple (2 h). The mixture was filtered and the filtrate was acidified by adding concentrated HCl to pH=1. The reaction was extracted with ethyl acetate (5×500 mL) and the combined organic layers were dried over sodium sulfate. After filtration and concentration, the target diacid was obtained (74 g, 87% yield) and taken on without further purification. MS found: MS found: (M+H)$^+$=339.

(59c) Sodium acetate (11.4 g, 138 mmol) was added to a solution of the dicarboxylic acid from reaction (59b) (57 g, 169 mmol) in acetic anhydride (43 g, 421 mmol) at rt. The reaction was refluxed for 2 h, and cooled to rt. Acetic anhydride was removed by rotary evaporation under reduced pressure. Water (600 mL) was added and the residue was extracted with ethyl acetate (1 L×2). The combined organic layers were dried over MgSO$_4$. After filtration and concentration, the crude ketone was obtained. Purification by silica gel column chromatography (Ethyl acetate 33% in hexane) furnished the target ketone (21 g, 45% yield). MS found: (M)$^+$=276.

(59d) The ketone from reaction (59c) (7 g, 25.3 mmol), ethylene glycol (15.7 g, 253.3 mmol) and p-toluenesulfonic acid monohydrate (481 mg, 2.5 mmol) were refluxed in benzene (507 mL) using Dean-Stark conditions for 1 h. After cooling, the reaction was quenched with saturated sodium bicarbonate solution (80 mL) and extracted with ethyl acetate (2×100 mL). The combined organic layers were washed with brine (80 mL), dried over magnesium sulfate, filtered and concentrated. The purification by silica gel column chromatography (Ethyl acetate 33% in hexane) furnished the target ketal (7.8 g, 97% yield). MS found: (M+H)$^+$=321.

(59e) The ketal from reaction (59d) (7.1 g, 22.3 mmol) and palladium hydroxide on carbon (20 wt %, 780 mg, 0.1 eq) were stirred in ethyl acetate (11 mL) under hydrogen (balloon) at rt for 45 min. After filtration and concentration, the target carboxylic acid (5.1 g, 99% yield) was obtained. MS found: (M+H)$^+$=231.

(59f) To a solution of the carboxylic acid from reaction (59e) (447 mg, 1.9 mmol) in acetone was added triethylamine (393 mg, 3.9 mmol) and ethyl chloroformate (316 mg, 2.9 mmol) at −25° C. under nitrogen. After stirring at rt for 10 min, sodium azide (316 mg, 4.9 mmol) dissolved in water (0.5 mL) was added to the mixture at −10° C. The reaction was stirred at rt for 1 h, and quenched with water (20 mL). It was extracted with CH$_2$Cl$_2$ (2×50 mL), washed with brine (30 mL), dried over MgSO$_4$, filtered, and concentrated. The crude azide was dissolved in benzene (2.6 mL) and refluxed for 1 h.

Benzyl alcohol (210 mg, 1.9 mmol) and p-toluenesulfonic acid (18 mg, 0.1 mmol) were added and the mixture was refluxed for 1 h. After cooling to rt, the reaction was quenched with water and extracted with CH$_2$Cl$_2$ (2×50 mL) The combined organic layer was washed with brine (50 mL), dried over MgSO$_4$, filtered, and concentrated. The crude was purified by silica gel column chromatography (33%EtOAc in hexane). The target amide (393 mg, 60% yield) was obtained. MS found: (M+H)$^+$=236.

(59g) The Cbz protected amine from reaction (59f) (3.8 g, 11.3 mmol), triethylamine (1.1 g, 11.3 mmol) and palladium hydrooxide on carbon (20 wt %, 400 mg, 0.56 mmol) were stirred in EtOAc (57 mL) under hydrogen (50 psi) at rt for 2 h. After filtration and concentration, the target amine was obtained (2.2 g, 96% yield). MS found: (M+H)$^+$=202.

(59h) To the solution of the amine from reaction (59g) (2.2 g, 11.3 mmol), 4-[(2-methyl-4-quinolinyl)methoxy] benzoic acid (3.49 g, 11.9 mmol) and diisopropylethylamine (3.7 g, 28.3 mmol) in DMF (57 mL) was added BOP reagent (6 g, 13.6 mmol) at 0° C. After stirring at rt for 3 h, the reaction was quenched with NH$_4$Cl (100 mL) at 0° C., extracted with EtOAc (300 mL×2), washed with brine (100 mL), dried over Na$_2$SO$_4$, filtered and concentrated. The crude (14 g) was purified by silica gel column chromatography (Gradient elution ethyl acetate/hexane, 1:1 to ethyl acetate) to give the target compound amide (5.4 g, 99% yield). MS found: (M+H)$^+$=477.

(59i) Using conditions analogous to (36b) and the ester from reaction (59h) (300 mg, 0.63 mmol) was converted to the desired hydroxamic acid (220 mg, 73% yield. (M+H)$^+$=478.

(59j) The compound from reaction (59i) (24 mg, 0.0511 mmol) was dissolved in TFA (5 mL). After 10 min stirring at rt, TFA was evaporated. The crude was dissolved in DMSO and purified by HPLC. The TFA salt of target hydroxyamine compound was obtained (28 mg, 99% yield). MS found: $(M+H)^+=434$.

Example 60

N-{(1R,2S,4R)-4-hydroxy-2-[(hydroxyamino) carbonyl]cyclopentyl}-4-[(2-methyl-4-quinolinyl) methoxy]benzamide trifluoracetate

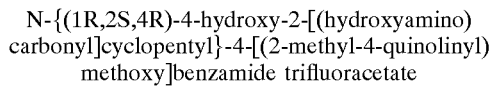

(60a) The compound from reaction (59h) (47 mg, 0.1 mmol) in THF (0.4 mL) was treated with HCl (3N solution, 0.4 mL) at rt for 3 h. The reaction was quenched with saturated NaHCO3 to basic solution at 0° C. The mixture was extracted with ethyl acetate (20 mL×2), washed with brine (10 mL), dried over $Na_2SO_4$, filtered, and concentrated. Silica gel chromatography (dichloromethane/methanol, 20:1) provided the desired ketone (25 mg, 59% yield). MS found: $(M+H)^+=231$ (60b) To a solution of the ketone from reaction (60a) (520 mg, 1.2 mmol) in MeOH (120 mL) was added $NaBH_4$ at 0° C. The reaction was stirred at rt for 20 min. MeOH was evaporated. The reaction was diluted with ethyl acetate and quenched with saturated aqueous $NH_4Cl$ at 0° C. White solid was filtered and the filtrate was extracted with EtOAc (200 mL×2), dried over $Na_2SO_4$, filtered and concentrated. The crude alcohol was purified by silica gel column chromatography (5% MeOH in $CH_2Cl_2$) to give two diastereomers. Major diastereomer (380 mg, 73% yield) and minor one (95 mg, 18%) were obtained. MS found: $(M+H)^+=435$.

(60c) Using conditions analogous to (36b) and the major diastereomer from reaction (60b) (50 mg, 0.12 mmol) was converted to the desired hydroxamic acid (29 mg, 46% yield. $(M+H)^+=436$.

Example 61

N-{(1R,2S,4S)-4-hydroxy-2-[(hydroxyamino) carbonyl]cyclopentyl}-4-[(2-methyl-4-quinolinyl) methoxy]benzamide trifluoracetate (61a) Using conditions analogous to (36b) the minor diastereomer from reaction (60b) (50 mg, 0.12 mmol) was converted to the desired hydroxamic acid (57 mg, 91% yield. $(M+H)^+=436$.

Example 62

(3S,4S)-N-hydroxy-4-({4-[(2-methyl-4-quinolinyl) methoxy]benzoyl}amino)-1-tetrahydro-2H-pyran-4-yl-3-pyrrolidinecarboxamide bis(trifluoroacetate)

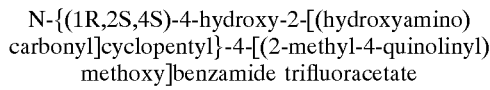

(62a) Using analogous procedures to (16h and 36b), the amine from reaction (16g) (205 mg, 0.49 mmol) and tetrahydro-4H-pyran-4-one (0.068 mL, 1.5 eq) were converted to the desired amine and then to the desired hydroxamic acid (100 mg, 28%, 2 steps). MS Found: $(M+H)^+=505$.

Example 63 methyl (3S,4S)-3-[(hydroxyamino)carbonyl]-4-({4-[(2-methyl-4-quinolinyl)methoxy]benzoyl}amino)-1-pyrrolidinecarboxylate trifluoroacetate

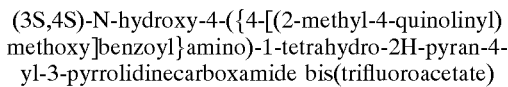

(63a) A BIO-RAD Poly-Prep® chromatography column (0.8×4 cm) vessel was charged with a solution of the free base of the amine from reaction (16g) (0.1 g, 0.24 mmol) in dichloromethane (6 mL). The mixture was then treated with PS-DIEA resin (Argonaut Technologies) (215 mg, 3 eq) followed by methylchloroformate (0.028 mL, 1.5 eq). The vessel was sealed and rotated on a Labquake® rotisserie (Barnstead/Thermolyne) for 6 h. PS-Trisamine resin (Argonaut Technologies) (300 mg, 3 eq) was then added, the vessel sealed and rotated for 16 h. The reaction mixture was then filtered and the resins rinsed with dichloromethane (4 mL). The filtrate was concentrated in a test tube to give the desired carbamate as a white solid that was taken on without further purification. MS found: $(M+H)^+=478$.

(63b) The crude carbamate from reaction (49a), in a test tube, was treated with a 1.64M solution of $NH_2OH$/NaOMe/MeOH, as prepared in example (36b) (2.9 mL, 20 eq), at 0° C. and warmed to ambient temperature while agitating on a Vortex (1 h). The mixture was quenched with 1N HCl (2.9 ml) and the ensuing precipitate filtered affording a white solid. The product was converted to its TFA salt by dissolution in 0.2 N TFA (5 mL), filtration through a $0.45\mu$ PTFE membrane, and freeze-drying yielding the desired hydroxamate as a white amorphous solid (119 mg, 84% yield, 2 steps). MS Found: $(M+H)^+=479$.

Example 64 ethyl (3S,4S)-3-[(hydroxyamino)carbonyl]-4-({4-[(2-methyl-4-quinolinyl)methoxy]benzoyl}amino)-1-pyrrolidinecarboxylate trifluoracetate

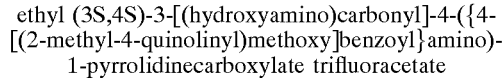

(64a) Using procedures analogous to (63a)–(63b), the free base of the amine from reaction (16g) (0.1 g, 0.24 mmol) and ethylchloroformate (0.034 mL, 1.5 eq) were converted to the desired carbamate and then to the desired hydroxamic acid (136 mg, 94% yield, 2 steps). MS Found $(M+H)^+=493$.

Example 65 propyl (3S,4S)-3-[(hydroxyamino)carbonyl]-4-({4-[(2-methyl-4-quinolinyl)methoxy]benzoyl}amino)-1-pyrrolidinecarboxylate trifluoroacetate

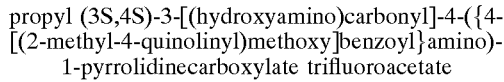

(65a) Using procedures analogous to (63a)–(63b), the free base of the amine from reaction (16g) (0.1 g, 0.24 mmol) and propylchloroformate (0.040 mL, 1.5 eq) were converted to the desired carbamate and then to the desired hydroxamic acid (134 mg, 90% yield, 2 steps). MS Found $(M+H)^+=507$.

Example 66 allyl (3S,4S)-3-[(hydroxyamino)carbonyl]-4-({4-[(2-methyl-4-quinolinyl)methoxy]benzoyl}amino)-1-pyrrolidinecarboxylate trifluoroacetate

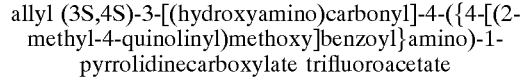

(66a) Using procedures analogous to (63a)–(63b), the free base of the amine from reaction (16g) (0.1 g, 0.24 mmol) and allylchloroformate (0.038 mL, 1.5 eq) were converted to the desired carbamate and then to the desired hydroxamic acid (122 mg, 82% yield, 2 steps). MS Found $(M+H)^+=505$.

Example 67 isopropyl (3S,4S)-3-[(hydroxyamino)carbonyl]-4-({4-[(2-methyl-4-quinolinyl)methoxy] benzoyl}amino)-1-pyrrolidinecarboxylate trifluoroacetate

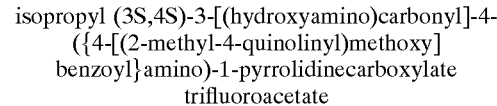

(67a) Using procedures analogous to (63a)–(63b), the free base of the amine from reaction (16g) (0.1 g, 0.24 mmol)

Example 68

2-propynyl (3S,4S)-3-[(hydroxyamino)carbonyl]-4-({4-[(2-methyl-4-quinolinyl)methoxy]benzoyl}amino)-1-pyrrolidinecarboxylate trifluoroacetate (68a) Using procedures analogous to (63a)–(63b), the free base of the amine from reaction (16g) (0.1 g, 0.24 mmol) and 2-propynylchloroformate (0.035 mL, 1.5 eq) were converted to the desired carbamate and then to the desired hydroxamic acid (88 mg, 60% yield, 2 steps). MS Found $(M+H)^+=503$.

Example 69

2-butynyl (3S,4S)-3-[(hydroxyamino)carbonyl]-4-({4-[(2-methyl-4-quinolinyl)methoxy]benzoyl}amino)-1-pyrrolidinecarboxylate trifluoroacetate (69a) Using procedures analogous to (63a)–(63b), the free base of the amine from reaction (16g) (0.1 g, 0.24 mmol) and 2-butynylchloroformate (0.041 mL, 1.5 eq) were converted to the desired carbamate and then to the desired hydroxamic acid (96 mg, 63% yield, 2 steps). MS Found $(M+H)^+=517$.

Example 70

3-butenyl (3S,4S)-3-[(hydroxyamino)carbonyl]-4-({4-[(2-methyl-4-quinolinyl)methoxy]benzoyl}amino)-1-pyrrolidinecarboxylate trifluoroacetate (70a) Using procedures analogous to (63a)–(63b), the free base of the amine from reaction (16g) (0.1 g, 0.24 mmol) and 3-butenylchloroformate (0.045 mL, 1.5 eq) were converted to the desired carbamate and then to the desired hydroxamic acid (109 mg, 72% yield, 2 steps). MS Found $(M+H)^+=519$.

Example 71 benzyl (3S,4S)-3-[(hydroxyamino)carbonyl]-4-({4-[(2-methyl-4-quinolinyl)methoxy]benzoyl}amino)-1-pyrrolidinecarboxylate trifluoroacetate (71a) Using procedures analogous to (63a)–(63b), the free base of the amine from reaction (16g) (0.1 g, 0.24 mmol) and benzylchloroformate (0.051, 1.5 eq) were converted to the desired carbamate and then to the desired hydroxamic acid (98 mg, 61% yield, 2 steps). MS Found $(M+H)^+=554$.

Example 72

N-{(1R,2S)-4-(dimethylamino)-2-[(hydroxyamino)carbonyl]cyclopentyl}-4-[(2-methyl-4-quinolinyl)methoxy]benzamide bis(trifluoroacetate (72a) Using procedures analogous to examples (36a) and (36b) the ketone from example (60a) (50 mg, 0.12 mmol) and dimethyl amine were converted to the desired amine and then the desired hydroxamic acid (74 mg, 27% yield). MS found: $(M+H)^+=463$

Example 73

(3S,4S)-4-{[4-(2-butynyloxy)benzoyl]amino}-N-hydroxy-1-isopropyl-3-pyrrolidinecarboxamide (73a) The amide from reaction (16g) (510 mg, 1.10 mmol) in AcOH (2 mL) and dichloromethane (4 mL) was treated with zinc dust (217 mg, 3 eq)) and stirred for 24 h at ambient temperature. The remaining zinc was filtered off and the filtrate neutralized with saturated aqueous NaHCO3 (5 mL) and extracted with ethyl acetate (3×10 mL). The combined extracts were dried (MgSO$_4$) and concentrated. Silica gel chromatography (ethyl acetate) provided the desired phenol (259 mg, 77%). MS Found: (M+H)+307.

(73b) 2-Butyn-1-ol (105 mg, 1.5 eq)) was treated with triphenylphosphine (393 mg, 1.5 eq.) and diethylazodicarboxylate (0.24 mL, 1.5 eq) in benzene (10 mL). The phenol from reaction (73a) (307 mg, 1.0 mmol) in benzene (5 mL) was added via cannula and the mixture stirred for 12 h. The mixture was quenched with water (20 mL) and extracted with ethyl acetate (3×30 mL). The combined organic layers were dries (MgSO$_4$), filtered and concentrated. Silica gel chromatography (ethyl acetate) provided the desired ether (200 mg, 45%). MS Found: $(M+H)^+=459$.

(73c) Using procedures analogous to (36b), the ester from reaction (73b) (200 mg, 0.44 mmol) was converted to the desired hydroxamic acid (57 mg, 28% yield). MS Found $(M+H)^+=360$.

Example 74

N-{(1R,2S)-4,4-difluoro-2-[(hydroxyamino)carbonyl]cyclopentyl}-4-[(2-methyl-4-quinolinyl)methoxy]benzamide trifluoroacetate (74a) To a heterogeneous solution of the ketone from example (60a) (50 mg, 0.12 mmol) in toluene (0.5 mL) was added diethylaminosulfur trifluoride (47 mg, 0.29 mmol) at 0° C. The reaction was stirred at rt for 3 days. The mixture was poured into ice water, extracted with EtOAc (10 mL×2), dried over Na$_2$SO$_4$, filtered and concentrated. Crude 60 mg was purified by silica gel column chromatography (EtOAc 90% in hexane). The target difluoride compound (18 mg, 34% yield) was obtained. MS found: $(M+H)^+=455$.

(74b) Using conditions analogous to (36b) and the ester from example (74a) (18 mg, 0.0.04 mmol) was converted to the desired hydroxamic acid (11 mg, 49% yield. $(M+H)^+=456$.

Example 75

(3S,4S)-N-hydroxy-1-isopropyl-4-{[4-(2-methylphenoxy)benzoyl]amino}-3-pyrrolidinecarboxamide trifluoroacetate (75a) Using procedures analogous to (2a) and (36b), The phenol from reaction (73a) (100 mg, 0.33 mmol) and 2-methylphenylboronic acid (135 mg, 0.4 mmol) were converted the desired ester and then hydroxamic acid (23 mg, 41% yield). MS Found: $(M+H)^+=398$.

Example 100 cis-N-hydroxy-2-[[[4-[(2-methyl-4-quinolinyl)methoxy]phenyl]carbonyl]amino]-1-cyclopentanecarboxamide trifluoroacetate (100a) A mixture of methyl (+/-)-cis-2-aminocyclopentanecarboxylate hydrochloride (150 mg, 0.83 mmol), 4-(2-methyl-4-quinolinylmethoxy)benzoic acid (250 mg, 1 eq), DIEA (0.43 mL, 3 eq) and BOP (0.31 g, 1.2 eq) in DMF (4 mL) was stirred at rt for 2 h. Following addition of sat $NH_4Cl$, the mixture was extracted with ethyl acetate. The extracts were washed with sat $NaHCO_3$, brine, dried ($MgSO_4$) and concentrated in vacuo. Silica gel chromatography (ethyl acetate-hexane, 60:40 then 80:20) provided the desired amide (330 mg, 95%). MS $(M+H)^+=419$.

(100b) The freshly prepared 1.76 M solution of hydroxylamine (3.0 mL, 9 eq) was added to the ester from (100a) (240 mg, 0.57 mmol) at rt. After 30 min at this temperature, the mixture was acidified to pH 5 with 4 N HCl. The desired hydroxamic acid precipitated out and collected by filtration (146 mg, 61%). The free base was then converted to the trifluoroacetate salt in quantitative yield by reaction with TFA. MS found: $(M+H)^+=420$.

Example 101 trans-N-hydroxy-2-[[[4-[(2-methyl-4-quinolinyl)methoxy]phenyl]carbonyl]amino]-1-cyclopentanecarboxamide trifluoroacetate (101a) The cis-isomer from (100a) (90 mg, 215 mmol) was dissolved in toluene (10 mL) and heated to reflux for 45 h. The mixture was filtered through a pad of silica gel and filter pad washed with EtOAc until free of product. The filtrate was concentrated to give a 1:1 mixture of trans and cis isomers (77.2 mg, 86%). MS found: $(M+H)^+=419$.

(101b) Following a procedure similar to that used for step (100b), the title compound was prepared. The two isomers were separated by reverse phase HPLC on a Vydac C-18 semiprep column eluting an acetonitrile:water:TFA gradient, to give the trans hydroxamic acid product (25%). MS $(M+H)^+=420$.

Example 102

(1S,2R)-N-hydroxy-2-[[[4-[(2-methyl-4-quinolinyl)methoxy]phenyl]carbonyl]amino]-1-cyclopentanecarboxamide trifluoroacetate (102a–b) Following the procedures similar to that used for steps (100a–b), but using methyl (1S,2R)-2-aminocyclopentanecarboxylate hydrochloride (Davies, S. G.; Ichihara, O.; Lenoir, I.; Walters, A. S. J. Chem. Soc. Perkin Trans. 1994, 1411), the title compound was prepared. The product was purified by reverse phase HPLC on a Vydac C-18 semiprep column eluting an acetonitrile-:water:TFA gradient, to give the hydroxamic acid product. MS $(M+H)^+=420$.

Example 103

(1R,2S)-N-hydroxy-2-[[[4-[(2-methyl-4-quinolinyl)methoxy]phenyl]carbonyl]amino]-1-cyclopentanecarboxamide trifluoroacetate (103a–b) Following the procedures similar to that used for steps (100a–b), but using methyl (1R,2S)-2-aminocyclopentanecarboxylate hydrochloride (Davies, S. G.; Ichihara, O.; Lenoir, I.; Walters, A. S. J. Chem. Soc. Perkin Trans. 1994, 1411), the title compound was prepared. The product was purified by reverse phase HPLC on a Vydac C-18 semiprep column eluting an acetonitrile-:water:TFA gradient, to give the hydroxamic acid product. MS $(M+H)^+=420$.

Example 104 cis-N-hydroxy-2-[[[4-[(2-methyl-4-quinolinyl)methoxy]phenyl]carbonyl]amino]-1-cyclohexanecarboxamide trifluoroacetate (104a–b) Following the procedures similar to that used for steps (100a–b), but using (+/−)-cis-2-aminocyclohexanecarboxylate hydrochloride, the title compound was prepared. The product was purified by reverse phase HPLC on a Vydac C-18 semiprep column eluting an acetonitrile:water:TFA gradient, to give the hydroxamic acid product. MS $(M+H)^+=434$.

Example 105 trans-N-hydroxy-2-[[[4-[(2-methyl-4-quinolinyl)methoxy]phenyl]carbonyl]amino]-1-cyclohexanecarboxamide trifluoroacetate (105a–b) Following the procedures similar to that used for steps (101a–b), but using the cyclohexane analogue, the title compound was prepared. The product was purified by reverse phase HPLC on a Vydac C-18 semiprep column eluting an acetonitrile:water:TFA gradient, to give the hydroxamic acid product. MS $(M+H)^+=434$.

Example 108 trans-1-[[(1,1-dimethylethyl)oxy]carbonyl]-N-hydroxy-3-[[[4-[(2-methyl-4-quinolinyl)methoxy]phenyl]carbonyl]amino]-4-pyrrolidinecarboxamide trifluoroacetate (108a) A solution of benzyl methyl fumarate (26.4 g, 113 mmol) in toluene (200 mL) was heated to reflux. A suspension of glycine (11.0 g, 1.3 eq) and paraformaldehyde (4.40 g, 1.3 eq) in toluene (50 mL) was added over 1 h. The mixture was maintained at reflux for 2 h after completion of addition. Additional amount of paraformaldehyde (1 eq) and glycine (1 eq) were added. After additional 30 min at reflux, the mixture was cooled and filtered. The filtrate was diluted with ethyl acetate (300 mL) and washed with sat Na2CO3 (2×10 mL), brine (10 mL), dried ($MgSO_4$) and concentrated. The crude material was used in the next step without purification. MS $(M+H)^+=278$.

(108b) DIEA (34.8 mL, 1.8 eq) and $(BOC)_2O$ (36.3 mL, 1.5 eq) were added to a solution of the crude amine from (108a) in $CH_2Cl_2$ (600 mL) at 0° C. After 2 days at rt, additional amount of DIEA (1 eq) and $(BOC)_2O$ (1 eq) were added. After a total of 3 days, the mixture was washed with sat $NaHCO_3$ (2×20 mL), brine (20 mL), dried ($MgSO_4$) and concentrated in vacuo. Silica gel chromatography (ethyl acetate-hexane, 10:90 then 20:80) provided the desired product (7.60 g, 20% over 2 steps). MS $(M+H)^+=378$.

(108c) A mixture of the benzyl ester from (108b) (7.40 g, 19.6 mmol) and $Pd(OH)_2$ on carbon (1.90 g) in methanol (150 mL) was purged with hydrogen and stirred under balloon pressure hydrogen for 3 h. The catalyst was removed by filtration and the filtrate was concentrated to give the desired carboxylic acid (5.64 g, 100%). MS $(2M-H)^-=573$.

(108d) $Et_3N$ (3.7 mL, 1.5 eq) and DPPA (4.6 mL, 1.2 eq) were added to a solution of the carboxylic acid from (108c) (5.12 g, 17.8 mmol) in benzene (150 mL). After 2 h at rt, benzyl alcohol (2.2 mL, 1.2 eq) was added. The mixture was heated to reflux for 1 h, cooled to rt, washed with sat NaHCO$_3$ (2×10 mL), brine (10 mL), dried (MgSO$_4$) and concentrated in vacuo. Silica gel chromatography (ethyl acetate-hexane, 20:80 then 30:70) provided the desired product (4.50 g, 64%). MS (M+H)$^+$= 393.

(108e) A mixture of the Cbz-protected intermediate from (108d) (2.30 g, 5.86 mmol) and Pd on carbon (0.60 g) in methanol (100 mL) was purged with hydrogen and stirred under balloon pressure hydrogen for 2 h. The catalyst was removed by filtration and the filtrate was concentrated to give the desired amine (1.52 g, 100%). MS (2M+H)$^+$= 517.

(108f) Following the procedures similar to that used for step (100a), but using the amine from (108e) (1.35 g, 523 mmol), the amide was prepared. Silica gel chromatography (ethyl acetate-hexane, 50:50 then 60:40) provided the desired product (2.70 g, 85%). MS (M+H)$^+$=534.

(108g) Following the procedures similar to that used for step (100b), the ester from (108f) (165 mg, 260 mmol) was converted to the title compound. The product was purified by reverse phase HPLC on a Vydac C-18 semiprep column eluting an acetonitrile:water:TFA gradient, to give the hydroxamic acid product (85 mg, 52%). MS (M+H)$^+$= 521.

Example 109 trans-N-hydroxy-3-[[[4-[(2-methyl-4-quinolinyl) methoxy]phenyl]carbonyl]amino]-4-pyrrolidinecarboxamide bis(trifluoroacetate)

(109a) The product from example 108 (50 mg, 0.079 mmol) was mixed with TFA (1 mL) and CH$_2$Cl$_2$ (2 mL) and stirred for 1 h. Concentration in vacuo provided the title compound (52 mg, 100%). MS (M+H)$^+$=421.

Example 110 cis-1-[[(1,1-dimethylethyl)oxy]carbonyl]-N-hydroxy-3-[[[4-[(2-methyl-4-quinolinyl)methoxy] phenyl]carbonyl]amino]-4-pyrrolidinecarboxamide trifluoroacetate (110a–b) Following the procedures similar to that used for steps (101a–b), the intermediate from (108f) was converted to the title compound. The product was purified by reverse phase HPLC on a Vydac C-18 semiprep column eluting an acetonitrile:water:TFA gradient, to give the hydroxamic acid product. MS (M+H)$^+$=521.

Example 111 cis-N-hydroxy-3-[[[4-[(2-methyl-4-quinolinyl) methoxy]phenyl]carbonyl]amino]-4-pyrrolidinecarboxamide bis(trifluoroacetate)

(111a) Following the procedure similar to that used for step (109a), the product from (110a) was converted to the title compound. MS (M+H)$^+$=421.

Example 112

(3S,4R)-1-[[(1,1-dimethylethyl)oxy]carbonyl]-N-hydroxy-4-[[[4-[(2-methyl-4-quinolinyl)methoxy] phenyl]carbonyl]amino]-3-piperidinecarboxamide trifluoroacetate (112a) DIEA (82 mL, 2.5 eq) and (BOC)$_2$O (36.0 g, 1.3 eq) were added to a solution of methyl 4-oxo-3-piperidinecarboxylate (24.6 g, 137 mmol) in CH$_2$Cl$_2$ (600 mL) at 0° C. After at rt overnight, sat NaHCO$_3$ (50 mL) was added. The mixture was washed with water (2×30 mL), brine (30 mL), dried (MgSO4) and concentrated in vacuo. Silica gel chromatography (ethyl acetate-hexane, 50:50) provided the desired product (29.8 g, 93%).

(112b) Yb(OTf)$_3$ (1.41 g, 0.02 eq) was added to a mixture of the intermediate from (112a) (29.2 g, 113 mmol) and (R)-α-methylbenzylamine (16.1 mL, 1.1 eq) in benzene. The mixture was heated to reflux for 3 h with azotropic removal of water using a Dean-Stark trap. The mixture was concentrated in vacuo. The residue was filtered through a silica gel pad and the filter cake washed with ethyl acetate-hexane (10:90) until free of product. The filtrated was concentrated to give the desired enamine product (40.8 g, 100%). MS (M+H)$^+$=361.

(112c) NaHB(OAc)3 (58.8 g, 2.5 eq) was added to a solution of the enamine from (112b) (40.0 g, 111 mmol) in acetic acid (180 mL) and acetonitrile (180 mL) at 0° C. After 2 h at 0° C., the mixture was concentrated in vacuo. The residue was diluted with CH$_2$Cl$_2$ (1 L), washed with Na$_2$CO$_3$ (3×50 mL), brine (50 mL), dried (MgSO$_4$) and concentrated in vacuo. Silica gel chromatography (ethyl acetate-hexane, 10:90 then 20:80) provided the desired amine product as a 5:1 mixture of two diastereomers as judged by $^1$H NMR (37.0 g, 92%). MS (M+H)$^+$=363.

(112d) Pd(OH)$_2$ on C (6.0 g) was added to the amine from (112c) (36.8 g, 101 mmol) in methanol (600 mL), water (60 mL) and acetic acid (15 mL). The mixture was purged with hydrogen and stirred under balloon pressure hydrogen overnight. Following removal of catalyst by filtration, the filtrate was concentrated to give the desired amine (22.8 g, 87%). MS (M+H)$^+$=259.

(112e) Following the procedure similar to that used for steps (100a), the amine from (112d) (10.0 g, 38.7 mmol) was coupled with 4-(2-methyl-4-quinolinylmethoxy)benzoic acid. Silica gel chromatography (ethyl acetate-hexane, 50:50 then 70:30) gave the desired amide (10.4 g, 50%). The enantiomeric purity of the amide was improved to >99% ee by crystallization with CHCl$_3$ (80 mL), ethyl acetate (10 mL) and hexane (10 mL). The material recovery from the crystalization was 63%. MS (M+H)$^+$= 534.

(112f) Following the procedure similar to that used for steps (100b), the intermediate from (112e) (80 mg, 0.150 mmol) was converted to the hydroxamic acid. The product was purified by reverse phase HPLC on a Vydac C-18 semiprep column eluting an acetonitrile:water:TFA gradient, to give the desired hydroxamic acid product (43 mg, 44%). MS (M+H)$^+$=535.

Example 113

(3S,4S)-1-[[(1,1-dimethylethyl)oxy]carbonyl]-N-hydroxy-4-[[[4-[(2-methyl-4-quinolinyl)methoxy] phenyl]carbonyl]amino]-3-piperidinecarboxamide trifluoroacetate (113a–d) Following the procedures similar to that used for steps (112b–e), but using (S)-α-methylbenzylamine in step (112b), the (3R,4S) amide enantiomer was prepared. MS (M+H)$^+$=534.

(113e–f) Following the procedures similar to that used for steps (101a–b), the amide from (113d) was converted to the title compound. The product was purified by reverse phase HPLC on a Vydac C-18 semiprep column eluting an acetonitrile:water:TFA gradient, to give the desired hydroxamic acid product. MS (M+H)$^+$=535.

Example 114

(3S,4S)-N-hydroxy-4-[[[4-[(2-methyl-4-quinolinyl)methoxy]phenyl]carbonyl]amino]-3-piperidinecarboxamide bis(trifluoroacetate)

(114a) Following the procedure similar to that used for step (109a), the product from (113f) was converted to the title compound. MS (M+H)$^+$=435.

Example 115

(3S,4R)-N-hydroxy-4-[[[4-[(2-methyl-4-quinolinyl)methoxy]phenyl]carbonyl]amino]-3-piperidinecarboxamide bis(trifluoroacetate)

(115a) Following the procedure similar to that used for step (109a), the product from (112f) was converted to the title compound. MS (M+H)$^+$=435.

Example 116

(3S,4R)-1-[(butoxy)carbonyl]-N-hydroxy-4-[[[4-[(2-methyl-4-quinolinyl)methoxy]phenyl]carbonyl]amino]-3-piperidinecarboxamide trifluoroacetate (116a) Following the procedure similar to that used for step (109a), the intermediate from (112e) (2.24 g, 4.20 mmol) was converted to the desired amine bis-TFA salt (3.16 g, 100%). MS (M+H)$^+$=434.

(116b) DIEA (0.17 mL, 5 eq) and n-butyl chloroformate (30 mg, 1.1 eq) were added to the amine from (116a) (150 mg, 0.199 mmol) in $CH_2Cl_2$. After 30 min at rt, ethyl acetate (100 mL) and sat $NaHCO_3$ (3 mL) were added. The mixture was washed with water (2×3 mL) and brine (3 mL), dried ($MgSO_4$) and concentrated in vacuo. The crude material was taken to the next step without further purification. MS (M+H)$^+$=534.

(116c) Following the procedures similar to that used for step (100b), the crude material from (116b) was converted to the title compound. The product was purified by reverse phase HPLC on a Vydac C-18 semiprep column eluting an acetonitrile:water:TFA gradient, to give the desired hydroxamic acid product (38 mg, 29% for two steps). MS (M+H)$^+$=535.

Example 117

(3S,4R)-N-hydroxy-1-[[(1-methylethyl)oxy]carbonyl]-4-[[[4-[(2-methyl-4-quinolinyl)methoxy]phenyl]carbonyl]amino]-3-piperidinecarboxamide trifluoroacetate (117a–b) Following the procedures similar to that used for steps 116b and 100b, but with isopropyl chloroformate in step (116b), the title compound was prepared. The product was purified by reverse phase HPLC on a Vydac C-18 semiprep column eluting an acetonitrile:water:TFA gradient, to give the hydroxamic acid product. MS (M+H)$^+$=521.

Example 118

(3S,4R)-N-hydroxy-1-(methylsulfonyl)-4-[[[4-[(2-methyl-4-quinolinyl)methoxy]phenyl]carbonyl]amino]-3-piperidinecarboxamide trifluoroacetate (118a–b) Following the procedures similar to that used for steps 116b and 100b, but with MsCl in step (116b), the title compound was prepared. The product was purified by reverse phase HPLC on a Vydac C-18 semiprep column eluting an acetonitrile:water:TFA gradient, to give the hydroxamic acid product. MS (M+H)$^+$=513.

Example 119

(3S,4R)-N-hydroxy-4-[[[4-[(2-methyl-4-quinolinyl)methoxy]phenyl]carbonyl]amino]-1-(phenylsulfonyl)-3-piperidinecarboxamide trifluoroacetate (119a–b) Following the procedures similar to that used for steps 116b and 100b, but with benzenesulfonyl chloride in step (116b), the title compound was prepared. The product was purified by reverse phase HPLC on a Vydac C-18 semiprep column eluting an acetonitrile:water:TFA gradient, to give the hydroxamic acid product. MS (M+H)$^+$=575.

Example 120

(3S,4R)-1-acetyl-N-hydroxy-4-[[[4-[(2-methyl-4-quinolinyl)methoxy]phenyl]carbonyl]amino]-3-piperidinecarboxamide trifluoroacetate (120a–b) Following the procedures similar to that used for steps 116b and 100b, but with acetic anhydride in step (116b), the title compound was prepared. The product was purified by reverse phase HPLC on a Vydac C-18 semiprep column eluting an acetonitrile:water:TFA gradient, to give the hydroxamic acid product. MS (M+H)$^+$=477.

Example 121

(3S,4R)-1-benzoyl-N-hydroxy-4-[[[4-[(2-methyl-4-quinolinyl)methoxy]phenyl]carbonyl]amino]-3-piperidinecarboxamide trifluoroacetate (121a–b) Following the procedures similar to that used for steps 116b and 100b, but with benzoyl chloride in step (116b), the title compound was prepared. The product was purified by reverse phase HPLC on a Vydac C-18 semiprep column eluting an acetonitrile:water:TFA gradient, to give the hydroxamic acid product. MS (M+H)$^+$=539.

Example 122

(3S,4R)-1-(2,2-dimethylpripionyl)-N-hydroxy-4-[[[4-[(2-methyl-4-quinolinyl)methoxy]phenyl]carbonyl]amino]-3-piperidinecarboxamide trifluoroacetate (122a–b) Following the procedures similar to that used for steps 116b and 100b, but with trimethylacetyl chloride in step (116b), the title compound was prepared. The product was purified by reverse phase HPLC on a Vydac C-18 semiprep column eluting an acetonitrile:water:TFA gradient, to give the hydroxamic acid product. MS (M+H)$^+$=519.

Example 123

(3S,4R)-1-(3,3-dimethylbutanoyl)-N-hydroxy-4-[[[4-[(2-methyl-4-quinolinyl)methoxy]phenyl]carbonyl]amino]-3-piperidinecarboxamide trifluoroacetate (123a–b) Following the procedures similar to that used for steps 116b and 100b, but with 3,3-dimethylbutyryl chlo-

Example 124

(3S,4R)-N-hydroxy-4-[[[4-[(2-methyl-4-quinolinyl)methoxy]phenyl]carbonyl]amino]-1-(4-morpholinecarbonyl)-3-piperidinecarboxamide trifluoroacetate (124a–b) Following the procedures similar to that used for steps 116b and 100b, but with 4-morpholinecarbonyl chloride in step (116b), the title compound was prepared. The product was purified by reverse phase HPLC on a Vydac C-18 semiprep column eluting an acetonitrile:water:TFA gradient, to give the hydroxamic acid product. MS $(M+H)^+=548$.

Example 125

(3S,4R)-1-(dimethylcarbamyl)-N-hydroxy-4-[[[4-[(2-methyl-4-quinolinyl)methoxy]phenyl]carbonyl]amino]-3-piperidinecarboxamide trifluoroacetate (125a–b) Following the procedures similar to that used for steps 116b and 100b, but with dimethylcarbamyl chloride in step (116b), the title compound was prepared. The product was purified by reverse phase HPLC on a Vydac C-18 semiprep column eluting an acetonitrile:water:TFA gradient, to give the hydroxamic acid product. MS $(M+H)^+=506$.

Example 126

(3S,4R)-N-hydroxy-1-methyl-4-[[[4-[(2-methyl-4-quinolinyl)methoxy]phenyl]carbonyl]amino]-3-piperidinecarboxamide bis(trifluoroacetate)

(126a) DIEA (0.23 mL, 5 eq) and 37% aqueous formaldehyde (24 mg, 1.1 eq) were added to the amine intermediate from (116a) (200 mg, 0.258 mmol) in 1,2-dichloroethane (6 mL). After 30 min at rt, NaHB(OAc)$_3$ (82 mg, 1.5 eq) was added. After additional 1 h at rt, sat NaHCO$_3$ (3 mL) and ethyl acetate (100 mL) were added. The mixture was washed with water (2×5 mL) and brine (5 mL), dried (MgSO$_4$) and concentrated in vacuo. The crude material was used in the next step without further purification. MS $(M+H)^+=448$.

(126b) Following the procedures similar to that used for step (100b), the crude intermediate from (126a) was converted to the title compound. The product was purified by reverse phase HPLC on a Vydac C-18 semiprep column eluting an acetonitrile:water:TFA gradient, to give the desired hydroxamic acid (50 mg, 32% for two steps). MS $(M+H)^+=449$.

Example 127

(3S,4R)-1-ethyl-N-hydroxy-4-[[[4-[(2-methyl-4-quinolinyl)methoxy]phenyl]carbonyl]amino]-3-piperidinecarboxamide bis(trifluoroacetate)

(127a–b) Following the procedures similar to that used for steps 126a and 100b, but with acetaldehdye in step (126b), the title compound was prepared. The product was purified by reverse phase HPLC on a Vydac C-18 semiprep column eluting an acetonitrile:water:TFA gradient, to give the hydroxamic acid product. MS $(M+H)^+=463$.

Example 128

(3S,4R)-N-hydroxy-4-[[[4-[(2-methyl-4-quinolinyl)methoxy]phenyl]carbonyl]amino]-1-propyl-3-piperidinecarboxamide bis(trifluoroacetate)

(128a–b) Following the procedures similar to that used for steps 126a and 100b, but with propionaldehyde in step (126b), the title compound was prepared. The product was purified by reverse phase HPLC on a Vydac C-18 semiprep column eluting an acetonitrile:water:TFA gradient, to give the hydroxamic acid product. MS $(M+H)^+=477$.

Example 129

(3S,4R)-N-hydroxy-1-(1-methylethyl)-4-[[[4-[(2-methyl-4-quinolinyl)methoxy]phenyl]carbonyl]amino]-3-piperidinecarboxamide bis(trifluoroacetate)

(129a–b) Following the procedures similar to that used for steps 126a and 100b, but with acetone in step (126b), the title compound was prepared. The product was purified by reverse phase HPLC on a Vydac C-18 semiprep column eluting an acetonitrile:water:TFA gradient, to give the hydroxamic acid product. MS $(M+H)^+=477$.

Example 130

(3S,4R)-1-(cyclopropylmethyl)-N-hydroxy-4-[[[4-[(2-methyl-4-quinolinyl)methoxy]phenyl]carbonyl]amino]-3-piperidinecarboxamide bis(trifluoroacetate)

(130a–b) Following the procedures similar to that used for steps 126a and 100b, but with cyclopropanecarboxaldehyde in step (126b), the title compound was prepared. The product was purified by reverse phase HPLC on a Vydac C-18 semiprep column eluting an acetonitrile:water:TFA gradient, to give the hydroxamic acid product. MS $(M+H)^+=489$.

Example 131

(3S,4R)-1-(2,2-dimethylpropyl)-N-hydroxy-4-[[[4-[(2-methyl-4-quinolinyl)methoxy]phenyl]carbonyl]amino]-3-piperidinecarboxamide bis(trifluoroacetate)

(131a–b) Following the procedures similar to that used for steps 126a and 100b, but with trimethylacetaldehyde in step (126b), the title compound was prepared. The product was purified by reverse phase HPLC on a Vydac C-18 semiprep column eluting an acetonitrile:water:TFA gradient, to give the hydroxamic acid product. MS $(M+H)^+=505$.

Example 132

(3S,4R)-1-benzyl-N-hydroxy-4-[[[4-[(2-methyl-4-quinolinyl)methoxy]phenyl]carbonyl]amino]-3-piperidinecarboxamide bis(trifluoroacetate)

(132a–b) Following the procedures similar to that used for steps 126a and 100b, but with benzaldehyde in step

--- ride in step (116b), the title compound was prepared. The product was purified by reverse phase HPLC on a Vydac C-18 semiprep column eluting an acetonitrile:water:TFA gradient, to give the hydroxamic acid product. MS $(M+H)^+=533$.

(126b), the title compound was prepared. The product was purified by reverse phase HPLC on a Vydac C-18 semi-prep column eluting an acetonitrile:water:TFA gradient, to give the hydroxamic acid product. MS (M+H)$^+$=525.

Example 133

(3S,4R)-1-(2-thiazolylmethyl)-N-hydroxy-4-[[[4-[(2-methyl-4-quinolinyl)methoxy]phenyl]carbonyl]amino]-3-piperidinecarboxamide bis(trifluoroacetate)

(133a–b) Following the procedures similar to that used for steps 126a and 100b, but with 2-thiazolecarboxaldehyde in step (126b), the title compound was prepared. The product was purified by reverse phase HPLC on a Vydac C-18 semiprep column eluting an acetonitrile:water:TFA gradient, to give the hydroxamic acid product. MS (M+H)$^+$=532.

Example 134

(3S,4S)-1-[[(1,1-dimethylethyl)oxy]carbonyl]-N-hydroxy-3-[[[4-[(2-methyl-4-quinolinyl)methoxy]phenyl]carbonyl]amino]-4-piperidinecarboxamide trifluoroacetate (134a). A mixture of ethyl 1-benzyl-3-oxo-4-piperidinecarboxylate hydrochloride (50 g, 168 mmol), (BOC)$_2$O (50 g, 1.36 eq), Et$_3$N (35.2 mL, 1.5 eq), Pd(OH)$_2$ on C (10 g) and ethanol (400 mL) was hydrogenated at 50 psi overnight. Following removal of catalyst by filtration, the filtrate was concentrated, diluted with ethyl acetate (1 L), washed with 0.5 N HCl (300 mL), sat NaHCO$_3$ (150 mL), brine (100 mL), dried (MgSO$_4$) and concentrated in vacuo. Silica gel chromatography (ethyl acetate-hexane, 5:95 then 10:90) provided the desired product (39.0 g, 86%). MS (M+H)$^+$=272.

(134b–e) Following the procedures similar to that used for steps (112b–e), the intermediate from (134a) was converted to the desired amide. The material obtained through this route was 40% ee as determined by analytical chiral HPLC. The enantiomeric purity of the major enantiomer was improved to >99% ee using preparative chiral HPLC. The minor enantiomer was also collected. MS (M+H)$^+$=548.

(134f) Following the procedures similar to that used for step (100b), the major enantiomer from (134e) (100 mg, 0.180 mmol) was converted to the title compound. The product was purified by reverse phase HPLC on a Vydac C-18 semiprep column eluting an acetonitrile:water:TFA gradient, to give the desired hydroxamic acid product (83.5 mg, 72%). MS (M+H)$^+$=535.

Example 135

(3R,4S)-1-[[(1,1-dimethylethyl)oxy]carbonyl]-N-hydroxy-3-[[[4-[(2-methyl-4-quinolinyl)methoxy]phenyl]carbonyl]amino]-4-piperidinecarboxamide trifluoroacetate (135a–b) Following the procedures similar to that used for steps (101a–b), the minor enantiomer from (134e) was converted to the title compound. The product was purified by reverse phase HPLC on a Vydac C-18 semiprep column eluting an acetonitrile:water:TFA gradient, to give the hydroxamic acid product. MS (M+H)$^+$=535.

Example 136

(3R,4S)-N-hydroxy-3-[[[4-[(2-methyl-4-quinolinyl)methoxy]phenyl]carbonyl]amino]-4-piperidinecarboxamide bis(trifluoroacetate)

(136a) Following the procedure similar to that used for step (109a), the product from (135b) was converted to the title compound. MS (M+H)$^+$=435.

Example 137

(3S,4S)-N-hydroxy-3-[[[4-[(2-methyl-4-quinolinyl)methoxy]phenyl]carbonyl]amino]-4-piperidinecarboxamide bis(trifluoroacetate)

(137a) Following the procedure similar to that used for step (109a), the product from (134f) was converted to the title compound. MS (M+H)$^+$=435.

Example 138

(3S,4S)-N-hydroxy-1-[[(2-methylpropyl)oxy]carbonyl]-3-[[[4-[(2-methyl-4-quinolinyl)methoxy]phenyl]carbonyl]amino]-4-piperidinecarboxamide trifluoroacetate (138a) Following the procedure similar to that used for step (109a), the major enantiomer from (134e) (500 mg, 0.913 mmol) was converted to the desired amine bis-TFA salt (616 mg, 100%). MS (M+H)$^+$=448.

(138b–c) Following the procedures similar to that used for steps 116b and 100b, but with the amine from (138a) and isobutyl chloroformate in step (116b), the title compound was prepared. The product was purified by reverse phase HPLC on a Vydac C-18 semiprep column eluting an acetonitrile:water:TFA gradient, to give the hydroxamic acid product. MS (M+H)$^+$=535.

Example 139

(3S,4S)-N-hydroxy-1-(methoxycarbonyl)-3-[[[4-[(2-methyl-4-quinolinyl)methoxy]phenyl]carbonyl]amino]-4-piperidinecarboxamide trifluoroacetate (139a–b) Following the procedures similar to that used for steps 116b and 100b, but with the amine from (138a) and methyl chloroformate in step (116b), the title compound was prepared. The product was purified by reverse phase HPLC on a Vydac C-18 semiprep column eluting an acetonitrile:water:TFA gradient, to give the hydroxamic acid product. MS (M+H)$^+$=493.

Example 140

(3S,4S)-N-hydroxy-1-[(1-methylethoxy)carbonyl]-3-[[[4-[(2-methyl-4-quinolinyl)methoxy]phenyl]carbonyl]amino]-4-piperidinecarboxamide trifluoroacetate (140a–b) Following the procedures similar to that used for steps 116b and 100b, but with the amine from (138a) and isopropyl chloroformate in step (116b), the title compound was prepared. The product was purified by reverse phase HPLC on a Vydac C-18 semiprep column eluting an acetonitrile:water:TFA gradient, to give the hydroxamic acid product. MS (M+H)$^+$=521.

Example 141

(3S,4S)-N-hydroxy-1-(methylsulfonyl)-3-[[[4-[(2-methyl-4-quinolinyl)methoxy]phenyl]carbonyl]amino]-4-piperidinecarboxamide trifluoroacetate (141a–b) Following the procedures similar to that used for steps 116b and 100b, but with the amine from (138a) and methanesulfonyl chloride in step (116b), the title compound was prepared. The product was purified by reverse phase HPLC on a Vydac C-18 semiprep column eluting an acetonitrile:water:TFA gradient, to give the hydroxamic acid product. MS (M+H)$^+$=513.

Example 142

(3S,4S)-N-hydroxy-3-[[[4-[(2-methyl-4-quinolinyl)methoxy]phenyl]carbonyl]amino]-1-(phenylsulfonyl)-4-piperidinecarboxamide trifluoroacetate (142a–b) Following the procedures similar to that used for steps 116b and 100b, but with the amine from (138a) and benzenesulfonyl chloride in step (116b), the title compound was prepared. The product was purified by reverse phase HPLC on a Vydac C-18 semiprep column eluting an acetonitrile:water:TFA gradient, to give the hydroxamic acid product. MS (M+H)$^+$=575.

Example 147

(3S,4S)-1-(3,3-dimethylbutanoyl)-N-hydroxy-3-[[[4-[(2-methyl-4-quinolinyl)methoxy]phenyl]carbonyl]amino]-4-piperidinecarboxamide trifluoroacetate (147a–b) Following the procedures similar to that used for steps 116b and 100b, but with the amine from (138a) and t-butylacetyl chloride in step (116b), the title compound was prepared. The product was purified by reverse phase HPLC on a Vydac C-18 semiprep column eluting an acetonitrile:water:TFA gradient, to give the hydroxamic acid product. MS (M+H)$^+$=533.

Example 148

(3S,4S)-1-(2,2-dimethylpropionyl)-N-hydroxy-3-[[[4-[(2-methyl-4-quinolinyl)methoxy]phenyl]carbonyl]amino]-4-piperidinecarboxamide trifluoroacetate (148a–b) Following the procedures similar to that used for steps 116b and 100b, but with the amine from (138a) and trimethylacetyl chloride in step (116b), the title compound was prepared. The product was purified by reverse phase HPLC on a Vydac C-18 semiprep column eluting an acetonitrile:water:TFA gradient, to give the hydroxamic acid product. MS (M+H)$^+$=519.

Example 149

(3S,4S)-1-benzoyl-N-hydroxy-3-[[[4-[(2-methyl-4-quinolinyl)methoxy]phenyl]carbonyl]amino]-4-piperidinecarboxamide trifluoroacetate (149a–b) Following the procedures similar to that used for steps 116b and 100b, but with the amine from (138a) and benzoyl chloride in step (116b), the title compound was prepared. The product was purified by reverse phase HPLC on a Vydac C-18 semiprep column eluting an acetonitrile:water:TFA gradient, to give the hydroxamic acid product. MS (M+H)$^+$=539.

Example 150

(3S,4S)-1-[(pyridin-3-yl)carbonyl]-N-hydroxy-3-[[[4-[(2-methyl-4-quinolinyl)methoxy]phenyl]carbonyl]amino]-4-piperidinecarboxamide bis(trifluoroacetate)

(150a–b) Following the procedures similar to that used for steps 116b and 100b, but with the amine from (138a) and nicotinoyl chloride in step (116b), the title compound was prepared. The product was purified by reverse phase HPLC on a Vydac C-18 semiprep column eluting an acetonitrile:water:TFA gradient, to give the hydroxamic acid product. MS (M+H)$^+$=540.

Example 151

(3S,4S)-N-hydroxy-3-[[[4-[(2-methyl-4-quinolinyl)methoxy]phenyl]carbonyl]amino]-1-(2-thiophenecarbonyl)-4-piperidinecarboxamide trifluoroacetate (151a–b) Following the procedures similar to that used for steps 116b and 100b, but with the amine from (138a) and 2-thiophenecarbonyl chloride in step (116b), the title compound was prepared. The product was purified by reverse phase HPLC on a Vydac C-18 semiprep column eluting an acetonitrile:water:TFA gradient, to give the hydroxamic acid product. MS (M+H)$^+$=545.

Example 152

(3S,4S)-1-(dimethylcarbamyl)-N-hydroxy-3-[[[4-[(2-methyl-4-quinolinyl)methoxy]phenyl]carbonyl]amino]-4-piperidinecarboxamide trifluoroacetate (152a–b) Following the procedures similar to that used for steps 116b and 100b, but with the amine from (138a) and dimethylcarbamyl chloride in step (116b), the title compound was prepared. The product was purified by reverse phase HPLC on a Vydac C-18 semiprep column eluting an acetonitrile:water:TFA gradient, to give the hydroxamic acid product. MS (M+H)$^+$=506.

Example 153

(3S,4S)-N-hydroxy-3-[[[4-[(2-methyl-4-quinolinyl)methoxy]phenyl]carbonyl]amino]-1-(4-morpholinecarbonyl)-4-piperidinecarboxamide trifluoroacetate (153a–b) Following the procedures similar to that used for steps 116b and 100b, but with the amine from (138a) and 4-morpholinecarbonyl chloride in step (116b), the title compound was prepared. The product was purified by reverse phase HPLC on a Vydac C-18 semiprep column eluting an acetonitrile:water:TFA gradient, to give the hydroxamic acid product. MS (M+H)$^+$=548.

Example 154

(3S,4S)-N-hydroxy-3-[[[4-[(2-methyl-4-quinolinyl)methoxy]phenyl]carbonyl]amino]-1-[[2-(2-thienyl)ethyl]carbamyl]-4-piperidinecarboxamide trifluoroacetate (154a–b) Following the procedures similar to that used for steps 116b and 100b, but with the amine from (138a) and 2-(thien-2-yl)ethyl isocyanate in step (116b), the title compound was prepared. The product was purified by reverse phase HPLC on a Vydac C-18 semiprep column eluting an acetonitrile:water:TFA gradient, to give the hydroxamic acid product. MS (M+H)$^+$=588.

Example 155

(3S,4S)-1-[(1,1-dimethylethyl)carbamyl]-N-hydroxy-3-[[[4-[(2-methyl-4-quinolinyl)methoxy]phenyl]carbonyl]amino]-4-piperidinecarboxamide trifluoroacetate (155a–b) Following the procedures similar to that used for steps 116b and 100b, but with the amine from (138a) and t-butyl isocyanate in step (116b), the title compound was prepared. The product was purified by reverse phase HPLC on a Vydac C-18 semiprep column eluting an acetonitrile:water:TFA gradient, to give the hydroxamic acid product. MS (M+H)$^+$=534.

Example 156

(3S,4S)-N-hydroxy-1-methyl-3-[[[4-[(2-methyl-4-quinolinyl)methoxy]phenyl]carbonyl]amino]-4-piperidinecarboxamide bis(trifluoroacetate)

(156a–b) Following the procedures similar to that used for steps 126a and 100b, but with the amine from (138a) and para-formaldehyde in step (126a), the title compound was prepared. The product was purified by reverse phase HPLC on a Vydac C-18 semiprep column eluting an acetonitrile:water:TFA gradient, to give the hydroxamic acid product. MS (M+H)$^+$=449.

Example 157

(3S,4S)-1-ethyl-N-hydroxy-3-[[[4-[(2-methyl-4-quinolinyl)methoxy]phenyl]carbonyl]amino]-4-piperidinecarboxamide bis(trifluoroacetate)

(157a–b) Following the procedures similar to that used for steps 126a and 100b, but with the amine from (138a) and acetaldehyde in step (126a), the title compound was prepared. The product was purified by reverse phase HPLC on a Vydac C-18 semiprep column eluting an acetonitrile:water:TFA gradient, to give the hydroxamic acid product. MS (M+H)$^+$=463.

Example 158

(3S,4S)-N-hydroxy-3-[[[4-[(2-methyl-4-quinolinyl)methoxy]phenyl]carbonyl]amino]-1-propyl-4-piperidinecarboxamide bis(trifluoroacetate)

(158a–b) Following the procedures similar to that used for steps 126a and 100b, but with the amine from (138a) and propionaldehyde in step (126a), the title compound was prepared. The product was purified by reverse phase HPLC on a Vydac C-18 semiprep column eluting an acetonitrile:water:TFA gradient, to give the hydroxamic acid product. MS (M+H)$^+$=477.

Example 159

(3S,4S)-N-hydroxy-1-(1-methylethyl)-3-[[[4-[(2-methyl-4-quinolinyl)methoxy]phenyl]carbonyl]amino]-4-piperidinecarboxamide bis(trifluoroacetate)

(159a–b) Following the procedures similar to that used for steps 126a and 100b, but with the amine from (138a) and acetone in step (126a), the title compound was prepared. The product was purified by reverse phase HPLC on a Vydac C-18 semiprep column eluting an acetonitrile:water:TFA gradient, to give the hydroxamic acid product. MS (M+H)$^+$=477.

Example 160

(3S,4S)-1-cyclobutyl-N-hydroxy-3-[[[4-[(2-methyl-4-quinolinyl)methoxy]phenyl]carbonyl]amino]-4-piperidinecarboxamide bis(trifluoroacetate)

(160a–b) Following the procedures similar to that used for steps 126a and 100b, but with the amine from (138a) and cyclobutanone in step (126a), the title compound was prepared. The product was purified by reverse phase HPLC on a Vydac C-18 semiprep column eluting an acetonitrile:water:TFA gradient, to give the hydroxamic acid product. MS (M+H)$^+$=489.

Example 161

(3S,4S)-1-butyl-N-hydroxy-3-[[[4-[(2-methyl-4-quinolinyl)methoxy]phenyl]carbonyl]amino]-4-piperidinecarboxamide bis(trifluoroacetate)

(161a–b) Following the procedures similar to that used for steps 126a and 100b, but with the amine from (138a) and butyraldehyde in step (126a), the title compound was prepared. The product was purified by reverse phase HPLC on a Vydac C-18 semiprep column eluting an acetonitrile:water:TFA gradient, to give the hydroxamic acid product. MS (M+H)$^+$=491.

Example 162

(3S,4S)-N-hydroxy-3-[[[4-[(2-methyl-4-quinolinyl)methoxy]phenyl]carbonyl]amino]-1-(2-methylpropyl)-4-piperidinecarboxamide bis(trifluoroacetate)

(162a–b) Following the procedures similar to that used for steps 126a and 100b, but with the amine from (138a) and isobutyraldehyde in step (126a), the title compound was prepared. The product was purified by reverse phase HPLC on a Vydac C-18 semiprep column eluting an acetonitrile:water:TFA gradient, to give the hydroxamic acid product. MS (M+H)$^+$=491.

Example 163

(3S,4S)-1-(cyclopropylmethyl)-N-hydroxy-3-[[[4-[(2-methyl-4-quinolinyl)methoxy]phenyl]carbonyl]amino]-4-piperidinecarboxamide bis(trifluoroacetate)

(163a–b) Following the procedures similar to that used for steps 126a and 100b, but with the amine from (138a) and cyclopropanecarboxaldehyde in step (126a), the title compound was prepared. The product was purified by reverse phase HPLC on a Vydac C-18 semiprep column eluting an acetonitrile:water:TFA gradient, to give the hydroxamic acid product. MS (M+H)$^+$=489.

Example 164

(3S,4S)-1-(2,2-dimethylpropyl)-N-hydroxy-3-[[[4-[(2-methyl-4-quinolinyl)methoxy]phenyl]carbonyl]amino]-4-piperidinecarboxamide bis(trifluoroacetate)

(164a–b) Following the procedures similar to that used for steps 126a and 100b, but with the amine from (138a) and trimethylacetaldehyde in step (126a), the title compound was prepared. The product was purified by reverse phase HPLC on a Vydac C-18 semiprep column eluting an acetonitrile:water:TFA gradient, to give the hydroxamic acid product. MS (M+H)$^+$=505.

Example 165

(3S,4S)-1-cyclopentyl-N-hydroxy-3-[[[4-[(2-methyl-4-quinolinyl)methoxy]phenyl]carbonyl]amino]-4-piperidinecarboxamide bis(trifluoroacetate)

(165a–b) Following the procedures similar to that used for steps 126a and 100b, but with the amine from (138a) and cyclopentanone in step (126a), the title compound was prepared. The product was purified by reverse phase HPLC on a Vydac C-18 semiprep column eluting an acetonitrile:water:TFA gradient, to give the hydroxamic acid product. MS (M+H)$^+$=503.

Example 166

(3S,4S)-N-hydroxy-3-[[[4-[(2-methyl-4-quinolinyl) methoxy]phenyl]carbonyl]amino]-1-(4-tetrahydropyranyl)-4-piperidinecarboxamide bis (trifluoroacetate)

(166a–b) Following the procedures similar to that used for steps 126a and 100b, but with the amine from (138a) and tetrahydro-4H-pyran-4-one in step (126a), the title compound was prepared. The product was purified by reverse phase HPLC on a Vydac C-18 semiprep column eluting an acetonitrile:water:TFA gradient, to give the hydroxamic acid product. MS (M+H)$^+$=519.

Example 167

(3S,4S)-1-benzyl-N-hydroxy-3-[[[4-[(2-methyl-4-quinolinyl)methoxy]phenyl]carbonyl]amino]-4-piperidinecarboxamide bis(trifluoroacetate)

(167a–b) Following the procedures similar to that used for steps 126a and 100b, but with the amine from (138a) and benzaldehyde in step (126a), the title compound was prepared. The product was purified by reverse phase HPLC on a Vydac C-18 semiprep column eluting an acetonitrile:water:TFA gradient, to give the hydroxamic acid product. MS (M+H)$^+$=525.

Example 168

(3S,4S)-N-hydroxy-3-[[[4-[(2-methyl-4-quinolinyl) methoxy]phenyl]carbonyl]amino]-1-(2-thiazolylmethyl)-4-piperidinecarboxamide bis (trifluoroacetate)

(168a–b) Following the procedures similar to that used for steps 126a and 100b, but with the amine from (138a) and 2-thiazolecarboxaldehyde in step (126a), the title compound was prepared. The product was purified by reverse phase HPLC on a Vydac C-18 semiprep column eluting an acetonitrile:water:TFA gradient, to give the hydroxamic acid product. MS (M+H)$^+$=532.

Example 169

(3S,4S)-N-hydroxy-3-[[[4-[(2-methyl-4-quinolinyl) methoxy]phenyl]carbonyl]amino]-1-(4-pyridinylmethyl)-4-piperidinecarboxamide bis (trifluoroacetate)

(169a–b) Following the procedures similar to that used for steps 126a and 100b, but with the amine from (138a) and 4-pyridinecarboxaldehyde in step (126a), the title compound was prepared. The product was purified by reverse phase HPLC on a Vydac C-18 semiprep column eluting an acetonitrile:water:TFA gradient, to give the hydroxamic acid product. MS (M+H)$^+$=526.

Example 170

(3S,4S)-N-hydroxy-3-[[[4-[(2-methyl-4-quinolinyl) methoxy]phenyl]carbonyl]amino]-1-(2-pyridinylmethyl)-4-piperidinecarboxamide bis (trifluoroacetate)

(170a–b) Following the procedures similar to that used for steps 126a and 100b, but with the amine from (138a) and 2-pyridinecarboxaldehyde in step (126a), the title compound was prepared. The product was purified by reverse phase HPLC on a Vydac C-18 semiprep column eluting an acetonitrile:water:TFA gradient, to give the hydroxamic acid product. MS (M+H)$^+$=526.

Example 171

(3S,4S)-N-hydroxy-3-[[[4-[(2-methyl-4-quinolinyl) methoxy]phenyl]carbonyl]amino]-1-(3-pyridinylmethyl)-4-piperidinecarboxamide bis (trifluoroacetate)

(171a–b) Following the procedures similar to that used for steps 126a and 100b, but with the amine from (138a) and 3-pyridinecarboxaldehyde in step (126a), the title compound was prepared. The product was purified by reverse phase HPLC on a Vydac C-18 semiprep column eluting an acetonitrile:water:TFA gradient, to give the hydroxamic acid product. MS (M+H)$^+$=526.

Example 172

(3S,4S)-N-hydroxy-3-[[[4-[(2-methyl-4-quinolinyl) methoxy]phenyl]carbonyl]amino]-1-(trans-3-phenyl-2-propenyl)-4-piperidinecarboxamide bis (trifluoroacetate)

(172a–b) Following the procedures similar to that used for steps 126a and 100b, but with the amine from (138a) and trans-cinnamaldehyde in step (126a), the title compound was prepared. The product was purified by reverse phase HPLC on a Vydac C-18 semiprep column eluting an acetonitrile:water:TFA gradient, to give the hydroxamic acid product. MS (M+H)$^+$=551.

Example 173

(3S,4S)-N-hydroxy-3-[[[4-[(2-methyl-4-quinolinyl) methoxy]phenyl]carbonyl]amino]-1-phenyl-4-piperidinecarboxamide bis(trifluoroacetate)

(173a) A mixture of the amine from (138a) (100 mg, 0.223 mmol, free base), benzeneboronic acid (54.5 mg, 2 eq), copper(II) acetate monohydrate (133.8 mg, 3 eq), pyridine (0.054 mL, 3 eq), 4 A molecular sieve (165 mg) and CH$_2$Cl$_2$ (2 mL) were stirred overnight with the flask open to the atmosphere. The mixture was filtered and the filtrate concentrated in vacuo. Silica gel chromatography (ethyl acetate-hexane, 60:40 then 70:30) provided the desired product (94 mg, 80%). MS (M+H)$^+$=524.

(173b) Following the procedures similar to that used for step (100b), the intermediate from (173a) (94 mg, 0.180 mmol) was converted to the title compound. The product was purified by reverse phase HPLC-on a Vydac C-18 semiprep column eluting an acetonitrile:water:TFA gradient, to give the desired hydroxamic acid (74 mg, 56%). MS (M+H)$^+$=511.

Example 174

(3R, 4S)-1-(2,2-dimethylpropionyl)-N-hydroxy-3-[[[4-[(2-methyl-4-quinolinyl)methoxy]phenyl] carbonyl]amino]-4-piperidinecarboxamide trifluoroacetate (174a–b) Following the procedures similar to that used for steps 101a and 109a, the minor enantiomer from (134e)

was epimerized with DBU and deprotected. The product was purified by reverse phase HPLC on a Vydac C-18 semiprep column eluting an acetonitrile:water:TFA gradient, to give the trans isomer. MS (M+H)$^+$=448.

(174c–d) Following the procedures similar to that used for steps 116b and 100b, but with the amine from (174b) and trimethylacetyl chloride in step (116b), the title compound was prepared. The product was purified by reverse phase HPLC on a Vydac C-18 semiprep column eluting an acetonitrile:water:TFA gradient, to give the desired hydroxamic acid. MS (M+H)$^+$=519.

Example 175

(3R,4S)-N-hydroxy-3-[[[4-[(2-methyl-4-quinolinyl)methoxy]phenyl]carbonyl]amino]-1-methyl-4-piperidinecarboxamide bis(trifluoroacetate)

(175a–b) Following the procedures similar to that used for steps 126a and 100b, but with the amine from (174b) and para-formaldehyde in step (126a), the title compound was prepared. The product was purified by reverse phase HPLC on a Vydac C-18 semiprep column eluting an acetonitrile:water:TFA gradient, to give the hydroxamic acid product. MS (M+H)$^+$=449.

Example 176

(3R,4S)-1-(dimethylcarbamyl)-N-hydroxy-3-[[[4-[(2-methyl-4-quinolinyl)methoxy]phenyl]carbonyl]amino]-4-piperidinecarboxamide trifluoroacetate (176a–b) Following the procedures similar to that used for steps 116b and 100b, but with the amine from (174b) and dimethylcarbamyl chloride in step (116b), the title compound was prepared. The product was purified by reverse phase HPLC on a Vydac C-18 semiprep column eluting an acetonitrile:water:TFA gradient, to give the hydroxamic acid product. MS (M+H)$^+$=506.

Example 177

(3S,4S)-1-hexyl-N-hydroxy-3-[[[4-[(2-methyl-4-quinolinyl)methoxy]phenyl]carbonyl]amino]-4-piperidinecarboxamide bis(trifluoroacetate)

(177a–b) Following the procedures similar to that used for steps 126a and 100b, but using the amine from (138a) and hexanal in step (126a), the title compound was prepared. The product was purified by reverse phase HPLC on a Vydac C-18 semiprep column eluting an acetonitrile:water:TFA gradient, to give the hydroxamic acid product. MS (M+H)$^+$=519.

Example 178

(3S,4S)-1-(2-fluoroethyl)-N-hydroxy-3-[[[4-[(2-methyl-4-quinolinyl)methoxy]phenyl]carbonyl]amino]-4-piperidinecarboxamide bis(trifluoroacetate)

(178a) A mixture of the amine from (138a) (800 mg, 1.20 mmol), 1-bromo-2-fluoroehtane (0.27 mL), 3 eq), K$_2$CO$_3$ (1.20 g, 10 eq) and NaI (580 mg, 3 eq) in acetone (20 mL) was heated to reflux for 6 h, cooled to rt and filtered. The filtrate was concentrated and purified by silica gel chromatography (methanol-dichloromethane, 5:95) to give the desired product (450 mg, 76%). MS (M+H)$^+$=538.

(178b) Following the procedures similar to that used for step (100b), the intermediate from (178a) (350 mg, 0.710 mmol) was converted to the title compound. The product was purified by reverse phase HPLC on a Vydac C-18 semiprep column eluting an acetonitrile:water:TFA gradient, to give the desired hydroxamic acid (170 mg, 34%). MS (M+H)$^+$=481.

Example 179

(3S,4S)-1-(2,2-difluoroethyl)-N-hydroxy-3-[[[4-[(2-methyl-4-quinolinyl)methoxy]phenyl]carbonyl]amino]-4-piperidinecarboxamide bis(trifluoroacetate)

(179a–b) Following the procedures similar to that used for steps (178a and 100b), but the amine from (138a) and 2-bromo-1,1-difluoroethane in step (178a), the title compound was prepared. The product was purified by reverse phase HPLC on a Vydac C-18 semiprep column eluting an acetonitrile:water:TFA gradient, to give the hydroxamic acid product. MS (M+H)$^+$=499.

Example 180

(3S,4S)-N-hydroxy-1-(1-methylpropyl)-3-[[[4-[(2-methyl-4-quinolinyl)methoxy]phenyl]carbonyl]amino]-4-piperidinecarboxamide bis(trifluoroacetate)

(180a–b) Following the procedures similar to that used for steps (126a and 100b), but using the amine from (138a) and 2-butanone in step (126a), the title compound was prepared. The product was purified by reverse phase HPLC on a Vydac C-18 semiprep column eluting an acetonitrile:water:TFA gradient, to give the hydroxamic acid product. MS (M+H)$^+$=491.

Example 181

(3S,4S)-1-(1-ethylpropyl)-N-hydroxy-3-[[[4-[(2-methyl-4-quinolinyl)methoxy]phenyl]carbonyl]amino]-4-piperidinecarboxamide bis(trifluoroacetate)

(181a–b) Following the procedures similar to that used for steps (126a and 100b), but using the amine from (138a) and 3-pentanone in step (126a), the title compound was prepared. The product was purified by reverse phase HPLC on a Vydac C-18 semiprep column eluting an acetonitrile:water:TFA gradient, to give the hydroxamic acid product. MS (M+H)$^+$=505.

Example 182

(3S,4S)-1-[1-[[(1,1-dimethylethyl)oxy]carbonyl]-4-tetrahydropiperidinyl]-N-hydroxy-3-[[[4-[(2-methyl-4-quinolinyl)methoxy]phenyl]carbonyl]amino]-4-piperidinecarboxamide bis(trifluoroacetate)

(182a–b) Following the procedures similar to that used for steps (126a and 100b), but using the amine from (138a) and Boc-4-piperidone in step (126a), the title compound was prepared. The product was purified by reverse phase HPLC on a Vydac C-18 semiprep column eluting an acetonitrile:water:TFA gradient, to give the hydroxamic acid product. MS (M+H)$^+$=618.

Example 183

(3S,4S)-N-hydroxy-3-[[[4-[(2-methyl-4-quinolinyl)methoxy]phenyl]carbonyl]amino]-1-(4-tetrahydropiperidinyl)-4-piperidinecarboxamide tris(trifluoroacetate)

(183a) Following the procedure similar to that used for step (109a), the product from (182b) was converted to the title compound. MS (M+H)$^+$=518.

Example 184

(3S,4S)-1-[1-[[(1,1-dimethylethyl)oxy]carbonyl]-3-tetrahydropyrrolidinyl]-N-hydroxy-3-[[[4-[(2-methyl-4-quinolinyl)methoxy]phenyl]carbonyl]amino]-4-piperidinecarboxamide bis (trifluoroacetate)

(184a–b) Following the procedures similar to that used for steps (126a and 100b), but using the amine from (138a) and N-Boc-3-pyrrolidinone in step (126a), the title compound was prepared. The product was purified by reverse phase HPLC on a Vydac C-18 semiprep column eluting an acetonitrile:water:TFA gradient, to give the hydroxamic acid product. MS (M+H)$^+$=604.

Example 185

(3S,4S)-N-hydroxy-3-[[[4-[(2-methyl-4-quinolinyl)methoxy]phenyl]carbonyl]amino]-1-(3-tetrahydropyrrolidinyl)-4-piperidinecarboxamide tris (trifluoroacetate)

(185a) Following the procedure similar to that used for step (109a), the product from (184b) was converted to the title compound. MS (M+H)$^+$=505.

Example 186

(3S,4S)-1-(1,1-dimethyl-2-propynyl)-N-hydroxy-3-[[[4-[(2-methyl-4-quinolinyl)methoxy]phenyl]carbonyl]amino]-4-piperidinecarboxamide bis (trifluoroacetate)

(186a) A solution of 3-chloro-3-methyl-1-butyne (0.51 ml, 1 eq) in dichloromethane (2 mL) was added dropwise to a mixture of the amine from (138a) (2.00 g, 4.47 mmol), CuCl (1 mg), Cu (1 mg), Et$_3$N (1.30 mL, 2 eq), water (15 mL) and dichloromethane (30 mL). After stirring under N$_2$ for 4 days, the mixture was diluted with dichloromethane and water. The organic phase was separated and purified by silica gel chromatography (methanol-dichloromethane, 5:95) to give the desired product (1.76 g, 76%). MS (M+H)$^+$=514.

(186b) Following the procedures similar to that used for step (100b), the intermediate from (186a) (200 mg, 0.389 mmol) was converted to the title compound. The product was purified by reverse phase HPLC on a Vydac C-18 semiprep column eluting an acetonitrile:water:TFA gradient, to give the desired hydroxamic acid (95 mg, 33%). MS (M+H)$^+$=501.

Example 187

(3S,4S)-N-hydroxy-3-[[[4-[(2-methyl-4-quinolinyl)methoxy]phenyl]carbonyl]amino]-1-(3-thiophenylmethyl)-4-piperidinecarboxamide bis (trifluoroacetate)

(187a–b) Following the procedures similar to that used for steps (126a and 100b), but using the amine from (138a) and 3-thiophenecarboxaldehyde in step (126a), the title compound was prepared. The product was purified by reverse phase HPLC on a Vydac C-18 semiprep column eluting an acetonitrile:water:TFA gradient, to give the hydroxamic acid product. MS (M+H)$^+$=531.

Example 188

(3S,4S)-N-hydroxy-1-(1-methylethyl)-3-[[[4-[(2-methyl-4-quinolinyl)methoxy]phenyl]carbonyl]amino]-1-oxo-4-piperidinecarboxamide trifluoroacetate (188a) Following the procedures similar to that used for steps (126a), but using the amine from (138a) (4.00 g, 5.92 mmol) and acetone, the title compound was prepared. Silica gel chromatography (methanol-dichloromethane, 5:95 then 7:93) gave the desired product (2.36 g, 81%). MS (M+H)$^+$=490.

(188b) m-CPBA (102 mg, 1 eq, 55% pure) was added to a solution of the tert-amine from (188a) (160 mg, 0.327 mmol) in dichloromethane (4 mL). After 30 min at rt, the mixture was treated with saturated NaHSO$_3$ (1.5 mL) and saturated NaHCO$_3$ (1.5 mL), and immediately extracted with ethyl acetate. The extracts were washed with brine, dried and concentrated (MgSO$_4$). Silica gel chromatography (methanol-dichloromethane, 5:95 then 10:90) gave the tertiary amine N-oxide (140 mg, 85%). MS (M+H)$^+$=506.

(188c) Following the procedures similar to that used for step (100b), the intermediate from (188b) (30 mg, 0.059 mmol) was converted to the title compound. The product was purified by reverse phase HPLC on a Vydac C-18 semiprep column eluting an acetonitrile:water:TFA gradient, to give the desired hydroxamic acid (25 mg, 69%). MS (M+H)$^+$=493.

Example 189

(3S,4S)-N-hydroxy-1-(1-methylethyl)-3-[[[4-[(2-methyl-1-oxo-4-quinolinyl)methoxy]phenyl]carbonyl]amino]-4-piperidinecarboxamide trifluoroacetate (189a) The momo-N-oxide from (188b) (110 mg, 0.218 mmol) was dissolved in dichloromethane. (2 mL) and treated with m-CPBA (68.3 mg, 1 eq, 55% pure) for 30 min. TLC showed clean conversion to the bis-N-oxide product. The mixture was treated with saturated NaHSO$_3$ (1.5 mL) and saturated NaHCO$_3$ (1.5 mL), and extracted with ethyl acetate. The NaHSO$_3$ treatment resulted in partial reduction of the tertiary amine N-oxide and therefore gave a mixture of bis-N-oxide and quinoline mono-N-oxide. The extracts were washed with brine, dried and concentrated (MgSO$_4$). Silica gel chromatography (methanol-dichloromethane, 5:95 then 8:92 then 10:90 then 15:85) gave the mono-N-oxide at the quinoline nitrogen (50 mg, 44%) and bis-N-oxide (40 mg, 35%). MS for mono-N-oxide (M+H)$^+$=506, for bis-N-oxide (M+H)$^+$=522.

(189b) Following the procedures similar to that used for step (100b), the mono-N-oxide from (189a) (48 mg, 0.095 mmol) was converted to the title compound. The product was purified by reverse phase HPLC on a Vydac C-18 semiprep column eluting an acetonitrile:water:TFA gradient, to give the desired hydroxamic acid (30 mg, 52%). MS (M+H)$^+$=493.

Example 190

(3S,4S)-N-hydroxy-1-(1-methylethyl)-3-[[[4-[(2-methyl-1-oxo-4-quinolinyl)methoxy]phenyl]carbonyl]amino]-1-oxo-4-piperidinecarboxamide (190a) Following the procedures similar to that used for step (100b), the bis-N-oxide from (189a) (38 mg, 0.073 mmol) was converted to the title compound. The product was purified by reverse phase HPLC on a Vydac C-18 semiprep column eluting an acetonitrile:water:TFA gradient, to give the desired hydroxamic acid (23 mg, 62%). MS (M+H)$^+$=509.

Example 191

(3S,4S)-N-hydroxy-3-[[[4-[(2-methyl-4-quinolinyl)methoxy]phenyl]carbonyl]amino]-1-[2-(4-morpholinyl)-2-oxoethyl]-4-piperidinecarboxamide bis(trifluoroacetate)

(191a) A mixture of the amine from (138a) (2.00 g, 2.96 mmol), t-butyl bromoacetate (1.15 g, 2 eq), Cs2CO3 (4.82 g, 5 eq) and DMSO (25 mL) was stirred at rt for 1 h. Following addition of sat NH$_4$Cl (15 mL) and ethyl acetate (200 mL), the mixture was washed with water (2×10 mL), brine (10 mL), dried (MgSO$_4$) and concentrated. Silica gel chromatography (ethyl acetate) provided the desired product (1.40 g, 80%). MS (M+H)$^+$=562.

(191b) The t-butyl eater from (191a) (1.20 g, 2.14 mmol) was treated with TFA (5 mL) in dichloromethane (5 mL) for 3 h and concentrated to give the desired carboxylic acid (1.70 g, 100%). MS (M+H)$^+$=506.

(191c) Following the procedure similar to that used for steps (100a), The acid from (191b) (300 mg, 0.378 mmol) was coupled with morpholine. Silica gel chromatography (methanol-dichloromethane, 5:95) gave the desired amide (130 mg, 59%). MS (M+H)$^+$=575.

(191d) Following the procedures similar to that used for step (100b), the product from (191c) (130 mg, 0.223 mmol) was converted to the title compound. The product was purified by reverse phase HPLC on a Vydac C-18 semi-prep column eluting an acetonitrile:water:TFA gradient, to give the desired hydroxamic acid (70 mg, 53%). MS (M+H)$^+$=562.

Example 192

(3S,4S)-1-[2-(N,N-dimethylamino)-2-oxoethyl]-N-hydroxy-3-[[[4-[(2-methyl-4-quinolinyl)methoxy]phenyl]carbonyl]amino]-4-piperidinecarboxamide bis(trifluoroacetate)

(192a–b) Following the procedures similar to that used for steps (100a–b), but using the acid from (191b) and dimethylamine in step (100a), the title compound was prepared. The product was purified by reverse phase HPLC on a Vydac C-18 semiprep column eluting an acetonitrile:water:TFA gradient, to give the hydroxamic acid product. MS (M+H)$^+$=520.

Example 193

(3S,4S)-1-(t-butylsulfonyl)-N-hydroxy-3-[[[4-[(2-methyl-4-quinolinyl)methoxy]phenyl]carbonyl]amino]-4-piperidinecarboxamide trifluoroacetate (193a) A precooled solution (0° C.) of t-Butylsulfinyl chloride (210 mg, 2 eq) in dichloromethane (10 mL) was added dropwise to a solution of triethylamine (1.03 mL, 10 eq) and the amine from (138a) (500 mg, 0.74 mmol) in dichloromethane (10 mL) at 0° C. After 1 h at 0° C., the mixture was quenched with sat NaHCO$_3$ and extracted with dichloromethane. The extracts were dried (MgSO$_4$) and concentrated. Silica gel chromatography (methanol-dichloromethane, 5:95) gave the desired sulfinamide (400 mg, 98%) as a 1:1 mixture epimeric at sulfur center. MS (M+H)$^+$=552.

(193b) Ruthenium(III) chloride monohydrate (0.4 mg) and NaIO$_4$ (46 mg, 1.2 eq) were added to a mixture of the sulfinamide from (193a) (100 mg, 0.180 mmol), dichloromethane (2 mL), acetonitrile (2 mL) and water (3 mL) at 0° C. After 1 h at 0° C., the mixture was extracted with dichloromethane. The combined extracts were dried (MgSO$_4$) and concentrated to give the desired sulfonamide as a crude material. MS (M+H)$^+$=568.

(193c) Following the procedures similar to that used for step (100b), the crude product from (193b) was converted to the title compound. The product was purified by reverse phase HPLC on a Vydac C-18 semiprep column eluting an acetonitrile:water:TFA gradient, to give the desired hydroxamic acid (47 mg, 39% for two steps). MS (M+H)$^+$=555.

Example 194

(3S,4S)-1-(t-butylsulfonyl)-N-hydroxy-3-[[[4-[(2-methyl-1-oxo-4-quinolinyl)methoxy]phenyl]carbonyl]amino]-4-piperidinecarboxamide (194a) Following a procedure similar to that used for step (189a), the sulfinamide from (193a) (220 mg, 0.400 mmol) was oxidized to the sulfonamide quinoline N-oxide (250 mg crude weight). MS (M+H)$^+$=584.

(194b) Following the procedures similar to that used for step (100b), the crude product from (194a) (100 mg) was converted to the title compound. The product was purified by reverse phase HPLC on a Vydac C-18 semiprep column eluting an acetonitrile:water:TFA gradient, to give the desired hydroxamic acid (64 mg, 65% for two steps). MS (M+H)$^+$=571.

Example 195

(3S,4S)-1-(benzenesulfonyl)-N-hydroxy-3-[[[4-[(2-methyl-4-quinolinyl)methoxy]phenyl]carbonyl]amino]-4-piperidinecarboxamide trifluoroacetate (195a–b) Following the procedures similar to that used for steps (116b and 100b), but using the amine from (138a) and benzenesulfonyl chloride in step (116b), the title compound was prepared. The product was purified by reverse phase HPLC on a Vydac C-18 semiprep column eluting an acetonitrile:water:TFA gradient, to give the hydroxamic acid product. MS (M+H)$^+$=575.

Example 196

(3S,4S)-1-(t-butylsulfinyl)-N-hydroxy-3-[[[4-[(2-methyl-4-quinolinyl)methoxy]phenyl]carbonyl]amino]-4-piperidinecarboxamide trifluoroacetate (196a) Following the procedures similar to that used for step (100b), the 1:1 mixture of sulfinamide from (193a) was converted to the title compound. The two isomers were separated by reverse phase HPLC on a Vydac C-18 semiprep column eluting an acetonitrile:water:TFA gradient, to give the desired hydroxamic acids. MS (M+H)$^+$=539.

Example 197

(3S,4S)-N-hydroxy-1-(2-hydroxylethyl)-3-[[[4-[(2-methyl-4-quinolinyl)methoxy]phenyl]carbonyl]amino]-4-piperidinecarboxamide bis (trifluoroacetate)

(197a) Following the procedure similar to that used for step (126a), the amine from (138a) (225 mg, 0.333 mmol) was reacted with (t-butyldimethylsilyloxy)acetaldehyde via reductive amination. Silica gel chromatography (ethyl acetate-hexane, 30:70, then methanol-dichloromethane, 5:95) gave the desired product (150 mg, 74%) MS (M+H)$^+$=606.

(197b) A 1 M THF solution of TBAF (0.50 mL, 2 eq) was added to the product from (197a) (150 mg, 0.248 mmol) in THF (6 mL). The mixture was stirred for 30 min, diluted with sat NH$_4$Cl (5 mL) and ethyl acetate (100 mL), washed with water (5 mL), brine (5 mL), dried (MgSO$_4$) and concentrated. Silica gel chromatography (methanol-dichloromethane, 5:95) gave the desired alcohol (100 mg, 82%). MS (M+H)$^+$=492.

(197c) Following the procedures similar to that used for step (100b), the product from (197b) (100 mg, 0.203 mmol) was converted to the title compound. Purification by reverse phase HPLC on a Vydac C-18 semiprep column eluting an acetonitrile:water:TFA gradient, gave the desired hydroxamic acid (35 mg, 24%). MS (M+H)$^+$=479.

Example 198

(3S,4S)-1-[2-[[[(1,1-dimethylethyl)oxy]carbonyl]amino]ethyl]-N-hydroxy-3-[[[4-[(2-methyl-4-quinolinyl)methoxy]phenyl]carbonyl]amino]-4-piperidinecarboxamide bis(trifluoroacetate)

(198a) Following the procedure similar to that used for step (126a), the amine from (138a) (200 mg, 0.296 mmol) was reacted with t-butyl N-(2-oxoethyl)carbamate via reductive amination. Silica gel chromatography (methanol-dichloromethane, 5:95) gave the desired product (150 mg, 86%). MS (M+H)$^+$=591.

(198b) Following the procedures similar to that used for step (100b), the product from (198a) (120 mg, 0.203 mmol) was converted to the title compound. The product was purified by reverse phase HPLC on a Vydac C-18 semiprep column eluting an acetonitrile:water:TFA gradient, to give the hydroxamic acid product (80 mg, 49%). MS (M+H)$^+$=578.

Example 199

(3S,4S)-1-(2-aminoethyl)-N-hydroxy-3-[[[4-[(2-methyl-4-quinolinyl)methoxy]phenyl]carbonyl]amino]-4-piperidinecarboxamide tris (trifluoroacetate)

(199a) Following the procedure similar to that used for step (109a), the product from (198b) was converted to the title compound. MS (M+H)$^+$=478.

Example 200

(3S,4S)-1-[2-(N,N-dimethylamino)ethyl]-N-hydroxy-3-[[[4-[(2-methyl-4-quinolinyl)methoxy]phenyl]carbonyl]amino]-4-piperidinecarboxamide tris(trifluoroacetate)

(200a) Following the procedure similar to that used for step (109a), the product from (198a) (380 mg, 0.643 mmol) was deprotected to give the desired product (550 mg, 100%). MS (M+H)$^+$=491.

(200b) Following the procedure similar to that used for step (126a), the amine from (200a) (300 mg, 0.351 mmol) was reacted with formaldehyde via reductive amination. Silica gel chromatography (methanol-dichloromethane-ammonium hydroxide, 10:90:0 then 10:88:2) gave the dimethylamino product (160 mg, 88%). MS (M+H)$^+$=519.

(200c) Following the procedure similar to that used for step (100b), the product from (200b) (150 mg, 0.289 mmol) was converted to the title compound. The product was purified by reverse phase HPLC on a Vydac C-18 semiprep column eluting an acetonitrile:water:TFA gradient, to give the hydroxamic acid product (140 mg, 57%). MS (M+H)$^+$=506.

Example 201

(3S,4S)-1-[(2S)-2-aminopropyl]-N-hydroxy-3-[[[4-[(2-methyl-4-quinolinyl)methoxy]phenyl]carbonyl]amino]-4-piperidinecarboxamide tris (trifluoroacetate)

(201a–c) Following the procedures similar to that used for steps (126a, 100b and 109a), but using the amine from (138a) and N-t-Boc-L-alaninal in step (126a), the title compound was prepared. The product was purified by reverse phase HPLC on a Vydac C-18 semiprep column eluting an acetonitrile:water:TFA gradient, to give the hydroxamic acid product. MS (M+H)$^+$=492.

Example 202

(3S,4S)-1-[(2R)-2-amino-3-hydroxypropyl]-N-hydroxy-3-[[[4-[(2-methyl-4-quinolinyl)methoxy]phenyl]carbonyl]amino]-4-piperidinecarboxamide tris(trifluoroacetate)

(202a–c) Following the procedures similar to that used for steps (126a, 100b and 109a), but using the amine from (138a) and S-(–)-3-tert-butoxycarbonyl-4-formyl-2,2-dimethyl-1,3-oxazolidine in step (126a), the title compound was prepared. The product was purified by reverse phase HPLC on a Vydac C-18 semiprep column eluting an acetonitrile:water:TFA gradient, to give the hydroxamic acid product. MS (M+H)$^+$=508.

Example 203

(3S,4S)-N-hydroxy-3-[[[4-[(2-methyl-4-quinolinyl)methoxy]phenyl]carbonyl]amino]-1-[[(2R)-2-pyrrolidinyl]methyl]-4-piperidinecarboxamide tris (trifluoroacetate)

(203a–c) Following the procedures similar to that used for steps (126a, 100b and 109a), but using the amine from (138a) and N-(tert-butoxycarbonyl)-D-prolinal in step (126a), the title compound was prepared. The product was purified by reverse phase HPLC on a Vydac C-18 semiprep column eluting an acetonitrile:water:TFA gradient, to give the hydroxamic acid product. MS (M+H)$^+$=518.

Example 204

(3S,4R)-N-hydroxy-1-(2-hydroxylethyl)-4-[[[4-[(2-methyl-4-quinolinyl)methoxy]phenyl]carbonyl]amino]-3-piperidinecarboxamide bis (trifluoroacetate)

(204a–c) Following the procedures similar to that used for steps (126a, 197b and 100b), but using the amine from (116a) and (t-butyldimethylsilyloxy)acetaldehyde in step (126a), the title compound was prepared. The product was purified by reverse phase HPLC on a Vydac C-18 semiprep column eluting an acetonitrile:water:TFA gradient, to give the hydroxamic acid product. MS (M+H)$^+$=479.

Example 205

(3S,4R)-1-(2-aminoethyl)-N-hydroxy-4-[[[4-[(2-methyl-4-quinolinyl)methoxy]phenyl]carbonyl]amino]-3-piperidinecarboxamide tris (trifluoroacetate)

(205a–c) Following the procedures similar to that used for steps (126a, 100b and 109a), but using the amine from (116a) and t-butyl N-(2-oxoethyl)carbamate in step (126a), the title compound was prepared. The product was purified by reverse phase HPLC on a Vydac C-18 semiprep column eluting an acetonitrile:water:TFA gradient, to give the hydroxamic acid product. MS (M+H)$^+$=478.

Example 206

(3S,4R)-1-cyclobutyl-N-hydroxy-4-[[[4-[(2-methyl-4-quinolinyl)methoxy]phenyl]carbonyl]amino]-3-piperidinecarboxamide bis(trifluoroacetate)

(206a–b) Following the procedures similar to that used for steps (126a and 100b), but using the amine from (116a)

and cyclobutanone in step (126a), the title compound was prepared. The product was purified by reverse phase HPLC on a Vydac C-18 semiprep column eluting an acetonitrile:water:TFA gradient, to give the hydroxamic acid product. MS (M+H)$^+$=489.

Example 207

(3R,4R)-N-hydroxy-4-({4-[(2-methyl-4-quinolinyl)methoxy]benzoyl}amino)tetrahydro-2H-pyran-3-carboxamide (207a) LiHMDS (1.0 M in THF, 52.5 mL, 1.05 eq) was added dropwise to a −78° C. solution of tetrahydro-4H-pyran-4-one (5.0 g, 50 mmol) in THF (200 mL). The resulting solution was stirred at −20° C. for 1 h, then cooled back to −78° C. To this mixture was added methyl cyanoformate (4.75 mL, 1.2 eq) dropwise. Ten min after completion of the addition, the reaction was quenched with aqueous NH$_4$Cl and extracted with ether (200 mL). The organic layer was washed with brine (100 mL), dried (MgSO$_4$), and concentrated. Silica gel column chromatography (ether-hexane, 1:4, 2:3, then 3:2) yielded an oil containing both ketone and enol forms of the product (5.4 g, ca. 30% purity). MS found: (M+H)$^+$=159.1.

(207b) The ester from (207a) was dissolved in benzene (200 mL) and treated with (R)-α-methylbenzylamine (3 mL) and ytterbium(III) trifluoromethanesulfonate (200 mg). The mixture was heated to reflux under Dean-Stark conditions for 2 h, concentrated, and purified by silica gel column chromatography (ethyl acatete-hexane, 1:4) to yield the desired enamine as a white solid (3.6 g, 27.5% for 2 steps).

(207c) The enamine from (207b) (3.5 g, 13.4 mmol) in acetonitrile-acetic acid (1:1, 80 mL) was treated with NaBH(OAc)$_3$ and stirred for 2 h at 0° C. Following concentration in vacuo, the residue was dissolved in ether (200 mL), washed with saturated NaHCO$_3$ until the aqueous phase was basic, dried (MgSO$_4$), and concentrated to yield an oil (3.39 g, 96%). MS Found: (M+H)$^+$=264.3.

(207d) The intermediate from (207c) (1.86 g, 7.06 mmol) in methanol (100 mL) was treated with 10% palladium hydroxide on carbon (0.6 g, 3.5% mol) and aqueous 1N hydrochloric acid (10 mL, 1.4 eq) and stirred under a H$_2$-balloon for 72 h. The catalyst was removed by filtration. Removal of solvent provided the desired amine as hydrochloric acid salt (1.42 g, 100%). MS Found: (M+H)$^+$=160.3.

(207e) To a mixture of the amine from (207d) (1.0 g, 5.11 mmol) and 4-[(2-methyl-4-quinolinyl)methoxy]benzoic acid (1.50 g, 1.0 eq) in N,N-dimethylformamide (20 ml) was added BOP reagent (2.30 g, 1.02 eq) and N,N-diisopropylethylamine (2.2 mL, 2.5 eq) at room temperature. After 2 h at room temperature, saturated aqueous NaHCO$_3$ (50 ml) was added and the mixture extracted with ethyl acetate (2×50 mL), washed with brine (20 mL), dried (MgSO$_4$) and concentrated. Silica gel column chromatography (ethyl acetate-hexane, 3:2 then 4:1) yielded the desired amide (1.6 g, 72%). The above amide was submitted for a chiral HPLC separation (OJ, hexane-isopropanol-methanol, 60:20:20, 1.2 mL/min @ 240 nM and ambient temperature) to provide the (3R,4R) isomer in enantiomerically pure form (980 mg, 58% recovery, >99% ee). MS Found: (M+H)$^+$=435.1.

(207f) Freshly prepared 1.76 M hydroxylamine solution (example 1d) (20 mL, 20 eq.) was added to the methyl ester (0.78 g, 1.80 mmol) from reaction (207e) and stirred at room temperature for 10 min. The mixture was adjusted to pH 7 with 1 N hydrochloric acid. The resulting precipitate was collected by filtration and recrystallized from hot methanol (80 mL) to yield the free base form of the hydroxamic acid. The free base was treated with dichloromethane (30 mL) and trifluoroacetic acid (0.1 mL, 1.5 eq) and stirred until homogeneous. The mixture was concentrated and lyophilized to afford the TFA salt of the desired hydroxamic acid (0.50 g, 50%). MS Found: (M+H)$^+$=436.1.

Example 208

(3S,4S)-1-tert-butyl-N-hydroxy-3-({4-[(2-methyl-4-quinolinyl)methoxy]benzoyl}amino)-4-piperidinecarboxamide bis(trifluoroacetate)

(208a) To a solution of the alcohol (0.95 g, 3.09 mmol) from reaction (222a) in dichloromethane (30 mL) was added, at 0° C., triethylamine (0.65 mL, 1.5 eq), and methanesulfonyl chloride (0.29 mL, 1.2 eq). After 15 min at 0° C., the reaction was quenched with saturated NaHCO$_3$ (10 mL), extracted with dichloromethane, washed with brine, dried (MgSO$_4$), concentrated and purified by silica gel chromatography (40% then 50% ethyl acetate/hexane) to yield the mesylate (0.99 g, 83%). MS found: (M+Na)$^+$=408.

(208b) To a −78° C. solution of the mesylate (0.90 g, 2.33 mmol) from reaction (208a) in dichloromethane (100 mL) was bubbled ozone until the reaction solution turned blue. The reaction was purged with nitrogen until colorless. Triphenylphosphine (0.73 g, 1.2 eq) was added, and the mixture was stirred at ambient temperature for 2 h, concentrated and purified by silica gel chromatography (60% ethyl acetate/hexane) to yield the desired aldehyde (0.81 g, 90%). MS found: (M+Na)$^+$=410.

(208c) A mixture of the aldehyde (0.81 mg, 2.09 mmol) from the reaction (208b), tert-butylamine (1.14 mL, 5.2 eq) and sodium triacetoxyborohydride (1.33 g, 3.0 eq) in dichloroethane (40 mL) was stirred in a sealed flask at room temperature for 4 h, then 80° C. overnight. The reaction was quenched with saturated NaHCO$_3$, extracted with dichloromethane (2×50 mL), washed with brine (50 mL), dried (MgSO$_4$), concentrated and purified twice by silica gel chromatography (60% ethyl acetate/hexane) to yield the desired cyclized tertiary amine (0.37 g, 40%). MS found: (M+H)$^+$=349.

(208d) A mixture of the amine (0.32 g, 0.92 mmol) from reaction (208c), Pd/C (64 mg, 20% wt) and 1 N hydrogen chloride in ethyl ether (1.0 mL) in methanol (20 mL) was stirred under a hydrogen-balloon for 1 h. After removal of catalyst by filtration, the filtrate was concentrated to afford the deprotected amine hydrochloride (0.23 g, 100%). MS found: (M+H)$^+$=215.

(208e) Following a procedure analogous to that used in reaction (16f), the amine hydrochloride (0.23 g, 0.92 mmol) from reaction (208d) was coupled with 4-(2-methyl-4-quinolinylmethoxy)benzoic acid. Silica gel chromatography (3% methanol/dichloromethane) provided the desired amide (0.37 g, 82%). MS found: (M+H)$^+$=490.

(208f) Following a procedure analogous to that used in reaction (1d), the methyl ester (0.25 g, 0.51 mmol) from reaction (208e) was treated with hydroxylamine solution. Purification by reverse phase HPLC (15–40% acetonitrile/water) yielded the desired hydroxamic acid (0.26 g, 71%). MS found: (M+H)$^+$=491.

Example 209 tert-butyl 2-[(3S,4S)-4-[(hydroxyamino)carbonyl]-3-({4-[(2-methyl-4-quinolinyl)methoxy]benzoyl}amino)piperidinyl]-2-methylpropanoate bis(trifluoroacetate)

(209a) The amine from reaction (138a) (250 mg, 0.370 mmol), tert-butyl 2-bromoisobutyrate (0.69 mL, 10 eq)

and potassium carbonate (760 mg, 15 eq) were added to acetone (20 mL) and heated to reflux for 24 h. The mixture was cooled to rt and concentrated in vacuo. Purification of the residue by silica gel column chromatography (5:95, methanol:methylene chloride) gave the desired tertiary amine (50 mg, 23%). MS found: $(M+H)^+=590$.

(209b) Following a procedure similar to that used for reaction (100b), the tertiary amine from reaction (209a) (50 mg, 0.0848 mmol) was treated with hydroxylamine. Purification by reverse phase HPLC, using acetonitrile:water:TFA as eluant, provided the title hydroxamic acid (22 mg, 32%) as bis-TFA salt. MS found: $(M+H)^+=577$.

Example 210

2-[(3S,4S)-4-[(hydroxyamino)carbonyl]-3-({4-[(2-methyl-4-quinolinyl)methoxy]benzoyl}amino) piperidinyl]-2-methylpropanoic acid bis (trifluoroacetate)

(210a) Following a procedure similar to that used for reaction (109a), the hydroxamic acid from reaction (209b) was treated with TFA. Purification by reverse phase HPLC, using acetonitrile:water:TFA as eluant, provided the title hydroxamic acid (8 mg, 58%) as bis-TFA salt. MS found: $(M+H)^+=521$.

Example 211 methyl 2-[(3S,4S)-4-[(hydroxyamino)carbonyl]-3-({4-[(2-methyl-4-quinolinyl)methoxy] benzoyl}amino)piperidinyl]-2-methylpropanoate bis (trifluoroacetate)

(211a) Following a procedure similar to that used for reaction (209a), The amine from reaction (138a) (200 mg, 0.296 mmol) was treated with methyl 2-bromoisobutyrate (0.55 mL, 10 eq). Purification of the residue by silica gel column chromatography (5:95, methanol:methylene chloride) gave the desired tertiary amine (150 mg, 93%). MS found: $(M+H)^+=548$.

(211b) Following a procedure similar to that used for reaction (100b), the tertiary amine from reaction (211a) (150 mg, 0.274 mmol) was treated with hydroxylamine. Purification by reverse phase HPLC, using acetonitrile:water:TFA as eluant, provided the title hydroxamic acid (40 mg, 20%) as bis-TFA salt. MS found: $(M+H)^+=535$.

Example 212

(3S,4S)-N-hydroxy-3-({4-[(2-methyl-4-quinolinyl) methoxy]benzoyl}amino)-1-[2-(4-morpholinyl)-2-oxoethyl]-4-piperidinecarboxamide bis (trifluoroacetate)

(212a) Following a procedure similar to that used for reaction (209a), The amine from reaction (138a) (2.00 g, 2.96 mmol) was treated with tert-butyl bromoacetate (1.15 g, 2 eq). Purification of the residue by silica gel column chromatography (ethyl acetate) gave the desired tertiary amine (1.40 g, 80%). MS found: $(M+H)^+=562$.

(212b) Following a procedure similar to that used for reaction (109a), the tertiary amine from reaction (212a) (1.20 g, 2.14 mmol) was treated with TFA. The mixture was concentrated in vacuo to provide the desired carboxylic acid (1.70 g, 100%) as bis-TFA salt. MS found: $(M+H)^+=506$.

(212c) Following a procedure similar to that used for reaction (16f), the carboxylic acid from reaction (212b) (300 mg, 0.378 mmol) was treated with morpholine. Purification of the residue by silica gel column chromatography (5:95, methanol:methylene chloride) gave the desired amide (130 mg, 60%). MS found: $(M+H)^+=575$.

(212d) Following a procedure similar to that used for reaction (100b), the amide from reaction (212c) (130 mg, 0.226 mmol) was treated with hydroxylamine. Purification by reverse phase HPLC, using acetonitrile:water:TFA as eluant, provided the title hydroxamic acid (70 mg, 40%) as bis-TFA salt. MS found: $(M+H)^+=562$.

Example 213

(3S,4S)-1-[2-(dimethylamino)-2-oxoethyl]-N-hydroxy-3-({4-[(2-methyl-4-quinolinyl)methoxy] benzoyl}amino)-4-piperidinecarboxamide bis (trifluoroacetate)

(213a) Following a procedure similar to that used for reaction (16f), the carboxylic acid from reaction (212b) (300 mg, 0.378 mmol) was treated with dimethylamine hydrogen chloride. The crude amide (200 mg) was used for the next step without further purification. MS found: $(M+H)^+=533$.

(213b) Following a procedure similar to that used for reaction (100b), the amide from reaction (213a) (200 mg, 0.378 mmol) was treated with hydroxylamine. Purification by reverse phase HPLC, using acetonitrile:water:TFA as eluant, provided the title hydroxamic acid (90 mg, 32% for two steps) as bis-TFA salt. MS found: $(M+H)^+=520$.

Example 214

(3S,4S)-1-(1,1-dimethyl-2-propenyl)-N-hydroxy-3-({4-[(2-methyl-4-quinolinyl)methoxy] benzoyl}amino)-4-piperidinecarboxamide bis (trifluoroacetate)

(214a) A mixture of the intermediate from (186a) (1.0 g, 1.95 mmol) and Pd/BaSO$_4$ (0.10 g, 5% wt.) in ethanol (50 mL) was stirred under a hydrogen balloon for 40 min. After removal of catalyst by filtration, the filtrate was concentrated and purified by silica gel chromatography (5% methanol/dichloromethane) to yield the alkene (0.87 g, 87%). MS found: $(M+H)^+=516$.

(214b) Following a procedure analogous to that used in reaction (1d), the ethyl ester (0.15 g, 0.29 mmol) from reaction (214a) was treated with hydroxylamine solution. Purification by reverse phase HPLC (15–40% acetonitrile/water) yielded the desired hydroxamic acid (0.09 g, 43%). MS found: $(M+H)^+=503$.

Example 215

(3S,4S)-N-hydroxy-3-({4-[(2-methyl-4-quinolinyl) methoxy]benzoyl}amino)-1-tert-pentyl-4-piperidinecarboxamide bis(trifluoroacetate)

(215a) A mixture of the intermediate from (214a) (0.20 g, 0.388 mmol) and Rh/C (20 mg, 5% wt.) in ethanol (20 mL) was stirred under a hydrogen balloon for 4 h. After removal of catalyst by filtration, the filtrate was purified by silica gel chromatography (5% methanol/dichloromethane) to yield the alkane (0.176 g, 88%). MS found: $(M+H)^+=518$.

(215b) Following a procedure analogous to that used in reaction (1d), the ethyl ester (0.12 g, 0.23 mmol) from reaction (215a) was treated with hydroxylamine solution. Purification by reverse phase HPLC (15–40% acetonitrile/water) yielded the desired hydroxamic acid (82 mg, 48%). MS found: (M+H)$^+$=505.

Example 216

(3S,4S)-N-hydroxy-3-({4-[(2-methyl-4-quinolinyl)methoxy]benzoyl}amino)-1-(2-propynyl)-4-piperidinecarboxamide bis(trifluoroacetate)

(216a) A mixture of the free base of the intermediate from (138a) (0,30 g, 0.67 mmol), propargyl bromide (80% wt. in toluene, 0.1 mL, 0.90 mmol), potassium carbonate (0.46 g, 5 eq) and sodium iodide (0.135 g, 1.35 eq) in acetone (10 mL) was refluxed for 2 h. The mixture was then cooled to room temperature, quenched with saturated NH$_4$Cl (20 mL), extracted with ethyl acetate (2×20 mL), washed with brine (10 mL), dried (MgSO$_4$) and concentrated. Silica gel chromatography (5% methanol/dichloromethane) yielded the desired product (0.27 g, 83%). MS found: (M+H)$^+$=486.

(216b) Following a procedure analogous to that used in reaction (1d), the ethyl ester (0.25 g, 0.52 mmol) from reaction (216a) was treated with hydroxylamine solution. Purification by reverse phase HPLC (15–40% acetonitrile/water) yielded the desired hydroxamic acid (0.26 g, 72%). MS found: (M+H)$^+$=473.

Example 217

(3S,4S)-1-allyl-N-hydroxy-3-({4-[(2-methyl-4-quinolinyl)methoxy]benzoyl}amino)-4-piperidinecarboxamide bis(trifluoroacetate)

(217a–b) Following procedures analogous to that used in reaction (186a) and (1d), the intermediate from reaction (138a) (0.20 g, 0.45 mmol) was alkylated with allyl bromide, then treated with hydroxylamine solution. Purification by reverse phase HPLC (15–40% acetonitrile/water) yielded the desired hydroxamic acid (75 mg, 26% for 2 steps). MS found: (M+H)$^+$=475.

Example 218

(3S,4S)-N-hydroxy-1-(1-methyl-2-propynyl)-3-({4-[(2-methyl-4-quinolinyl)methoxy]benzoyl}amino)-4-piperidinecarboxamide bis(trifluoroacetate)

(218a–b) Following procedures analogous to that used in reaction (186a) and (1d), the intermediate from reaction (138a) (0.20 g, 0.45 mmol) was alkylated with 3-chloro-1-butyne, then treated with hydroxylamine solution. Purification by reverse phase HPLC (15–40% acetonitrile/water) yielded the desired hydroxamic acid (100.5 mg, 40% for 2 steps). MS found: (M+H)$^+$=487.

Example 219

(3S,4S)-N-hydroxy-1-(1-methyl-2-propenyl)-3-({4-[(2-methyl-4-quinolinyl)methoxy]benzoyl}amino)-4-piperidinecarboxamide bis(trifluoroacetate)

(219a) A mixture of hydroxamic acid from example 218 (20 mg, 0.028 mmol) and 5% wt. Pd/BaSO$_4$ (4 mg, 20% wt.) in methanol (2 mL) was stirred under a hydrogen-balloon for 20 min. After removal of catalyst by filtration, the filtrate was concentrated and lyophilized to yield the title product (17 mg, 87%). MS found: (M+H)$^+$=489.

Example 220

N-{(1R,2S)-4,5-dihydroxy-2-[(hydroxyamino)carbonyl]cyclohexyl}-4-[(2-methyl-4-quinolinyl)methoxy]benzamide trifluoroacetate (220a) To a −20° C. solution of 1-methyl-(1S,2R)-(+)-cis-1,2,3,6-tetrahydrophthalate (2.21 g, 12.0 mmol) and triethylamine (3.34 mL, 2.0 eq) in tetrahydrofuran (30 mL) was added ethyl chloroformate (1.72 mL, 1.5 eq). After 5 min at −20° C., the CCl$_4$/dry ice bath was replaced with ice-water bath. A solution of sodium azide (1.95 g, 2.5 mmol) in water (10 mL) was added. The mixture was stirred at ambient temperature for 30 min, diluted with water (50 mL), extracted with ethyl acetate (2×100 mL), washed with brine (50 mL), dried (MgSO$_4$), and concentrated. The oil residue was treated with benzene (30 mL) and heated to reflux for 1 h. The mixture was finally treated with 1 N hydrochloric acid (24 mL) and stirred at room temperature for 40 h. The aqueous layer was separated, washed with ethyl ether (2×5 mL), concentrated and pumped in vacuo to yield the desired amine hydrochloride (1.40 g, 61%).

(220b) Following a procedure analogous to that used in reaction (16f), the amine hydrochloride (1.20 g, 5.72 mmol) from reaction (220a) was coupled with 4-(2-methyl-4-quinolinylmethoxy)benzoic acid. Silica gel chromatography (60% then 70% ethyl acetate/hexane) provided the desired amide (1.40 g, 57%). MS found: (M+H)$^+$=431.

(220c) To a mixture of the amide from reaction (220b) (0.30 g, 0.70 mmol) in water (1 mL) and acetone (8 mL) was added 4-methylmorpholine N-oxide (0.16 g, 2 eq) and OsO$_4$ (4% in water, 0.2 mL, 0.05 eq). After 4 h at room temperature, the reaction was quenched with 30% NaHSO$_3$ (3 mL), and stirred for 30 min before extracted with ethyl acetate (2×50 mL). The extracts were combined, washed with water (10 mL), brine (10 mL), dried (MgSO$_4$), and concentrated. Purification by silica gel chromatography (5% methanol/dichloromethane) and recrystallization from methanol yielded the lower Rf isomer as the desired diol (0.16 g, 50%). MS found: (M+H)$^+$=465.

(220d) Following a procedure analogous to that used in reaction (1d), the diol from reaction (220c) (0.15 g, 0.30 mmol) was treated with hydroxylamine solution. Purification by reverse phase HPLC (15–40% acetonitrile/water) yielded the desired hydroxamic acid (98 mg, 55%). MS found: (M+H)$^+$=466.

Example 221

(5S)-N-hydroxy-5-({4-[(2-methyl-4-quinolinyl)methoxy]benzoyl}amino)-2-oxo-4-piperidinecarboxamide trifluoroacetate (221a) A solution of benzyl (S)-(−)-tetrahydro-5-oxo-3-furanyl carbamate (2.00 g, 8.50 mmol) in THF (50 mL) was added dropwise to LDA (17.9 mmol, 2.1 eq) in THF (150 mL) at −78° C. over 10 minutes. After additional 10 min at that temperature, tert-butyl bromoacetate (3.77 mL, 3 eq) was added. The mixture was stirred at −78° C. for 1 h, quenched with a solution of acetic acid (1 mL) in THF (4 mL) and warmed to rt. Following removal of solvent in vacuo, the residue was diluted with ethyl acetate (300 mL), washed with water (2×10 mL), and brine (10 mL), dried (MgSO$_4$) and concentrated. 1H NMR analysis of the crude material indicated presence of two isomers in 3:2 ratio. Silica gel column chromatography (2:8, ethyl acetate:hexanes) gave the major lactone (950 mg, 32%). MS found: (M+Na)+=506.

(221b) The lactone from reaction (221a) (2.70 g, 7.72 mmol) in THF (40 mL) was treated with 1 N LiOH (10 mL, 1.3 eq) at 0° C. and stirred at that temperature for 1 h. The mixture was adjusted to pH4–5 with 1 N HCl and concentrated. The residue was diluted with ethyl acetate (200 mL), washed with water (10 mL), brine (10 mL), dried (MgSO$_4$) and concentrate in vacuo. The crude carboxylic acid (3.00 g) was taken to the next step without further purification. MS found: (M+Na)+=390.

(221c) The crude carboxylic acid from reaction (221b) (3.00 g) in methanol (20 mL) and benzene (80 mL) was treated with 2.0 M hexane solution of (trimethylsilyl) diazomethane (5 mL, 1.3 eq) at rt. After 10 min at rt, the mixture was concentrated and purified by silica gel column chromatography (3:7, ethyl acetate:hexanes) to provide the desired methyl ester (1.46 g, 50% for two steps). MS found: (M+Na)+=404.

(221d) The ester from reaction (221c) (780 mg, 2.04 mmol) in methylene chloride (20 mL) was treated with triethylamine (0.43 mL, 1.5 eq) and methanesulfonyl chloride (0.19 mL, 1.3 eq) at 0° C. and stirred at that temperature for 1 h. The mixture was quenched with saturated NaHCO$_3$ (10 mL) and diluted with ethyl acetate (200 mL). The mixture was washed with water (10 mL), and brine (10 mL), dried (MgSO$_4$) and concentrated. The residue was purified by silica gel column chromatography (3:7, ethyl acetate:hexanes) to provide the desired mesylate (870 mg, 93%). MS found: (M+H)+=460.

(221e) The mesylate from reaction (221d) (700 mg, 1.52 mmol) and sodium azide (990 mg, 10 eq) were dissolved in DMF (10 mL) and heated to 90° C. for 1 h. The mixture was cooled down to rt, treated with saturated NaHCO$_3$ (5 mL) and ethyl acetate (200 mL), washed with water (10 mL), brine (10 mL), dried (MgSO$_4$) and concentrate in vacuo. Purification of the residue by silica gel column chromatography (2:8, ethyl acetate:hexanes) gave the desired azide (580 mg, 94%). 1H NMR showed a 4:1 mixture due to partial epimerization at alpha position of the ester. MS found: (M+H)+=407.

(221f) The azide from reaction (221e) (190 mg, 0.467 mmol) in methanol (4 mL) was treated with tin(II) chloride (177 mg, 2 eq) and stirred at rt for 2 h. Additional portion of tin(II) chloride (177 mg, 2 eq) was added and the mixture stirred for 2 h. Following addition of saturated NaHCO$_3$ (5 mL) and ethyl acetate (100 mL), the mixture was washed with water (2×5 mL), and brine (5 mL), dried (MgSO$_4$), treated with 1 N HCl in ether (1 mL) and concentrated. The crude amine hydrochloride salt (220 mg) was taken to the next step without further purification. MS found: (M+H)+=381.

(221g) Following a procedure similar to that used for reaction (109a), the amine from reaction (221f) (220 mg) was treated with TFA. The crude carboxylic acid (250 mg) was taken to the next step without further purification. MS found: (M+H)+=325.

(221h) Following a procedure similar to that used for reaction (16f), the carboxylic acid from reaction (212g) (280 mg) was treated with BOP reagent. Purification of the residue by silica gel column chromatography (7:3 ethyl acetate:hexane, then 5:95 methanol:methylene chloride) gave the desired lactam (29 mg, 20% for 3 steps). MS found: (M+Na)+=329.

(221i) The lactam from reaction (221h) (29 mg, 0.0948 mmol) in methanol (8 mL) was treated with 20% Pd(OH)$_2$ on carbon (20 mg) and stirred under hydrogen balloon for 2 h. The mixture was filtered and the filtrate was concentrated to provide the desired amine (16 mg, 100%). MS found: (M+CH$_3$CN)+=205.

(221j) Following a procedure similar to that used for reaction (16f), the amine from reaction (212i) (15 mg, 0.0871 mmol) was coupled with 4-(2-methyl-4-quinolinylmethoxy)benzoic acid. Purification of the residue by silica gel column chromatography (7:3 ethyl acetate:hexanes, then 5:95 methanol:methylene chloride) gave the amide compound (25 mg, 64%). MS found: (M+H)+=448.

(221k) Following a procedure similar to that used for reaction (100b), the intermediate from reaction (221j) (25 mg, 0.0559 mmol) was treated with hydroxylamine. Purification by reverse phase HPLC, using acetonitrile:water:TFA as eluant, provided the title hydroxamic acid (6.5 mg, 21%) as bis-TFA salt. MS found: (M+H)+=449.

Example 222

(3S,4S)-N-hydroxy-3-({4-[(2-methyl-4-quinolinyl) methoxy]benzoyl}amino)-2-oxo-4-piperidinecarboxamide trifluoroacetate (222a) Isobutylene (100 mL) was condensed into a solution of L-ASP(OMe)-OH hydrogen chloride (10.0 g, 54.4 mmol) in dioxane (100 mL) and sulfuric acid (10 mL) in a 350-mL pressure bottle. The resultant mixture was shaken mechanically at rt for 4 h and poured into a cold mixture of 1 N NaOH (500 mL) and ether (250 mL). The aqueous phase was extracted with ethyl acetate (3×200 mL). The combined organic extracts were washed with brine (30 mL), dried (MgSO$_4$) and concentrated to provide the desired ester (2.10 g, 19%). MS found: (M+H)+=204.

(222b) Following a procedure similar to that used for reaction (126a), the ester from reaction (222a) (2.10 g, 10.3 mmol) was treated with benzaldehyde (1.26 mL, 1.2 eq). Purification of the residue by silica gel column chromatography (3:7 ethyl acetate:hexanes) gave the desired amine (2.00 g, 66%). MS found: (M+H)+=294.

(222c) A mixture of the amine for reaction (222b) (2.60 g, 8.86 mmol), potassium phosphate (3.76 g, 2 eq), Lead(II) nitrate (2.35 g, 0.8 eq) and 9-phenylfluorenyl-9-bromide (3.13 g, 1.1 eq) in acetonitrile (100 mL) was shaken at rt for 15 h. Following addition of methylene chloride (200 mL and the mixture was filtered through a silica gel pad. The filtrate was concentrated and purified by silica gel column chromatography (1:9 ethyl acetate:hexanes) to provide the desired tertiary amine (4.80 g, 100%). MS found: (M+Na)+=556.

(222d) A 0.5 M toluene solution of potassium bis (trimethylsilyl)amide (32.2 mL, 2 eq) and allyl iodide (1.47 mL, 2 eq) were added sequentially to a solution of the amine from reaction (222c) (4.30 g, 8.06 mmol) in THF (100 mL) at −20° C. After 2 h at −20° C., the mixture was quenched with pH7 phosphate buffer (30 mL). The aqueous phase was extracted with ethyl acetate (2×100 mL). The combined organic layers were washed with brine (20 mL), dried (MgSO$_4$) and concentrated. $^1$H NMR analysis of the crude material showed a 5:1 mixture of two isomers. Silica gel column chromatography (5:95 ethyl acetate:hexanes) gave the major isomer (3.00 g, 78%). MS found: (M+Na)+=596.

(222e) O$_3$ was bubbled into a solution of the intermediate from reaction (222d) (500 mg, 0.872 mmol) in methylene chloride (30 mL) at −78° C. until the solution turned blue (approximately 2 min). The mixture was bubbled with N₂ until the blue color disappeared, and then treated with triphenylphosphine (458 mg, 2 eq). After 4 h at rt, the mixture was concentrated and purified by silica gel column chromatography (1:9 ethyl acetate:hexanes) to provide the desired aldehyde (380 mg, 76%). MS found: (M+Na)$^+$=598.

(222f) Sodium triacetoxyborohydride (423 mg, 6 eq) was added to a solution of the aldehyde from reaction (222e) (190 mg, 0.330 mmol) and ammonium acetate (255 mg, 10 eq) in acetic acid (2 mL) and acetonitrile (2 mL) at 0° C. After 30 minutes at 0° C., another portion of sodium triacetoxyborohydride (282 mg, 4 eq) was added. After an additional 30 minutes at 0° C., the mixture was diluted with ethyl acetate (100 mL) and washed with saturated ammonium chloride (5 mL), brine (5 mL), dried (MgSO₄) and concentrated. Purification of the residue by silica gel column chromatography (1:1 ethyl acetate:hexanes, then 1:9 methanol:methylene chloride) gave the desired primary amine (80 mg, 42%). MS found: (M+H)$^+$=577.

(222g) The amine from reaction (222f) (80 mg, 0.139 mmol) was treated with TFA (2 mL) at rt for 3 h and concentrated. The crude carboxylic acid (70 mg) was taken to the next step without further purification. MS found: (M+H)$^+$=281.

(222h) Following a procedure similar to that used for reaction (16f), the carboxylic acid from reaction (222g) (70 mg) was treated with BOP reagent. Purification of the residue by silica gel column chromatography (1:1 ethyl acetate:hexane, then 5:95 methanol:methylene chloride) gave the desired lactam (25 mg, 69% for 2 steps). MS found: (M+H)$^+$=263.

(222i-k) Following the procedure similar to that used for steps from (221i–k), but using the lactam from reaction (222h) (25 mg, 0.0953 mmol), the title compound was prepared. The product was purified by reverse phase HPLC, using acetonitrile:water:TFA as eluant, to provide the desired hydroxamic acid (6.5 mg, 13% for 3 steps) as bis-TFA salt. MS found: (M+H)$^+$=449.

Example 223

(3S,4S)-3-{[4-(2-butynyloxy)benzoyl]amino}-N-hydroxy-1-isopropyl-4-piperidinecarboxamide trifluoroacetate (223a) The intermediate from reaction (134e) (1.0 g, 1.83 mmol) was treated with Pd(OH)₂/C (0.20 g, 20% wt.) and ethanol (20 mL). The resulting mixture stirred under hydrogen balloon overnight. After removal of catalyst by filtration, the filtrate was concentrated and purified by silica gel chromatography to yield the phenol (0.60 g, 84%). MS found: (M+H)$^+$=393.

(223b) The phenol from reaction (223a) (0.10 g, 0.26 mmol) was alkylated with 1-bromo-2-butyne (0.03 mL, 1.3 eq) and K₂CO₃ (0.18 g, 5 eq) in acetonitrile (5 mL) at reflux for 3 h. The mixture was cooled to room temperature and partitioned between water (10 mL) and ethyl acetate (50 mL). The organic layer was separated, dried (MgSO₄), concentrated and purified by silica gel chromatography (40% ethyl acetate/hexane) to yield the desired product (0.11 g, 99%). MS found: (M+H)$^+$=445.

(223c) The intermediate from reaction (223b) (0.10 g, 0.23 mmol) was treated with dichloromethane (2 mL) and trifluoroacetic acid (1 mL) at room temperature for 1 h, then concentrated and pumped in vacuo overnight to give the amine TFA salt (0.1 g, 100%). MS found: (M+H)$^+$=345.

(223d–e) Following procedures analogous to that used in reaction (16h) and (1d), the intermediate from reaction (223c) (72 mg, 0.16 mmol) was converted to the title compound (37 mg, 71%). MS found: (M+H)$^+$=374.

Example 224

(3S,4S)-3-{[4-(2-butynyloxy)benzoyl]amino}-N-hydroxy-4-piperidinecarboxamide trifluoroacetate (224a) Following a procedure analogous to that used in reaction (1d), the intermediate from reaction (223c) (27 mg, 0.08 mmol) was converted to the title compound (10 mg, 28%). MS found: (M+H)$^+$=332.

Example 225 tert-butyl (3S,4S)-4-[(hydroxyamino)carbonyl]-3-({4-[(2-methyl-3-pyridinyl)methoxy]benzoyl}amino)-1-piperidinecarboxylate trifluoroacetate (225a) To a 0° C. solution of the phenol from reaction (223a) (0.10 g, 0.255 mmol) and 2-methyl-3-hydroxymethylpyridine (38 mg, 1.2 eq) in THF (2 mL) was added triphenylphosphine (80 mg, 1.2 eq) and diethyl azodicarboxylate (0.05 mL, 1.2 eq). After stirred at room temperature overnight, the mixture was quenched with saturated NH₄Cl, extracted with ethyl acetate (2×20 mL), dried (MgSO₄), concentrated and purified by silica gel chromatography (80% ethyl acetate/hexane) to yield the desired product (0.12 g, 100%). MS found: (M–H)$^-$=496.

(225b) Following a procedure analogous to that used in reaction (1d), the intermediate from reaction (225a) (0.12 g, 0.25 mmol) was treated with hydroxylamine solution. Purification by reverse phase HPLC (25–50% acetonitrile/water) yielded the desired hydroxamic acid (67 mg, 52%). MS found: (M+H)$^+$=485.

Example 226

(3S,4S)-N-hydroxy-3-({4-[(2-methyl-3-pyridinyl)methoxy]benzoyl}amino)-4-piperidinecarboxamide bis(trifluoroacetate)

(226a) The hydroxamic acid from reaction (225b) (20 mg, 0.033 mmol) was treated with dichloromethane (2 mL) and trifluoroacetic acid (0.2 mL) at room temperature for 1 h. After removal of solvent in vacuo, the residue was purified by reverse phase HPLC (5–30% acetonitrile/water) to yield the titled compound (10 mg, 49%). (M+H)$^+$=385.

Example 227 tert-butyl (3S,4S)-3-({4-[(2,5-dimethylbenzyl)oxy]benzoyl}amino)-4-[(hydroxyamino)carbonyl]-1-piperidinecarboxylate (227a) To a mixture of the phenol from reaction (223a) (0.10 g, 0.255 mmol) and 2,5-dimethylbenzyl chloride (0.05 mL, 1.3 eq) in DMSO (1 mL) was added sodium iodide (51 mg, 1.3 eq) and Cs₂CO₃ (0.25 g, 3.0 eq). After 2 h at room temperature, the reaction mixture was quenched with saturated NH₄Cl, extracted with ethyl acetate (2×20 mL), dried (MgSO₄), concentrated and purified by silica gel chromatography (50% ethyl acetate/hexane) to yield the desired product (0.10 g, 77%). MS found: (M+H)$^+$=511.

(227b) Following a procedure analogous to that used in reaction (1d), the intermediate from reaction (227a) (0.10 g, 0.20 mmol) was converted to the desired hydroxamic acid (92 mg, 97%). MS found: (M−H)⁻=496.

Example 228

(3S,4S)-3-({4-[(2,5-dimethylbenzyl)oxy]benzoyl}amino)-N-hydroxy-4-piperidinecarboxamide trifluoroacetate (228a) The hydroxamic acid from reaction (227b) (26 mg, 0.053 mmol) was treated with dichloromethane (2 mL) and trifluoroacetic acid (1 mL) at room temperature for 1 h. After removal of solvent in vacuo, the residue was purified by reverse phase HPLC (30–55% acetonitrile/water) to yield the titled compound (9.5 mg, 35%). (M+H)⁺=398.

Example 301

(cis,cis)-3-Amino-2-[[[4-[(2-methyl-4-quinolinyl)methoxy]phenyl]carbonyl]amino]-(N-hydroxy)cyclohexylcarboxamide bis-trifluoroacetate salt (301a) To a solution of 3-hydroxy-2-nitrobenzoic acid (10 g, 54.6 mmol) in EtOH (150 mL) and benzene (150 mL) was added concentrated sulfuric acid (40 mL). The mixture was heated at reflux for 48 hours with azeotropic removal of water and concentrated on a rotary evaporator. The residue was dissolved in EtOAc (200 mL) and the resulting solution was washed with saturated NaHCO₃ (2×100 mL) and brine (2×100 mL). The organic layer was dried (MgSO₄) and concentrated on a rotary evaporator to give the ethyl ester (11 g, 95%) as a solid. MS-ESI (M+H)⁺=212.1.

(301b) The above compound (11 g, 52.1 mmol) was mixed with 0.5% aqueous HCl (200 mL) and PtO₂ (2.2 g) in a Parr bottle. The mixture was hydrogenated on a Parr shaker at 55 psi for 24 hours. The catalyst was filtered off and the filtrate was concentrated on a rotary evaporator. The residue was dried in vacuo to give the crude ethyl 2-amino-3-hydroxycyclohexylcarboxylate (12 g, 100%). MS-ESI (M+H)⁺=188.1

(301c) To a solution of 301b (1.8 g, 8 mmol) and 4-[(2-methyl-4-quinolinyl)methoxy]benzoic acid (1.7 g, 6 mmol) in DMF (10 mL) cooled in an ice bath was added BOP (3.1 g, 7 mmol) followed by N-methylmorpholine (3 g, 30 mmol). The mixture was stirred at room temperature overnight. EtOAc (100 mL) was added and the solution was washed with brine (2×50 mL), NaHCO₃ (2×50 mL) and brine (2×50 mL), dried (MgSO₄) and concentrated on a rotary evaporator. The crude product was chromatographed on a silica gel column (10% MeOH/CH₂Cl₂) to provide 301c (0.8 g, 30%) as a solid. MS-ESI (M+H)⁺=449.2.

(301d) Compound 301c (350 mg, 0.78 mmol) was dissolved in chloroform (10 mL)/TFA (0.5 mL). To it was added Dess-Martin periodinane (365 mg, 0.86 mmol) and the solution was stirred for 2 hours. Insoluble material was filtered off and the filtrate was concentrated on a rotary evaporator to provide the crude ketone product as a solid. MS-ESI (M+H)⁺=461.2.

(301e) To a solution of 301d (120 mg, 0.21 mmol) in DMF (2 mL) was added acetic acid (0.2 mL) followed by NH₄OAc (90 mg, 1.2 mmol) and Na(OAc)₃BH (120 mg, 0.6 mmol). The mixture was stirred at room temperature for 3 hours and purified using reverse phase HPLC to provide the amino product (55 mg, 40%) as a powder. MS-ESI (M+H)⁺=462.3.

(301f) Compound 301e (40 mg, 0.058 mmol) was dissolved in DMF (1 mL) and to it was added N-methylmorpholine (40 mg, 0.4 mmol) followed by di-tert-butyl-dicarbonate (22 mg, 0.1 mmol). The mixture was stirred at room temperature for 5 hours and purified using reverse phase HPLC to provide the Boc-protected product (20 mg, 51%) as a powder. MS-ESI (M+H)⁺=562.3.

(301g) A mixture of 301f (20 mg, 0.03 mmol) in MeOH (2 mL) and 1 N KOH (0.5 mL) was heated at 60° C. for 1 hour and the solution was concentrated on a rotary evaporator. The residue was dissolved in DMSO/HOAc and purified using reversed phase HPLC to provide the carboxylic acid (16 mg, 83%) as a powder. MS-ESI (M+H)⁺=534.2.

(301h) To a solution of 301g (15 mg, 0.023 mmol) in DMF (1 mL) was added N-methylmorpholine (20 mg, 0.2 mmol) followed by hydroxylamine hydrochloride (10 mg, 0.14 mmol). After all solid was dissolved, the solution was cooled in an ice bath and to it was added BOP (22 mg, 0.05 mmol). The mixture was stirred for 30 min at room temperature. Purification using reversed phase HPLC provided the hydroxamic acid (10 mg, 67%) as a powder. MS-ESI (M+H)⁺=549.3.

(301i) Compound 301h (10 mg) was dissolved in a mixed solvent of 40% TFA in CH₂Cl₂ (1 mL) and after 30 min, the solvent was removed by evaporation. The residue was dissolved in water/acetonitrile. Lyophilization provided the desired product as a powder. MS-ESI (M+H)⁺=449.3.

Example 302

(cis,cis)-3-Methylamino-2-[[[4-[(2-methyl-4-quinolinyl)methoxy]phenyl]carbonyl]amino]-(N-hydroxy)cyclohexylcarboxamide bis-trifluoroacetate salt (302a) To a solution of 301d (100 mg, 0.17 mmol) in DMF (1 mL) was added HOAc (48 mg, 0.8 mmol) followed by methylamine (2 M solution in THF, 0.4 mL, 0.8 mmol) and Na(OAc)₃BH (80 mg, 0.4 mmol). The mixture was stirred for 3 hours at room temperature. Purification using reversed phase HPLC provided the methylamino product (70 mg, 58%) as a powder. MS-ESI (M+H)⁺=476.3.

(302b) Compound 302a (70 mg, 0.1 mmol) was reacted with di-tert-butyl-dicarbonate using the procedure described in (301f) to provide the Boc-protected product (55 mg, 80%) as a powder. MS-ESI (M+H)⁺=576.3.

(302c) The final product was obtained by saponification of the ethyl ester 302b followed by coupling of the carboxylic acid with hydroxylamine hydrochloride and removal of the Boc group using procedures similar to those described in (301g)–(301i). MS-ESI (M+H)⁺=463.3.

Example 303

(cis,cis)-3-Dimethylmino-2-[[[4-[(2-methyl-4-quinolinyl)methoxy]phenyl]carbonyl]amino]-1-(N-hydroxy)cyclohexylcarboxamide bis-trifluoroacetate salt (303a) To a solution of 302a (100 mg, 0.14 mmol) in DMF (1 mL) was added formaldehyde (37% aqueous solution, 82 mg, 1 mmol) followed by N-methylmorpholine (100 mg, 1 mmol) and Na(OAc)₃BH (84 mg, 0.4 mmol). The mixture was stirred for 2 hours at room temperature. Purification using reversed phase HPLC provided the dimethylamino product (100 mg, 99%) as a powder. MS-ESI (M+H)$^+$=490.2.

(303b) The final compound was obtained by saponification of the ethyl ester 303a followed by coupling the resulting carboxylic acid with hydroxylamine hydrochloride using procedures similar to those described in (301g) and (301h). MS-ESI (M+H)$^+$=477.3.

Example 304

(cis,trans)-3-Amino-2-[[[4-[(2-methyl-4-quinolinyl)methoxy]phenyl]carbonyl]amino]-1-(N-hydroxy)cyclohexylcarboxamide bis-trifluoroacetate salt (304a) To a solution of 301b (3.6 g, 16 mmol) and 4-benzyloxybenzoic acid (3.7 g, 16 mmol) in DMF (10 mL) cooled in an ice bath was added BOP (8 g, 18 mmol) followed by N-methylmorpholine (7.4 mL, 64 mmol). The mixture was stirred at room temperature overnight and diluted with EtOAc (150 mL). The resulting solution was washed with NaHCO$_3$ (2×70 mL) and brine (2×70 mL), dried (MgSO$_4$) and concentrated on a rotary evaporator. The residue was chromatographed on a silica gel column (5% MeOH/CH$_2$Cl$_2$) to provide the amide product (2.3 g, 36%) as a solid. MS-ESI (M+H)$^+$=398.2.

(304b) To a solution of 304a (2.3 g, 5.8 mmol) in CHCl$_3$ (15 mL) cooled in an ice bath was added N-methylmorpholine (1.1 mL, 10 mmol) followed by methanesulfonyl chloride (0.7 g, 6 mmol). The mixture was stirred in the ice bath for 2 hours and at room temperature overnight. The solvent was removed by concentration and the residue was dissolved in EtOAc. The resulting solution was washed with brine, dried (MgSO$_4$) and concentrated. Chromatography on a silica gel column (50% EtOAc/hexane) provided the mesylate (1.6 g, 60%) as a solid. MS-ESI (M+H)$^+$=476.2.

(304c) A mixture of 304b (1.2 g, 2.5 mmol) and sodium azide (0.33 g, 5.1 mmol) in DMF (15 mL) was heated at 100° C. for 5 hours. DMF was removed by evaporation in vacuo. The residue was dissolved in EtOAc and the resulting solution was washed with brine, dried (MgSO$_4$) and concentrated. Chromatography on a silica gel column (40% EtOAc/hexane) provided the azido product (0.69 g, 65%) as a solid. MS-ESI (M+H)$^+$=423.1.

(304d) Compound 304c (0.69 g, 1.6 mmol) was dissolved in MeOH (20 mL) in a Parr bottle and to it was added 4 N HCl in dioxane (0.5 mL) followed by 10% Pd—C (0.1 g). The mixture was hydrogenated on a Parr shaker at 50 psi for 4 hours. The catalyst was filtered off and the filtrate was concentrated on a rotary evaporator to provide the amino product (0.55 g, 99%) as a solid. MS-ESI (M+H)$^+$= 307.2.

(304e) To a solution of 304d (0.55 g, 1.6 mmol) in THF (15 mL) and water (2 mL) cooled in an ice bath was added 1 N NaOH (1.6 mL) followed by NaHCO$_3$ (0.5 g, 6 mmol) and di-tert-butyl-dicarbonate (0.35 g, 1.6 mmol). The mixture was stirred 4 hours at room temperature. EtOAc (150 mL) was added and the solution was washed with brine (2×60 mL), dried (MgSO$_4$) and concentrated on a rotary evaporator to give the crude Boc-protected product that was used for the next reaction without purification. MS-ESI (M+H)$^+$=407.2.

(304f) A mixture of 304e (0.65 g, 1.6 mmol), 4-chloromethyl-2-methylquinoline (0.36 g, 1.6 mmol) and K$_2$CO$_3$ (1 g, 7.2 mmol) in acetone (15 mL) was heated at reflux for 4 hours. EtOAc (150 mL) was added and the resulting solution was washed with brine (2×60 mL), dried (MgSO$_4$), and concentrated on a rotary evaporator. Purification using reversed phase HPLC provided 304f (0.68 g, 67%) as a powder. MS-ESI (M+H)$^+$=562.3.

(304g) Compound 304f (0.37 g, 0.65 mmol) was dissolved in MeOH (5 mL) and KOH (0.15 g) in water (1 mL) was added. The mixture was heated at 50° C. for 1 hour and acidified with 0.2 mL HOAc. Purification on reversed phase HPLC provided the carboxylic acid (0.25 g, 70%) as a powder. MS-ESI (M+H)$^+$=534.2.

(304h) To a solution of 304g (58 mg, 0.1 mmol) in DMF (2 mL) was added hydroxylamine hydrochloride (32 mg, 0.4 mmol) followed by N-methylmorpholine (0.06 mL, 0.5 mmol). After all solid was dissolved, the solution was cooled in an ice bath. To it was added BOP (54 mg, 0.12 mmol) and the mixture was stirred for 1 hour. Purification on reversed phase HPLC provided the hydroxamic acid as a powder. MS-ESI (M+H)$^+$=549.2.

(304i) Compound 304h (30 mg) was treated with TFA (1 mL)/CH$_2$Cl$_2$ (3 mL) for 20 min and the solution was concentrated on a rotary evaporator. The residue was taken up in water/acetonitrile. Lyophilization provided the final product as a powder. MS-ESI (M+H)$^+$=449.2.

Example 305

(cis,trans)-3-Dimethylmino-2-[[[4-[(2-methyl-4-quinolinyl)methoxy]phenyl]carbonyl]amino]-(N-hydroxy)cyclohexylcarboxamide bis-trifluoroacetate salt (305a) Compound 304g (160 mg) was treated with TFA (1 mL)/CH$_2$Cl$_2$ (3 mL) for 20 min and the solution was concentrated on a rotary evaporator. MS-ESI (M+H)$^+$= 434.2.

(305b) To a solution of 305a (50 mg, 0.075 mmol) in THF (2 mL) was added formaldehyde (37% aqueous solution, 0.04 mL, 0.42 mmol) followed by N-methylmorpholine (40 mg, 0.4 mmol) and NaBH$_3$CN (24 mg, 0.4 mmol). After stirring at room temperature for 1 hour, the mixture was purified on reversed phase HPLC to provide the dimethylamino product (48 mg, 92%) as a powder. MS-ESI (M+H)$^+$=462.2.

(305c) Coupling of 305b with hydroxylamine hydrochloride using a procedure similar to that described in (304h) provided the hydroxamic acid as a powder. MS-ESI (M+H)$^+$=477.3.

Example 306

(cis,trans)-3-(1-Methyl-1-ethylmino)-2-[[[4-[(2-methyl-4-quinolinyl)methoxy]phenyl]carbonyl]amino]-(N-hydroxy)cyclohexylcarboxamide bis-trifluoroacetate salt (306a) To a solution of compound 305a (52 mg, 0.08 mmol) in THF (2 mL) was added acetone (0.1 mL) followed by N-methylmorpholine (40 mg, 0.4 mmol) and Na(OAc)$_3$BH (25 mg, 0.12 mmol). The mixture was stirred at room temperature overnight. Concentration on a rotary evaporator followed by purification on reversed phase HPLC provided the desired product (45 mg, 80%) as a powder. MS-ESI (M+H)$^+$=476.2.

(306b) Coupling of 306a with hydroxylamine hydrochloride using a procedure similar to that described in (304h) provided the hydroxamic acid as a powder. MS-ESI (M+H)$^+$=491.3.

Example 307

(cis,trans)-3-Methylamino-2-[[[4-[(2-methyl-4-quinolinyl)methoxy]phenyl]carbonyl]amino]-(N-hydroxy)cyclohexylcarboxamide bis-trifluoroacetate salt (307a) To a solution of compound 304d (0.166 g, 0.39 mmol) and benzaldehyde (0.042 g, 0.4 mmol) in THF (5 mL) was added Na(OAc)$_3$BH (0.1 g, 0.5 mmol). The mixture was stirred for 1 hour at room temperature. The product formed was a bis-benzylated product. More benzaldehyde (0.042 g, 0.4 mmol) and Na(OAc)$_3$BH were added. The mixture was stirred for another hour and purified on reversed phase HPLC to provide the bis-benzylated product (0.15 g, 78%) as a powder. MS-ESI (M+H)$^+$=487.3.

(307b) Compound 307a (0.15 g, 0.3 mmol) was dissolved in MeOH (10 mL) and 10% Pd—C (30 mg) was added. The mixture was hydrogenated at atmospheric pressure for 3 hours. The catalyst was filtered off and the filtrate was concentrated on a rotary evaporator. Purification on reversed phase HPLC provided the mono-benzylated product (114 mg, 75%) as a powder. MS-ESI (M+H)$^+$=397.2.

(307c) To a solution of 307b (81 mg, 0.16 mmol) and Na(OAc)$_3$BH (20 g, 0.32 mmol) in THF (2 mL) was added N-methylmorpholine (40 mg, 0.4 mmol) followed by formaldehyde (37% aqueous solution, 25 mg, 0.3 mmol). The mixture was stirred for 1 hour and concentrated on a rotary evaporator. Chromatography on a silica gel column (10% MeOH/CH$_2$Cl$_2$) provided the N-benzyl-N-methyl product (60 mg, 94%)-as a solid. MS-ESI (M+H)$^+$=411.2.

(307d) Compound 307c (60 mg, 0.15 mmol) was dissolved in EtOH (5 mL) in a Parr bottle and to it was added 4 N HCl in dioxane (0.1 mL) followed by 10% Pd—C (10 mg). The mixture was hydrogenated on a Parr shaker at 50 psi for 4 hours. The catalyst was filtered off and the filtrate was concentrated on a rotary evaporator to provide the methylamino product as a solid. MS-ESI (M+H)$^+$=321.2.

(307e) To a solution of 307d (46 mg, 0.13 mmol) in THF (4 mL)/saturated aqueous NaHCO$_3$ solution (1 mL) cooled in an ice bath was added 1 N NaOH (0.13 mL) followed by di-tert-butyl-dicarbonate (28 mg, 0.13 mmol). The mixture was stirred at room temperature overnight. EtOAc (50 mL) was added and the solution was washed with brine (2×20 mL), dried (MgSO$_4$) and concentrated on a rotary evaporator. MS-ESI (M+H)$^+$=421.1.

(307f) A mixture of the crude product 307e, 4-chloromethyl-2-methylquinoline (30 mg, 0.13 mmol), K$_2$CO$_3$ (138 mg, 1 mmol) and Bu$_4$NI (20 mg, 0.13 mmol) in DMF (2 mL) was heated at 60° C. for 5 hours. Purification using reversed phase HPLC provided the desired product (68 mg, 90%) as a powder. MS-ESI (M+H)$^+$=576.3.

(307g) The final product was obtained by saponification of the ethyl ester 307f followed by acid deprotection of the Boc group using procedures similar to those described in (304g)–(304i). MS-ESI (M+H)$^+$=463.2.

Example 308

(cis,cis)-3-Hydroxy-2-[[[4-[(2-methyl-4-quinolinyl)methoxy]phenyl]carbonyl]amino]-(N-hydroxy) cyclohexylcarboxamide trifluoroacetate salt This compound was obtained by saponification of the ethyl ester intermediate 301c followed by coupling the resulting carboxylic acid with hydroxylamine hydrochloride using procedures similar to those described in (304g) and (304h). MS-ESI (M+H)$^+$=450.2.

Example 309

N-{cis-2-[(Hydroxyamino)carbonyl]cyclopentyl}-4-{[(2-methyl-4-quinolinyl)methyl]amino}benzamide (309a) A mixture of methyl 4-aminobenzoate (1.51 g, 10 mmol), 4-chloromethyl-2-methylquinoline hydrochloride (2.28 g, 10 mmol) and K$_2$CO$_3$ (3.2 g, 25 mmol) in DMF (20 mL) was stirred at 100° C. overnight. EtOAc (200 mL) was added. The solution was washed with water 2×, brine 2×, dried (MgSO$_4$) and concentrated. Flash chromatography on silica eluting with EtOAc/hexanes (2:1) provided the desired product (600 mg, 20%). MS m/z 307.1 (M+H)$^+$.

(309b) To a solution of 309a (400 mg, 1.3 mmol) in MeOH (5 mL) and THF (5 mL) was added 1 N KOH (5 mL). The solution was stirred at 80° C. for 3 h and concentrated. The residue was taken up in 1 N HCl solution (4 mL) and the solvent was removed under reduced pressure. The resulting residue was dissolved in MeOH. Insoluble materials were filtered off and the filtrate was concentrated to give the desired carboxylic acid product that was used for the next reaction without purification. MS m/z 293.2 (M+H)$^+$.

(309c) To a solution of 309b (200 mg, 0.684 mmol), ethyl cis-2-aminocyclopentanecarboxylate hydrochloride (108 mg, 0.6 mmol) and triethylamine (303 mg, 3 mmol) in DMF (3 mL) cooled in an ice bath was added BOP (266 mg, 0.6 mmol). The solution was stirred at room temperature for 2 h. Purification by reversed phase HPLC provided the desired product (130 mg, 34%) as a bis-trifluoroacetate. MS m/z 418.2 (M+H)$^+$.

(309d) Compound 309c (120 mg, 0.186 mmol) was dissolved in a 1.7 M hydroxylamine solution (3 mL). The reaction was stirred at room temperature for 20 min and quenched with a solution of 4 N HCl in dioxane (0.5 mL). The solvents were removed under reduced pressure and the residue was purified by reversed phase HPLC to give the desired product (90 mg, 75%) as a powder. MS m/z 419.1 (M+H)$^+$.

Example 310

N-{cis-2-[(Hydroxyamino)carbonyl]cyclopentyl}-4-{methyl[(2-methyl-4-quinolinyl)methyl] amino}benzamide (310a) This compound was prepared using procedures analogous to those described for Example 309. MS m/z 433.2 (M+H)$^+$.

Example 311

N-{cis-2-[(Hydroxyamino)carbonyl]cyclopentyl}-4-(3-phenyl-4,5-dihydro-5-isoxazolyl )benzamide (311a) To a stirred solution of benzaldehyde oxime (605 mg, 5 mmol) and methyl 4-vinylbenzoate (810 mg, 5 mmol) in CH$_2$Cl$_2$ (20 mL) was added a bleach solution (30 mL). The mixture was stirred at room temperature for 4 h and diluted with CH$_2$Cl$_2$. The organic phase was separated, washed with brine 2×, dried (MgSO$_4$) and concentrated. Chromatography on a silica gel column eluting with EtOAc/hexanes (1:2) provided the desired product (500 mg, 36%) as a solid. MS m/z 323.2 (M+H)$^+$.

(311b) To a solution of 3a (500 mg, 1.78 mmol) in THF (10 mL) was added 1 N KOH (5 mL). The solution was stirred at room temperature overnight and acidified with 1 N HCl to pH=3. The resulting solution was extracted with EtOAc 2×. The combined organic phase was washed with brine 2×, dried (MgSO$_4$) and concentrated to give the desired acid (400 mg, 84%). MS m/z 268.2 (M+H)$^+$.

(311c) To a solution of 3b (133 mg, 0.5 mmol), ethyl cis-2-aminocyclopentanecarboxylate hydrochloride (116 mg, 0.6 mmol) and triethylamine (303 mg, 3 mmol) in DMF (3 mL) cooled in an ice bath was added BOP (253 mg, 0.6 mmol). The solution was stirred at room temperature for 2 h. Purification by reversed phase HPLC provided the desired product (170 mg, 84%) as a powder. MS m/z 407.1 (M+H)$^+$.

(311d) Compound 3c (170 mg, 0.41 mmol) was dissolved in a 1.7 M hydroxylamine solution (3 mL). After stirring at room temperature for 20 min, a solution of TFA (0.3 mL) in $CH_2Cl_2$ (2 mL) was added slowly. The solvents were removed under reduced pressure and the residue was purified by reversed phase HPLC to give the desired product (90 mg, 56%) as a powder. MS m/z 394.1 (M+H)$^+$.

Example 312

N-{cis-2-[(Hydroxyamino)carbonyl]cyclopentyl}-4-[3-(4-pyridinyl)-4,5-dihydro-5-isoxazolyl]benzamide (312a) This compound was prepared using procedures analogous to those described for Example 311. MS m/z 395.1 (M+H)$^+$.

Example 313

N-{cis-2-[(Hydroxyamino)carbonyl]cyclopentyl}-4-[3-(3-pyridinyl)-4,5-dihydro-5-isoxazolyl]benzamide (313a) This compound was prepared using procedures analogous to those described for Example 311. MS m/z 395.2 (M+H)$^+$.

Example 314

N-{cis-2-[(Hydroxyamino)carbonyl]cyclopentyl}-4-[3-(2-pyridinyl)-4,5-dihydro-5-isoxazolyl]benzamide (314a) This compound was prepared using procedures analogous to those described for Example 311. MS m/z 395.2 (M+H)$^+$.

Example 315

N-{cis-2-[(Hydroxyamino)carbonyl]cyclopentyl}-4-[3-(4-quinolinyl)-4,5-dihydro-5-isoxazolyl]benzamide (315a) This compound was prepared using procedures analogous to those described for Example 311. MS m/z 445.1 (M+H)$^+$.

Example 316

4-[3-(2,6-Dimethyl-4-pyridinyl)-4,5-dihydro-5-isoxazolyl]-N-{cis-2-[(hydroxyamino)carbonyl]cyclopentyl}benzamide (316a) This compound was prepared using procedures analogous to those described for Example 311. MS m/z 423.1 (M+H)$^+$.

Example 317

N-{cis-2-[(Hydroxyamino)carbonyl]cyclopentyl}-3-methoxy-4-[3-(4-pyridinyl)-4,5-dihydro-5-isoxazolyl]benzamide (317a) This compound was prepared using procedures analogous to those described for Example 311. MS m/z 425.1 (M+H)$^+$.

Example 318

3-Hydroxy-N-{cis-2-[(hydroxyamino)carbonyl]cyclopentyl}-4-[3-(4-pyridinyl)-4,5-dihydro-5-isoxazolyl]benzamide (318a) This compound was prepared using procedures analogous to those described for Example 311. MS m/z 411.1 (M+H)$^+$.

Example 319

N-{cis-2-[(Hydroxyamino)carbonyl]cyclopentyl}-4-[5-(2-pyridinyl)-4,5-dihydro-3-isoxazolyl]benzamide (319a) To a solution of methyl 4-formylbenzoate (10 g, 61 mmol) in MeOH (100 mL) was added hydroxylamine hydrochloride (7 g, 100 mmol) followed by triethylamine (13.9 mL, 100 mmol). The mixture was stirred at room temperature overnight. The solvent was removed under reduced pressure and the residue was taken up in EtOAc (300 mL). The solution was washed with brine 3×, dried ($MgSO_4$), and concentrated. Flash chromatography on silica eluting with EtOAc/hexanes (2:1) provided the desired oxime product (2.5 g, 23%) as a solid. MS m/z 180.1 (M+H)$^+$.

(319b) To a solution of 11a (716 mg, 4 mmol) and 2-vinylpyridine (525 mg, 5 mmol) in $CH_2Cl_2$ (20 mL) was added a solution of bleach (30 mL). The solution was stirred at room temperature overnight and diluted with $CH_2Cl_2$. The organic phase was separated, washed with brine 2×, dried ($MgSO_4$) and concentrated. Chromatography on a silica gel column eluting with EtOAc/hexanes (2:1) provided the desired product (800 mg, 73%) as a solid. MS m/z 283.2 (M+H)$^+$.

(319c) To a solution of 11b (800 mg, 2.83 mmol) in THF (5 mL) and MeOH (3 mL) was added a solution of 1 N KOH (5 mL). The solution was stirred at room temperature for 4 h and acidified with a solution of 1 N HCl (6 mL). The solvents were removed under reduced pressure. The residue was dissolved in MeOH, the insoluble materials were filtered off and the filtrate was concentrated to give the desired carboxylic acid that was used for the next reaction without purification. MS m/z 269.2 (M+H)$^+$.

(319d) To a solution of 11c (152 mg, 0.5 mmol), ethyl cis-2-aminocyclopentanecarboxylic acid hydrochloride (116 mg, 0.6 mmol) and triethylamine (303 mg, 3 mmol) in DMF (3 mL) cooled in an ice bath was added BOP (253 mg, 0.6 mmol). The solution was stirred at room temperature for 4 h. Purification by reversed phase HPLC provided the desired product (190 mg, 73%) as a TFA salt. MS m/z 408.1 (M+H)$^+$.

(319e) Treatment of 11d with a solution of hydroxylamine following the procedure described in (311d) provided the desired hydroxamic acid. MS m/z 395.1 (M+H)$^+$.

Example 320

N-{cis-2-[(Hydroxyamino)carbonyl]cyclopentyl}-4-[5-(4-pyridinyl)-4,5-dihydro-3-isoxazolyl]benzamide (320a) This compound was prepared using procedures analogous to those described for Example 319. MS m/z 395.1 (M+H)$^+$.

Example 501

N-{4-[(hydroxyamino)carbonyl]-3-pyrrolidinyl}-1-[(2-methyl-4-quinolinyl)methyl]-1H-indole-5-carboxamide bis(trifluoroacetate)

(501a) Indole 5-carboxylic acid (0.5 g, 3.1 mmol) was added to a suspension of sodium hydride (0.27 g, 6.8 mmol, 60% oil dispersion) (washed with hexanes) in DMF (20 mL) cooled to 0° C. The reaction was allowed to stir for 1 h and the 4-chloromethyl-2-methyl-quinoline (0.72 g, 3.8 mmol) was added. The reaction was allowed to warm to room temperature and stirred overnight. The reaction was neutralized with 1 N HCl and extracted with ethyl acetate. The combined organic layer was washed with brine, dried over magnesium sulfate and concentrated to give the 1-[(2-methyl-5,8-dihydro-4-quinolinyl)methyl]-1H-indole-5-carboxylic acid (0.68 g, 69%) as a brown residue, MS (M+H)+=317.

(501b) Thionyl chloride (5 mL) was added to a suspension of the 1-[(2-methyl-5,8-dihydro-4-quinolinyl)methyl]-1H-indole-5-carboxylic acid from step (501a) (0.67 g, 2.1 mmol) in methylene chloride (15 mL) and was heated to reflux for 2 h. The reaction was cooled to room temperature, concentrated in vacuo to give the 1-[(2-methyl-5,8-dihydro-4-quinolinyl)methyl]-1H-indole-5-carbonyl chloride (0.68 g, 80%) as a yellow solid.

(501c) The 1-tert-butyl 3-methyl 4-amino-1,3-pyrrolidinedicarboxylate (0.10 g, 0.41 mmol) was combined with the acid chloride from step (501b) (0.10 g, 0.32 mmol) in methylene chloride (15 mL) and water saturated sodium bicarbonate (15 mL). The reaction was stirred for 3.5 h, partitioned between methylene chloride and water. The organic layer was washed with brine, dried over magnesium sulfate and concentrated to give a solid. This was purified by flash chromatography on silica gel eluting hexane: ethyl acetate (30:60, v:v) to give the 1-tert-butyl 3-methyl 4-[({1-[(2-methyl-4-quinolinyl)methyl]-1H-indol-5-yl}carbonyl)amino]-1,3-pyrrolidinedicarboxylate (0.120 g, 70%) as a solid, MS (M+H)+=543.

(501d) TFA (2 mL) was added to a solution of the coupled product (0.11 g, 0.2 mmol) from step (501c) in methylene chloride (3 mL) at room temperature. The reaction was complete after stirring for 2 h and was concentrated to give methyl 4-[({1-[(2-methyl-4-quinolinyl)methyl]-1H-indol-5-yl}carbonyl)amino]-3-pyrrolidinecarboxylate (0.165 g, 100%) as an oil, MS (M+2H)++=222.

(501e) Following a procedure analogous to that used in example (1d) for the conversion to the hydroxamic acid, but using the methyl ester step (501d) the title compound (0.065 g. 23%) was prepared as a white amorphous solid, MS (M+H)+=444.

Example 502

N-{2-[(hydroxyamino)carbonyl]cyclopentyl}-1-[(2-methyl-4-quinolinyl)methyl]-1H-indole-5-carboxamide trifluoroacetate (502a) Following a procedure analogous to that used in example (501) but using the methyl 2-aminocyclopentanecarboxylate, the title compound (0.038 g. 32%) was prepared as a solid, MS (M+H)+=443.

Example 503

N-hydroxy-3-({6-[(2-methyl-4-quinolinyl)methoxy]-1-naphthoyl}amino)-4-piperidinecarboxamide bis(trifluoroacetate)

(503a) Following a procedure analogous to that used in example (501) but using the methyl 3-amino-4-piperidinecarboxylate and 6-hydroxy-1-naphthoic acid, the title compound (0.015 g. 39%) was prepared as a white amorphous solid, MS (M+H)+=485.

Example 504

N-{2-[(hydroxyamino)carbonyl]cyclopentyl}-6-[(2-methyl-4-quinolinyl)methoxy]-1-naphthamide trifluoroacetate (504a) Following a procedure analogous to that used in example (501) but using the methyl 2-aminocyclopentanecarboxylate and 6-hydroxy-1-naphthoic acid, the title compound (0.11 g. 57%) was prepared as a white amorphous solid, MS (M+H)+=470.

Example 505

N-{2-[(hydroxyamino)carbonyl]cyclopentyl}-6-[(2-methyl-4-quinolinyl)methoxy]-2-naphthamide trifluoroacetate (505a) Following a procedure analogous to that used in example (501) but using the methyl 2-aminocyclopentanecarboxylate and 6-hydroxy-2-naphthoic acid, the title compound (0.06 g. 23%) was prepared as a white amorphous solid, MS (M+H)+=470.

Example 506

N-{2-[(hydroxyamino)carbonyl]cyclopentyl}-6-[(2-methyl-4-quinolinyl)methoxy]-1,2,3,4-tetrahydro-1-isoquinolinecarboxamide bis(trifluoroacetate)

(506a) Following a procedure analogous to that used in example (501) but using the methyl 2-aminocyclopentanecarboxylate and 2-(tert-butoxycarbonyl)-6-hydroxy-1,2,3,4-tetrahydro-1-isoquinolinecarboxylic acid the title compound (0.050 g. 29%) was prepared as a white amorphous solid, MS (M+H)+=475.

Example 507

N-{2-[(hydroxyamino)carbonyl]cyclopentyl}-1-[(2-methyl-4-quinolinyl)methyl]-1H-benzimidazole-5-carboxamide trifluoroacetate (507a) Following a procedure analogous to that used in example (501) but using the methyl 2-aminocyclopentanecarboxylate and 1H-benzimidazole-5-carboxylic acid the title compound (0.020 g. 5%) was prepared as a white amorphous solid, MS (M+H)+=444.

Example 508

N-{2-[(hydroxyamino)carbonyl]cyclopentyl}-1-[(2-methyl-4-quinolinyl)methyl]-1H-indole-4-carboxamide trifluoroacetate (508a) Following a procedure analogous to that used in example (501) but using the methyl 2-aminocyclopentanecarboxylate and 1H-indole-4-carboxylic acid, the title compound (0.085 g. 56%) was prepared as a white amorphous solid, MS (M+H)+=443.

Example 700

(±)-cis-N-hydroxy-2-[[4-[(2-methyl-4-quinolinyl)methoxy]benzoyl]amino]-1-cycloheptanecarboxamide, trifluoroacetate (700a) Chlorosulfonylisocyanate (4.80 g, 33.9 mmol) in methylene chloride (2 mL) was added dropwise to cycloheptene in methylene chloride (25 mL) then heated to reflux under nitrogen for 10 h. The reaction was quenched by dropwise addition of water then extracted with methylene chloride (2x). The combined organic layers were washed with water (1x) and brine (1x) then dried over magnesium sulfate. The solvent was evaporated in vacuo and the residue diluted with ether (15 mL). The ether solution was added dropwise to a solution of 10% sodium sulfite/ether (2:1, 75 mL) maintaining the pH between 7 and 8 with 10% sodium hydroxide. After the addition was complete stirring was continued for 0.5 h then the reaction was extracted with ether (3×). The combined organic layers were washed with water (1×) and brine (1×) then dried over magnesium sulfate. The solvent was evaporated in vacuo to provide 700a (3.76 g, 87%) as a waxy yellow solid. MS: APc [M+(CH$_3$CN+H)]+=181.

(700b) Chlorotrimethylsilane (5.87 g, 54 mmol) was added dropwise to 700a (3.76 g, 27.0 mmol) in methanol (75 mL) at room temperature under nitrogen. After stirring for 2 h the solvent was evaporated in vacuo and the residue titurated with ether. The white solid was filtered then dried under vacuum for 24 h to provide 700b (4.52 g, 81%). MS: ESI [M+H]$^+$=172.

(700c) N-Methyl morpholine (0.73 g, 7.22 mmol) was added dropwise to 700b (0.5 g, 2.41 mmol), BOP reagent (1.17 g, 2.65 mmol), and 4-[(2-methyl-4-quinolinyl)methoxy] benzoic acid (0.71 g, 2.41 mmol) in dimethylformamide (10 mL) at 0° C. under nitrogen. The reaction was allowed to warm to room temperature then stirred overnight. The solvent was removed in vacuo and the residue taken up in ethyl acetate (100 mL). The solution was washed with water (2×), saturated sodium bicarbonate (2×), and brine (1×) then dried over magnesium sulfate. The solvent was removed in vacuo and the residue purified by flash chromatography (SiO$_2$, 75%–100% ethyl acetate/hexanes) to provide 700c (0.963 g, 89%) as a viscous light yellow oil. MS: ESI [M+H]$^+$=447.

(700d) A solution of basic hydroxylamine was prepared by adding potassium hydroxide (2.81 g, 50.2 mmol) in methanol (7 mL) to hydroxylamine hydrochloride (2.34 g, 33.7 mmol) in hot methanol (12 mL). The solution was allowed to cool to ambient temperature and the solid potassium chloride was filtered. The hydroxylamine solution (15 mL) was added in one portion to 700c (0.25 g, 0.56 mmol) and stirred for 6 h. The reaction was quenched with 1N hydrogen chloride (~15 mL) until the pH was approximately 6. The solvent was removed in vacuo and the residue taken up in 1N hydrogen chloride/methanol (1:1) then purified by C$_{18}$ HPLC to provide example 700(88 mg, 32%). MS: ESI [M+H]$^+$=448.

Example 701

(±)-trans-N-hydroxy-2-[[4-[(2-methyl-4-quinolinyl) methoxy]benzoyl]amino]-1-cycloheptanecarboxamide, trifluoroacetate (701a) Diazabicyclo[5.4.0]undec-5-ene (0.39 g, 2.58 mmol) was added to 700c (0.23 g, 0.52 mmol) in xylenes (10 mL) then heated at 100° C. for 8 h and 110° C. for 14 h. The solvent was evaporated in vacuo and the residue purified by flash chromatography (SiO$_2$, 65% ethyl acetate/hexanes) to provide 701a (103 mg, 45%) with >90% isomeric purity. MS: ESI [M+H]$^+$=447.

(701b) Example 701 was prepared in a procedure analogous to 700d. MS: ESI [M+H]$^+$=448.

Example 702

(4S,5R)-N-hydroxy-5-({4-[(2-methyl-4-quinolinyl) methoxy]benzoyl}amino)-2-oxohexahydro-1H-azepine-4-carboxamide trifluoroacetate (702a) Diphenylphosphoryl azide (4.72 g, 17.1 mmol) was added dropwise to 1-methyl (1S,2R)-(+)-cis-1,2,3,6-tetrahydrophthalate (2.63 g, 14.3 mol) and triethylamine (2.17 g, 41.2 mmol) in benzene (20 mL) at room temperature. After stirring for 2 h benzyl alcohol (1.85 g, 17.1 mmol) was added and the reaction was heated to reflux for 3 h. The mixture was cooled to room temperature and diluted with ethyl acetate (150 mL). The solution was washed with water (1×), 10% citric acid (1×), saturated sodium bicarbonate (1×), and brine (1×) then dried over magnesium sulfate. The solvent was evaporated in vacuo and the residue purified by flash chromatography (SiO$_2$, 20–30% ethyl acetate/hexanes as solvent. The product 702a (2.69, 65%) was isolated as a brittle foam. MS: ESI [M+H]$^+$=290.

(702b) Borane:tetrahydrofuran (1M, 9.66 mL, 9.66 mmol) was added dropwise to 702a (2.15 g, 7.43 mmol) in anhydrous tetrahydrofuran (20 mL) at 0° C. under nitrogen. The reaction was allowed to warm to room temperature over 1.5 h then cooled again to 0° C. and quenched by the dropwise addition of a with of 30% hydrogen peroxide (4.5 mL) and 1N sodium hydroxide (10 mL). After the addition was completed the mixture was stirred 15 m then quenched with 10% sodium sulfite. The solution was extracted with ethyl acetate (3×) and the combined organic extracts were washed with 10% sodium sulfite (2×) and brine (1×). After drying over magnesium sulfate the solvent was removed in vacuo and the product 702b (2.35 g, 100%) was carried forward without further purification. MS: APc [M+H]$^+$=308.

(702c) Pyridinium dichromate (4.19 g. 11.1 mmol) was added in one portion to 702b(7.43 mmol) and powdered 3 A molecular sieves (5 g) in methylene chloride (30 mL) then stirred for 3 h at ambient temperature. The reaction was filtered through celite under vacuum washing with methylene chloride. The solvent was evaporated in vacuo and the residue purified by flash chromatography (SiO$_2$, 50% ethyl acetate/hexanes) to provide 702c (1.68 g, 74%) as a viscous light yellow oil. MS: APc [M+H]$^+$=306.

(702d) Hydroxylamine hydrochloride (1.53 g, 22.0 mmol) was added in one portion to 702c (1.68 g, 5.50 mmol) and sodium bicarbonate (1.53 g, 18.2 mmol) in methanol (25 mL) then heated to reflux for 3 h. The mixture was cooled to ambient temperature then diluted with water (50 mL) and extracted with chloroform (4×). The combined organic extracts were washed with brine (1×) then dried over magnesium sulfate. The solvent was evaporated in vacuo and the residue purified by flash chromatography (SiO$_2$, 50% ethyl acetate/hexanes) to provide 702d (1.46 g, 83%) as a viscous light yellow oil. MS: ESI [M+H]$^+$= 321.

(702e) 702d(1.46 g, 4.56 mmol) in methylene chloride (10 mL) was added dropwise to p-toluenesulfonyl chloride (1.04 g, 5.47 mmol) and pyridine (0.54 g, 6.84 mmol) in methylene chloride (20 mL) at room temperature. The reaction was stirred for 14 h then diluted with methylene chloride (80 mL). The solution was washed with 1N hydrochloric acid (2×), saturated sodium bicarbonate (2×), and brine (1×) then dried over magnesium sulfate. The solvent was evaporated in vacuo and the tosylate ([M+H]$^+$=475) was taken up in ethanol free chloroform (40 mL) and added to dry silica gel (20 g). The reaction was stirred for 4 h then poured onto the top of a flash column (SiO$_2$, 80 g, 50% ethyl acetate hexanes to 50% methanol/ethyl acetate) and eluted. The mixture of four regioisomeric lactams were purified by C$_{18}$ HPLC (CH$_3$CN/water, 0.1% trifluoroacetic acid) to provide 702e-a, 702e-b, 702e-c, and 702e-d (410 mg, 267 mg, 364, mg, 195 mg, respectively, 85%). MS: APc [M+H]$^+$= 321 for all samples.

(702f) Methanol (10 mL) was carefully added to 10% Pd on C (0.17 g) and 702e-c (264 mg, 1.14 mmol) under a bed of nitrogen. A hydrogen balloon was attached via a three-way stopcock and the atmosphere was removed and replaced with hydrogen three times. After 0.5 h the hydrogen was removed and replaced with nitrogen then the catalyst removed by vacuum. filtration through celite. The solvent was removed in vacuo to provide 702f (239 mg, 100%) as a viscous oil. MS: ESI [M+H]$^+$=187.

(702g) In a procedure analogous to 700c, 702f was coupled to 4-[(2-methyl-4-quinolinyl)methoxy]benzoic acid to provide 702g (0.28 g, 53%)as a viscous clear oil. MS: ESI [M+H]$^+$=462.

(702h) In a procedure analogous to 700d, 702g was converted to the hydroxamic acid example 702 were the regiochemistry was proven by 2D $^1$HNMR. MS: ESI [M+H]$^+$=463.

Example 703 and Example 704

(3S,4S)-N-hydroxy-3-({4-[(2-methyl-4-quinolinyl) methoxy]benzoyl}amino)-7-oxohexahydro-1H-azepine-4-carboxamide trifluoroacetate and (3S, 4R)-N-hydroxy-4-({4-[(2-methyl-4-quinolinyl) methoxy]benzoyl}amino)-7-oxohexahydro-1H-azepine-3-carboxamide trifluoroacetate and (4S, 5R)-N-hydroxy-5-({4-[(2-methyl-4-quinolinyl) methoxy]benzoyl}amino)-7-oxohexahydro-1H-azepine-4-carboxamide trifluoroacetate (703a) In a series of procedures analogous to steps 702f through 702h, 702e-a was converted to example 703.
(704) In a series of procedures analogous to steps 702f through 702h 702e-b was converted example 704.

Example 705 and Example 706

(2S,3R)-N-hydroxy-3-({4-[(2-methyl-4-quinolinyl) methoxy]benzoyl}amino)-2-pyrrolidinecarboxamide ditrifluoroacetate and (2R,3R)-N-hydroxy-3-({4-[(2-methyl-4-quinolinyl)methoxy]benzoyl}amino)-2-pyrrolidinecarboxamide ditrifluoroacetate (705a,706a) Di-t-butyl dicarbonate (8.60 g, 39.4 mmol) in tetrahydrofuran (20 mL) was added dropwise to trans-3-hydroxy-L-proline (5.16 g, 39.4 mmol) in mixture of 1N sodium hydroxide (43.3 mL) and tetrahydrofuran (20 mL) at ambient temperature. The solution was stirred overnight then extracted with pet ether (2x). The pet ether extracts were washed with saturated sodium bicarbonate (3x) then the combined aqueous layers were carefully acidified with sodium hydrogensulfate monohydate. The aqueous solution was extracted with ethyl acetate (3x) and the combined organic layers were dried over magnesium sulfate. The solvent was removed in vacuo to give 706a/707a (8.29 g, 91%). MS: ESI$^-$[M-H]$^-$=230.

(705b,706b) N-Methyl morpholine (7.25 g, 71.7 mmol) was added in a slow stream to 705a,706a (8.29 g, 35.8 mmol), BOP reagent (17.4 g, 39.4 mmol), and N-benzylhydroxylamine hydrochloride (7.44 g, 46.6 mmol) in dimethylformamide (75 mL) under nitrogen. The reaction was stirred overnight and the solvent was evaporated in vacuo. The residue was taken up in ethyl acetate (300 mL) and washed with water (2x), 10% citric acid (2x), saturated sodium bicarbonate (2x), and brine (1x) then dried over magnesium sulfate. The solvent was removed in vacuo and the residue purified by flash chromatography (SiO$_2$, 50%–80% ethyl acetate/hexanes) to provide 706b,707b(6.11 g, 51%) as a viscous oil. MS: ESI [M+H]$^+$=337.

(705c,706c) Diazoethyldicarboxylate (3.16 g, 18.2 mmol) was added dropwise to 705b,706b (6.11 g, 18.2 mmol) and triphenylphosphine (5.24 g, 20.0 mmol) in anhydrous tetrahydrofuran (50 mL) at room temperature under nitrogen. After stirring overnight the solvent was evaporated in vacuo and the residue purified by flash chromatography (SiO$_2$, 20%–30% ethyl acetate/hexanes) to provide 706c, 707c (4.61 g, 80%). MS: APc [M+H]$^+$=319.

(705d,706d) Methanol (75 mL) was carefully added to 705c,706c(4.61 g, 14.5 mmol) and Pd on C(10%, 1.3 g) under a bed of nitrogen. A hydrogen balloon was attached via a 3-way stopcock and the atmosphere was removed and replace with hydrogen three times. After 1.5 h the hydrogen was removed and the reaction was vented with nitrogen. The catalyst was removed by vacuum filtration through celite and the sovent was removed in vacuo to provide 706d,707d (3.09 g, 93%). MS: APc {M+H]$^+$=229.

(705e,706e) Sodium acetate (23.8 g, 290 mmol) was added to 705d,706d (3.09 g, 13.5 mmol) in water/tetrahydrofuran (200 mL, 1/1) at room temperature. Titanium trichloride (36.7 g, 12 wt % in 21% HCl(aq), 29.0 mmol) was added dropwise and stirring was continued for 3 h at room temperature. The reaction mixture was extracted with ethyl acetate (1x) then titanium dioxide was removed from the aqueous layer by vacuum filtration through celite. The aqueous layer was extracted again with ethyl acetate (2x) and the combined ethyl acetate layers were washed with brine (1x). The solvent was removed in vacuo and the resulting solid was recrystallized from ethyl acetate/hexanes to provide 706e,707e (1.64 g, 57%). MS: CI [(M–C$_4$H$_8$)+H]$^+$=157.

(705f,706f) Chlorotrimethylsilane (256 mg, 2.36 mmol) was added dropwise to 705e,706e (250 mg, 1.18 mmol) in methanol (2 mL) at room temperature under nitrogen. After stirring for 2 h the solvent was evaporated in vacuo and the residue titurated with ether. The white solid was filtered then dried under vacuum for 24 h to provide an inseparable mixture of Boc protected β-amino acid and Boc deprotected β-amino acid 706f,707f (235 mg) that was taken forward without further purification. MS: CI [(M–NH$_3$)+H]$^+$=128.

(705g,706g) In a procedure analogous to 700c, 705f,706f (281 mg) was coupled to 4-[(2-methyl-4-quinolinyl) methoxy]benzoic acid to provide 706g,707g-a(Boc deprotected, 78 mg, MS ESI: [M+H]$^+$=420) and 706g, 707g-b (Boc protected, 29 mg, [M+H]$^+$=520).

(705h,706h) Examples 706 and 707 were prepared from 705g,706g-a using a procedure analogous to 700d. Example 707 was the first off the C$_{18}$ HPLC column(MS: ESI[M+H]$^+$=421) and example 706 was the first(MS: ESI [M+H]$^+$=421).

Example 707 tert-butyl (2S,3R)-2-[(hydroxyamino)carbonyl]-3-({4-[(2-methyl-4-quinolinyl)methoxy] benzoyl}amino)-1-pyrrolidinecarboxylate trifluoroacetate (707a) Example 707 was prepared from 705g,705g-b using a procedure analogous to 700d. Example 708 was isolated as a single diastereomer. MS: ESI [M+H]$^+$=521.

TABLE 1
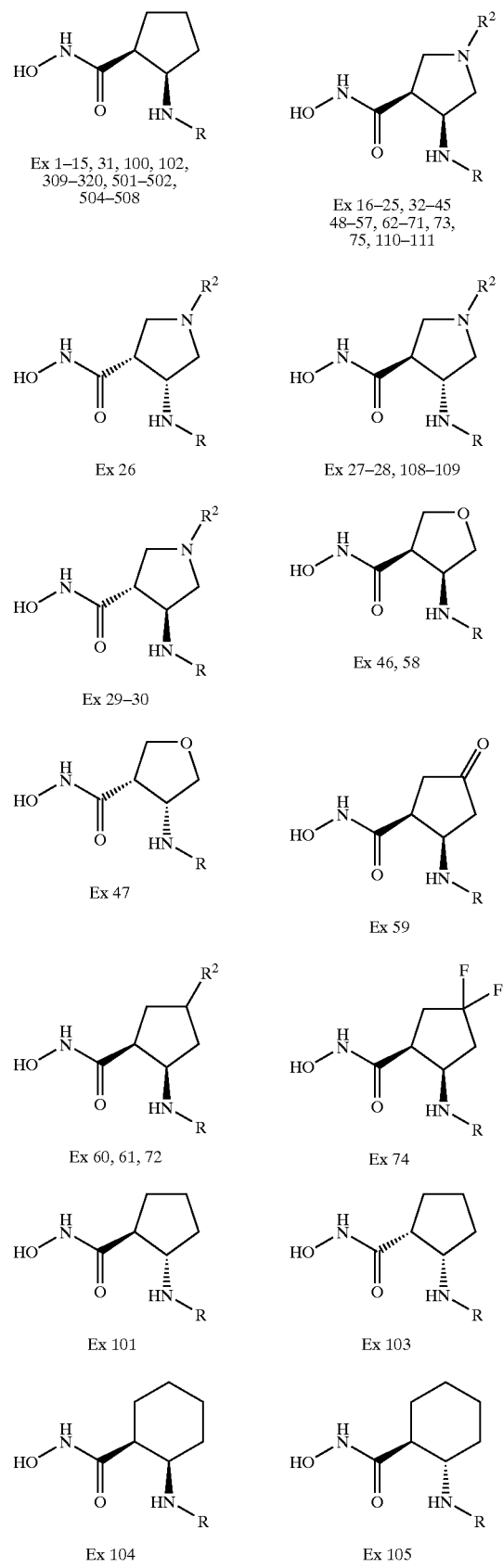
TABLE 1-continued
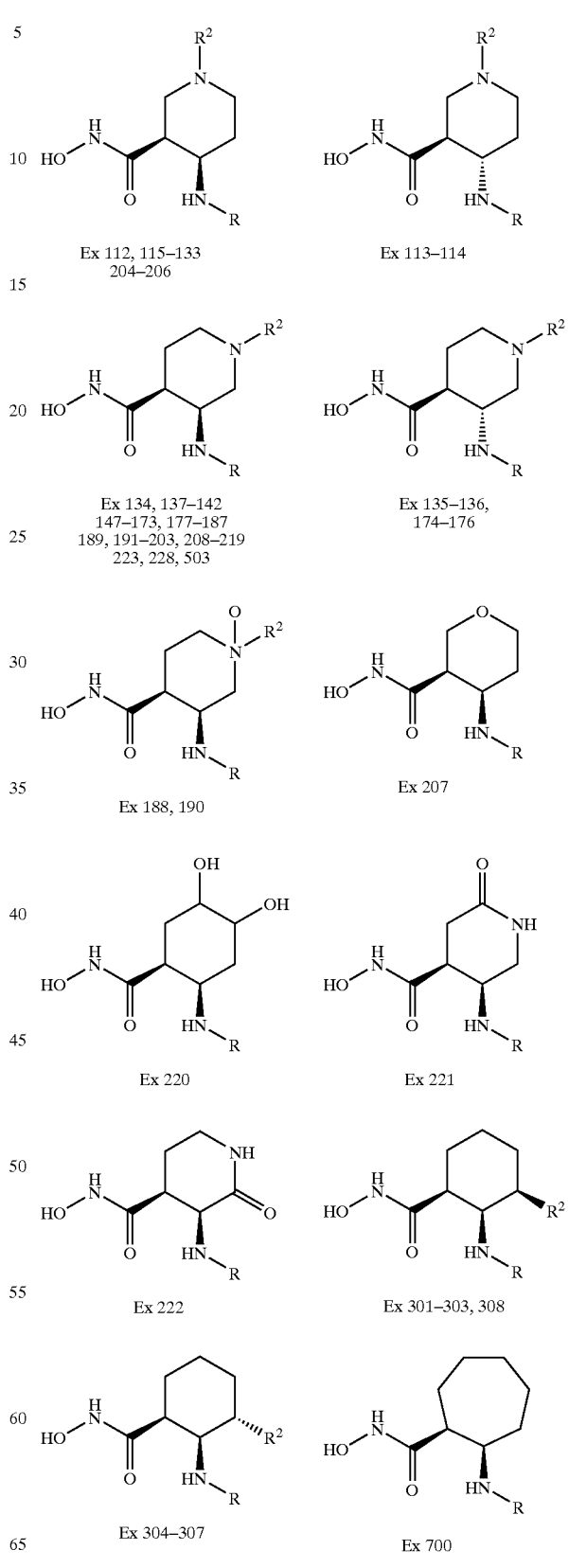

TABLE 1-continued

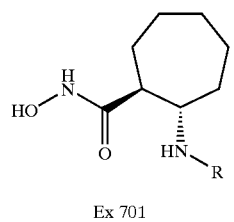

Ex 701    Ex 702

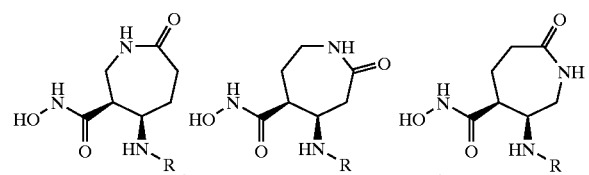

Example 703 (1 of 3 structures)    Example 704 (1 of remaining 2)

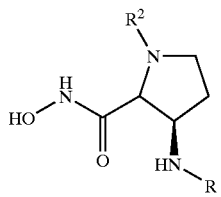

Ex 705–707

| Ex | R | R² | MS [M + H] |
|---|---|---|---|
| 1 | 4-(2-trifluoromethylphenyl)benzoyl | — | 393 |
| 2 | 4-(2-trifluoromethylphenoxy)benzoyl | — | 409 |
| 3 | 4-(3-methyl-2-pyridinyl)benzoyl | — | 340 |
| 4 | 4-phenylbenzoyl | — | 325 |
| 5 | 4-phenoxybenzoyl | — | 341 |
| 6 | 4-benzyloxybenzoyl | — | 355 |
| 7 | 4-(2-methoxyphenyl)benzoyl | — | 355 |
| 8 | 4-(2-methylphenyl)benzoyl | — | 339 |
| 9 | 4-(2-methoxyphenoxy)benzoyl | — | 371 |
| 10 | 4-(2-methylphenoxy)benzoyl | — | 355 |
| 11 | 4-(3-methylphenyl)benzoyl | — | 339 |
| 12 | 4-(4-quinolinyl)benzoyl | — | 376 |
| 13 | 4-(3,5-dimethylphenyl)benzoyl | — | 353 |
| 14 | 5-[2-(2-methylphenyl)]pyridinylcarbonyl | — | 340 |
| 15 | 5-[2-(2-methoxyphenyl)]pyridinylcarbonyl | — | 356 |
| 16 | 4-(2-methyl-4-quinolinylmethoxy)benzoyl | Isopropyl | 463 |
| 17 | 4-(2-methyl-4-quinolinylmethoxy)benzoyl | 2,2-dimethylpropionyl | 505 |
| 18 | 4-(2-methyl-4-quinolinylmethoxy)benzoyl | methanesulfonyl | 499 |
| 19 | 4-(2-methyl-4-quinolinylmethoxy)benzoyl | Methyl | 435 |
| 20 | 4-(2-methyl-4-quinolinylmethoxy)benzoyl | (1,1-dimethyl-ethoxy)carbonyl | 521 |
| 21 | 4-(2-methyl-4-quinolinylmethoxy)benzoyl | H | 421 |
| 22 | 4-(2-methyl-4-quinolinylmethoxy)benzoyl | 4-[N-(1,1-dimethyl-ethoxy)carbonyl]piperidinyl | 604 |
| 23 | 4-(2-methyl-4-quinolinylmethoxy)benzoyl | 4-piperidinyl | 504 |
| 24 | 4-(2-methyl-4-quinolinylmethoxy)benzoyl | 3-[N-(1,1-dimethyl-ethoxy)carbonyl]pyrrolidinyl | 590 |
| 25 | 4-(2-methyl-4-quinolinylmethoxy)benzoyl | pyrrolidinyl | 490 |
| 26 | 4-(2-methyl-4-quinolinylmethoxy)benzoyl | (1,1-dimethyl-ethoxy)carbonyl | 521 |
| 27 | 4-(2-methyl-4-quinolinylmethoxy)benzoyl | (1,1-dimethyl-ethoxy)carbonyl | 521 |
| 28 | 4-(2-methyl-4-quinolinylmethoxy)benzoyl | H | 421 |
| 29 | 4-(2-methyl-4-quinolinylmethoxy)benzoyl | (1,1-dimethyl-ethoxy)carbonyl | 521 |
| 30 | 4-(2-methyl-4-quinolinylmethoxy)benzoyl | H | 421 |
| 31 | 4-(4-pyridinyl)benzoyl | — | 326 |
| 32 | 4-(2-methyl-4-quinolinylmethoxy)benzoyl | 1,1-dimethyl-2-propynyl | 487 |
| 33 | 4-(2-methyl-4-quinolinylmethoxy)benzoyl | 2-propynyl | 459 |
| 34 | 4-(2-methyl-4-quinolinylmethoxy)benzoyl | 2-propenyl | 461 |
| 35 | 4-(2-methyl-4-quinolinylmethoxy)benzoyl | propyl | 463 |
| 36 | 4-(2-methyl-4-quinolinylmethoxy)benzoyl | 2-methyl-2-propenyl | 475 |
| 37 | 4-(2-methyl-4-quinolinylmethoxy)benzoyl | 1,1-dimethyl-2-propenyl | 489 |
| 38 | 4-(2-methyl-4-quinolinylmethoxy)benzoyl | 1,1-dimethylpropyl | 491 |
| 39 | 4-(2-methyl-4-quinolinylmethoxy)benzoyl | 3-methylbutyl | 491 |
| 40 | 4-(2-methyl-4-quinolinylmethoxy)benzoyl | 2,2-dimethylpropyl | 491 |
| 41 | 4-(2-methyl-4-quinolinylmethoxy)benzoyl | butyl | 477 |
| 42 | 4-(2-methyl-4-quinolinylmethoxy)benzoyl | 3-butenyl | 475 |
| 43 | 4-(2-methyl-4-quinolinylmethoxy)benzoyl | 2-butynyl | 473 |
| 44 | 4-(2-methyl-4-quinolinylmethoxy)benzoyl | 2-furylmethyl | 501 |
| 45 | 4-(2-methyl-4-quinolinylmethoxy)benzoyl | (5-methyl-2-furyl)methyl | 515 |
| 46 | 4-(2-methyl-4-quinolinylmethoxy)benzoyl | — | 422 |
| 47 | 4-(2-methyl-4-quinolinylmethoxy)benzoyl | — | 422 |
| 48 | 4-(2-methyl-4-quinolinylmethoxy)benzoyl | 1,3-thiazol-2-ylmethyl | 518 |
| 49 | 4-(2-methyl-4-quinolinylmethoxy)benzoyl | acetyl | 463 |
| 50 | 4-(2-methyl-4-quinolinylmethoxy)benzoyl | isobutyryl | 491 |
| 51 | 4-(2-methyl-4-quinolinylmethoxy)benzoyl | 3-methylbutanoyl | 505 |
| 52 | 4-(2-methyl-4-quinolinylmethoxy)benzoyl | cyclopropylcarbonyl | 489 |
| 53 | 4-(2-methyl-4-quinolinylmethoxy)benzoyl | cyclobutylcarbonyl | 503 |
| 54 | 4-(2-methyl-4-quinolinylmethoxy)benzoyl | methoxyacetyl | 493 |
| 55 | 4-(2-methyl-4-quinolinylmethoxy)benzoyl | 2-furoyl | 515 |
| 56 | 4-(2-methyl-4-quinolinylmethoxy)benzoyl | 2-thienylcarbonyl | 531 |
| 57 | 4-(2-methyl-4-quinolinylmethoxy)benzoyl | propionyl | 477 |
| 58 | 4-(2-butynyloxy)benzoyl | — | 319 |
| 59 | 4-(2-methyl-4-quinolinylmethoxy)benzoyl | — | 434 |

TABLE 1-continued

| | | | |
|---|---|---|---|
| 60 | 4-(2-methyl-4-quinolinylmethoxy)benzoyl | OH | 436 |
| 61 | 4-(2-methyl-4-quinolinylmethoxy)benzoyl | OH | 436 |
| 62 | 4-(2-methyl-4-quinolinylmethoxy)benzoyl | tetrahydro-2H-pyran-4-yl | 505 |
| 63 | 4-(2-methyl-4-quinolinylmethoxy)benzoyl | methoxycarbonyl | 479 |
| 64 | 4-(2-methyl-4-quinolinylmethoxy)benzoyl | ethoxycarbonyl | 493 |
| 65 | 4-(2-methyl-4-quinolinylmethoxy)benzoyl | propyloxycarbonyl | 507 |
| 66 | 4-(2-methyl-4-quinolinylmethoxy)benzoyl | 2-propenyloxycarbonyl | 505 |
| 67 | 4-(2-methyl-4-quinolinylmethoxy)benzoyl | isopropyloxycarbonyl | 507 |
| 68 | 4-(2-methyl-4-quinolinylmethoxy)benzoyl | 2-propynyloxycarbonyl | 503 |
| 69 | 4-(2-methyl-4-quinolinylmethoxy)benzoyl | 2-butynyloxycarbonyl | 517 |
| 70 | 4-(2-methyl-4-quinolinylmethoxy)benzoyl | 3-butenyloxycarbonyl | 519 |
| 71 | 4-(2-methyl-4-quinolinylmethoxy)benzoyl | benzyloxycarbonyl | 554 |
| 72 | 4-(2-methyl-4-quinolinylmethoxy)benzoyl | dimethylamino | 463 |
| 73 | 4-(2-butynyloxy)benzoyl | isopropyl | 360 |
| 74 | 4-(2-methyl-4-quinolinylmethoxy)benzoyl | — | 456 |
| 75 | 4-(2-methylphenoxy)benzoyl | isopropyl | 398 |
| 100 | 4-(2-methyl-4-quinolinylmethoxy)benzoyl | — | 420 |
| 101 | 4-(2-methyl-4-quinolinylmethoxy)benzoyl | — | 420 |
| 102 | 4-(2-methyl-4-quinolinylmethoxy)benzoyl | — | 420 |
| 103 | 4-(2-methyl-4-quinolinylmethoxy)benzoyl | — | 420 |
| 104 | 4-(2-methyl-4-quinolinylmethoxy)benzoyl | — | 434 |
| 105 | 4-(2-methyl-4-quinolinylmethoxy)benzoyl | — | 434 |
| 108 | 4-(2-methyl-4-quinolinylmethoxy)benzoyl | (1,1-dimethyl-ethoxy)carbonyl | 521 |
| 109 | 4-(2-methyl-4-quinolinylmethoxy)benzoyl | H | 421 |
| 110 | 4-(2-methyl-4-quinolinylmethoxy)benzoyl | (1,1-dimethyl-ethoxy)carbonyl | 521 |
| 111 | 4-(2-methyl-4-quinolinylmethoxy)benzoyl | H | 421 |
| 112 | 4-(2-methyl-4-quinolinylmethoxy)benzoyl | (1,1-dimethyl-ethoxy)carbonyl | 535 |
| 113 | 4-(2-methyl-4-quinolinylmethoxy)benzoyl | (1,1-dimethyl-ethoxy)carbonyl | 535 |
| 114 | 4-(2-methyl-4-quinolinylmethoxy)benzoyl | H | 435 |
| 115 | 4-(2-methyl-4-quinolinylmethoxy)benzoyl | H | 435 |
| 116 | 4-(2-methyl-4-quinolinylmethoxy)benzoyl | butoxycarbonyl | 535 |
| 117 | 4-(2-methyl-4-quinolinylmethoxy)benzoyl | (1-methyl-ethoxy)carbonyl | 521 |
| 118 | 4-(2-methyl-4-quinolinylmethoxy)benzoyl | methanesulfonyl | 513 |
| 119 | 4-(2-methyl-4-quinolinylmethoxy)benzoyl | benzenesulfonyl | 575 |
| 120 | 4-(2-methyl-4-quinolinylmethoxy)benzoyl | acetyl | 477 |
| 121 | 4-(2-methyl-4-quinolinylmethoxy)benzoyl | benzoyl | 539 |
| 122 | 4-(2-methyl-4-quinolinylmethoxy)benzoyl | 2,2-dimethylpropionyl | 519 |
| 123 | 4-(2-methyl-4-quinolinylmethoxy)benzoyl | 3,3-dimethylbutanoyl | 533 |
| 124 | 4-(2-methyl-4-quinolinylmethoxy)benzoyl | 4-morpholinecarbonyl | 548 |
| 125 | 4-(2-methyl-4-quinolinylmethoxy)benzoyl | dimethylcarbamyl | 506 |
| 126 | 4-(2-methyl-4-quinolinylmethoxy)benzoyl | methyl | 449 |
| 127 | 4-(2-methyl-4-quinolinylmethoxy)benzoyl | ethyl | 463 |
| 128 | 4-(2-methyl-4-quinolinylmethoxy)benzoyl | n-propyl | 477 |
| 129 | 4-(2-methyl-4-quinolinylmethoxy)benzoyl | isopropyl | 477 |
| 130 | 4-(2-methyl-4-quinolinylmethoxy)benzoyl | cyclopropylmethyl | 489 |
| 131 | 4-(2-methyl-4-quinolinylmethoxy)benzoyl | 2,2-dimethylpropyl | 505 |
| 132 | 4-(2-methyl-4-quinolinylmethoxy)benzoyl | benzyl | 525 |
| 133 | 4-(2-methyl-4-quinolinylmethoxy)benzoyl | 2-thiazolylmethyl | 532 |
| 134 | 4-(2-methyl-4-quinolinylmethoxy)benzoyl | (1,1-dimethyl-ethoxy)carbonyl | 535 |
| 135 | 4-(2-methyl-4-quinolinylmethoxy)benzoyl | (1,1-dimethyl-ethoxy)carbonyl | 535 |
| 136 | 4-(2-methyl-4-quinolinylmethoxy)benzoyl | H | 435 |
| 137 | 4-(2-methyl-4-quinolinylmethoxy)benzoyl | H | 435 |
| 138 | 4-(2-methyl-4-quinolinylmethoxy)benzoyl | (2-ethyl-propyloxy)carbonyl | 535 |
| 139 | 4-(2-methyl-4-quinolinylmethoxy)benzoyl | methoxycarbonyl | 493 |
| 140 | 4-(2-methyl-4-quinolinylmethoxy)benzoyl | (1-methyl-ethoxy)carbonyl | 521 |
| 141 | 4-(2-methyl-4-quinolinylmethoxy)benzoyl | methanesulfonyl | 513 |
| 142 | 4-(2-methyl-4-quinolinylmethoxy)benzoyl | benzenesulfonyl | 575 |
| 147 | 4-(2-methyl-4-quinolinylmethoxy)benzoyl | 3,3-dimethylbutanoyl | 533 |
| 148 | 4-(2-methyl-4-quinolinylmethoxy)benzoyl | 2,2-dimethylpropionyl | 519 |
| 149 | 4-(2-methyl-4-quinolinylmethoxy)benzoyl | benzoyl | 539 |
| 150 | 4-(2-methyl-4-quinolinylmethoxy)benzoyl | nicotinoyl | 540 |
| 151 | 4-(2-methyl-4-quinolinylmethoxy)benzoyl | 2-thiophenecarbonyl | 545 |
| 152 | 4-(2-methyl-4-quinolinylmethoxy)benzoyl | dimethylcarbamyl | 506 |
| 153 | 4-(2-methyl-4-quinolinylmethoxy)benzoyl | 4-morpholinecarbonyl | 548 |
| 154 | 4-(2-methyl-4-quinolinylmethoxy)benzoyl | [2-(2-thienyl)ethyl]carbamyl | 588 |
| 155 | 4-(2-methyl-4-quinolinylmethoxy)benzoyl | (1,1-dimethyl-ethyl)carbamyl | 534 |
| 156 | 4-(2-methyl-4-quinolinylmethoxy)benzoyl | Methyl | 449 |
| 157 | 4-(2-methyl-4-quinolinylmethoxy)benzoyl | Ethyl | 463 |
| 158 | 4-(2-methyl-4-quinolinylmethoxy)benzoyl | n-propyl | 477 |
| 159 | 4-(2-methyl-4-quinolinylmethoxy)benzoyl | isopropyl | 477 |
| 160 | 4-(2-methyl-4-quinolinylmethoxy)benzoyl | cyclobutyl | 489 |
| 161 | 4-(2-methyl-4-quinolinylmethoxy)benzoyl | n-butyl | 491 |
| 162 | 4-(2-methyl-4-quinolinylmethoxy)benzoyl | 2-methylpropyl | 491 |
| 163 | 4-(2-methyl-4-quinolinylmethoxy)benzoyl | cyclopropylmethyl | 489 |
| 164 | 4-(2-methyl-4-quinolinylmethoxy)benzoyl | 2,2-dimethylpropyl | 505 |
| 165 | 4-(2-methyl-4-quinolinylmethoxy)benzoyl | cyclopentyl | 503 |
| 166 | 4-(2-methyl-4-quinolinylmethoxy)benzoyl | 4-tetrahydropyranyl | 519 |
| 167 | 4-(2-methyl-4-quinolinylmethoxy)benzoyl | Benzyl | 525 |
| 168 | 4-(2-methyl-4-quinolinylmethoxy)benzoyl | 2-thiazolylmethyl | 532 |

TABLE 1-continued

| # | | | |
|---|---|---|---|
| 169 | 4-(2-methyl-4-quinolinylmethoxy)benzoyl | 4-picolyl | 526 |
| 170 | 4-(2-methyl-4-quinolinylmethoxy)benzoyl | 2-picolyl | 526 |
| 171 | 4-(2-methyl-4-quinolinylmethoxy)benzoyl | 3-picolyl | 526 |
| 172 | 4-(2-methyl-4-quinolinylmethoxy)benzoyl | Trans-cinnamyl | 551 |
| 173 | 4-(2-methyl-4-quinolinylmethoxy)benzoyl | Phenyl | 511 |
| 174 | 4-(2-methyl-4-quinolinylmethoxy)benzoyl | Pivolyl | 519 |
| 175 | 4-(2-methyl-4-quinolinylmethoxy)benzoyl | Methyl | 449 |
| 176 | 4-(2-methyl-4-quinolinylmethoxy)benzoyl | dimethylcarbamyl | 506 |
| 177 | 4-(2-methyl-4-quinolinylmethoxy)benzoyl | n-hexyl | 519 |
| 178 | 4-(2-methyl-4-quinolinylmethoxy)benzoyl | 2-fluoroethyl | 481 |
| 179 | 4-(2-methyl-4-quinolinylmethoxy)benzoyl | 2,2-difluoroethyl | 499 |
| 180 | 4-(2-methyl-4-quinolinylmethoxy)benzoyl | 1-methylpropyl | 491 |
| 181 | 4-(2-methyl-4-quinolinylmethoxy)benzoyl | 2-ethylpropyl | 505 |
| 182 | 4-(2-methyl-4-quinolinylmethoxy)benzoyl | 4-[N-(1,1-dimethyl-ethoxy)carbonyl]piperidinyl | 618 |
| 183 | 4-(2-methyl-4-quinolinylmethoxy)benzoyl | 4-piperidinyl | 518 |
| 184 | 4-(2-methyl-4-quinolinylmethoxy)benzoyl | 3-[N-(1,1-dimethyl-ethoxy)carbonyl]pyrrolidinyl | 604 |
| 185 | 4-(2-methyl-4-quinolinylmethoxy)benzoyl | Pyrrolidinyl | 505 |
| 186 | 4-(2-methyl-4-quinolinylmethoxy)benzoyl | 1,1-dimethyl-2-propynyl | 501 |
| 187 | 4-(2-methyl-4-quinolinylmethoxy)benzoyl | (3-thiophenyl)methyl | 531 |
| 188 | 4-(2-methyl-4-quinolinylmethoxy)benzoyl | Isopropyl | 493 |
| 189 | 4-(2-methyl-1-oxo-4-quinolinylmethoxy)benzoyl | Isopropyl | 493 |
| 190 | 4-(2-methyl-1-oxo-4-quinolinylmethoxy)benzoyl | Isopropyl | 509 |
| 191 | 4-(2-methyl-4-quinolinylmethoxy)benzoyl | 2-oxo-2-(4-morpholinyl)ethyl | 562 |
| 192 | 4-(2-methyl-4-quinolinylmethoxy)benzoyl | 2-dimethylamino-2-oxoethyl | 520 |
| 193 | 4-(2-methyl-4-quinolinylmethoxy)benzoyl | t-butylsulfonyl | 555 |
| 194 | 4-(2-methyl-1-oxo-4-quinolinylmethoxy)benzoyl | t-butylsulfonyl | 571 |
| 195 | 4-(2-methyl-4-quinolinylmethoxy)benzoyl | Benzenesulfonyl | 575 |
| 196 | 4-(2-methyl-4-quinolinylmethoxy)benzoyl | t-butylsulfinyl | 539 |
| 197 | 4-(2-methyl-4-quinolinylmethoxy)benzoyl | 2-hydroxyethyl | 479 |
| 198 | 4-(2-methyl-4-quinolinylmethoxy)benzoyl | 2-[(1,1-dimethyl-ethoxy)carbonyl]aminoethyl | 578 |
| 199 | 4-(2-methyl-4-quinolinylmethoxy)benzoyl | 2-aminoethyl | 478 |
| 200 | 4-(2-methyl-4-quinolinylmethoxy)benzoyl | 2-(N,N-dimethylamino)ethyl | 506 |
| 201 | 4-(2-methyl-4-quinolinylmethoxy)benzoyl | 2-aminopropyl | 492 |
| 202 | 4-(2-methyl-4-quinolinylmethoxy)benzoyl | 2-amino-3-hydroxypropyl | 508 |
| 203 | 4-(2-methyl-4-quinolinylmethoxy)benzoyl | (2-pyrrolidinyl)methyl | 518 |
| 204 | 4-(2-methyl-4-quinolinylmethoxy)benzoyl | 2-hydroxyethyl | 479 |
| 205 | 4-(2-methyl-4-quinolinylmethoxy)benzoyl | 2-aminoethyl | 478 |
| 206 | 4-(2-methyl-4-quinolinylmethoxy)benzoyl | Cyclobutyl | 489 |
| 207 | 4-(2-methyl-4-quinolinylmethoxy)benzoyl | — | 436 |
| 208 | 4-(2-methyl-4-quinolinylmethoxy)benzoyl | tert-butyl | 491 |
| 209 | 4-(2-methyl-4-quinolinylmethoxy)benzoyl | tert-butyloxy-2-methylpropanoate | 577 |
| 210 | 4-(2-methyl-4-quinolinylmethoxy)benzoyl | 2-methylpropanoic acid | 521 |
| 211 | 4-(2-methyl-4-quinolinylmethoxy)benzoyl | methyl-2-methylpropanoate | 535 |
| 212 | 4-(2-methyl-4-quinolinylmethoxy)benzoyl | 2-(4-morpholinyl)-2-oxoethyl | 562 |
| 213 | 4-(2-methyl-4-quinolinylmethoxy)benzoyl | 2-(dimethylamino)-2-oxo | 520 |
| 214 | 4-(2-methyl-4-quinolinylmethoxy)benzoyl | 1,1-dimethyl-2-propenyl | 503 |
| 215 | 4-(2-methyl-4-quinolinylmethoxy)benzoyl | tert-pentyl | 505 |
| 216 | 4-(2-methyl-4-quinolinylmethoxy)benzoyl | 2-propynyl | 473 |
| 217 | 4-(2-methyl-4-quinolinylmethoxy)benzoyl | 2-propenyl | 475 |
| 218 | 4-(2-methyl-4-quinolinylmethoxy)benzoyl | 1-methyl-2-propynyl | 487 |
| 219 | 4-(2-methyl-4-quinolinylmethoxy)benzoyl | 1-methyl-2-propenyl | 489 |
| 220 | 4-(2-methyl-4-quinolinylmethoxy)benzoyl | — | 466 |
| 221 | 4-(2-methyl-4-quinolinylmethoxy)benzoyl | — | 449 |
| 222 | 4-(2-methyl-4-quinolinylmethoxy)benzoyl | — | 449 |
| 223 | 4-(2-butynyloxy)benzoyl | isopropyl | 374 |
| 224 | 4-(2-butynyloxy)benzoyl | H | 332 |
| 225 | 4-[(2-methyl-3-pyridinyl)methoxy]benzoyl | (1,1-dimethyl-ethoxy)carbonyl | 485 |
| 226 | 4-[(2-methyl-3-pyridinyl)methoxy]benzoyl | H | 385 |
| 227 | 4-(2,5-dimethylbenzyl)oxy]benzoyl | (1,1-dimethyl-ethoxy)carbonyl | 496 |
| 228 | 4-(2,5-dimethylbenzyl)oxy]benzoyl} | H | 398 |
| 301 | 4-(2-methyl-4-quinolinylmethoxy)benzoyl | NH$_2$ | 449 |
| 302 | 4-(2-methyl-4-quinolinylmethoxy)benzoyl | NHMe | 463 |
| 303 | 4-(2-methyl-4-quinolinylmethoxy)benzoyl | NMe$_2$ | 477 |
| 304 | 4-(2-methyl-4-quinolinylmethoxy)benzoyl | NH$_2$ | 449 |
| 305 | 4-(2-methyl-4-quinolinylmethoxy)benzoyl | NMe$_2$ | 477 |
| 306 | 4-(2-methyl-4-quinolinylmethoxy)benzoyl | NH-i-Pr | 491 |
| 307 | 4-(2-methyl-4-quinolinylmethoxy)benzoyl | NHMe | 463 |
| 308 | 4-(2-methyl-4-quinolinylmethoxy)benzoyl | OH | 450 |
| 309 | 4-{[(2-methyl-4-quinolinyl)methyl]amino}benzoyl | — | 419 |
| 310 | 4-{methyl[(2-methyl-4-quinolinyl)methyl]amino}benzoyl | — | 433 |
| 311 | 4-(3-phenyl-4,5-dihydro-5-isoxazolyl)benzoyl | — | 394 |
| 312 | 4-[3-(4-pyridinyl)-4,5-dihydro-5-isoxazolyl]benzoyl | — | 395 |
| 313 | }-4-[3-(3-pyridinyl)-4,5-dihydro-5-isoxazolyl]benzoyl | — | 395 |
| 314 | 4-[3-(2-pyridinyl)-4,5-dihydro-5-isoxazolyl]benzoyl | — | 395 |
| 315 | 4-[3-(4-quinolinyl)-4,5-dihydro-5-isoxazolyl]benzoyl | — | 445 |

TABLE 1-continued

| | | | |
|---|---|---|---|
| 316 | 4-[3-(2,6-Dimethyl-4-pyridinyl)-4,5-dihydro-5-isoxazolyl]benzoyl | — | 423 |
| 317 | 3-methoxy-4-[3-(4-pyridinyl)-4,5-dihydro-5-isoxazolyl]benzoyl | — | 425 |
| 318 | 4-[3-(4-pyridinyl)-4,5-dihydro-5-isoxazolyl]benzoyl | — | 411 |
| 319 | 4-[5-(2-pyridinyl)-4,5-dihydro-3-isoxazolyl]benzoyl | — | 395 |
| 320 | 4-[5-(4-pyridinyl)-4,5-dihydro-3-isoxazolyl]benzoyl | — | 395 |
| 501 | 1-[(2-methyl-4-quinolinyl)methyl]-1H-indole-5-carbonyl | H | 444 |
| 502 | 1-[(2-methyl-4-quinolinyl)methyl]-1H-indole-5-carbonyl | — | 443 |
| 503 | 6-[(2-methyl-4-quinolinyl)methoxy]-1-naphthoyl | H | 485 |
| 504 | 6-[(2-methyl-4-quinolinyl)methoxy]-1-naphthoyl | — | 470 |
| 505 | 6-[(2-methyl-4-quinolinyl)methoxy]-2-naphthoyl | — | 470 |
| 506 | 6-[(2-methyl-4-quinolinyl)methoxy]-1,2,3,4-tetrahydro-1-isoquinolinecarbonyl | — | 475 |
| 507 | 1-[(2-methyl-4-quinolinyl)methyl]-1H-benzimidazole-5-carbonyl | — | 444 |
| 508 | 1-[(2-methyl-4-quinolinyl)methyl]-1H-indole-4-carboxamide | — | 443 |
| 701 | 4-(2-methyl-4-quinolinylmethoxy)benzoyl | — | 448 |
| 702 | 4-(2-methyl-4-quinolinylmethoxy)benzoyl | — | 463 |
| 703 | 4-(2-methyl-4-quinolinylmethoxy)benzoyl | — | 463 |
| 704 | 4-(2-methyl-4-quinolinylmethoxy)benzoyl | — | 463 |
| 705 | 4-(2-methyl-4-quinolinylmethoxy)benzoyl | H | 421 |
| 706 | 4-(2-methyl-4-quinolinylmethoxy)benzoyl | H | 421 |
| 707 | 4-(2-methyl-4-quinolinylmethoxy)benzoyl | (1,1-dimethylethoxy)carbonyl | 521 |

The following tables contain representative examples of the present invention. Each entry in each table is intended to be paired with each formula at the start of the table. For example, example 1 is intended to be paired with each of formulae A-AG.

TABLE 2

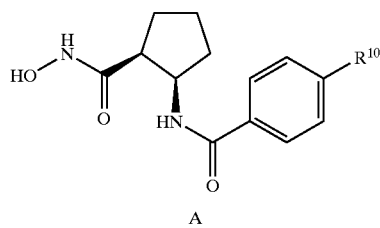

A

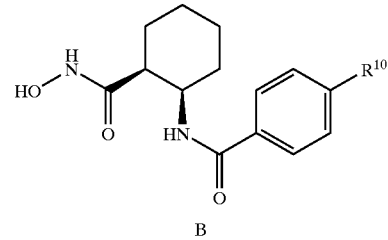

B

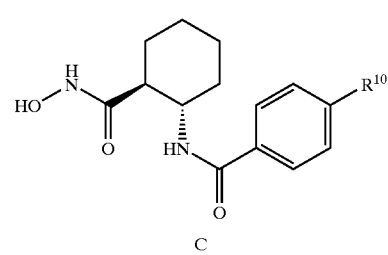

C

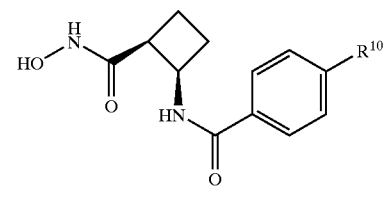

D

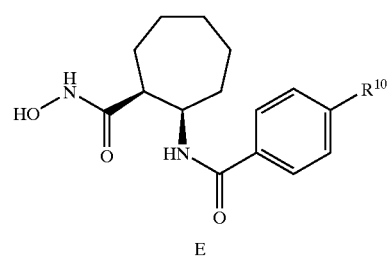

E

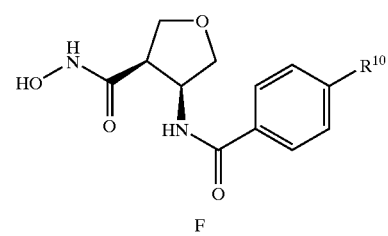

F

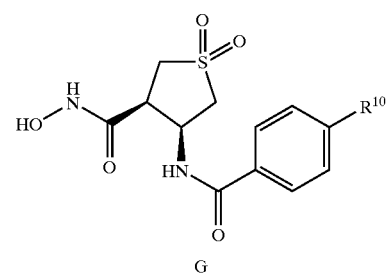

G

TABLE 2-continued
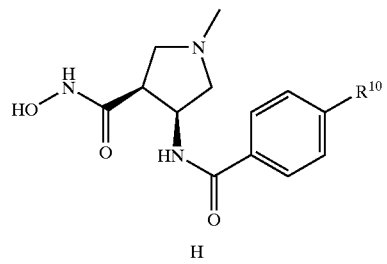
H
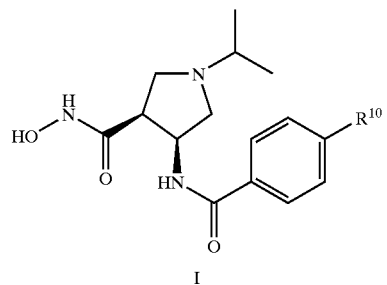
I
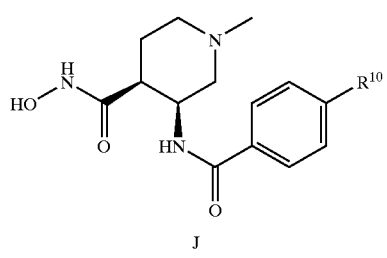
J
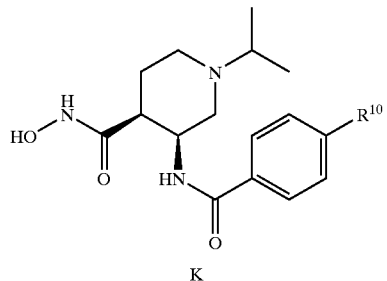
K
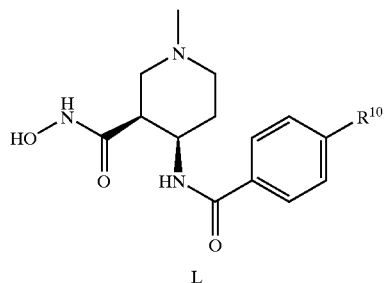
L
TABLE 2-continued
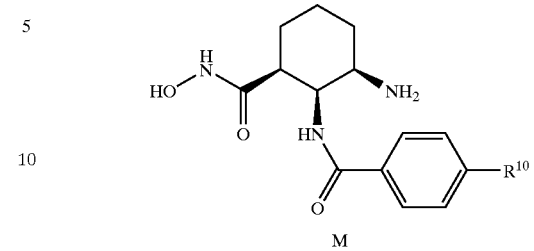
M
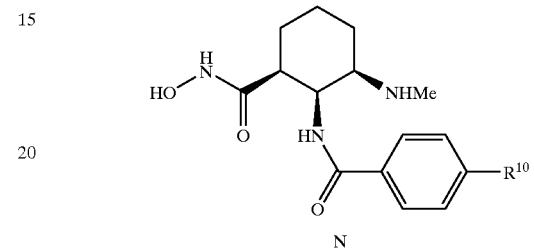
N
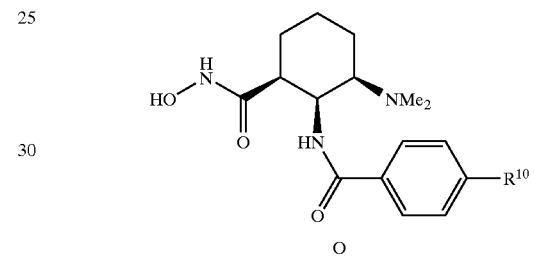
O
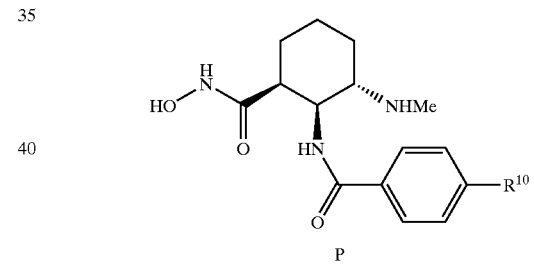
P
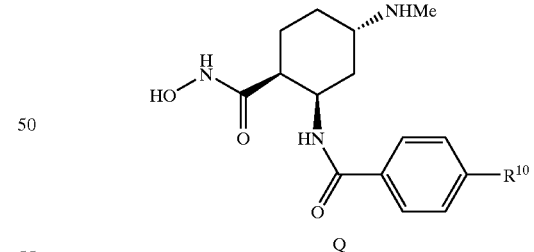
Q
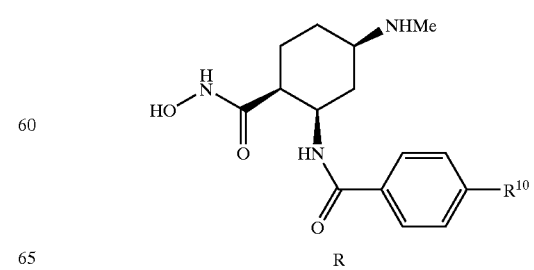
R TABLE 2-continued
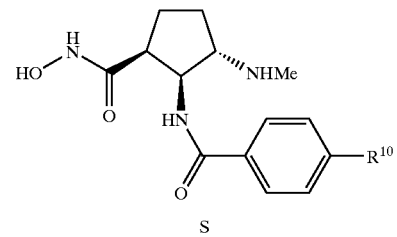
S
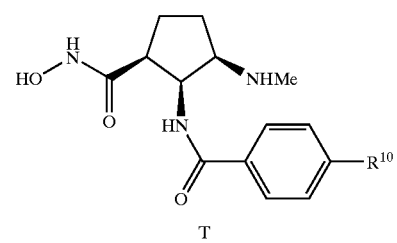
T
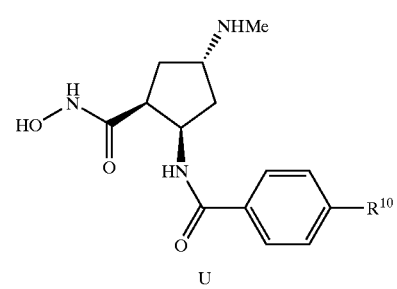
U
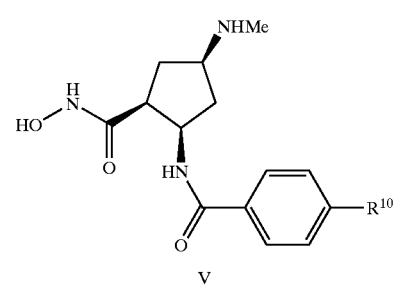
V
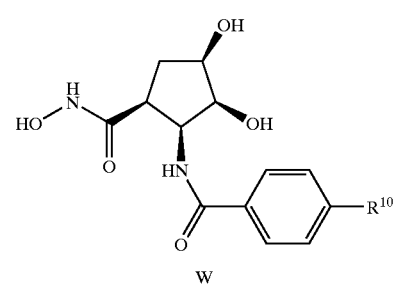
W
TABLE 2-continued
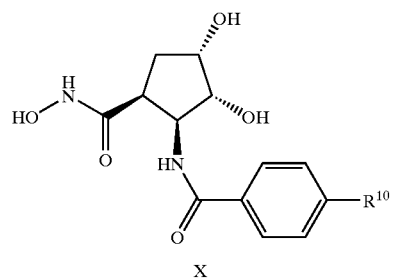
X
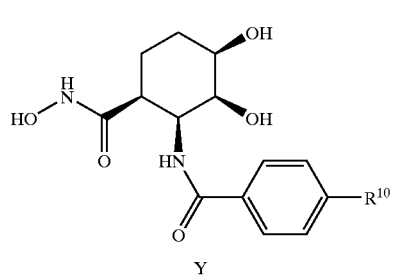
Y
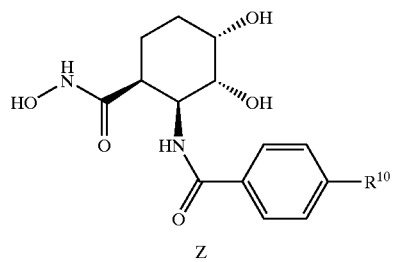
Z
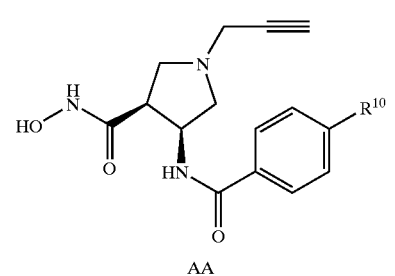
AA
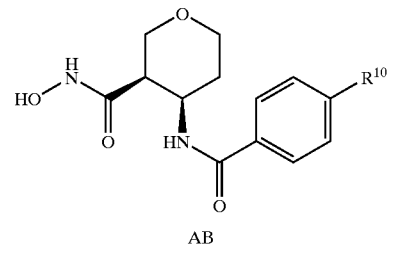
AB TABLE 2-continued

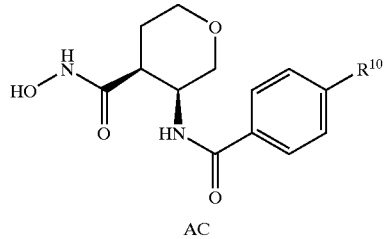

AC

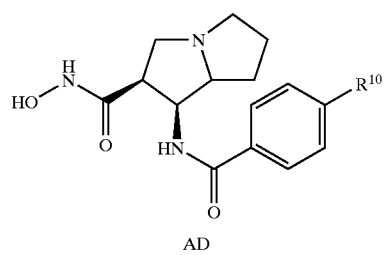

AD

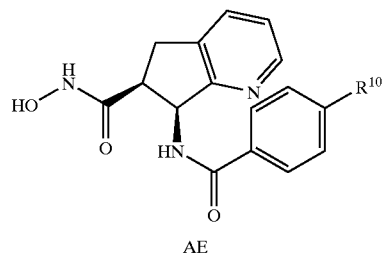

AE

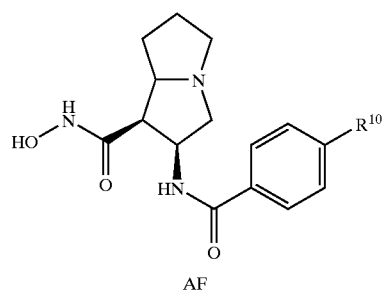

AF

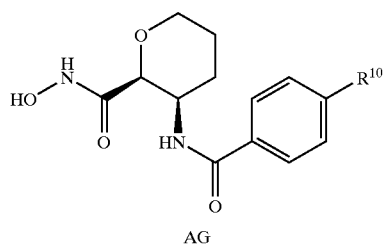

AG

| Ex # | R$^{10}$ |
|---|---|
| 1 | H |
| 2 | methyl |
| 3 | methoxy |
| 4 | 1-methylethyl |
| 5 | 1-methylethoxy |
| 6 | phenyl |
| 7 | [1,1'-biphenyl]-4-yl |
| 8 | phenoxy |
| 9 | 2-phenylethyl |
| 10 | 2-(3,5-dimethylphenyl)ethyl |
| 11 | 1-(2,6-dimethylphenyl)ethyl |
| 12 | 2-phenylethenyl |
| 13 | phenoxymethyl |
| 14 | (2-methylphenyl)methoxy |
| 15 | (3-methylphenyl)methoxy |
| 16 | 3-methylphenoxy |
| 17 | 2,6-dimethylphenoxy |
| 18 | (2,6-dimethylphenyl)methoxy |
| 19 | 3,5-dimethylphenoxy |
| 20 | (3,5-dimethylphenyl)methoxy |
| 21 | 2-(3,5-dimethylphenyl)ethyl |
| 22 | 2-(3,5-dimethylphenyl)ethenyl |
| 23 | (3-amino-5-methylphenyl)methoxy |
| 24 | (2-amino-6-methylphenyl)methoxy |
| 25 | (3-cyano-5-methylphenyl)methoxy |
| 26 | (3-cyano-5-methylphenoxy)methyl |
| 27 | (3-cyano-5-nitrophenyl)methoxy |
| 28 | (3,5-diethoxyphenyl)methoxy |
| 29 | (3,5-dimethoxyphenyl)methoxy |
| 30 | 3,5-dimethoxyphenoxy |
| 31 | 2-(3,5-dimethoxyphenyl)ethyl |
| 32 | 1-(3,5-dimethoxyphenyl)ethoxy |
| 33 | (3,5-dichlorophenyl)methoxy |
| 34 | (2,6-dichlorophenyl)methoxy |
| 35 | (3,5-dibromophenyl)methoxy |
| 36 | 3,5-dibromophenoxy |
| 37 | (3-amino-5-cyanophenyl)methoxy |
| 38 | [2,6-bis(trifluoromethyl)phenyl]methoxy |
| 39 | 2,6-bis(trifluoromethyl)phenoxy |
| 40 | (3-aminocarbonyl-5-methylphenyl)methoxy |
| 41 | ([1,1'-biphenyl]-2-yl)methoxy |
| 42 | ([1,1'-biphenyl]-3-yl)methoxy |
| 43 | [5-methyl-3-(methylsulfonyl)phenyl]methoxy |
| 44 | 5-methyl-3-(methylsulfonyl)phenoxy |
| 45 | (2-pyridinyl)methoxy |
| 46 | (4-pyridinyl)methoxy |
| 47 | (2,6-dimethyl-4-pyridinyl)methoxy |
| 48 | 2,6-dimethyl-4-pyridinyloxy |
| 49 | 1-(2,6-dimethyl-4-pyridinyl)ethoxy |
| 50 | (3,5-dimethyl-4-pyridinyl)methoxy |
| 51 | (2,6-diethyl-4-pyridinyl)methoxy |
| 52 | (2,6-dichloro-4-pyridinyl)methoxy |
| 53 | (2,6-dimethoxy-4-pyridinyl)methoxy |
| 54 | (2-chloro-6-methyl-4-pyridinyl)methoxy |
| 55 | (2-chloro-6-methoxy-4-pyridinyl)methoxy |
| 56 | (2-methoxy-6-methyl-4-pyridinyl)methoxy |
| 57 | (1-naphthalenyl)methoxy |
| 58 | 1-naphthalenyloxy |
| 59 | (2-naphthalenyl)methoxy |
| 60 | (2-methyl-1-naphthalenyl)methoxy |
| 61 | (4-methyl-2-naphthalenyl)methoxy |
| 62 | (4-quinolinyl)methoxy |
| 63 | 1-(4-quinolinyl)ethoxy |
| 64 | 4-quinolinyloxy |
| 65 | (4-quinolinyloxy)methyl |
| 66 | 2-(4-quinolinyl)ethyl |
| 67 | (2-methyl-4-quinolinyl)methoxy |
| 68 | 2-methyl-4-quinolinyloxy |
| 69 | (2-chloro-4-quinolinyl)methoxy |
| 70 | (2-methoxy-4-quinolinyl)methoxy |
| 71 | (2-hydroxy-4-quinolinyl)methoxy |
| 72 | (2-trifluoromethyl-4-quinolinyl)methoxy |
| 73 | (2-phenyl-4-quinolinyl)methoxy |
| 74 | (2,6-dimethyl-4-quinolinyl)methoxy |
| 75 | (2,7-dimethyl-4-quinolinyl)methoxy |
| 76 | (5-quinolinyl)methoxy |
| 77 | (7-methyl-5-quinolinyl)methoxy |
| 78 | (7-methoxy-5-quinolinyl)methoxy |
| 79 | (8-quinolinyl)methoxy |
| 80 | 2-(1,2,3-benzotriazol-1-yl)ethyl |
| 81 | (2-benzimidazolyl)methoxy |
| 82 | (1,4-dimethyl-5-imidazolyl)methoxy |
| 83 | (3,5-dimethyl-4-isoxazolyl)methoxy |
| 84 | (4,5-dimethyl-2-oxazolyl)methoxy |
| 85 | (2,5-dimethyl-4-thiazolyl)methoxy |
| 86 | (3,5-dimethyl-1-pyrazolyl)ethyl |
| 87 | (1,3-benzodioxo-4-yl)methoxy |
| 88 | (1,3,5-trimethyl-4-pyrazolyl)methoxy |
| 89 | (2,6-dimethyl-4-pyrimidinyl)methoxy |

TABLE 2-continued
| | |
|---|---|
| 90 | (4,5-dimethyl-2-furanyl)methoxy |
| 91 | (4,5-dimethyl-2-thiazolyl)methoxy |
| 92 | 2-(2-oxazolyl)ethyl |
| 93 | 2-butynyloxy |
| 94 | 4-hydroxy-2-butynyloxy |
| 95 | 4-pyridyl |
| 96 | 4-pyridoxy |
| 97 | (2-methyl-4-quinolinyl)methylamino |
| 98 | 3-phenyl-4,5-dihydro-5-isoxazolyl |
| 99 | 3-(4-pyridinyl)-4,5-dihydro-5-isoxazolyl |
| 100 | 5-(4-pyridinyl)-4,5-dihydro-3-isoxazolyl |
TABLE 3
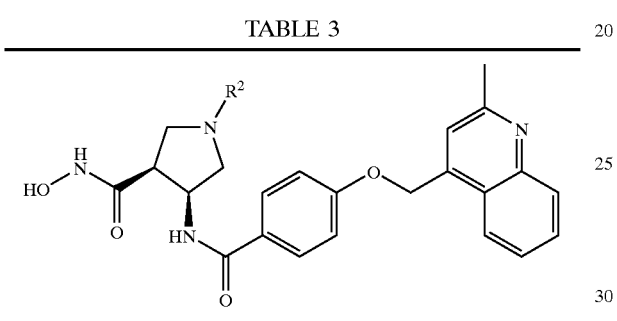
A
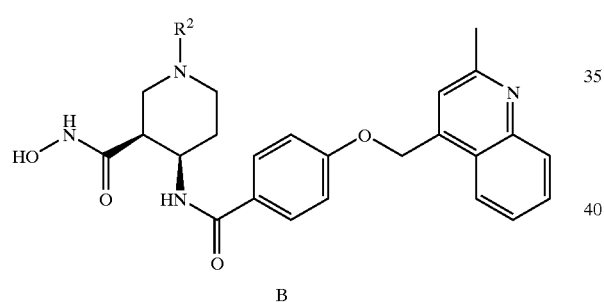
B
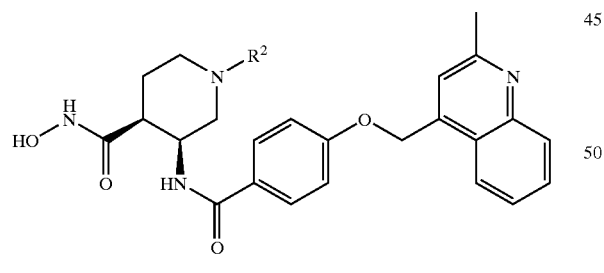
C
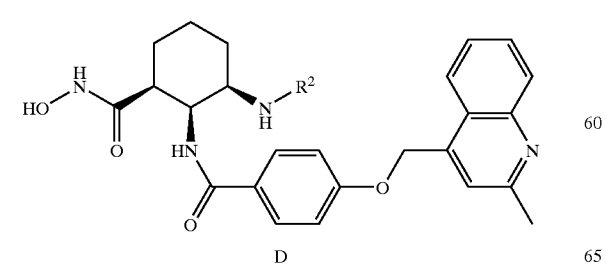
D
TABLE 3-continued
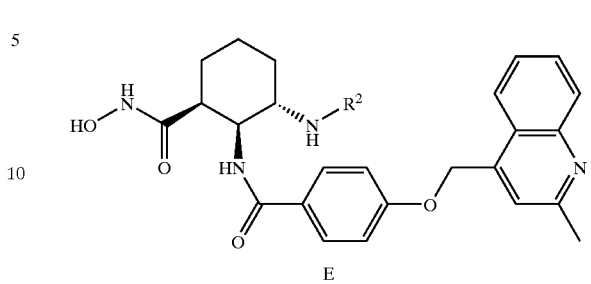
E
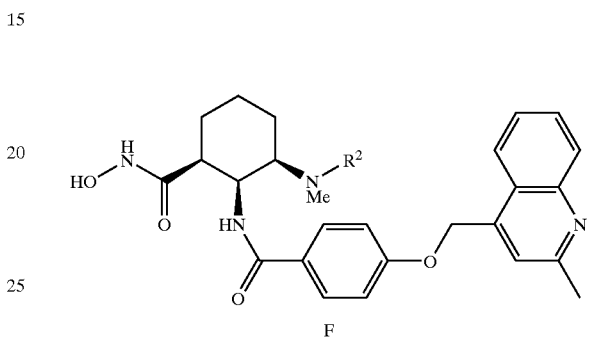
F
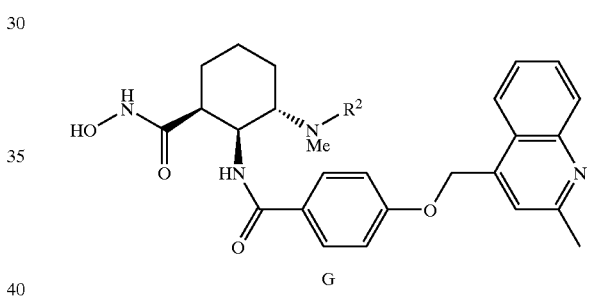
G
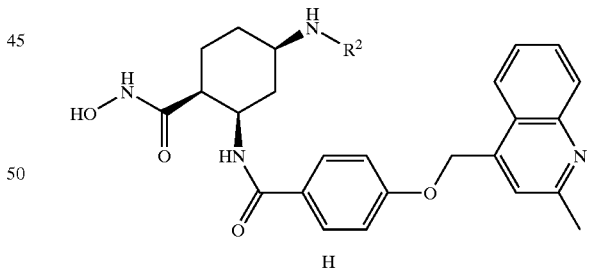
H
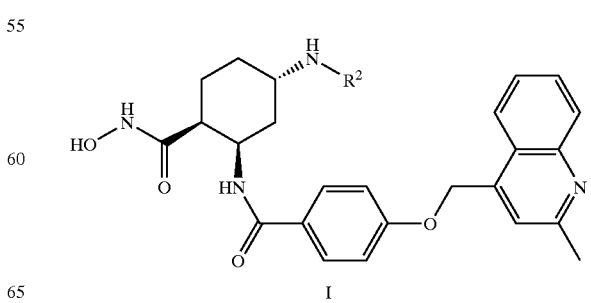
I TABLE 3-continued

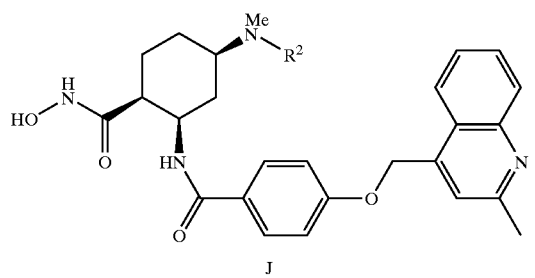

J

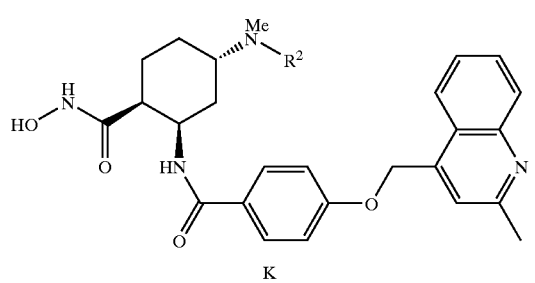

K

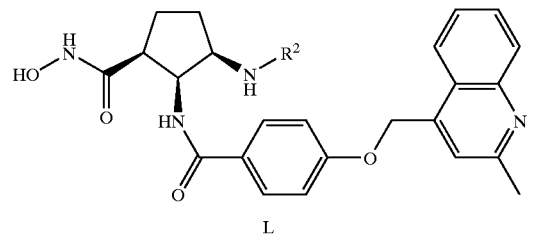

L

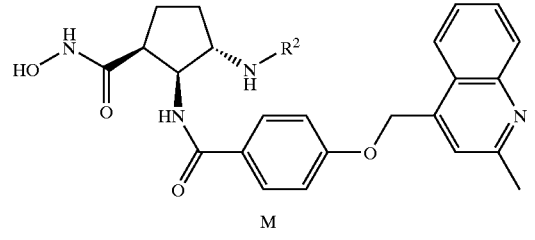

M

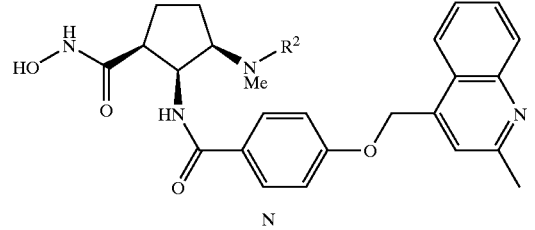

N

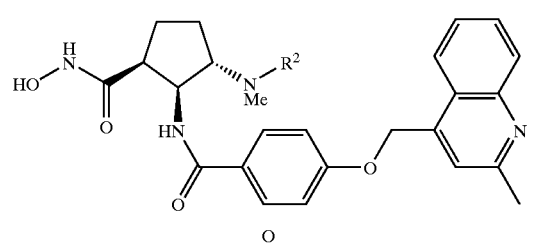

O

TABLE 3-continued

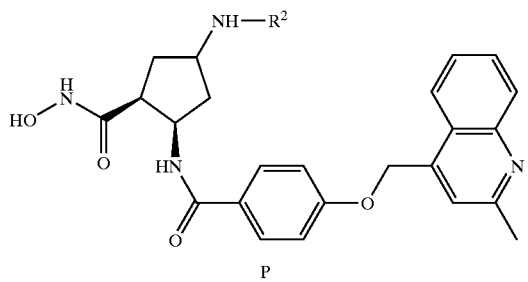

P

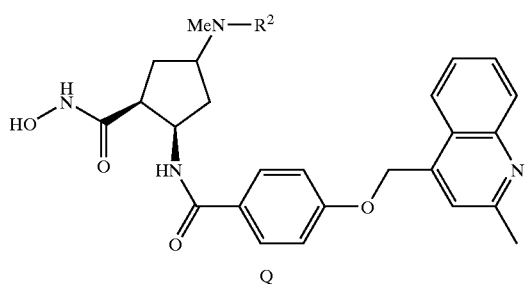

Q

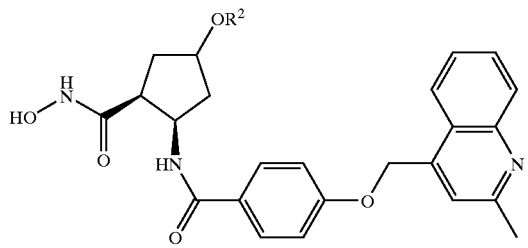

R

| Ex # | R² |
|---|---|
| 1 | H |
| 2 | methyl |
| 3 | ethyl |
| 4 | 1-methylethyl |
| 5 | cyclobutyl |
| 6 | n-butyl |
| 7 | 2,2-dimethylpropyl |
| 8 | cyclopropylmethyl |
| 9 | 2-methoxyethyl |
| 10 | 2-hydroxyethyl |
| 11 | 2-aminoethyl |
| 12 | 2-dimethylaminoethyl |
| 13 | 2-(4-morpholinyl)ethyl |
| 14 | 2-(1-piperidinyl)ethyl |
| 15 | 2-(1-piperizinyl)ethyl |
| 16 | phenyl |
| 17 | benzyl |
| 18 | 3-picolyl |
| 19 | formyl |
| 20 | acetyl |
| 21 | pivaloyl |
| 22 | benzoyl |
| 23 | nicotinoyl |
| 24 | methanesulfonyl |
| 25 | benzenesulfonyl |
| 26 | t-butylsulfonyl |
| 27 | methoxycarbonyl |
| 28 | t-butoxycarbonyl |
| 29 | isopropyloxycarbonyl |
| 30 | Dimethylcarbamyl |
| 31 | 4-morpholinecarbonyl |
| 32 | 2-thiophenecarbonyl |
| 33 | 2-fluoroethyl |

TABLE 3-continued

| | |
|---|---|
| 34 | 2,2-difluoroethyl |
| 35 | 2-(dimethylamino)-2-oxoethyl |
| 36 | 2-oxo-2-(4-morphorlinyl)ethyl |
| 37 | tert-butyl |
| 38 | 1,1-dimethylpropyl |
| 39 | 2-propenyl |
| 40 | 1-methyl-2-propenyl |
| 41 | 1,1-dimethyl-2-propenyl |
| 42 | 2-propynyl |
| 43 | 1-methyl-2-propynyl |
| 44 | 1,1-dimethyl-2-propynyl |
| 45 | (2-pyrrolidinyl)methyl |

Utility

The compounds of formula I are expected to possess matrix metalloprotease and/or aggrecanase and/or TNF-α inhibitory activity. The MMP inhibitory activity of the compounds of the present invention is demonstrated using assays of MMP activity, for example, using the assay described below for assaying inhibitors of MMP activity. The compounds of the present invention are expected to be bioavailable in vivo as demonstrated, for example, using the ex vivo assay described below. The compounds of formula I are expected to have the ability to suppress/inhibit cartilage degradation in vivo, for example, as demonstrated using the animal model of acute cartilage degradation described below.

The compounds provided by this invention should also be useful as standards and reagents in determining the ability of a potential pharmaceutical to inhibit MPs. These would be provided in commercial kits comprising a compound of this invention.

Metalloproteases have also been implicated in the degradation of basement membranes to allow infiltration of cancer cells into the circulation and subsequent penetration into other tissues leading to tumor metastasis (Stetler-Stevenson, Cancer and Metastasis Reviews, 9, 289–303, 1990). The compounds of the present invention should be useful for the prevention and treatment of invasive tumors by inhibition of this aspect of metastasis.

The compounds of the present invention should also have utility for the prevention and treatment of osteopenia associated with matrix metalloprotease-mediated breakdown of cartilage and bone that occurs in osteoporosis patients.

Compounds that inhibit the production or action of TNF and/or Aggrecanase and/or MMP's are potentially useful for the treatment or prophylaxis of various inflammatory, infectious, immunological or malignant diseases or conditions. Thus, the present invention relates to a method of treating various inflammatory, infectious, immunological or malignant diseases. These include acute infection, acute phase response, age related macular degeneration, alcoholism, anorexia, asthma, autoimmune disease, autoimmune hepatitis, Bechet's disease, cachexia (including cachexia resulting from cancer or HIV), calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthropathy (including inflammatory bowl disease), Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pydoderma gangrenosum, relapsing polychondritis, Reiter's syndrome, rheumatic fever, rheumatoid arthritis (including juvenile rheumatoid arthritis and adult rheumatoid arthritis), sarcoidosis, scleroderma, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

Some compounds of the present invention have been shown to inhibit TNF production in lipopolysacharride stimulated mice, for example, using the assay for TNF induction in mice and in human whole blood as described below.

Some compounds of the present invention have been shown to inhibit aggrecanase, a key enzyme in cartilage breakdown, as determined by the aggrecanase assay described below.

As used herein "ug" denotes microgram, "mg" denotes milligram, "g" denotes gram, "$\mu$L" denotes microliter, "mL" denotes milliliter, "L" denotes liter, "nM" denotes nanomolar, "pM" denotes micromolar, "mM" denotes millimolar, "M" denotes molar and "nm" denotes nanometer. "Sigma stands for the Sigma-Aldrich Corp. of St. Louis, Mo.

A compound is considered to be active if it has an $IC_{50}$ or $K_i$ value of less than about 10 $\mu$M for the inhibition of a desired MP. Preferred compounds of the present invention have $K_i$'s or $IC_{50}$'s of $\leq 1$ $\mu$M. More preferred compounds of the present invention have $K_i$'s or $IC_{50}$'s of $\leq 0.1$ $\mu$M. Even more preferred compounds of the present invention have $K_i$'s or $IC_{50}$'s of $\leq 0.01$ pM. Still more preferred compounds of the present invention have $K_i$'s or $IC_{50}$'s of $\leq 0.001$ $\mu$M.

Aggrecanase Enzymatic Assay

A novel enzymatic assay was developed to detect potential inhibitors of aggrecanase. The assay uses active aggrecanase accumulated in media from stimulated bovine nasal cartilage (BNC) or related cartilage sources and purified cartilage aggrecan monomer or a fragment thereof as a substrate.

The substrate concentration, amount of aggrecanases time of incubation and amount of product loaded for Western analysis were optimized for use of this assay in screening putative aggrecanase inhibitors. Aggrecanase is generated by stimulation of cartilage slices with interleukin-1 (IL-1), tumor necrosis factor alpha (TNF-α) or other stimuli. Matrix metalloproteases (MMPs) are secreted from cartilage in an inactive, zymogen form following stimulation, although active enzymes are present within the matrix. We have shown that following depletion of the extracellular aggrecan matrix, active MMPs are released into the culture media (Tortorella, M. D. et. al. Trans. Ortho. Res. Soc. 20, 341, 1995). Therefore, in order to accumulate BNC aggrecanase in culture media, cartilage is first depleted of endogenous aggrecan by stimulation with 500 ng/ml human recombinant IL-β for 6 days with media changes every 2 days. Cartilage is then stimulated for an additional 8 days without media change to allow accumulation of soluble, active aggrecanase in the culture media. In order to decrease the amount of other matrix metalloproteases released into the media during aggrecanase accumulation, agents which inhibit MMP-1, -2, -3, and -9 biosynthesis are included during stimulation. This BNC conditioned media, containing aggrecanase activity is then used as the source of aggrecanase for the assay. Aggrecanase enzymatic activity is detected by monitoring production of aggrecan fragments produced exclusively by cleavage at the Glu373-Ala374 bond within the aggrecan core protein by Western analysis using the monoclonal antibody, BC-3 (Hughes, C E, et al., Biochem J 306:799–804, 1995). This antibody recognizes aggrecan fragments with the N-terminus, 374ARGSVIL, generated upon cleavage by aggrecanase. The BC-3 antibody recognizes this neoepitope only when it is at the N-terminus and not when it is present internally within aggrecan fragments or within the aggrecan protein core. Other proteases produced by cartilage in response to IL-1 do not cleave aggrecan at the Glu373-Ala374 aggrecanase site; therefore, only products produced upon cleavage by aggrecanase are detected. Kinetic studies using this assay yield a Km of 1.5+/−0.35 uM for aggrecanase.

To evaluate inhibition of aggrecanase, compounds are prepared as 10 mM stocks in DMSO, water or other solvents and diluted to appropriate concentrations in water. Drug (50 ul) is added to 50 ul of aggrecanase-containing media and 50 ul of 2 mg/ml aggrecan substrate and brought to a final volume of 200 ul in 0.2 M Tris, pH 7.6, containing 0.4 M NaCl and 40 mM $CaCl_2$. The assay is run for 4 hr at 37° C., quenched with 20 mM EDTA and analyzed for aggrecanase-generated products. A sample containing enzyme and substrate without drug is included as a positive control and enzyme incubated in the absence of substrate serves as a measure of background.

Removal of the glycosaminoglycan side chains from aggrecan is necessary for the BC-3 antibody to recognize the ARGSVIL epitope on the core protein. Therefore, for analysis of aggrecan fragments generated by cleavage at the Glu373-Ala374 site, proteoglycans and proteoglycan fragments are enzymatically deglycosylated with chondroitinase ABC (0.1 units/10 ug GAG) for 2 hr at 37° C. and then with keratanase (0.1 units/10 ug GAG) and keratanase II (0.002 units/10 ug GAG) for 2 hr at 37° C. in buffer containing 50 mM sodium acetate, 0.1 M Tris/HCl, pH 6.5. After digestion, aggrecan in the samples is precipitated with 5 volumes of acetone and resuspended in 30 ul of Tris glycine SDS sample buffer (Novex) containing 2.5% beta mercaptoethanol. Samples are loaded and then separated by SDS-PAGE under reducing conditions with 4–12% gradient gels, transferred to nitrocellulose and immunolocated with 1:500 dilution of antibody BC3. Subsequently, membranes are incubated with a 1:5000 dilution of goat anti-mouse IgG alkaline phosphatase second antibody and aggrecan catabolites visualized by incubation with appropriate substrate for 10–30 minutes to achieve optimal color development. Blots are quantitated by scanning densitometry and inhibition of aggrecanase determined by comparing the amount of product produced in the presence versus absence of compound.

TNF PBMC Assay

Human peripheral blood mononuclear cells (PBMC) were obtained from normal donor blood by leukophoresis and isolated by Ficoll-Paque density separation. PBMCs were suspended in 0.5 ml RPMI 1640 with no serum at $2 \times 10^6$ cells/ml in 96 well polystyrene plates. Cells were preincubated 10 minutes with compound, then stimulated with 1 ug/ml LPS (Lipopolysaccharide, Salmonella typhimurium) to induce TNF production. After an incubation of 5 hours at 37° C. in 95% air, 5% $CO_2$ environment, culture supernatants were removed and tested by standard sandwich ELISA for TNF production.

TNF Human Whole Blood Assay

Blood is drawn from normal donors into tubes containing 143 USP units of heparin/10 ml. 225 ul of blood is plated directly into sterile polypropylene tubes. Compounds are diluted in DMSO/serum free media and added to the blood samples so the final concentration of compounds are 50, 10, 5, 1, 0.5, 0.1, and 0.01 $\mu$M. The final concentration of DMSO does not exceed 0.5%. Compounds are preincubated for 15 minutes before the addition of 100 ng/ml LPS. Plates are incubated for 5 hours in an atmosphere of 5% $CO_2$ in air. At the end of 5 hours, 750 ul of serum free media is added to each tube and the samples are spun at 1200RPM for 10 minutes. The supernatant is collected off the top and assayed for TNF-alpha production by a standard sandwich ELISA. The ability of compounds to inhibit TNF-alpha production by 50% compared to DMSO treated cultures is given by the IC50 value.

TNF Induction in Mice

Test compounds are administered to mice either I.P. or P.O. at time zero. Immediately following compound administration, mice receive an I.P. injection of 20 mg of D-galactosamine plus 10 $\mu$g of lipopolysaccharide. One hour later, animals are anesthetized and bled by cardiac puncture. Blood plasma is evaluated for TNF levels by an ELISA specific for mouse TNF. Administration of representative compounds of the present invention to mice results in a dose-dependent suppression of plasma TNF levels at one hour in the above assay.

MMP Assays

The enzymatic activities of recombinant MMP-1, 2, 3, 7, 8, 9, 13, 14, 15, and 16 were measured at 25° C. with a fluorometric assay (Copeland, R. A.; Lombardo, D.; Giannaras, J. and Decicco, C. P. *Bioorganic Med. Chem. Lett.* 1995, 5, 1947–1952). Final enzyme concentrations in the assay were between 0.05 and 10 nM depending on the enzyme and the potency of the inhibitor tested. The permissive peptide substrate, MCA-Pro-Leu-Gly-Leu-DPA-Ala-Arg-$NH_2$, was present at a final concentration of 10 uM in all assays. Initial velocities, in the presence or absence of inhibitor, were measured as slopes of the linear portion of the product progress curves. IC50 values were determined by plotting the inhibitor concentration dependence of the fractional velocity for each enzyme, and fitting the data by non-linear least squares methods to the standard isotherm equation (Copeland, R. A. Enzymes: *A practical Introduction to Structure, Mechanism and Data Analysis*, Wiley-VHC, New York, 1996, pp 187–223). All of the compounds studied here were assumed to act as competitive inhibitors of the enzyme, binding to the active site Zn atom as previously demonstrated by crystallographic studies of MMP-3 complexed with related hydroxamic acids (Rockwell, A.; Melden, M.; Copeland, R. A.; Hardman, K.; Decicco, C. P. and DeGrado, W. F. *J. Am. Chem. Soc.* 1996, 118, 10337–10338). Based on the assumption of competitive inhibiton, the IC50 values were converted to Ki values as previously described.

Compounds tested in the above assay are considered to be active if they exhibit a $K_i$ of $\leq 10$ $\mu$M. Preferred compounds of the present invention have $K_i$'s of $\leq 1$ $\mu$M. More preferred compounds of the present invention have $K_i$'s of $\leq 0.1$ $\mu$M. Even more preferred compounds of the present invention have $K_i$'s of $\leq 0.01$ $\mu$M. Still more preferred compounds of the present invention have $K_i$'s of $\leq 0.001$ $\mu$M.

Using the methodology described above, a number of compounds of the present invention were found to exhibit $K_i$'s of $\leq 10$ $\mu$M, thereby confirming the utility of the compounds of the present invention.

Dosage and Formulation

The compounds of the present invention can be administered orally using any pharmaceutically acceptable dosage form known in the art for such administration. The active ingredient can be supplied in solid dosage forms such as dry powders, granules, tablets or capsules, or in liquid dosage forms, such as syrups or aqueous suspensions. The active ingredient can be administered alone, but is generally administered with a pharmaceutical carrier. A valuable treatise with respect to pharmaceutical dosage forms is Remington's Pharmaceutical Sciences, Mack Publishing.

The compounds of the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed as an antiinflammatory and antiarthritic agent.

The compounds of this invention can be administered by any means that produces contact of the active agent with the agent's site of action in the body of a mammal. They can be administered by any conventional. means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient,and the effect desired. An ordinarily skilled physician or veterinarian can readily determine and prescribe the effective amount of the drug required to prevent, counter, or arrest the progress of the condition.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. For a normal male adult human of approximately 70 kg of body weight, this translates into a dosage of 70 to 1400 mg/day. Intravenously, the most preferred doses will range from about 1 to about 10 mg/kg/minute during a constant rate infusion. Advantageously, compounds of the present invention may be administered in a single daily dose, or the total daily dosage may be administered in divided doses of two, three, or four times daily.

The compounds for the present invention can be administered in intranasal form via topical use of suitable intranasal vehicles, or via transdermal routes, using those forms of transdermal skin patches wall known to those of ordinary skill in that art. To be administered in the form of a transdermal delivery system, the dosage administration will, of course, be continuous rather than intermittant throughout the dosage regimen.

In the methods of the present invention, the compounds herein described in detail can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl-or propyl-paraben, and chlorobutanol.

Suitable pharmaceutical carriers are described in Remington's Pharmaceutical Sciences, Mack Publishing Company, a standard reference text in this field. Useful pharmaceutical dosage-forms for administration of the compounds of this invention can be illustrated as follows:

Capsules

Capsules are prepared by conventional procedures so that the dosage unit is 500 milligrams of active ingredient, 100 milligrams of cellulose and 10 milligrams of magnesium stearate.

A large number of unit capsules may also prepared by filling standard two-piece hard gelatin capsules each with 100 milligrams of powdered active ingredient, 150 milligrams of lactose, 50 milligrams of cellulose, and 6 milligrams magnesium stearate.

| Syrup | |
|---|---|
| | Wt. % |
| Active Ingredient | 10 |
| Liquid Sugar | 50 |
| Sorbitol | 20 |
| Glycerine | 5 |
| Flavor, Colorant and Preservative | as required |
| Water | as required |

The final volume is brought up to 100% by the addition of distilled water.

| Aqueous Suspension | |
|---|---|
| | Wt. % |
| Active Ingredient | 10 |
| Sodium Saccharin | 0.01 |
| Keltrol ® (Food Grade Xanthan Gum) | 0.2 |
| Liquid Sugar | 5 |
| Flavor, Colorant and Preservative | as required |
| Water | as required |

Xanthan gum is slowly added into distilled water before adding the active ingredient and the rest of the formulation ingredients. The final suspension is passed through a homogenizer to assure the elegance of the final products.

| Resuspendable Powder | |
|---|---|
| | Wt. % |
| Active Ingredient | 50.0 |
| Lactose | 35.0 |
| Sugar | 10.0 |
| Acacia | 4.7 |
| Sodium Carboxylmethylcellulose | 0.3 |

Each ingredient is finely pulverized and then uniformly mixed together. Alternatively, the powder can be prepared as a suspension and then spray dried.

| Semi-Solid Gel | |
|---|---|
| | Wt. % |
| Active Ingredient | 10 |
| Sodium Saccharin | 0.02 |
| Gelatin | 2 |
| Flavor, Colorant and Preservative | as required |
| Water | as required |

Gelatin is prepared in hot water. The finely pulverized active ingredient is suspended in the gelatin solution and then the rest of the ingredients are mixed in. The suspension is filled into a suitable packaging container and cooled down to form the gel.

| Semi-Solid Paste | |
|---|---|
| | Wt. % |
| Active Ingredient | 10 |
| Gelcarin ® (Carrageenin gum) | 1 |
| Sodium Saccharin | 0.01 |
| Gelatin | 2 |
| Flavor, Colorant and Preservative | as required |
| Water | as required |

Gelcarin® is dissolved in hot water (around 80° C.) and then the fine-powder active ingredient is suspended in this solution. Sodium saccharin and the rest of the formulation ingredients are added to the suspension while it is still warm. The suspension is homogenized and then filled into suitable containers.

| Emulsifiable Paste | |
|---|---|
| | Wt. % |
| Active Ingredient | 30 |
| Tween ® 80 and Span ® 80 | 6 |
| Keltrol ® | 0.5 |
| Mineral Oil | 63.5 |

All the ingredients are carefully mixed together to make a homogenous paste.

Soft Gelatin Capsules

A mixture of active ingredient in a digestable oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

Tablets may be prepared by conventional procedures so that the dosage unit is 500 milligrams of active ingredient, 150 milligrams of lactose, 50 milligrams of cellulose and 10 milligrams of magnesium stearate.

A large number of tablets may also be prepared by conventional procedures so that the dosage unit was 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is made isotonic with sodium chloride and sterilized.

Suspension

An aqueous suspension is prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

The compounds of the present invention may be administered in combination with a second therapeutic agent, especially non-steroidal anti-inflammatory drugs (NSAID's). The compound of Formula I and such second therapeutic agent can be administered separately or as a physical combination in a single dosage unit, in any dosage form and by various routes of administration, as described above.

The compound of Formula I may be formulated together with the second therapeutic agent in a single dosage unit (that is, combined together in one capsule, tablet, powder, or liquid, etc.). When the compound of Formula I and the second therapeutic agent are not formulated together in a single dosage unit, the compound of Formula I and the second therapeutic agent may be administered essentially at the same time, or in any order; for example the compound of Formula I may be administered first, followed by administration of the second agent. When not administered at the same time, preferably the administration of the compound of Formula I and the second therapeutic agent occurs less than about one hour apart, more preferably less than about 5 to 30 minutes apart.

Preferably the route of administration of the compound of Formula I is oral. Although it is preferable that the compound of Formula I and the second therapeutic agent are both administered by the same route (that is, for example, both orally), if desired, they may each be administered by different routes and in different dosage forms (that is, for example, one component of the combination product may be administered orally, and another component may be administered intravenously).

The dosage of the compound of Formula I when administered alone or in combination with a second therapeutic agent may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above. Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a lowviscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The present invention also includes pharmaceutical kits useful, for example, in the treatment or prevention of osteoarthritis or rheumatoid arthritis, which comprise one or more containers containing a pharmaceutical composition comprising a therapeutically effective amount of a compound of Formula I. Such kits may further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, may also be included in the kit.

In the present disclosure it should be understood that the specified materials and conditions are important in practicing the invention but that unspecified materials and conditions are not excluded so long as they do not prevent the benefits of the invention from being realized.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A compound of formula I:

$$\text{(Formula I structure shown)}$$

or a stereoisomer or pharmaceutically acceptable salt form thereof, wherein;

A is selected from —COR$^5$, —CO$_2$H, CH$_2$CO$_2$H, —CO$_2$R$^6$, —CONHOH, —CONHOR$^5$, —CONHOR$^6$, —N(OH)COR$^5$, —N(OH)CHO, —SH, —CH$_2$SH, —S(O)(=NH)R$^a$, —SN$_2$H$_2$R$^a$, —PO(OH)$_2$, and —PO(OH)NHR$^a$;

ring B is piperidinyl or pyridinyl;

Z is phenyl substituted with 0–4 R$^b$, naphthyl substituted with 0–5 R$^b$, or tetrahydronaphthyl substituted with 0–5 R$^b$;

U$^a$ is absent or is selected from: O, NR$^{a1}$, C(O), C(O)O, OC(O), C(O)NR$^{a1}$, NR$^{a1}$C(O), OC(O)O, OC(O)NR$^{a1}$, NR$^{a1}$C(O)O, NR$^{a1}$C(O)NR$^{a1}$, S(O)$_p$, S(O)$_p$NR$^{a1}$, NR$^{a1}$S(O)$_p$, and NR$^{a1}$SO$_2$NR$^{a1}$;

X$^a$ is absent or selected from C$_{1-10}$ alkylene, C$_{2-10}$ alkenylene, and C$_{2-10}$ alkynylene;

Y$^a$ is absent or selected from O, NR$^{a1}$, S(O)$_p$, and C(O);

Z$^a$ is pyridyl substituted with 0–4 R$^c$ or quinolinyl substituted with 0–5 R$^c$;

R$^1$ is selected from H, C$_{1-4}$ alkyl, phenyl, and benzyl;

R$^2$ is selected from O, Cl, F, C$_{1-10}$ alkylene-Q substituted with 0–3 R$^{b1}$, C$_{2-10}$ alkenylene-Q substituted with 0–3 R$^{b1}$, C$_{2-10}$ alkynylene-Q substituted with 0–3 R$^{b1}$, (CR$^a$R$^{a1}$)$_r$O(CR$^a$R$^{a1}$)$_r$-Q, (CR$^a$R$^{a1}$)$_r$NR$^a$(CR$^a$R$^{a1}$)$_r$-Q, (CR$^a$R$^{a1}$)$_{r1}$C(O)(CR$^a$R$^{a1}$)$_r$-Q, (CR$^a$R$^{a1}$)$_{r1}$C(O)O(CR$^a$R$^{a1}$)$_r$-Q, (CR$^a$R$^{a1}$)$_{r1}$C(O)O—C$_{2-5}$ alkenylene, (CR$^a$R$^{a1}$)$_{r1}$C(O)O—C$_{2-5}$ alkynylene, (CR$^a$R$^{a1}$)$_{r1}$OC(O)(CR$^a$R$^{a1}$)$_R$-Q, (CR$^a$R$^{a1}$)$_{r1}$C(O)NR$^a$(CR$^a$R$^{a1}$)$_r$-Q, (CR$^a$R$^{a1}$)$_{r1}$NR$^a$C(O)(CR$^a$R$^{a1}$)$_r$-Q, (CR$^a$R$^{a1}$)$_{r1}$OC(O)O(CR$^a$R$^{a1}$)$_r$-Q, (CR$^a$R$^{a1}$)$_{r1}$OC(O)NR$^a$(CR$^a$R$^{a1}$)$_r$-Q, (CR$^a$R$^{a1}$)$_{r1}$NR$^a$C(O)O(CR$^a$R$^{a1}$)$_r$-Q, (CR$^a$R$^{a1}$)$_{r1}$NR$^a$C(O)NR$^a$(CR$^a$R$^{a1}$)$_r$-Q, (CR$^a$R$^{a1}$)$_{r1}$S(O)$_p$(CR$^a$R$^{a1}$)$_r$-Q, (CR$^a$R$^{a1}$)$_{r1}$SO$_2$NR$^a$(CR$^a$R$^{a1}$)$_r$-Q, (CR$^a$R$^{a1}$)$_{r1}$NR$^a$SO$_2$(CR$^a$R$^{a1}$)$_r$-Q, and (CR$^a$R$^{a1}$)$_{r1}$NR$^a$SO$_2$NR$^a$(CR$^a$R$^{a1}$)$_r$-Q;

R$^{2a}$ is selected from H, C$_{1-6}$ alkyl, OR$^a$, NR$^a$R$^{a1}$, and S(O)$_p$R$^a$;

R$^{2b}$ is H or C$_{1-6}$ alkyl;

Q is selected from H, and a C$_{3-13}$ carbocycle substituted with 0–5 R$^d$

R$^3$ is selected from Q$^1$, Cl, F, C$_{1-6}$ alkylene-Q$^1$, C$_{2-6}$ alkenylene-Q$^1$, C$_{2-6}$ alkynylene-Q$^1$, (CR$^a$R$^{a1}$)$_{r1}$O(CR$^a$R$^{a1}$)$_r$-Q$^1$, (CR$^a$R$^{a1}$)$_{r1}$NR$^a$(CR$^a$R$^{a1}$)$_r$-Q$^1$, (CR$^a$R$^{a1}$)$_{r1}$NR$^a$C(O)(CR$^a$R$^{a1}$)$_r$-Q$^1$, (CR$^a$R$^{a1}$)$_{r1}$C(O)NR$^a$(CR$^a$R$^{a1}$)$_r$-Q$^1$, (CR$^a$R$^{a1}$)$_{r1}$C(O)(CR$^a$R$^{a1}$)$_r$-Q$^1$, (CR$^a$R$^{a1}$)$_{r1}$C(O)O(CR$^a$R$^{a1}$)$_r$-Q$^1$, (CR$^a$R$^{a1}$)$_{r1}$S(O)$_p$(CR$^a$R$^{a1}$)$_r$-Q$^1$, and (CR$^a$R$^{a1}$)$_{r1}$SO$_2$NR$^a$(CR$^a$R$^{a1}$)$_r$-Q$^1$;

Q$^1$ is selected from H, phenyl substituted with 0–3 R$^d$, and naphthyl substituted with 0–3 R$^d$ R$^a$, at each occurrence, is independently selected from H, C$_{1-4}$ alkyl, phenyl and benzyl;

R$^{a1}$, each occurrence, is independently selected from H and C$_{1-4}$ alkyl, alternatively, R$^a$ and R$^{a1}$ when attached to a nitrogen are taken together with the nitrogen to which they are attached to form a 5 or 6 membered ring comprising carbon atoms and from 0–1 additional heteroatoms selected from the group consisting of N, O, and S(O)$_p$;

R$^{a2}$, at each occurrence, is independently selected from C$_{1-4}$ alkyl, phenyl and benzyl;

R$^b$, at each occurrence, is independently selected from C$_{1-6}$ alkyl, OR$^a$, Cl, F, Br, I, =O, —CN, NO$_2$, NR$^a$R$^{a1}$, C(O)R$^a$, C(O)OR$^a$, C(O)NR$^a$R$^{a1}$, R$^a$NC(O)NR$^a$R$^{a1}$, OC(O)NR$^a$R$^{a1}$, R$^a$NC(O)O, S(O)$_2$NR$^a$R$^{a1}$, NR$^a$S(O)$_2$R$^{a2}$, NR$^a$S(O)$_2$NR$^a$R$^{a1}$, OS(O)$_2$NR$^a$R$^{a1}$, NR$^a$S(O)$_2$R$^{a2}$, S(O)$_p$R$^{a2}$, CF$_3$, and CF$_2$CF$_3$;

R$^{b1}$, at each occurrence, is independently selected from OR$^a$, Cl, F, Br, I, =O, —CN, NO$_2$, and NR$^a$R$^{a1}$;

R$^c$, at each occurrence, is independently selected from C$_{1-6}$ alkyl, OR$^a$, Cl, F, Br, I, =O, —CN, NO$_2$, NR$^a$R$^{a1}$, C(O)R$^a$, C(O)OR$^a$, C(O)NR$^a$R$^{a1}$, R$^a$NC(O)NR$^a$R$^{a1}$, OC(O)NR$^a$R$^{a1}$, R$^a$NC(O)O, S(O)$_2$NR$^a$R$^{a1}$, NR$^a$S(O)$_2$R$^{a2}$, NR$^a$S(O)$_2$NR$^a$R$^{a1}$, OS(O)$_2$NR$^a$R$^{a1}$, NR$^a$S(O)$_2$R$^{a2}$, S(O)$_p$R$^{a2}$, CF$_3$, CF$_2$CF$_3$, and C$_{3-10}$ carbocycle substituted with 0–3 R$^{c1}$;

R$^{c1}$, at each occurrence, is independently selected from C$_{1-6}$ alkyl, OR$^a$, Cl, F, Br, I, =O, —CN, NO$_2$, NR$^a$R$^a$, C(O)R$^a$, C(O)OR$^a$, C(O)NR$^a$R$^{a1}$, R$^a$NC(O)NR$^a$R$^{a1}$, OC(O)NR$^a$R$^{a1}$, R$^a$NC(O)O, S(O)$_2$NR$^a$R$^{a1}$, NR$^a$S(O)$_2$R$^{a2}$, NR$^a$S(O)$_2$NR$^a$R$^{a1}$, OS(O)$_2$NR$^a$R$^{a1}$, NR$^a$S(O)$_2$R$^{a2}$, S(O)$_p$R$^{a2}$, CF$_3$, and CF$_2$CF$_3$;

R$^d$, at each occurrence, is independently selected from C$_{1-6}$ alkyl, OR$^a$, Cl, F, Br, I, =O, —CN, NO$_2$, NR$^a$R$^a$, C(O)R$^a$, C(O)OR$^a$, C(O)NR$^a$R$^{a1}$, R$^a$NC(O)NR$^a$R$^{a1}$, OC(O)NR$^a$R$^{a1}$, R$^a$NC(O)O, S(O)$_2$NR$^a$R$^{a1}$, NR$^a$S(O)$_2$R$^{a2}$, NR$^a$S(O)$_2$NR$^a$R$^{a1}$, OS(O)$_2$NR$^a$R$^{a1}$, NR$^a$S(O)$_2$R$^{a2}$, S(O)$_p$R$^{a2}$, CF$_3$, CF$_2$CF$_3$, and C$_{3-10}$ carbocycle;

R$^5$, at each occurrence, is selected from C$_{1-10}$ alkyl substituted with 0–2 R$^b$, and C$_{1-8}$ alkyl substituted with 0–2 R$^e$;

R$^e$, at each occurrence, is selected from phenyl substituted with 0–2 R$^b$ and biphenyl substituted with 0–2 R$^b$;

R$^6$, at each occurrence, is selected from phenyl, naphthyl, C$_{1-10}$ alkyl-phenyl-C$_{1-6}$ alkyl-, C$_{3-11}$ cycloalkyl, C$_{1-6}$ alkylcarbonyloxy-C$_{1-3}$ alkyl-, C$_{1-6}$ alkoxycarbonyloxy-C$_{1-3}$ alkyl-, C$_{2-10}$ alkoxycarbonyl, C$_{3-6}$ cycloalkylcarbonyloxy-C$_{1-3}$ alkyl-, C$_{3-6}$ cycloalkoxycarbonyloxy-C$_{1-3}$ alkyl-, C$_{3-6}$ cycloalkoxycarbonyl, phenoxycarbonyl, phenyloxycarbonyloxy-C$_{1-3}$ alkyl-, phenylcarbonyloxy-C$_{1-3}$ alkyl-, C$_{1-6}$ alkoxy-C$_{1-6}$ alkylcarbonyloxy-C$_{1-3}$ alkyl-, [5-(C$_1$–C$_5$ alkyl)-1,3-dioxa-cyclopenten-2-one-yl]methyl, [5-(R$^a$)-1,3-dioxa-cyclopenten-2-one-yl]methyl, (5-aryl-1,3-dioxa-cyclopenten-2-one-yl)methyl, —C$_{1-10}$ alkyl-NR$^7$R$^{7a}$, —CH(R$^8$)OC(=O)R$^9$, and —CH(R$^8$)OC(=O)OR$^9$;

R$^7$ is selected from H and C$_{1-10}$ alkyl, C$_{2-6}$ alkenyl, C$_{3-6}$ cycloalkyl-C$_{1-3}$ alkyl-, and phenyl-C$_{1-6}$ alkyl-;

R$^{7a}$ is selected from H and C$_{1-10}$ alkyl, C$_{2-6}$ alkenyl, C$_{3-6}$ cycloalkyl-C$_{1-3}$ alkyl-, and phenyl-C$_{1-6}$ alkyl-;

R$^8$ is selected from H and C$_{1-4}$ linear alkyl;

R$^9$ is selected from H, C$_{1-8}$ alkyl substituted with 1–2 R$^f$, C$_{3-8}$ cycloalkyl substituted with 1–2 R$^f$, and phenyl substituted with 0–2 R$^b$;

R$^f$, at each occurrence, is selected from C$_{1-4}$ alkyl, C$_{3-8}$ cycloalkyl, C$_{1-5}$ alkoxy, and phenyl substituted with 0–2 R$^b$;

p, at each occurrence, is selected from 0, 1, and 2;

r, at each occurrence, is selected from 0, 1, 2, 3, and 4; and, $r^1$, at each occurrence, is selected from 0, 1, 2, 3, and 4.

2. A compound according to claim 1, wherein the compound is of formula II:

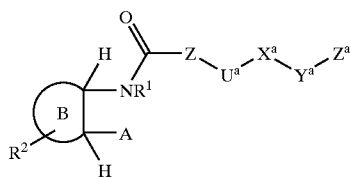

II or a stereoisomer or pharmaceutically acceptable salt form thereof, wherein;

A is selected from —$CO_2H$. $CH_2CO_2H$, —CONHOH, —CONHOR$^5$, —CONHOR$^6$, —N(OH)COR$^5$, —N(OH)CHO, —SH, and —$CH_2SH$;

ring B is piperidinyl or pyridinyl;

Z is phenyl substituted with 0–4 $R^b$, naphthyl substituted with 0–4 $R^b$, or tetrahydronaphthyl substituted with 0–4 $R^b$;

$U^a$ is absent or is selected from: O, $NR^{a^1}$, C(O), C(O)O, C(O)$NR^{a^1}$, $NR^{a^1}$C(O), S(O)$_p$, and S(O)$_p$$NR^{a^1}$;

$X^a$ is absent or selected from $C_{1-4}$ alkylene, $C_{2-4}$ alkenylene, and $C_{2-4}$ alkynylene;

$Y^a$ is absent or selected from O and $NR^{a^1}$;

$Z^a$ is pyridyl substituted with 0–4 $R^c$ or quinolinyl substituted with 0–5 $R^c$;

provided that Z, $U^a$, $Y^a$, and $Z^a$ do not combine to form a N—N, N—O, O—N, O—O, S(O)$_p$—O, O—S(O)$_p$ or S(O)$_p$—S(O)$_p$ group;

$R^1$ is selected from H, $C_{1-4}$ alkyl, phenyl, and benzyl;

$R^2$ is selected from O, $C_{1-6}$ alkylene-Q, $C_{2-6}$ alkenylene-Q, $C_{2-6}$ alkynylene-Q, $(CR^aR^{a^1})_{r^1}O(CR^aR^{a^1})_r$-Q, $(CR^aR^{a^1})_{r^1}NR^a(CR^aR^{a^1})_r$-Q, $(CR^aR^{a^1})_{r^1}C(O)(CR^aR^{a^1})_r$-Q, $(CR^aR^{a^1})_{r^1}C(O)O(CR^aR^{a^1})_r$-Q, $(CR^aR^{a^1})_rC(O)NR^aR^{a^1}$, $(CR^aR^{a^1})_{r^1}C(O)NR^a(CR^aR^{a^1})_r$-Q, $(CR^aR^{a^1})_{r^1}S(O)_p(CR^aR^{a^1})_r$-Q, and $(CR^aR^{a^1})_{r^1}SO_2NR^a(CR^aR^{a^1})_r$-Q;

Q is selected from H, and a $C_{3-6}$ carbocycle substituted with 0–5 $R^d$;

$R^a$, at each occurrence, is independently selected from H, $C_{1-4}$ alkyl, phenyl and benzyl;

$R^{a^1}$, at each occurrence, is independently selected from H and $C_{1-4}$ alkyl;

alternatively, $R^a$ and $R^{a^1}$ when attached to a nitrogen are taken together with the nitrogen to which they are attached to form a 5 or 6 memnbered ring comprising carbon atoms and from 0–1 additional heteroatoms selected from the group consisting of N, O, and S(O)$_p$;

$R^{a^2}$, at each occurrence, is independently selected from $C_{1-4}$ alkyl, phenyl and benzyl;

$R^b$, at each occurrence, is independently selected from $C_{1-6}$ alkyl, $OR^a$, Cl, F, Br, =O, —CN, $NR^aR^{a^1}$, C(O)$R^a$, C(O)$OR^a$, C(O)$NR^aR^{a^1}$, S(O)$_2NR^aR^{a^1}$, S(O)$_pR^{a^2}$, and $CF_3$;

$R^c$, at each occurrence, is independently selected from $C_{1-6}$ alkyl, $OR^a$, Cl, F, Br, =O, —CN, $NR^aR^{a^1}$, C(O)$R^a$, C(O)$OR^a$, C(O)$NR^aR^{a^1}$, S(O)$_2NR^aR^{a^1}$, S(O)$_pR^{a^2}$, $CF_3$, and $C_{3-6}$ carbocycle;

$R^d$, at each occurrence, is independently selected from $C_{1-6}$ alkyl, $OR^a$, Cl, F, Br, =O, —CN, $NR^aR^{a^1}$, C(O)$R^a$, C(O)$OR^a$, C(O)$NR^aR^{a^1}$, S(O)$_2NR^aR^{a^1}$, S(O)$_pR^{a^2}$, $CF_3$, and $C_{3-6}$ carbocycle;

$R^5$, at each occurrence, is selected from $C_{1-6}$ alkyl substituted with 0–2 $R^b$, and $C_{1-4}$ alkyl substituted with 0–2 $R^e$;

$R^e$, at each occurrence, is selected from phenyl substituted with 0–2 $R^b$ and biphenyl substituted with 0–2 $R^b$;

$R^6$, at each occurrence, is selected from phenyl, naphthyl, $C_{1-10}$ alkyl-phenyl-$C_{1-6}$ alkyl-, $C_{3-11}$ cycloalkyl, $C_{1-6}$ alkylcarbonyloxy-$C_{1-3}$ alkyl-, $C_{1-6}$ alkoxycarbonyloxy-$C_{1-3}$ alkyl-, $C_{2-10}$ alkoxycarbonyl, $C_{3-6}$ cycloalkylcarbonyloxy $C_{1-3}$ alky-, $C_{3-6}$ cycloalkoxycarbonyloxy-$C_{1-3}$ alkyl-, $C_{3-6}$ cycloalkoxycarbonyl, phenoxycarbonyl, phenoxycarbonyloxy-$C_{1-3}$ alkyl-, phenylcarbonyloxy-$C_{1-3}$ alkyl-, $C_{1-6}$ alkoxy-$C_{1-6}$ alkylcarbonyloxy-$C_{1-3}$ alkyl-, [5-($C_1$–$C_5$ alkyl)-1,3-dioxa-cyclopenten-2-one-yl]methyl, [5-($R^a$)-1,3-dioxa-cyclopenten-2-one-yl]methyl, (5-aryl-1,3-dioxa-cyclopenten-2-one-yl]methyl, —$C_{1-10}$ alkyl-$NR^7R^{7a}$, —CH($R^8$)OC(=O)$R^9$, and —CH($R^8$)OC(=O)$OR^9$;

$R^7$ is selected from H and $C_{1-6}$ alkyl, $C_{2-6}$ alkenyl, $C_{3-6}$ cycloalkyl-$C_{1-3}$ alkyl-, and phenyl-$C_{1-6}$ alkyl-;

$R^{7a}$ is selected from H and $C_{1-6}$ alkyl, $C_{2-6}$ alkenyl, $C_{3-6}$ cycloalkyl-$C_{1-3}$ alkyl-, and phenyl-$C_{1-6}$ alkyl-;

$R^8$ is selected from H and $C_{1-4}$ linear alkyl;

$R^9$ is selected from H, $C_{1-6}$ alkyl substituted with 1–2 $R^f$, $C_{3-6}$ cycloalkyl substituted with 1–2 $R^f$, and phenyl substituted with 0–2 $R^b$;

$R^f$, at each occurrence, is selected from $C_{1-4}$ alkyl, $C_{3-6}$ cycloalkyl, $C_{1-5}$ alkoxy, and phenyl substituted with 0–2 $R^b$;

p, at each occurrence, is selected from 0, 1, and 2;

r, at each occurrence, is selected from 0, 1, 2, 3, and 4; and, $r^1$, at each occurrence, is selected from 0, 1, 2, 3, and 4.

3. A compound according to claim 2, wherein the compound is of formula IIIa;

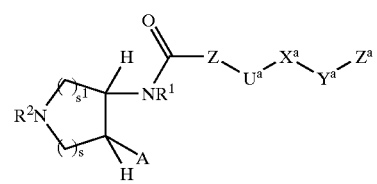

IIIa or a stereoisomer or pharmaceutically acceptable salt form thereof, wherein;

A is selected from —$CO_2H$, $CH_2CO_2H$, —CONHOH, —CONHOR$^5$, —N(OH)CHO, and —N(OH)COR$^5$;

Z is phenyl substituted with 0–3 $R^b$;

$U^a$ is absent or is selected from: O, $NR^{a^1}$, C(O), C(O)$NR^{a^1}$, S(O)$_p$, and S(O)$_p$$NR^{a^1}$;

$X^a$ is absent or selected from $C_{1-4}$ alkylene, $C_{2-4}$ alkenylene, and $C_{2-4}$ alkynylene $Y^a$ is absent or selected from O and $NR^{a^1}$;

$Z^a$ is pyridyl substituted with 0–3 $R^c$ or quinolinyl substituted with 0–3 $R^c$;

provided that Z, $U^a$, $Y^a$ and $Z^a$ do not combine to form a N—N, N—O, O—N, O—O, S(O)$_p$—O, O—S(O)$_p$ or S(O)$_p$—S(O)$_p$ group;

$R^1$ is selected from H, $C_{1-4}$ alkyl, phenyl, and benzyl;

$R^2$ is selected from Q, $C_{1-6}$ alkylene-Q, $C_{2-6}$ alkenylene-Q, $C_{2-6}$ alkynylene-Q, $(CR^aR^{a^1})_{r^1}C(O)(CR^aR^{a^1})_r$-Q, $(CR^aR^{a^1})_{r^1}C(O)O(CR^aR^{a^1})_r$-Q, $(CR^aR^{a^2})^{r^1}C(O)NR^aR^{a^1}$, $(CR^aR^{a^2})_{r^1}C(O)NR^a(CR^aR^{a^1})_r$-Q, and $(CR^aR^{a^1})_{r^1}S(O)_p(CR^aR^{a^1})_r$-Q;

Q is selected from H, and a $C_{3-6}$ carbocycle substituted with 0–3 $R^d$;

$R^a$, at each occurrence, is independently selected from H, $C_{1-4}$ alkyl, phenyl and benzyl;

$R^{a1}$, at each occurrence, is independently selected from H and $C_{1-4}$ alkyl;

$R^{a2}$, at each occurrence, is independently selected from $C_{1-4}$ alkyl, phenyl, and benzyl;

$R^b$, at each occurrence, is independently selected from $C_{1-4}$ alkyl, $OR^a$, Cl, F, =O, $NR^aR^{a^1}$, $C(O)R^a$, $C(O)OR^a$, $C(O)NR^aR^{a^1}$, $S(O)_2NR^aR^{a^1}$, $S(O)_pR^{a^2}$, and $CF_3$;

$R^c$, at each occurrence, is independently selected from $C_{1-6}$ alkyl, $OR^a$, Cl, F, Br, =O, $NR^aR^{a^1}$, $C(O)R^a$, $C(O)NR^aR^{a^1}$, $S(O)_2NR^aR^{a^1}$, $S(O)_pR^{a^2}$, and $CF_3$;

$R^d$, at each occurrence, is independently selected from $C_{1-6}$ alkyl, $OR^a$, Cl, F, Br, =O, $NR^aR^{a^1}$, $C(O)R^a$, $C(O)NR^aR^{a^1}$, $S(O)_2NR^aR^{a^1}$, $S(O)_pR^{a^2}$, $CF_3$, and phenyl;

$R^5$, at each occurrence, is selected from $C_{1-4}$ alkyl substituted with 0–2 $R^b$, and $C_{1-4}$ alkyl substituted with 0–2 $R^e$;

$R^e$, at each occurrence, is selected from phenyl substituted with 0–2 $R^b$ and biphenyl substituted with 0–2 $R^b$;

p, at each occurrence, is selected from 0, 1, and 2;

r, at each occurrence, is selected from 0, 1, 2, 3, and 4;

$r^1$, at each occurrence, is selected from 0, 1, 2, 3, and 4; and, s and $s^1$ combine to total 3.

4. A compound according to claim 3, wherein the compound is of formula IVa

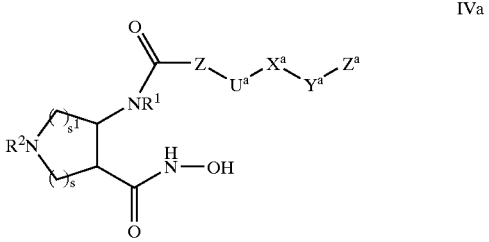

IVa or a stereoisomer or pharmaceutically acceptable salt form thereof, wherein; Z is phenyl substituted with 0–3 $R^b$;

$U^a$ is absent or is O;

$X^a$ is absent or is $CH_2$ or $CH_2CH_2$;

$Y^a$ is absent or is O;

$Z^a$ is pyridyl substituted with 0–3 $R^c$, or quinolinyl substituted with 0–3 $R^c$;

provided that Z, $U^a$, $Y^a$, and $Z^a$ do not combine to form a N—N, N—O, O—N, or O—O group;

$R^1$ is selected from H, $CH_3$, and $CH_2CH_3$;

$R^2$ is selected from Q, $C_{1-6}$ alkylene-Q, $C_{2-6}$ alkynylene-Q, $C(O)(CR^aR^{a^1})_r$-Q, $C(O)O(CR^aR^{a^1})_r$-Q, $C(O)NR^a(CR^aR^{a^1})_r$-Q, and $S(O)_p(CR^aR^{a^1})_r$-Q;

Q is selected from H, cycloprapyl substituted with 0–1 $R^d$, cyclobutyl substituted with 0–1 $R^d$, cyclopentyl substituted with 0–1 $R^d$, cyclohexyl substituted with 0–1 $R^d$, and phenyl substituted with 0–2 $R^d$;

$R^a$, at each occurrence, is independently selected from H, $CH_3$, and $CH_2CH_3$;

$R^{a1}$, at each occurrence, is independently selected from H, $CH_3$, and $CH_2CH_3$;

$R^{a2}$, at each occurrence, is independently selected from H, $CH_3$, and $CH_2CH_3$;

$R^b$, at each occurrence, is independently selected from $C_{1-4}$ alkyl, $OR^a$, Cl, F, =O, $NR^aR^{a^1}$, $C(O)R^a$, $C(O)OR^a$, $C(O)NR^aR^{a^1}$, $S(O)_2NR^aR^{a^1}$, $S(O)_pR^{a^2}$, and $CF_3$;

$R^c$, at each occurrence, is independently selected from $C_{1-6}$ alkyl, $OR^a$, Cl, F, Br, =O, $NR^aR^{a^1}$, $C(O)R^a$, $C(O)NR^aR^{a^1}$, $S(O)_2NR^aR^{a^1}$, $S(O)_pR^{a^2}$, and $CF_3$;

$R^d$, at each occurrence, is independently selected from $C_{1-6}$ alkyl, $OR^a$, Cl, F, Br, =O, $NR^aR^{a^1}$, $C(O)R^a$, $C(O)NR^aR^{a^1}$, $S(O)_2NR^aR^{a^1}$, $S(O)_pR^{a^2}$, $CF_3$ and phenyl;

p, at each occurrence, is selected from 0, 1, and 2;

r, at each occurrence, is selected from 0, 1, 2, and 3;

$r^1$, at each occurrence, is selected from 0, 1, 2, and 3; and, s and $s^1$ combine to total 3.

5. A compound according to claim 2, wherein;

A is selected from —$CO_2H$, $CH_2CO_2H$, —CONHOH, —$CONHOR^5$, —N(OH)CHO, and —$N(OH)COR^5$;

ring B is piperidinyl or pyridinyl;

Z is phenyl substituted with 0–3 $R^b$;

$U^a$ is absent or is selected from: O, $NR^{a^1}$, C(O), $C(O)NR^{a^1}$, $S(O)_p$, and $S(O)_pNR^{a^1}$;

$X^a$ is absent or selected from $C_{1-2}$ alkylene, $C_{2-4}$ alkenylene, and $C_{2-4}$ alkynylene $Y^a$ is absent or selected from O and $NR^{a^1}$;

$Z^a$ is pyridyl substituted with 0–3 $R^c$ or quinolinyl substituted with 0–3 $R^c$;

provided that Z, $U^a$, $Y^a$, and $Z^a$ do not combine to form a N—N, N—O, O—N, O—O, $S(O)_p$—O, O—$S(O)_p$ or $S(O)_p$—$S(O)_p$ group;

$R^1$ is selected from H, $C_{1-4}$ alkyl, phenyl, and benzyl;

$R^2$ is $(CR^aR^{a^1})_{r^1}O(CR^aR^{a^1})_r$-Q or $(CR^aR^{a^1})_{r^1}NR^a(CR^aR^{a^1})_r$-Q;

Q is selected from H, and a $C_{3-6}$ carbocycle substituted with 0–3 $R^d$;

$R^a$, at each occurrence, is independently selected from H, $C_{1-4}$ alkyl, phenyl and benzyl;

$R^{a1}$, at each occurrence, is independently selected from H and $C_{1-4}$ alkyl;

R,$a^2$, at each occurrence, is independently selected from $C_{1-4}$ alkyl, phenyl and benzyl;

$R^b$, at each occurrence, is independently selected from $C_{1-4}$ alkyl, $OR^a$, Cl, F, =O, $NR^aR^{a^1}$, $C(O)R^a$, $C(O)OR^a$, $C(O)NR^aR^{a^1}$, $S(O)_2NR^aR^{a^1}$, $S(O)_pR^{a^2}$, and $CF_3$;

$R^c$, at each occurrence, is independently selected from $C_{1-6}$ alkyl, $OR^a$, Cl, F, Br, =O, $NR^aR^{a^1}$, $C(O)R^a$, $C(O)NR^aR^{a^1}$, $S(O)_2NR^aR^{a^1}$, $S(O)_pR^{a^2}$, and $CF_3$;

$R^d$, at each occurrence, is independently selected from $C_{1-6}$ alkyl, $OR^a$, Cl, F, Br, =O, $NR^aR^{a^1}$, $C(O)R^a$, $C(O)NR^aR^{a^1}$, $S(O)_2NR^aR^{a^1}$, $S(O)_pR^{a^2}$, $CF_3$ and phenyl;

$R^5$, at each occurrence, is selected from $C_{1-4}$ alkyl substituted with 0–2 $R^b$, and $C_{1-4}$ alkyl substituted with 0–2 $R^e$;

$R^e$, at each occurrence, is selected from phenyl substituted with 0–2 $R^b$ and biphenyl substituted with 0–2 $R^b$;

p, at each occurrence, is selected from 0, 1, and 2;

r, at each occurrence, is selected from 0, 1, 2, 3, and 4; and, $r^1$ at each occurrence, is selected from 0, 1, 2, 3, and 4.

6. A compound according to claim 5, wherein;
A is —CONHOH;
ring B is piperidinyl or pyridinyl;
Z is phenyl substituted with 0–3 $R^b$;
$U^a$ is absent or is O;
$X^a$ is absent or is $CH_2$ or $CH_2CH_2$;
$Y^a$ is absent or is O;
$Z^a$ is pyridyl substituted with 0–3 $R^c$, or quinolinyl substituted with 0–3 $R^c$;
provided chat Z, $U^a$, $Y^a$, and $Z^a$ do not combine to form a N—N, N—O, O—N, or O—O group;
$R^1$ is selected from H, $CH_3$, and $CH_2CH_3$;
$R^2$ is $(CR^aR^{a^1})_{r^1}O(CR^aR^{a^1})_r$-Q or $(CR^aR^{a^1})_{r^1}NR^a(CR^aR^{a^1})_r$-Q;
Q is selected from H, cyclopropyl substituted with 0–1 $R^d$, cyclobutyl substituted with 0–1 $R^d$, cyclopentyl substituted with 0–1$R^d$;
$R^a$, at each occurrence, is independently selected from H, $CH_3$, and $CH_2CH_3$;
$R^{a^1}$, at each occurrence, is independently selected from H, $CH_3$, and $CH_2CH_3$;
$R^{a^2}$, at each occurrence, is independently selected from H, $CH_3$, and $CH_2CH_3$;
$R^b$, at each occurrence, is independently selected from $C_{1-4}$ alkyl, $OR^a$, Cl, F, =O, $NR^aR^{a^1}$, $C(O)R^a$, $C(O)OR^a$, $C(O)NR^aR^{a^1}$, $S(O)_2NR^aR^{a^1}$, $S(O)_pR^{a^2}$, and $CF_3$;
$R^c$, at each occurrence, is independently selected from $C_{1-6}$ alkyl, $OR^a$, Cl, F, Br, =O, $NR^aR^{a^1}$, $C(O)R^a$, $C(O)NR^aR^{a^1}$, $S(O)_2NR^aR^{a^1}$, $S(O)_pR^{a^2}$, and $CF_3$;
$R^d$, at each occurrence, is independently selected from $C_{1-6}$ alkyl, $OR^a$, Cl, F, Br, =O, $NR^aR^{a^1}$, $C(O)R^a$, $C(O)NR^aR^{a^1}$, $S(O)_2NR^aR^{a^1}$, $S(O)_pR^{a^2}$, $CF_3$ and phenyl;
p, at each occurrence, is selected from 0, 1, and 2;
r, at each occurrence, is selected from 0, 1, 2, and 3; and,
$r^1$, at each occurrence, is selected from 0, 1, 2, and 3.

7. A compound according to claim 1, wherein the compound is selected from the group:
(3S,4S)-N-hydroxy-4-[[[4-[(2-methyl-4-quinolinyl)methoxy]phenyl]carbonyl]aminol-3-piperidinecarboxamide;
(3S,4R)-N-hydroxy-4-[[[4-[(2-methyl-4-quinolinyl)methoxy]phenyl]carbonyl]amino]-3-piperidinecarboxamide;
(3S,4R)-1-[(butoxy)carbonyl]-N-hydroxy-4-[[[4-[(2-methyl-4-quinolinyl)methoxy]phenyl]carbonyl]amino]-3-piperidinecarboxamide;
(3S,4R)-N-hydroxy-1-[[(1-methylethyl)oxy]carbonyl]-4-[[[4-[(2-methyl-4-quinolinyl)methoxy]phenyl]carbonyl]amino]-3-piperidinecarboxamide;
(3S,4R)-N-hydroxy-1-(methylsulfonyl)-4-[[[4-[(2-methyl-4-quinolinyl)methoxy]phenyl]carbonyl]amino]-3-piperidinecarboxamide;
(3S,4R)-N-hydroxy-4-[[[4-[(2-methyl-4-quinolinyl)methoxy]phenyl]carbonyl]amino]-1-(phenylsulfonyl)-3-piperidinecarboxamide;
(3S,4R)-1-acetyl-N-hydroxy-4-[[[4-[(2-methyl-4-quinolinyl)methoxy]phenyl]carbonyl]amino]-3-piperidinecarboxamide;
(3S,4R)-1-benzoyl-N-hydroxy-4-[[[4-[(2-methyl-4-quinolinyl)methoxy]phenyl]carbonyl]amino]-3-piperidinecarboxamide;
(3S,4R)-1-(2,2-dimethylpripionyl)-N-hydroxy-4-[[[4-[(2-methyl-4-quinolinyl)methoxy]phenyl]carbonyl]amino]-3-piperidinecarboxamide;
(3S,4R)-1-(3,3-dimethylbutanoyl)-N-hydroxy-4-[[[4-[(2-methyl-4-quinolinyl)methoxy]phenyl]carbonyl]amino]-3-piperidinecarboxamide;
(3S,4R)-N-hydroxy-4-[[[4-[(2-methyl-4-quinolinyl)methoxy]phenyl]carbonyl]amino]-1-(4-morpholinecarbonyl)-3-piperidinecarboxamide;
(3S,4R)-1-(dimethylcarbamyl)-N-hydroxy-4-[[[4-[(2-methyl-4-quinolinyl)methoxy]phenyl]carbonyl]amino]-3-piperidinecarboxamide;
(3S,4R)-N-hydroxy-1-methyl-4-[[[4-[(2-methyl-4-quinolinyl)methoxy]phenyl]carbonyl]amino]-3-piperidinecarboxamide;
(3S,4R)-1-ethyl-N-hydroxy-4-[[[4-[(2-methyl-4-quinolinyl)methoxy]phenyl]carbonyl]amino]-3-piperidinecarboxamide;
(3S,4R)-N-hydroxy-4-[[[4-[(2-methyl-4-quinolinyl)methoxy]phenyl]carbonyl]amino]-1-propyl-3-piperidinecarboxamide;
(3S,4R)-N-hydroxy-1-(1-methylethyl)-4-[[[4-[(2-methyl-4-quinolinyl)methoxy]phenyl]carbonyl]amino]-3-piperidinecarboxamide;
(3S,4R)-1-(cyclopropylmethyl)-N-hydroxy-4-[[[4-[(2-methyl-4-quinolinyl)methoxy]phenyl]carbonyl]amino]-3-piperidinecarboxamide;
(3S,4R)-1-(2,2-dimethylpropyl)-N-hydroxy-4-[[[4-[(2-methyl-4-quinolinyl)methoxy]phenyl]carbonyl]amino]-3-piperidinecarboxamide;
(3S,4R)-1-benzyl-N-hydroxy-4-[[[4-[(2-methyl-4-quinolinyl)methoxy]phenyl]carbonyl]amino]-3-piperidinecarboxamide;
(3S,4S)-1-[[(1,1-dimethylethyl)oxy]carbonyl]-N-hydroxy-3-[[[4-[(2-methyl-4-quinolinyl)methoxy]phenyl]carbonyl]amino]-4-piperidinecarboxamide;
(3R,4S)-1-[[(1,1-dimethylethyl)oxy]carbonyl]-N-hydroxy-3-[[[4-[(2-methyl-4-quinolinyl)methoxy]phenyl]carbonyl]amino]-4-piperidinecarboxamide;
(3R,4S)-N-hydroxy-3-[[[4-[(2-methyl-4-quinolinyl)methoxy]phenyl]carbonyl]amino]-4-piperidinecarboxamide;
(3S,4S)-N-hydroxy-3-[[[4-[(2-methyl-4-quinolinyl)methoxy]phenyl]carbonyl]amino]-4-piperidinecarboxamide;
(3S,4S)-N-hydroxy-1-[[(2-methylpropyl)oxy]carbonyl]-3-[[[4-[(2-methyl-4-quinolinyl)methoxy]phenyl]carbonyl]amino]-4-piperidinecarboxamide;
(3S,4S)-N-hydroxy-1-(methoxycarbonyl)-3-[[[4-[(2-methyl-4-quinolinyl)methoxy]phenyl]carbonyl]amino]-4-piperidinecarboxamide;
(3S,4S)-N-hydroxy-1-[(1-methylethoxy)carbonyl]-3-[[[4-[(2-methyl-4-quinolinyl)methoxy]phenyl]carbonyl]amino]-4-piperidinecarboxamide;
(3S,4S)-N-hydroxy-1-(methylsulfonyl)-3-[[[4-[(2-methyl-4-quinolinyl)methoxy]phenyl]carbonyl]amino]-4-piperidinecarboxamide
(3S,4S)-N-hydroxy-3-[[[4-[(2-methyl-4-quinolinyl)methoxy]phenyl]carbonyl]amino]-1-(phenylsulfonyl)-4-piperidinecarboxamide;
(3S,4S)-1-(3,3-dimethylbutanoyl)-N-hydroxy-3-[[[4-[(2-methyl-4-quinolinyl)methoxy]phenyl]carbonyl]amino]-4-piperidinecarboxamide;
(3S,4S)-1-(2,2-dimethylpropionyl)-N-hydroxy-3-[[[4-[(2-methyl-4-quinolinyl)methoxy]phenyl]carbonyl]amino]-4-piperidinecarboxamide;

(3S,4S)-1-benzoyl-N-hydroxy-3-[[[4-[(2-methyl-4-quinolinyl)methoxy]phenyl]carbonyl]amino]-4-piperidinecarboxamide;

(3S,4S)-1-[(pyridin-3-yl)carbonyl]-N-hydroxy-3-[[[4-[(2-methyl-4-quinolinyl)methoxy]phenyl]carbonyl]amino]-4-piperidinecarboxamide;

(3S,4S)-1-(dimethylcarbamyl)-N-hydroxy-3-[[[4-[(2-methyl-4-quinolinyl)methoxy]phenyl]carbonyl]amino]-4-piperidinecarboxamide;

(3S,4S)-N-hydroxy-3-[[[4-[(2-methyl-4-quinolinyl)methoxy]phenyl]carbonyl]amino]-1-(4-morpholinecarbonyl)-4-piperidinecarboxamide;

(3S,4S)-1-[(1,1-dimethylethyl)carbamyl]-N-hydroxy-3-[[[4-[(2-methyl-4-quinolinyl)methoxy]phenyl]carbonyl]amino]-4-piperidinecarboxamide;

(3S,4S)-N-hydroxy-1-methyl-3-[[[4-[(2-methyl-4-quinolinyl)methoxy]phenyl]carbonyl]amino]-4-piperidinecarboxamide;

(3S,4S)-1-ethyl-N-hydroxy-3-[[[4-[(2-methyl-4-quinolinyl)methoxy]phenyl]carbonyl]amino]-4-piperidinecarboxamide;

(3S,4S)-N-hydroxy-3-[[[4-[(2-methyl-4-quinolinyl)methoxy]phenyl]carbonyl]amino]-1-propyl-4-piperidinecarboxamide;

(3S,4S)-N-hydroxy-1-(1-methylethyl)-3-[[[4-[(2-methyl-4-quinolinyl)methoxy]phenyl]carbonyl]amino]-4-piperidinecarboxamide;

(3S,4S)-1-cyclobutyl-N-hydroxy-3-[[[4-[(2-methyl-4-quinolinyl)methoxy]phenyl]carbonyl]amino]-4-piperidinecarboxamide;

(3S,4S)-1-butyl-N-hydroxy-3-[[[4-[(2-methyl-4-quinolinyl)methoxy]phenyl]carbonyl]amino]-4-piperidinecarboxamide;

(3S,4S)-N-hydroxy-3-[[[4-[(2-methyl-4-quinolinyl)methoxy]phenyl]carbonyl]amino]-1-(2-methylpropyl)-4-piperidinecarboxamide;

(3S,4S)-1-(cyclopropylmethyl)-N-hydroxy-3-[[[4-[(2-methyl-4-quinolinyl)methoxy]phenyl]carbonyl]amino]-4-piperidinecarboxamide;

(3S,4S)-1-(2,2-dimethylpropyl)-N-hydroxy-3-[[[4-[(2-methyl-4-quinolinyl)methoxy]phenyl]carbonyl]amino]-4-piperidinecarboxamide;

(3S,4S)-1-cyclopentyl-N-hydroxy-3-[[[4-[(2-methyl-4-quinolinyl)methoxy]phenyl]carbonyl]amino]-4-piperidinecarboxamide;

(3S,4S)-1-benzyl-N-hydroxy-3-[[[4-[(2-methyl-4-quinolinyl)methoxy]phenyl]carbonyl]amino]-4-piperidinecarboxamide;

(3S,4S)-N-hydroxy-3-[[[4-[(2-methyl-4-quinolinyl)methoxy]phenyl]carbonyl]amino]-1-(trans-3-phenyl-2-propenyl)-4-piperidinecarboxamide;

(3S,4S)-N-hydroxy-3-[[[4-[(2-methyl-4-quinolinyl)methoxy]phenyl]carbonyl]amino]-1-phenyl-4-piperidinecarboxamide;

(3R,4S)-1-(2,2-dimethylpropionyl)-N-hydroxy-3-[[[4-[(2-methyl-4-quinolinyl)methoxy]phenyl]carbonyl]amino]-4-piperidinecarboxamide;

(3R,4S)-N-hydroxy-3-[[[4-[(2-methyl-4-quinolinyl)methoxy]phenyl]carbonyl]amino]-1-methyl-4-piperidinecarboxamide;

(3R,4S)-1-(dimethylcarbamyl)-N-hydroxy-3-[[[4-[(2-methyl-4-quinolinyl)methoxy]phenyl]carbonyl]amino]-4-piperidinecarboxamide;

(3S,4S)-1-hexyl-N-hydroxy-3-[[[4-[(2-methyl-4-quinolinyl)methoxy]phenyl]carbonyl]amino]-4-piperidinecarboxamide;

(3S,4S)-1-(2-fluoroethyl)-N-hydroxy-3-[[[4-[(2-methyl-4-quinolinyl)methoxy]phenyl]carbonyl]amino]-4-piperidinecarboxamide;

(3S,4S)-1-(2,2-difluoroethyl)-N-hydroxy-3-[[[4-[(2-methyl-4-quinolinyl)methoxy]phenyl]carbonyl]amino]-4-piperidinecarboxamide;

(3S,4S)-N-hydroxy-1-(1-methylpropyl)-3-[[[4-[(2-methyl-4-quinolinyl)methoxy]phenyl]carbonyl]amino]-4-piperidinecarboxamide;

(3S,4S)-1-(1-ethylpropyl)-N-hydroxy-3-[[[4-[(2-methyl-4-quinolinyl)methoxy]phenyl]carbonyl]amino]-4-piperidinecarboxamide;

(3S,4S)-1-[1-[[(1,1-dimethylethyl)oxy]carbonyl]-4-tetrahydropiperidinyl]-N-hydroxy-3-[[[4-[(2-methyl-4-quinolinyl)methoxy]phenyl]carbonyl]amino]-4-piperidinecarboxamide;

(3S,4S)-N-hydroxy-3-[[[4-[(2-methyl-4-quinolinyl)methoxy]phenyl]carbonyl]amino]-1-(4-tetrahydropiperidinyl)-4-piperidinecarboxamide;

(3S,4S)-1-(1,1-dimethyl-2-propynyl)-N-hydroxy-3-[[[4-[(2-methyl-4-quinolinyl)methoxy]phenyl]carbonyl]amino]-4-piperidinecarboxamide;

(3S,4S)-N-hydroxy-1-(1-methylethyl)-3-[[[4-[(2-methyl-4-quinolinyl)methoxy]phenyl]carbonyl]amino]-1-oxo-4-piperidinecarboxamide;

(3S,4S)-N-hydroxy-1-(1-methylethyl)-3-[[[4-[(2-methyl-1-oxo-4-quinolinyl)methoxy]phenyl]carbonyl]amino]-4-piperidinecarboxamide;

(3S,4S)-N-hydroxy-1-(1-methylethyl)-3-[[[4-[(2-methyl-1-oxo-4-quinolinyl)methoxy]phenyl]carbonyl]amino]-1-oxo-4-piperidinecarboxamide;

(3S,4S)-N-hydroxy-3-[[[4-[(2-methyl-4-quinolinyl)methoxy]phenyl]carbonyl]amino]-1-[2-(4-morpholinyl)-2-oxoethyl]-4-piperidinecarboxamide;

(3S,4S)-1-[2-(N,N-dimethylamino)-2-oxoethyl]-N-hydroxy-3-[[[4-[(2-methyl-4-quinolinyl)methoxy]phenyl]carbonyl]amino]-4-piperidinecarboxamide;

(3S,4S)-1-(t-butylsulfonyl)-N-hydroxy-3-[[[4-[(2-methyl-4-quinolinyl)methoxy]phenyl]carbonyl]amino]-4-piperidinecarboxamide;

(3S,4S)-1-(t-butylsulfonyl)-N-hydroxy-3-[[[4-[(2-methyl-1-oxo-4-quinolinyl)methoxy]phenyl]carbonyl]amino]-4-piperidinecarboxamide;

(3S,4S)-1-(benzenesulfonyl)-N-hydroxy-3-[[[4-[(2-methyl-4-quinolinyl)methoxy]phenyl]carbonyl]amino]-4-piperidinecarboxamide;

(3S,4S)-1-(t-butylsulfinyl)-N-hydroxy-3-[[[4-[(2-methyl-4-quinolinyl)methoxy]phenyl]carbonyl]amino]-4-piperidinecarboxamide;

(3S,4S)-N-hydroxy-1-(2-hydroxyethyl)-3-[[[4-[(2-methyl-4-quinolinyl)methoxy]phenyl]carbonyl]amino]-4-piperidinecarboxamide;

(3S,4S)-1-[2-[[[(1,1-dimethylethyl)oxy]carbonyl]amino]ethyl]-N-hydroxy-3-[[[4-[(2-methyl-4-quinolinyl)methoxy]phenyl]carbonyl]amino]-4-piperidinecarboxamide;

(3S,4S)-1-(2-aminoethyl)-N-hydroxy-3-[[[4-[(2-methyl-4-quinolinyl)methoxy]phenyl]carbonyl]amino]-4-piperidinecarboxamide;

(3S,4S)-1-[2-(N,N-dimethylamino)ethyl]-N-hydroxy-3-[[[4-[(2-methyl-4-quinolinyl)methoxy]phenyl]carbonyl]amino]-4-piperidinecarboxamide;

(3S,4S)-1-[(2S)-2-aminopropyl]-N-hydroxy-3-[[[4-[(2-methyl-4-quinolinyl)methoxy]phenyl]carbonyl]amino]-4-piperidinecarboxamide;

(3S,4S)-1-[(2R)-2-amino-3-hydroxypropyl]-N-hydroxy-3-[[[4-[(2-methyl-4-quinolinyl)methoxy]phenyl]carbonyl]amino]-4-piperidinecarboxamide;

(3S,4R)-N-hydroxy-1-(2-hydroxyethyl)-4-[[[4-[(2-methyl-4-quinolinyl)methoxy]phenyl]carbonyl]amino]-3-piperidinecarboxamide;

(3S,4R)-1-(2-aminoethyl)-N-hydroxy-4-[[[4-[(2-methyl-4-quinolinyl)methoxy]phenyl]carbonyl]amino]-3-piperidinecarboxamide;

(3S,4R)-1-cyclobutyl-N-hydroxy-4-[[[4-[(2-methyl-4-quinolinyl)methoxy]phenyl]carbonyl]amino]-3-piperidinecarboxamide;

(3S,4S)-1-tert-butyl-N-hydroxy-3-({4-[(2-methyl-4-quinolinyl)methoxy]benzoyl}amino)-4-piperidinecarboxamide;

tert-butyl 2-[(3S,4S)-4-[(hydroxyamino)carbonyl]-3-({4-[(2-methyl-4-quinolinyl)methoxy]benzoyl}amino)piperidinyl]-2-methylpropanoate 2-[(3S,4S)-4-[(hydroxyamino)carbonyl]-3-({4-[(2-methyl-4-quinolinyl)methoxy]benzoyl}amino)piperidinyl]-2-methylpropanoic acid;

methyl 2-[(3S,4S)-4-[(hydroxyamino)carbonyl]-3-({4-[(2-methyl-4-quinolinyl)methoxy]benzoyl}amino)piperidinyl]-2-methylpropanoate;

(3S,4S)-N-hydroxy-3-({4-[(2-methyl-4-quinolinyl)methoxy]benzoyl}amino)-1-[2-(4-morpholinyl)-2-oxoethyl]-4-piperidinecarboxamide;

(3S,4S)-1-[2-(dimethylamino)-2-oxoethyl]-N-hydroxy-3-({4-[(2-methyl-4-quinolinyl)methoxy]benzoyl}amino)-4-piperidinecarboxamide;

(3S,4S)-1-(1,1-dimethyl-2-propenyl)-N-hydroxy-3-({4-[(2-methyl-4-quinolinyl)methoxy]benzoyl}amino)-4-piperidinecarboxamide;

(3S,4S)-N-hydroxy-3-({4-[(2-methyl-4-quinolinyl)methoxy]benzoyl}amino)-1-tert-pentyl-4-piperidinecarboxamide;

(3S,4S)-N-hydroxy-3-({4-[(2-methyl-4-quinolinyl)methoxy]benzoyl}amino)-1-(2-propynyl)-4-piperidinecarboxamide;

(3S,4S)-1-allyl-N-hydroxy-3-({4-[(2-methyl-4-quinolinyl)methoxy]benzoyl}amino)-4-piperidinecarboxamide;

(3S,4S)-N-hydroxy-1-(1-methyl-2-propynyl)-3-({4-[(2-methyl-4-quinolinyl)methoxy]benzoyl}amino)-4-piperidinecarboxamide;

(3S,4S)-N-hydroxy-1-(1-methyl-2-propenyl)-3-({4-[(2-methyl-4-quinolinyl)methoxy]benzoyl}amino)-4-piperidinecarboxamide;

(5S)-N-hydroxy-5-({4-[(2-methyl-4-quinolinyl)methoxy]benzoyl}amino)-2-oxo-4-piperidinecarboxamide;

(3S,4S)-N-hydroxy-3-({4-[(2-methyl-4-quinolinyl)methoxy]benzoyl}amino)-2-oxo-4-piperidinecarboxylate;

(3S,4S)-N-hydroxy-3-({4-[(2-methyl-3-pyridinyl)methoxy]benzoyl}amino)-4-piperidinecarboxamide;

N-hydroxy-3-({6-[(2-methyl-4-quinolinyl)methoxy]-1-naphthoyl}amino)-4-piperidinecarboxamide;

or a pharmaceutically acceptable salt form thereof.

8. A pharmaceutical composition, comprising: a pharmaceutically acceptable carrier and a therapeutically effective amount of a compound according to claim 1 or a pharmaceutically acceptable salt form thereof.

9. A method of treating a disease or condition selected from Crohn's disease, psoriasis, psoriatic arthritis, and rheumatoid arthritis, comprising administering to the mammal in need of such treatment a therapeutically effective amount of a compound according to claim 1.

10. A pharmaceutical composition, comprising: a pharmaceutically acceptable carrier and a therapeutically effective amount of a compound according to claim 2 or a pharmaceutically acceptable salt form thereof.

11. A pharmaceutical composition, comprising: a pharmaceutically acceptable carrier and a therapeutically effective amount of a compound according to claim 3 or a pharmaceutically acceptable salt form thereof.

12. A pharmaceutical composition, comprising: a pharmaceutically acceptable carrier and a therapeutically effective amount of a compound according to claim 4 or a pharmaceutically acceptable salt form thereof.

13. A pharmaceutical composition, comprising: a pharmaceutically acceptable carrier and a therapeutically effective amount of a compound according to claim 5 or a pharmaceutically acceptable salt form thereof.

14. A pharmaceutical composition, comprising: a pharmaceutically acceptable carrier and a therapeutically effective amount of a compound according to claim 6 or a pharmaceutically acceptable salt form thereof.

15. A pharmaceutical composition, comprising: a pharmaceutically acceptable carrier and a therapeutically effective amount of a conipound according to claim 7 or a pharmaceutically acceptable salt form thereof.

16. A method of treating a disease or condition selected from Crohn's disease, psoriasis, psoriatic arthritis, and rheumatoid arthritis, comprising administering to the mammal in need of such treatment a therapeutically effective amount of a compound according to claim 2.

17. A method of treating a disease or condition selected from Crohn's disease, psoriasis, psoriatic arthritis, and rheumatoid arthritis, comprising administering to the mammal in need of such treatment a therapeutically effective amount of a compound according to claim 3.

18. A method of treating a disease or condition selected from Crohn's disease, psoriasis, psoriatic arthritis, and rheumatoid arthritis, comprising administering to the mammal in need of such treatment a therapeutically effective amount of a compound according to claim 4.

19. A method of treating a disease or condition selected from Crotm's disease, psoriasis, psoriatic arthritis, and rheumatoid arthritis, comprising administering to the mammal in need of such treatment a therapeutically effective amount of a compound according to claim 5.

20. A method of treating a disease or condition selected from Crohn's disease, psoriasis, psonatic arthritis, and rheumatoid arthritis, comprising administering to the mammal in need of such treatment a therapeutically effective amount of a compound according to claim 6.

21. A method of treating a disease or condition selected from Crohn's disease, psoriasis, psonatic arthritis, and rheumatoid arthritis, comprising administering to the mammal in need of such treatment a therapeutically effective amount of a compound according to claim 7.

* * * * *